(12) United States Patent
Barry

(10) Patent No.: US 12,060,582 B2
(45) Date of Patent: Aug. 13, 2024

(54) ADENOVIRUSES AND METHODS FOR USING ADENOVIRUSES

(71) Applicant: MAYO FOUNDATION FOR MEDICAL EDUCATION AND RESEARCH, Rochester, MN (US)

(72) Inventor: Michael A. Barry, Rochester, MN (US)

(73) Assignee: MAYO FOUNDATION FOR MEDICAL EDUCATION AND RESEARCH, Rochester, MN (US)

(*) Notice: Subject to any disclaimer, the term of this patent is extended or adjusted under 35 U.S.C. 154(b) by 0 days.

(21) Appl. No.: 18/353,375

(22) Filed: Jul. 17, 2023

(65) Prior Publication Data

US 2024/0026307 A1    Jan. 25, 2024

Related U.S. Application Data

(62) Division of application No. 16/690,733, filed on Nov. 21, 2019, now Pat. No. 11,746,334.

(60) Provisional application No. 62/770,631, filed on Nov. 21, 2018.

(51) Int. Cl.
   *C12N 7/00* (2006.01)
   *A61K 35/761* (2015.01)

(52) U.S. Cl.
   CPC .............. *C12N 7/00* (2013.01); *A61K 35/761* (2013.01); *C12N 2750/14122* (2013.01); *C12N 2750/14132* (2013.01); *C12N 2750/14143* (2013.01)

(58) Field of Classification Search
   None
   See application file for complete search history.

(56) References Cited

U.S. PATENT DOCUMENTS

| | | | |
|---|---|---|---|
| 6,153,435 A | 11/2000 | Crystal | |
| 7,332,337 B2 | 2/2008 | Van Es | |
| 7,741,099 B2 | 6/2010 | Havenga et al. | |
| 7,951,585 B2 | 5/2011 | Ke | |
| 8,658,611 B2* | 2/2014 | Kumon | C07K 14/4747 514/44 R |
| 8,834,863 B2 | 9/2014 | Roy | |
| 9,546,206 B2 | 1/2017 | Ring et al. | |
| 9,562,087 B2 | 2/2017 | Ring et al. | |
| 9,683,025 B2 | 6/2017 | Zhang et al. | |
| 10,208,304 B2 | 2/2019 | Yamamoto | |
| 10,588,938 B2 | 3/2020 | Giaccia et al. | |

(Continued)

FOREIGN PATENT DOCUMENTS

| | | |
|---|---|---|
| EP | 1785488 | 5/2007 |
| EP | 1785488 | 9/2007 |

(Continued)

OTHER PUBLICATIONS

Zhang and Tao. "Antigenicity, immunogenicity, allergenicity." Allergy bioinformatics (2015): 175-186.*

(Continued)

*Primary Examiner* — Shanon A. Foley
(74) *Attorney, Agent, or Firm* — HUESCHEN AND SAGE

(57) ABSTRACT

This invention relates to methods and materials for nucleic acid delivery, vaccination, and/or treating cancer. More specifically, methods and materials for nucleic acid delivery, vaccination, and/or treating cancer using one or more recombinant adenoviruses (Ads) as an oncolytic agent are provided.

11 Claims, 83 Drawing Sheets

Specification includes a Sequence Listing.

(56) References Cited

U.S. PATENT DOCUMENTS

| | | |
|---|---|---|
| 10,800,830 B2 | 10/2020 | Ring et al. |
| 2002/0150557 A1 | 10/2002 | Ramachandra |
| 2003/0219899 A1 | 11/2003 | Korokhov |
| 2004/0191222 A1 | 9/2004 | Emini |
| 2005/0265973 A1 | 12/2005 | Harden |
| 2010/0303838 A1 | 12/2010 | Silvestre |
| 2011/0318373 A1 | 12/2011 | Sasikumar |
| 2012/0264192 A1 | 10/2012 | Yamamoto |
| 2013/0004461 A1 | 1/2013 | Roy |
| 2014/0348791 A1 | 11/2014 | Barouch |
| 2015/0250837 A1 | 9/2015 | Nolin |
| 2017/0157188 A1 | 6/2017 | Silvestre |
| 2018/0346571 A1 | 12/2018 | Gurney |
| 2019/0153471 A1 | 5/2019 | Paul |
| 2019/0382793 A1 | 12/2019 | Stewart |
| 2020/0157510 A1* | 5/2020 | Barry ............... A61K 39/12 |
| 2020/0339654 A1 | 10/2020 | Barry |
| 2021/0355453 A1 | 11/2021 | Barry |

FOREIGN PATENT DOCUMENTS

| | | |
|---|---|---|
| JP | 2008522630 | 7/2008 |
| JP | 2002527455 | 8/2008 |
| JP | 2015506372 | 3/2018 |
| KR | 10-2009-0007067 | 1/2009 |
| RU | 2017103162 | 8/2018 |
| WO | WO200022136 | 4/2000 |
| WO | WO2006065827 | 6/2006 |
| WO | WO 2011/043719 | 4/2011 |
| WO | WO 2012/083297 | 6/2012 |
| WO | WO2012083297 | 6/2012 |
| WO | WO2013112986 | 8/2013 |
| WO | WO2015166082 | 11/2015 |
| WO | WO2016008976 | 1/2016 |
| WO | WO2017075570 | 5/2017 |
| WO | WO2017220602 | 12/2017 |
| WO | WO2018006005 | 1/2018 |
| WO | WO 2018/111767 | 6/2018 |
| WO | WO2018157165 | 8/2018 |
| WO | WO2019202118 | 10/2019 |

OTHER PUBLICATIONS

Nguyen et al. (Oncolytic Virotherapy. (May 2018): 43-51).*
Howe et al. (PNAS. 1990; 87: 5883-5887).*
Badri, H., et al., "Optimization of radiation dosing schedules for proneural glioblastoma", J. Math. Biol., Jun. 21, 2015, pp. 1-36.
Baylot, Virginie, et al., "TCTP has a crucial role in the different stages of prostate cancer malignant progression", Springer International Publishing AG. Chapter 13, TCTP/TPt—Remodeling Signaling From Stem Cell to Disease, Results and Problems in Cell Differentiation 64 2017.
Tanque, Kiyornori, et al., "Armed oncolytic adenovirus expressing PD-L1 mini-body enhances anti-tumor effects of chimeric antigen receptor T-cells in solid tumors", Cancer Res., 77(8), Apr. 15, 2017, pp. 2040-2051.
Brahmer, et al. The New England Do Medicine, 366:2455-65, 2012.
Davison, AJ. Journal of General Virology, 84(11): 2885-2908, 2003.
Fromm, George, et al., "Agonist redirected checkpoint, PD1-Fc-OXAOL, for cancer immunotherapy", Journal for Immunotherapy of Cancer, 6:149, 2018, pp. 1-16.
Gao, Wenda, et al., "Stimulating PD-1-negative signals concurrent with blocking C0154 co-stimulation induces long-term islet allograft survival", Transplantation, vol. 78, No. 6, Sep. 1, 2003, pp. 994-999.
Iwai, et al. "Involvement of PD-1 on tumor cells in the escape from host immune system and tumor immunothespy by PD-L1 blockade", Proceedings of the National Academy of Sciences, 99(19):12293-97, 2002.
Maute, et al. Proceedings of the National Academy of Sciences, 112(47), E6506-F6514, published online Nov. 10, 2015.
Miao, et al. "Netralizing PD-LX and PD-L2 Enhances teh Efficacy of limone Checkpoint Inhibitors in Ovarian Cancer", biorxiv, published online Jan. 20, 2020.

Stepanenko, Aleksei, et al., "Tropism and transduction of oncolytic odenovirus 5 vectors in cancer therapy: focus on fiber chimerism and mosaicism, hexon and pIX", Virus Research, vol. 257, Sep. 1, 2018, pp. 40-51.
Wang, Gongze, et al., "Modification of sPD1 with CRT induces potent anti-tumor immune responses in vitro and in vivo", Biomedicine and Pharmacotherapy, vol. 76, Nov. 18, 2015, pp. 57-64.
Weaver, et al. Virology, 412(1):19-27, 2811.
Yoon, A-Rum, et al., "A vesicular stomatitis virus glycoprotein epitope-incorporated ontolytic adenovirus overcones CAR-dependency and shows markedly enhanced cancer cell killing and suppression of tumor growth", Oncotarget, vol. 6, No., 33, Oct. 27, 2015, pp. 34875-34891.
Barry, Michael, "Single-cycle adenovirus vectors in the current vaccine landscape", Expert Rev Vaccines, 17(2), Feb. 2018, pp. 163-173.
Boroviagin, et al., "Adenovirus-based vectors for the development of prophylactic and therapeutic vaccines", Novel Technologies for Vaccine Development, publisher-Springer-Verlag Wien, Chptr 8, pp. 203-271, 20114.
Chen, Christopher, Y. et al., "Targeting adenoviruses with factor x-single-chain antibody fusion proteins",Human Gene Therapy, vol. 21, No. 6, Jun. 1, 2010, pp. 733-749.
Cholanigiocarcinoma accessed Mar. 12, 2017 URL surgery.usc.edu/divisions/tumor/pancreasdiseases/web%20pages/BILIARY%20SYSTEM/cholaangiocaro 2 pages, 2017.
EESR For EP 22151052.2 dated Dec. 7, 2022.
Herrmann, Monika, et al., "Bifunctional PS-1 x aC03 x aC033 fusion protein reverses adaptive immune escape in acute myeloid leukemia", Blood, vol. 132, No. 23, Dec. 6, 2018, pp. 2484-2494.
Howe, et al., PNAS, 87, 1998, pp $883-5887.
International Search Report for PCT/US2019/062547 dated Feb. 5, 2020.
International Search Report for PCT/US2020/030240 dated Aug. 13, 2020.
Khare, et al., Molecular Therapy, 19(7), 2011, pp. 1254-1262.
Kiesler, "why a new immunotherapy for lung cancer works only for some people", accessed Feb. 12, 2018 at URL mskcc.org/blog/why-new-immunotherapy-lung-works-only-some-people, Apr. 2015, pp. 1-4.
Lu, Shao-Chia, et al., "Modulating oncolytic adenovirus Immunotherapy by driving two axes of the immune system by expressing 4-1BBL and C040L", Human Gene Therapy, vol. 33, No. 5-6, 2021, pp. 250-261.
Lukashev, et al. "Evidence of frequent recombination among human adenoviruses", Journal of Generel Virology, 2008, 89:386-388.
McDermott, et al., "PD-1 as a potential target in cancer therapy", Cancer Medicine 2(5): 662-673, 2013.
Merck Manual Bladder cancer accessed Aug. 21, 2014 URL merckmanuals.com/home/kidney_and_urinary_tract_disorders/cancers_of_the_kidney_and_genitourinary_ 2 pages, 2014.
Merck Manual Colorectal cancer accessed Aug. 21, 2014 URL merckmanuals.com/home/digestive,,disorders/tumors,,of,,the_digestive_system/colorectal_cancer.htm. 5 pages, 2013.
Merck Manual Prostate cancer accessed Aug. 21, 2014 URI merckmanuals.com/home/kidney_and_urinary_traer_disorders/cancers_of_the_kidney_an_genitourinary_cancer&alt/\sh, 8 pages, 2013.
Merck Manuals Lung carcinoma accessed Mar. 12, 2017 URL merckmanuals.com/professional/pulmonar-disorders/tumors -of-the-lungs/lung-carcinoma, 18 pages, 2017.
Merck Manuals Neuroblastoma accessed Mar. 12, 2017 URL merckmanuals.com/professional/pediatrics/pediatric-cancers/neuroblastoma, 4 page, 2017.
National Institute of Cancer—understanding and related topics, accessed Aug. 21, 20144 at URL cancer.gov/cancertopics/understandingcancer, 63 pages, 2017.
Nguyen, Tien, V., et al., "Onocolytic adenovirus Ad687 for systemic virotherapy against prostate cancer", Oncolvtic Virotherapy, vol. 7, May 1, 2018, pp. 43-51.
Partial EESR for EP 22151052.2 dated Sep. 2, 2022.
Renal Cell Carcinoma accessed Mar. 12, 2017 URL merckmanuals.com/professional/genitourinary-disorders/genitourinary-cancer/renal-cell-carcinoma, 6 pages, 2017.

(56) References Cited

OTHER PUBLICATIONS

Teng, et al., "Classifying cancers based on T-cell infiltration and PD-L1", Am. Assoc, Cancer Res. J., 75:2139-2145, 2015.
Thyroid Cancer accessed Mar. 12, 2017 URL www.merckmanuals.com/professional/endocinre-and-metabolic-disorders/thyroid-disorders-cancers, 4 pages, 2016.
Walsh, et al., Journal of Clinical Microbiology, 2011, pp. 3482-3490.

\* cited by examiner

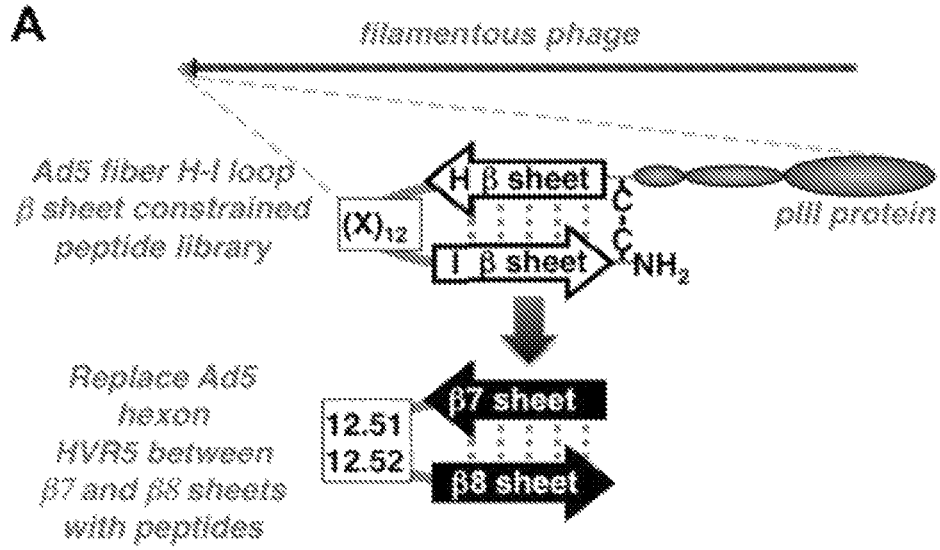
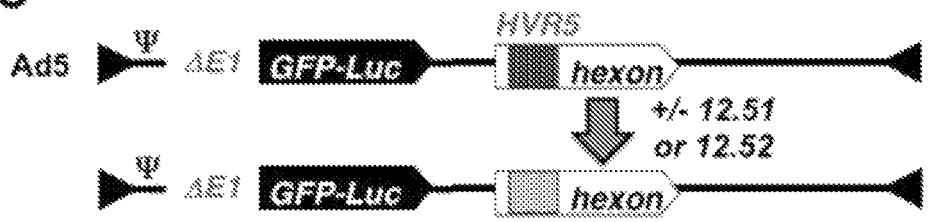
FIG. 1

|  | HVR 1 | |
|---|---|---|
| Ad5 hexon | YNALAPKGAPNPCEWDEAATL--ALEINLEEDDNEDEVDEQAEQKTHVFGDAPYSGI | |
| Ad6 hexon | YNALAPKGAPNSCEWDEEENEAQADELDEEENEAQADEQAKKTHVYAQAPLSGI | |
| Ad57 hexon | YNALAPKGAPNSCEWDEDDTQYVAEDDQDDEFEEQLQQNGKKTHVYAQAPFAGE | |

|  | HVR 2 | HVR 3 |
|---|---|---|
| Ad5 hexon | NITKEGLQIG....VEGQ.TPKYADKTFQPEPQIGESQWYETEINHAGGRVLKKTTPMK | |
| Ad6 hexon | KITKEGLQIGTADATNAGAKEIFADKTFQPEPQGESQWNEADATAGGRVLKKTTPMK | |
| Ad57 hexon | MFKNGLQIGTGNGAATEGNKEIYQPEPQIGESQWNEAEEGSVAGGRVLKKTTPMK | |

|  | HVR 4 | HVR 5 |
|---|---|---|
| Ad5 hexon | PCYGSYAKPTMENGGQRTLMQQNGKLESQVEMQFFSTTEATAGNDNLIPKVVLYSEDV | |
| Ad6 hexon | PCYGSYARPTNSNGGQSVMVEQ-NGKLESQVEMQFFSTNAINEVNNIQPTVVLYSEDV | |
| Ad57 hexon | PCYGSYARPTNSNGGQSVMVEQ-NGKLESQVEMQFFSTVNANNEAMLQPKMLYSEDV | |

|  | HVR 6 | HVR 7 |
|---|---|---|
| Ad5 hexon | DIETPDTHLSYKYFKNSRELLGGQSMPNRPNYIAFRDNFIGLMYYNSTGNMGVLAGQ | |
| Ad6 hexon | NMETPDTHLSYKEKMQDKAXVMLGGQAMPNRPNYIAFRDNFIGLMYYNSTGNMGVLAGQ | |
| Ad57 hexon | NMETPDTHLSYKEKSDQNSKAMLGGQSMPNRPNYIAFRDNFIGLMYYNSTGNMGVLAGQ | |

|  |  | |
|---|---|---|
| Ad5 hexon | ASQLNAVVDLQDRNTELSYQLLLDSIGDRTRAYFSMWNQAVDSYDPDVRIIENHGTEDELP | |
| Ad6 hexon | ASQLNAVVDLQDRNTELSYQLLLDSIGDRTRAYFSMWNQAVDSYDPDVRIIENHGTEDELP | |
| Ad57 hexon | ASQLNAVVDLQDRNTELSYQLLLDSIGDRTRAYFSMWNQAVDSYDPDVRIIENHGTEDELP | |

|  | HVR 7 | |
|---|---|---|
| Ad5 hexon | NYCFPLDGVINTETLTKVKPKTGQE----NGWEKDATEFSDKNEIGVGNNFAMEINLNAN | |
| Ad6 hexon | NYCFPLBGIQITDTFQAVKTTAANGDOGNTTWQKDS-TFAERNEIGVGNNFAMEINLNAN | |
| Ad57 hexon | NYCFPLBGIGVDTMQADKATWGNG-CATTMACDN-TFAERNEIGVGNNFLEAMEINLNAN | |

|  |  | |
|---|---|---|
| Ad5 hexon | LWRNFLYSNIALYLPDKLKYSPSNVHISDNPNTYDYMNKRVVAPGLVDCYINLGARWSLD | SEQ ID NO: 52 |
| Ad6 hexon | LWRNFLYSNIALYLPDKLKYNPTNVEISDNPNTYDYMNKRVVAPGLVDCYINLGARWSLE | SEQ ID NO: 53 |
| Ad57 hexon | LWRNFLYSNIALYLPDKLKYNPTNVEISDNPNTYDYMNKRVVAPGLVDCYINLGARWSLD | SEQ ID NO: 54 |

Week 40 F8 Binding IgG Antibodies (OD450)

Figure 25, continued
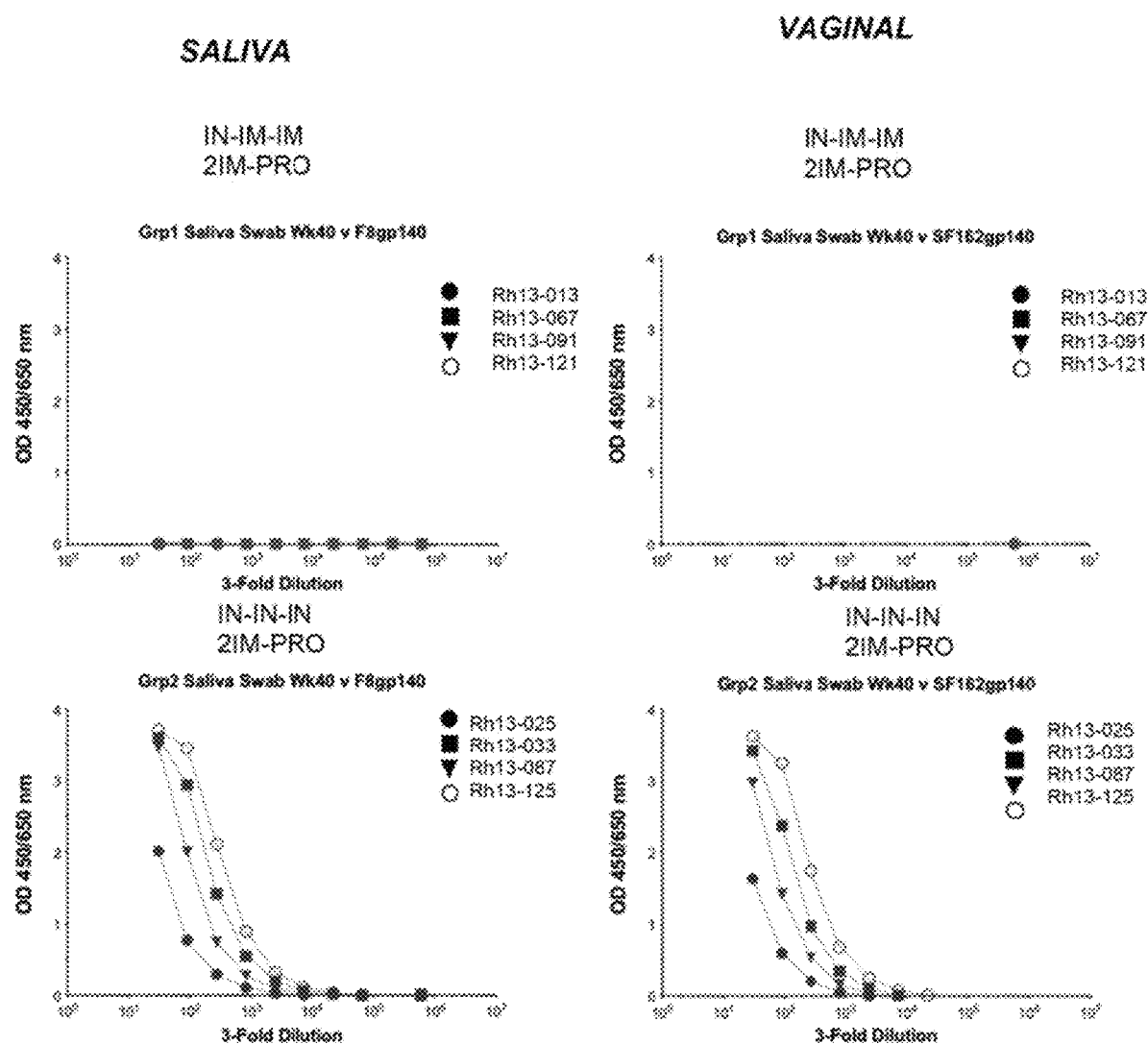

Combining different HVRs from Ad6 and Ad657 and inserting cell targeting and detargeting ligands
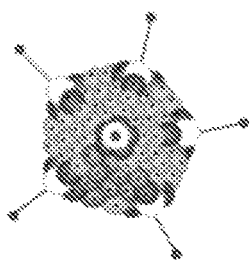
Insert combination of different HVRs
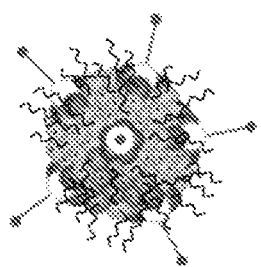
Insert peptides into different HVRs
FIG. 33

FIG. 34 (continued)

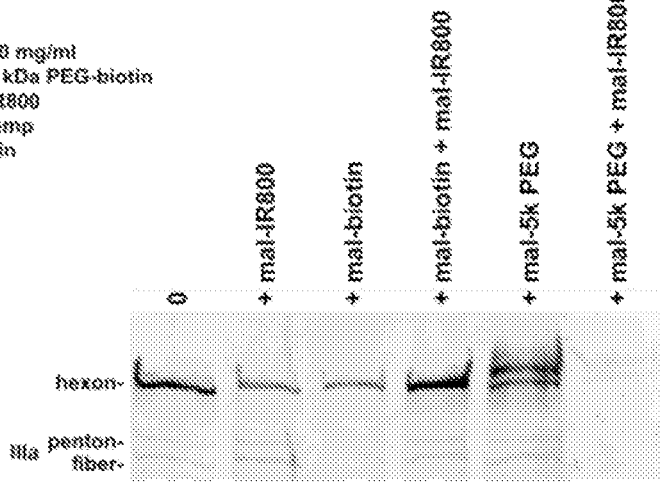
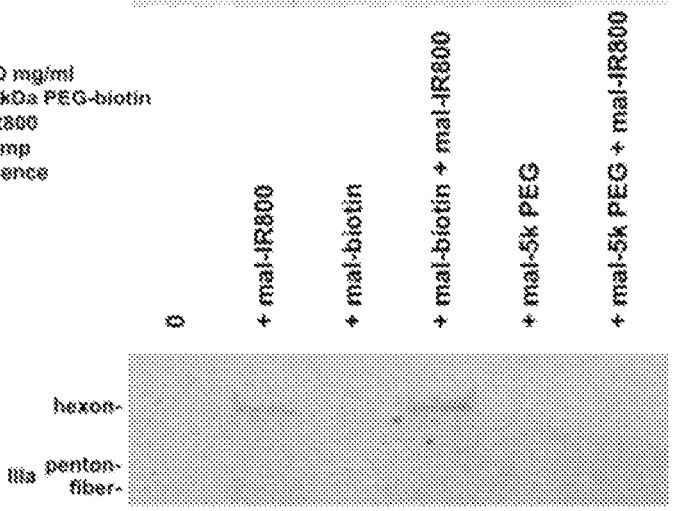
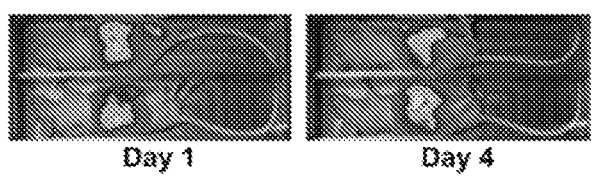
FIG. 37

RC-Ad

*E1 expression controlled by native E1 promoter*

CRAd-Probasin-E1A (Ad-PB)

*E1 expression
controlled by prostate-specific probasin promoter*

CRAd-dl1101

*p300 pathway binding ablated, susceptible to IFN pathway
in normal cells*

CRAd-dl1107

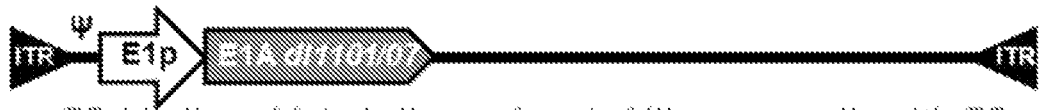

*pRB binding ablated allows virus to kill cancer cells with RB
pathway disruptions, but repressed in RB+ normal cells.*

CRAd-dl1101/07

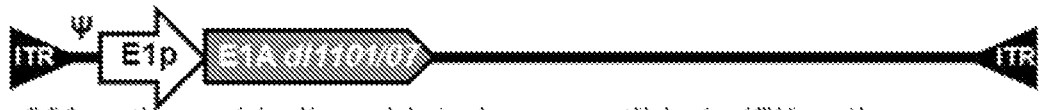

*p300 pathway binding ablated, susceptible to IFN pathway
pRB binding ablated allows virus to kill cancer cells with
RB pathway disruptions, but repressed in RB+
normal cells.*

Figure 43

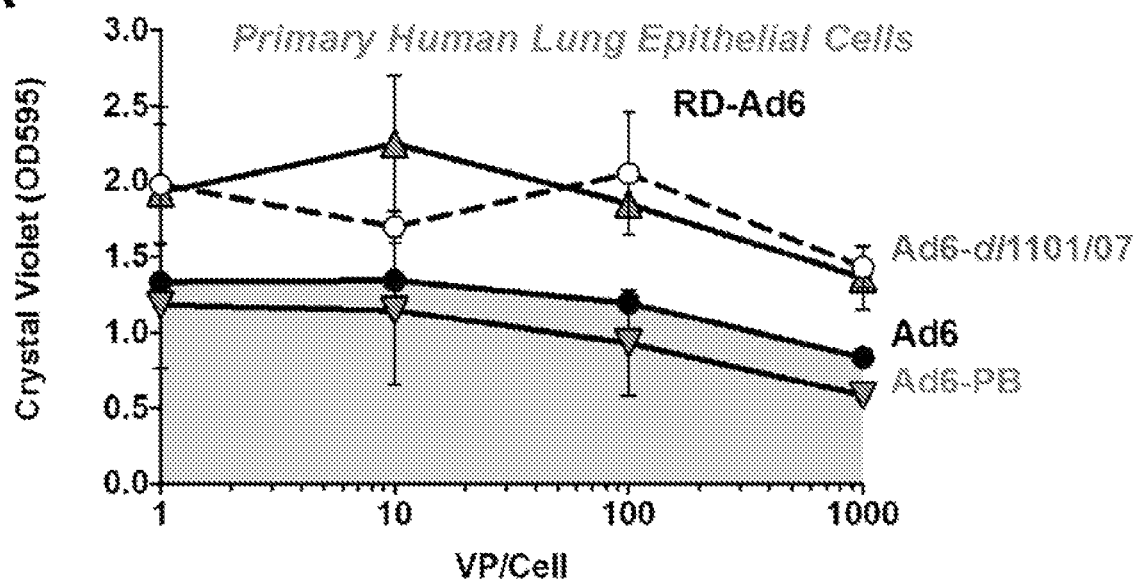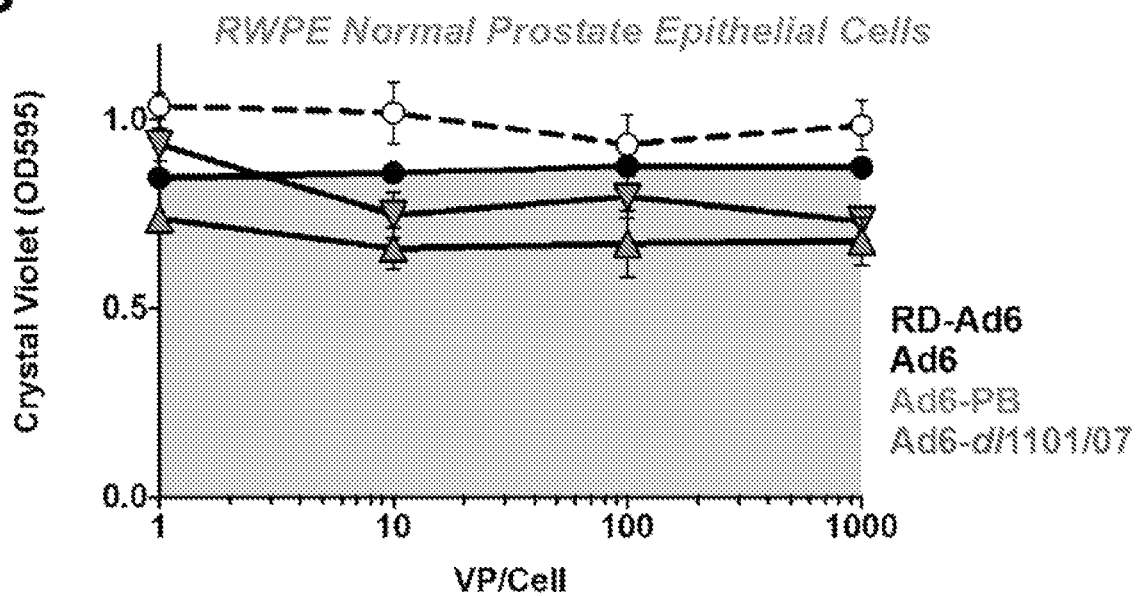
Figure 44

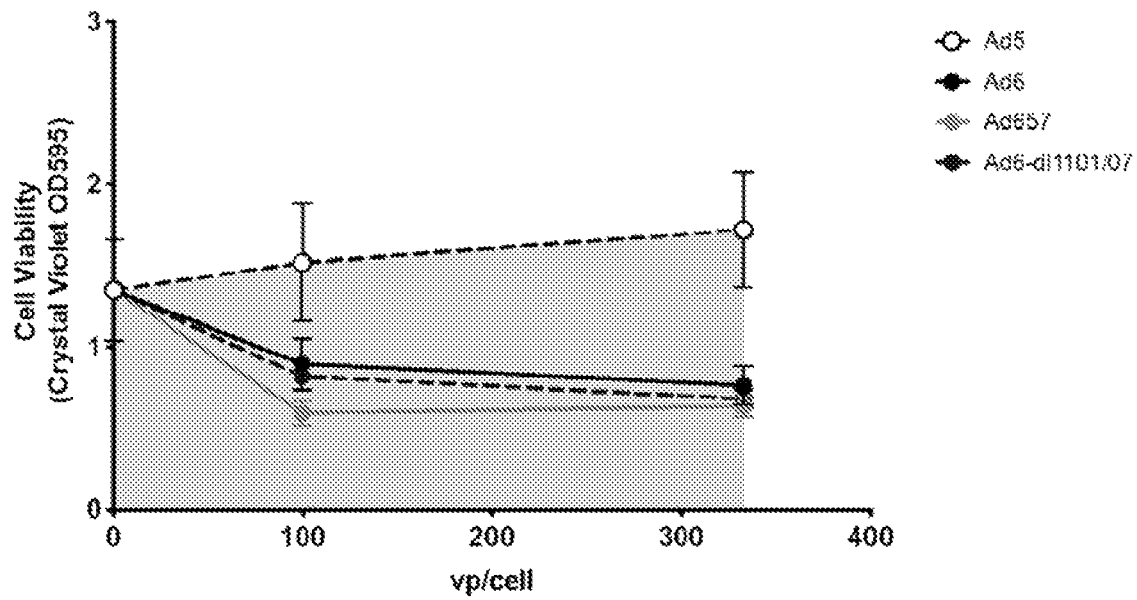
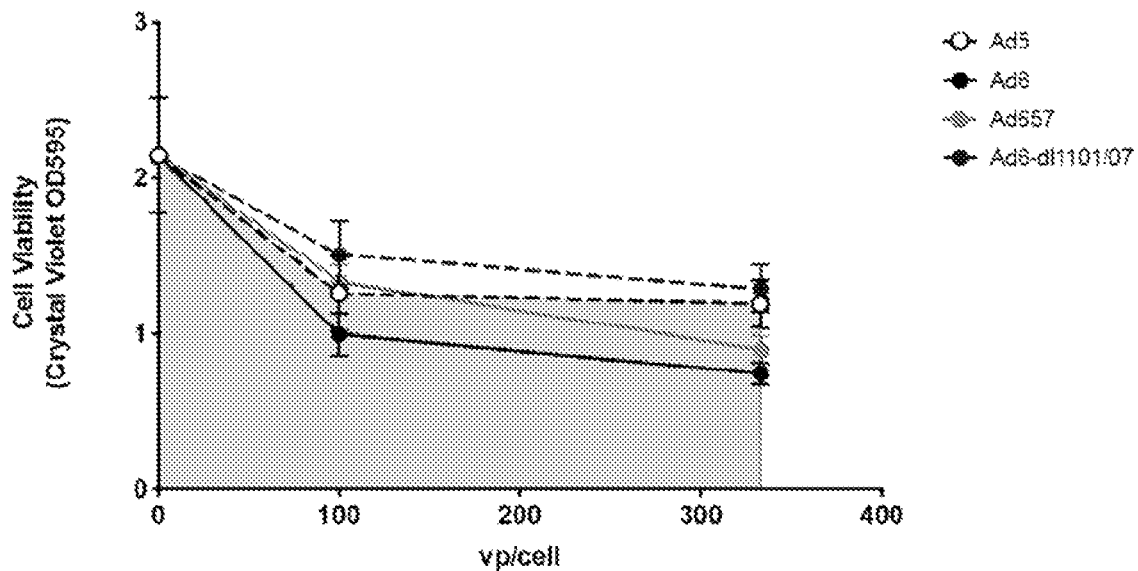
FIGURE 45

Figure 50
PBS
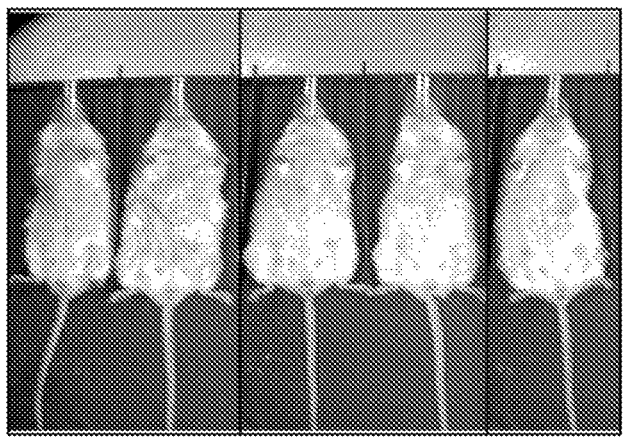
Ad-GL
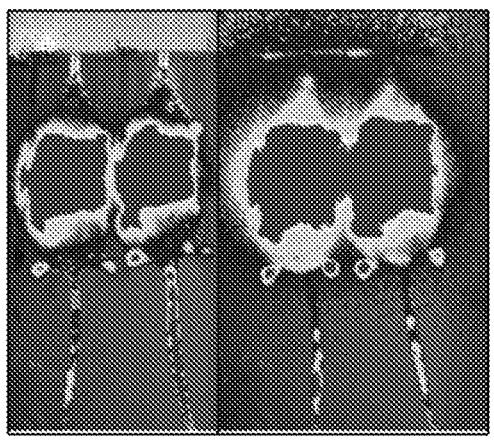
Ad-GL-
PEG2000-Biotin
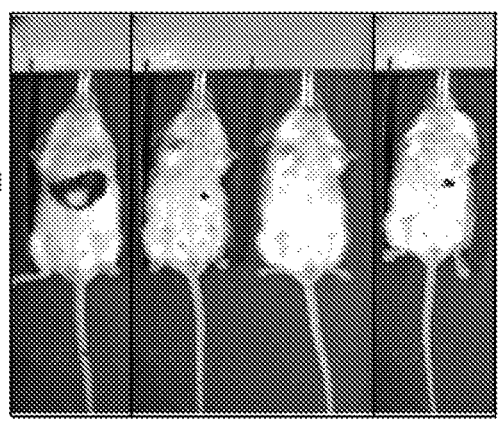

*E1 expression controlled by native E1 promoter*

CRAd-Probasin-E1A (Ad-PB)

*E1 expression controlled by prostate-specific probasin promoter*

**CRAd-*dl*1101**

*p300 pathway binding ablated, susceptible to IFN pathway in normal cells*

**CRAd-*dl*1107**

*pRB binding ablated allows virus to kill cancer cells with RB pathway disruptions, but repressed in RB+ normal cells.*

**CRAd-*dl*1101/07**

*p300 pathway binding ablated, susceptible to IFN pathway pRB binding ablated allows virus to kill cancer cells with RB pathway disruptions, but repressed in RB+ normal cells.* wild-type E1A N-terminus

MRHIICHGGVITEEMAASLLDQLIEEVLADNLPPPSHFEPPTLHELYDLDVT
APEDPNEEAVSQIFPESVMLAVQEGIDLFTFPPAPGSPEPPHLSRQPEQP
EQRALGPVSMPNLVPEVIDLTCHEAGFPPS (SEQ ID NO:42)

E1A dl1101 N-terminus

MRHIEEVLADNLPPPSHFEPPTLHELYDLDVTAPEDPNEEAVSQIFPESV
MLAVQEGIDLFTFPPAPGSPEPPHLSRQPEQPEQRALGPVSMPNLVPEVI
DLTCHEAGFPPS (SEQ ID NO:43)

E1A dl1107 N-terminus

MRHIICHGGVITEEMAASLLDQLIEEVLADNLPPPSHFEPPTLHELYDLDVT
APEDPNEEAVSQIFPESVMLAVQEGIDLFTFPPAPGSPEPPHLSRQPEQP
EQRALGPVCHEAGFPPS (SEQ ID NO:44)

E1A dl1101/1107 N-terminus

MRHIEEVLADNLPPPSHFEPPTLHELYDLDVTAPEDPNEEAVSQIFPESV
MLAVQEGIDLFTFPPAPGSPEPPHLSRQPEQPEQRALGPVCHEAGFPPS
(SEQ ID NO:45)

Figure 56

CRAd657

CRAd657 +/- Ad35 Fiber or Chimpanzee C68 Fiber +/- K7 peptide

CRAd657 +/- Ad35 Fiber or Chimpanzee C68 Fiber +/- K7 peptide Expressing Folate Receptor alpha CRAd657 +/- Ad35 Fiber or Chimpanzee C68 Fiber +/- K7 peptide Expressing GMCSF Ad6/57 with Ad6 HVR1 and Ad57 HVRs2-7 +/- Ad35 Fiber or Chimpanzee C68 Fiber +/- K7 peptide Ad6/57/6 with Ad6 HVR1, Ad57 HVRs2-6, Ad6 HVR7 +/- Ad35 Fiber or Chimpanzee C68 Fiber +/- K7 peptide Ad6/57/6 with Ad6 HVR1, Ad57 HVRs2-6, Ad6 HVR7 +/- Ad35 Fiber or Chimpanzee C68 Fiber +/- K7 peptide Expressing GFPLuciferase

ADENOVIRUSES AND METHODS FOR USING ADENOVIRUSES

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 112 KB file named "ADZE_1_SEQUENCE_LISTING_2023_FILED" created on 12 Jul. 2023.

STATEMENT REGARDING PRIOR DISCLOSURES BY THE INVENTOR OR A JOINT INVENTOR QUALIFYING FOR THE GRACE PERIOD PROVIDED UNDER 35 USC § 102(b)(1)

The applicant submits that the following disclosures qualify under the grace period provided as noted above: Nguyen, et al., Oncolytic Virotherapy 8:43-51, May 3, 2018; Nguyen, et al., Virology 514:118-123, 15 Jan. 2018; Matchett, et al., J Virol., 93:1-18, May 1, 2019.

BACKGROUND OF THE INVENTION

Technical Field of the Invention

This invention relates to methods and materials for nucleic acid delivery, vaccination, and/or treating cancer. For example, the invention encompasses adenoviruses (Ads) and methods for using adenoviruses to treat medical conditions such as cancer. In an aspect of the invention, an adenovirus provided herein can be used as an oncolytic agent.

Despite vast efforts, cancer remains a major public health issue in the United States with over 1.6 million new cases in 2017 alone (National Cancer Institute, "Cancer Stat Facts: Cancer of Any Site," seer.cancer.gov/statfacts/html/all.html). Traditional therapies, such as chemotherapeutics, radiation therapy and surgery, often fail, especially when cancer is advanced. One of the reasons is for this that cancer cells can eliminate or modify the components that are targeted by these therapies and effectively avoid being killed.

Oncolytic virotherapy can provide an alternative approach to cancer treatment by utilizing selectively replicating viruses to destroy tumors, activate adaptive immune responses, and ensure a life-long immunity against the tumors (Russell et al., 2017 Molecular Therapy 25:1107-1116).

This invention provides methods and materials for nucleic acid delivery, vaccination, and/or treating cancer. For example, this invention provides methods and materials for treating cancer by administering one or more recombinant Ads (e.g., one or more of Ad657 and variants thereof) as an oncolytic agent. In an embodiment, a recombinant Ad can be derived from a first Ad (e.g., can include a genome of a first Ad, such as Ad6, also referred to as the recombinant Ad backbone) and can include hexon HVRs from a second Ad such as Ad57. In cases where a recombinant Ad includes an Ad6 genome and Ad57 hexon HVRs, the recombinant Ad can be a chimeric Ad referred to as Ad657. (See Nguyen, et al. Oncolytic Virotherapy 7:43-51, 2018, the disclosure of which is incorporated by reference).

In an aspect, this invention provides methods for vaccinating against infectious disease using one or more recombinant Ads (e.g., one or more of Ad657 and variants thereof). In an aspect, this invention provides methods for treating cancer using one or more recombinant Ads (e.g., one or more of Ad657 and variants thereof) as an oncolytic agent. In some cases, one or more recombinant Ads (e.g., one or more Ad657s) can be used to reduce the number of cancer cells (e.g., by infecting and killing cancer cells) in a mammal. In some cases, one or more recombinant Ads (e.g., one or more of Ad657 and variants thereof) can be used to stimulate anti-cancer immune responses in a mammal. In some cases, one or more recombinant Ads (e.g., one or more of Ad657 and variants thereof) can be used to stimulate immune responses against infectious diseases in a mammal.

As demonstrated herein, when Ad657 is delivered by intravenous injection to mice having subcutaneous human DU145 prostate cancer tumors, Ad657 first infects the liver and then reaches distant tumors. Both Ad6 and Ad657 mediated significant delays in tumor growth and extension of survival with Ad6 mediating higher efficacy.

This invention provides methods and materials for nucleic acid delivery, vaccination, and/or treating cancer. For example, this invention provides methods and materials for treating cancer by administering one or more recombinant Ads (e.g., one or more of Ad657 and variants thereof) as an oncolytic agent. In an embodiment, a recombinant Ad can be derived from a first Ad (e.g., can include a genome of a first Ad, such as Ad6, also referred to as the recombinant Ad backbone) and can include hexon HVRs from a second Ad such as Ad57. In cases where a recombinant Ad includes an Ad6 genome and Ad57 hexon HVRs, the recombinant Ad can be a chimeric Ad referred to as Ad657. In an aspect, this invention provides methods for vaccinating against infectious disease using one or more recombinant Ads (e.g., one or more of Ad657 and variants thereof). In an aspect, this invention provides methods for treating cancer using one or more recombinant Ads (e.g., one or more of Ad657 and variants thereof) as an oncolytic agent. In some cases, one or more recombinant Ads (e.g., one or more Ad657s) can be used to reduce the number of cancer cells (e.g., by infecting and killing cancer cells) in a mammal. In some cases, one or more recombinant Ads (e.g., one or more of Ad657 and variants thereof) can be used to stimulate anti-cancer immune responses in a mammal. In some cases, one or more recombinant Ads (e.g., one or more of Ad657 and variants thereof) can be used to stimulate immune responses against infectious diseases in a mammal.

As demonstrated herein, when Ad657 is delivered by intravenous injection to mice having subcutaneous human DU145 prostate cancer tumors, Ad657 first infects the liver and then reaches distant tumors. Both Ad6 and Ad657 mediated significant delays in tumor growth and extension of survival with Ad6 mediating higher efficacy.

Moreover, liver sequestration is a considerable problem for virtually any oncolytic virus if it is used as an intravenous systemic therapy. If the virus infects hepatocytes and kills them, this will result in liver damage at low doses and death at higher doses. Notably, administration of the Ads of the invention, i.e., Ad657 chimeric vector and variants thereof, mediated unexpected lower liver damage than either Ad5 or Ad6. Thus the unique combination of Ad6 platform with the HVRs 1-7 of Ad657 mediated changes in biodistribution and therapy not observed in natural viruses.

Also, as demonstrated herein, immunization of rhesus macaques with replicating single-cycle adenovirus (SC-Ad657) vaccines expressing only clade B HIV-1 gp160 by intranasal (IN) and intramuscular (IM) routes was compared to mucosal and systemic routes of vaccination. SC-Ad vaccines by themselves generated significant circulating antibody titers against Env after only a single immunization. Animals immunized only by the IM route had high peripheral T follicular helper (pTfh) cells in blood, but low Tfh in lymph nodes, and had lower antibody-dependent cellular cytotoxicity (ADCC) antibody activity. Animals immunized by the IN route had high Tfh in lymph nodes, but low pTfh in the blood, and had higher ADCC antibodies. When immunized animals were challenged rectally with SHIV$_{SF162P3}$, they all became infected, but mucosally-primed animals had markedly lower viral loads their gastrointestinal tracts. Similarly, Ad657 carrying genes for hepatitis C antigens is able to generate cytotoxic T lymphocyte (CTL) responses against hepatitis and cytomegalovirus. Ad657 is able to delivery and express therapeutic genes including cytokines like 4-1BBL, granulocyte macrophage stimulating factor (GMCSF), and IL-21. The results provided herein demonstrate that recombinant Ads can be used as a local or systemic delivery vehicle for nucleic acid, vaccines, and/or oncolytic virotherapy for cancers.

BRIEF SUMMARY OF THE INVENTION

In general, one aspect of this invention features recombinant Ad comprising (a) an Ad genome from a first Ad strain and (b) a nucleic acid encoding a hexon polypeptide from a second Ad strain, where one or more of the hypervariable regions the hypervariable regions (HVRs) of the hexon polypeptide are different from the HVRs encoded by the Ad genome. The first Ad strain can be a first human Ad strain, and the second Ad strain can be a second human Ad strain which is different from the first human Ad strain. The first Ad strain and the second Ad strain can be serotypically distinct. The first Ad strain can be a human Ad6 strain, and the second Ad strain can be a human Ad57 strain. The recombinant Ad also can include one or more targeting polypeptides, antigenic polypeptides, enzymes, amino acid substitutions, PEGylation, ligands, tags and the like.

A recombinant Ad may be used as a vector for gene-based vaccination, for gene therapy application/delivery, or for oncolytic virotherapy.

In a further embodiment, the recombinant Ad comprises (a) an Ad genome from a first Ad strain and (b) a nucleic acid encoding at least one hexon polypeptide from one or more Ad strains, where the hypervariable regions (HVRs) of the hexon polypeptide from the one or more Ad strains are different from the HVRs encoded by the first Ad genome.

In a further embodiment, the recombinant Ad can be a replication competent or conditionally-replicating Ad (e.g., a CRAd).

In another aspect, this invention features a recombinant and/or chimeric Ad comprising (a) nucleic acid encoding a first hexon polypeptide and (b) a second hexon polypeptide, where the amino acid sequence of the first hexon polypeptide is different from the amino acid sequence of the second hexon polypeptide. The amino acid sequence of a hypervariable region (HVR) of the first hexon polypeptide can be different from the amino acid sequence of a hypervariable region of the second hexon polypeptide. The nucleic acid can be from a first Ad strain, and the second hexon polypeptide can be from a second Ad strain. The first Ad strain can be a first human Ad strain, and the second Ad strain can be a second human Ad strain different from the first human Ad strain. The first Ad strain and the second Ad strain can be serotypically distinct. The Ad strain can be a human Ad6 strain, and the second Ad strain can be a human Ad57 strain. The recombinant Ad also can include a targeting polypeptide. The targeting polypeptide can include the amino acid sequence TARGEHKEEELI (SEQ ID NO:1).

In a further embodiment, the recombinant Ad comprises a) nucleic acid encoding a first hexon polypeptide and (b) a second hexon polypeptide from one or more Ad strains, where the amino acid sequence of the first hexon polypeptide is different from the amino acid sequence of the second hexon polypeptide from the one or more Ad strains.

In a further embodiment, the recombinant Ad can be a replication competent Ad or conditionally-replicating Ad (e.g., a CRAd).

In another aspect, the invention provides materials and methods for treating a mammal having cancer. The methods can include, or consist essentially of, administering to a mammal having cancer, a recombinant Ad comprising (a) an Ad genome from a first Ad strain and (b) at least one hexon polypeptide from a one or more Ad strains, where one or more of the hypervariable regions (HVRs) of the hexon polypeptide are different from the HVRs encoded by the Ad genome and/or an Ad comprising (a) nucleic acid encoding a first hexon polypeptide and (b) a second hexon polypeptide, where the amino acid sequence of the first hexon polypeptide is different from the amino acid sequence of the second hexon polypeptide. The mammal can be a human. The cancer can be prostate cancer, ovarian cancer, lung cancer, hepatocellular carcinoma, pancreatic cancer, kidney cancer, melanoma, brain cancer, colon cancer, lymphoma, myeloma, lymphocytic leukemia, or myelogenous leukemia. The administering can include systemic or local administration (e.g. intravenous, intratumoral, intramuscular, intraorgan, intralymph node administration).

It is demonstrated herein that Ad657 and variants thereof are able to deliver therapeutic genes to cells for expression of therapeutic polypeptides. Thus, recombinant Ads, including chimeric Ads, can be used as a local or systemic delivery vehicle for nucleic acid, vaccines, and/or oncolytic virotherapy for cancers.

An aspect of the invention relates to recombinant adenovirus (Ad) comprising (a) an Ad genome encoding hexon polypeptides from a first Ad strain and (b) a nucleic acid encoding at least one hexon polypeptide from one or more different Ad strains, wherein at least one hypervariable region (HVR) of the hexon polypeptide is different from the HVRs encoded by the Ad genome of the first Ad strain.

A further aspect of the invention relates to such a recombinant Ad, wherein the first Ad strain and the one or more different Ad strains are serotypically distinct.

A further aspect of the invention relates to such a recombinant Ad, wherein the first Ad strain is a human Ad6 strain, and wherein a second Ad strain is a human Ad57 strain.

A further aspect of the invention relates to such a recombinant Ad further comprising a nucleic acid encoding a targeting polypeptide, antigen, enzyme, receptor, ligand or tag.

A further aspect of the invention relates to such a recombinant Ad, wherein the targeting polypeptide comprises an amino acid sequence selected from SEQ ID NO: 1-41 and SEQ ID NO:46-47.

A further aspect of the invention relates to such a recombinant Ad, wherein said recombinant Ad is a replication competent Ad.

A further aspect of the invention relates to such a recombinant Ad, wherein the replication competent Ad is a single-cycle Ad or conditionally-replicating Ad (CRAd).

A further aspect of the invention relates to such a recombinant adenovirus (Ad) comprising (a) Ad capsid polypeptides from a first Ad strain and (b) at least one hexon polypeptide from one or more different Ad strains, wherein hypervariable regions (HVRs) of the hexon polypeptide or capsid polypeptides are different from the HVRs or capsid polypeptides of the first Ad strain.

A further aspect of the invention relates to such a recombinant adenovirus (Ad) comprising (a) a nucleic acid encoding a first hexon polypeptide and (b) a nucleic acid encoding a second hexon polypeptide, wherein the amino acid sequence of the first hexon polypeptide is different from the amino acid sequence of the second hexon polypeptide.

A further aspect of the invention relates to such a recombinant Ad, wherein the nucleic acid encoding at least one hexon polypeptide is different from the amino acid sequence of a hypervariable region of said second hexon polypeptide.

A further aspect of the invention relates to such a recombinant Ad, wherein said nucleic acid is from a first Ad strain, and wherein said second hexon polypeptide is from a second Ad strain.

A further aspect of the invention relates to such a recombinant Ad, wherein said first Ad strain is a first human Ad strain, and wherein said second Ad strain is a second human Ad strain different from said first human Ad strain.

A further aspect of the invention relates to such a recombinant Ad, wherein said first Ad strain and said second Ad strain are serotypically distinct.

A further aspect of the invention relates to such a recombinant Ad, wherein said first Ad strain is a human Ad6 strain, and wherein said second Ad strain is a human Ad57 strain.

A further aspect of the invention relates to such a recombinant Ad, further comprising a targeting polypeptide.

A further aspect of the invention relates to such a recombinant Ad, wherein said targeting polypeptide comprises an amino acid sequence TARGEHKEEELI (SEQ ID NO:1).

A further aspect of the invention relates to such a recombinant Ad, wherein said recombinant Ad is a replication competent Ad.

A further aspect of the invention relates to such a recombinant Ad, wherein said replication competent Ad is a single-cycle Ad or conditionally-replicating Ad (CRAd).

A further aspect of the invention relates to a method for treating a mammal having cancer, wherein said method comprises administering, to said mammal, a recombinant adenovirus (Ad) as described herein.

A further aspect of the invention relates to such a method, wherein said cancer is selected from the group consisting of prostate cancer, ovarian cancer, lung cancer, hepatocellular carcinoma, pancreatic cancer, kidney cancer, melanoma, brain cancer, colon cancer, lymphoma, myeloma, lymphocytic leukemia, and myelogenous leukemia.

A further aspect of the invention relates to such a method, wherein said administering comprises systemic administration.

A further aspect of the invention relates to such a method, wherein in systemic administration comprises intramuscular, intranasal, or intravenous administration.

A further aspect of the invention relates to such a method, wherein said administering comprises local administration.

A further aspect of the invention relates to such a method, wherein said local administration comprises intratumoral injection.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 shows a translation of context-specific peptides from phage to adenovirus. A) Diagram of a phage display library containing the Ad5 fiber HI β sheets that structurally constrain a random 12-mer peptide library. Shown below is a depiction of the structurally similar site between the β7 and β8 sheets in the Ad5 HVR5 hexon. B) Primary amino acid alignments of 12.51 and 12.52 in the HI library and their location when inserted into HVR5 of hexon. C) Representation of Ad5 GFP-Luc expressing viruses modified with the peptides.

FIG. 16 shows plasma ADCC activity. Plasma samples were tested with CD16-KHYG-1 effector cells to kill CEM.NKR.CCR5.CD4+-Luc, target cells infected with SHIVSF162P3. Each dot represents the mean value for each animal. * $p<0.05$, * $p<0.001$, ** $p<0.0001$ by one-way ANOVA vs. the SC-Ad6-Ebov group.

FIG. 17 shows mucosal ADCC activity. Vaginal wash and saliva samples were tested with CD16-KHYG-1 effector cells to kill CEM.NKR.CCR5.CD4+-Luc, target cells infected with SHIVSF162P3. Each dot represents the mean value for each animal. * $p<0.05$ by one-way ANOVA vs. the SC-Ad6-Ebov group.

FIG. 21 shows protection against repeated rectal SHIV$_{SF162P3}$ challenge. The indicated groups were challenged rectally with 4.3 TCID50 (on rhesus PBMCs) of SHIVSF162P3 on a weekly basis. Plasma samples were analyzed for SHIV viral RNA copies. Animals with RNA copies above 10 were considered infected and the number of challenges required to infect that animal were used as events for Kaplan-Meier survival analysis.

FIG. 25 shows saliva and vaginal HIV env binding titrations. ELISA OD450 levels are shown for the indicated samples at the indicated dilutions when tested against F8. The low level of antibodies in these mucosal samples prevent reaching saturation of the assay. For this reason, EC50 values cannot be reliably calculated for most animals. Rhesus macaque Rh13-091 in the IN-IM-IM group was the only animal in which an EC50 could be calculated (EC50=4580). Similar results were observed in ELISAs using SF162 gp140.

FIG. 37 shows conjugation of polyethylene glycol (PEG) to Ad657-HVR5-C. A) SDS-PAGE of Ad proteins with and without PEGylation. B) Near infrared imaging of SDS-PAGE of Ad proteins with and without PEGylation and with and without the near infrared fluorescence imaging tag IR800. C) In vivo transduction after intraperitoneal injection of maleimide-PEGylated Ad657-HVR5-C by luciferase imaging.

FIG. 43 is a schematic of a replication competent Ad (RC-Ad), wherein E1 expression is controlled by the native E1 promoter; a variant CRAd-Probasin-E1A (Ad-PB), wherein E1 expression is controlled by prostate-specific probasin promoter; CRAd-dl1101, wherein p300 pathway binding ablated, susceptible to IFN pathway in normal cells; CRAd-dl1107, wherein pRB binding ablated allows virus to kill cancer cells with RB pathway disruptions, but is repressed in RB+normal cells; CRAd-dl1101/07, wherein p300 pathway binding ablated, susceptible to IFN pathway pRB binding ablated allows virus to kill cancer cells with RB pathway disruptions, but is repressed in RB+normal cells.

FIG. 44 (A and B) shows the effect of infection with replication-competent Ad5, Ad6, Ad657 on non-cancerous cells and modification of Ad6 and Ad657 to be conditionally-replicating Ads (CRAds).

FIG. 45 demonstrates killing of cancerous cells by replication-competent Ad5, Ad6, Ad657, and the indicated CRAds.

FIG. 50 demonstrates that PEGylation de-targets adenovirus to liver in vivo.

FIG. 55 is a schematic of variants of Ads having mutations in the E1 protein to convert the virus to a conditionally-replicating Ad (CRAd).

FIG. 56 shows amino acid sequences of the N-terminal portion of the wild-type E1A polypeptide and the E1A N-terminus of the CRAd variants, dl1101, dl1107 and dl1101/1107.

DETAILED DESCRIPTION OF THE INVENTION

Figure 2:
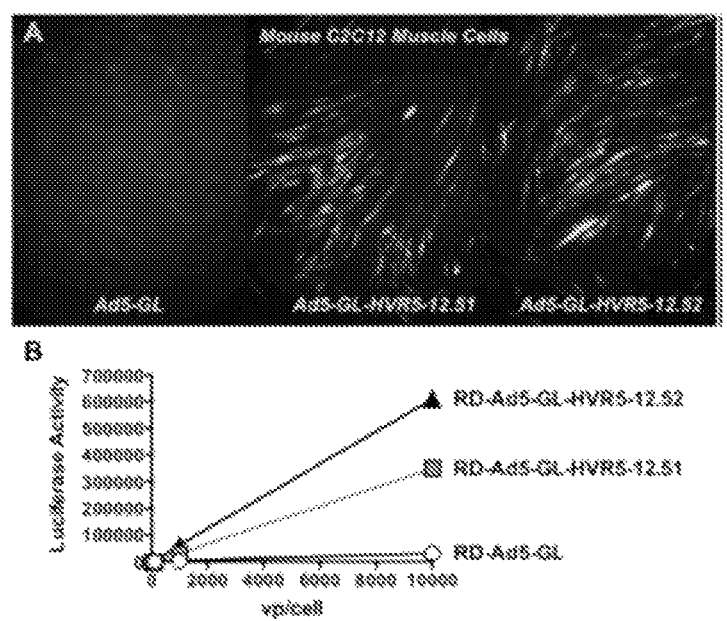
FIG. 2 shows in vitro transduction A) GFP expression by fluorescent microscopy of C2C12 cells infected with $10^4$ vp/cell of the indicated vectors 2 days after infection. B) Luciferase activity from C2C12 cells 2 days after infection with varied MOIs of the indicated Ads.

This invention provides methods and materials for nucleic acid delivery, vaccination, and/or treating cancer. For example, this invention provides methods and materials for nucleic acid delivery of proteins/polypeptides, vaccination, and/or treating cancer using one or more recombinant Ads (e.g., Ad657 and variants thereof) as an oncolytic agent.

An adenovirus icosahedron is made up of 720 copies of its hexon protein. The virus does not use this protein to bind receptors, but this nano-lattice of repeating proteins provides a matrix for interactions (e.g., natural interactions and unnatural interactions) with proteins, cells, and drugs. Antibodies that can neutralize Ads can target hypervariable regions (HVRs) of the hexon polypeptide on an Ads.

In some cases, this invention provides recombinant Ads having oncolytic anti-cancer activity. For example, a recombinant Ad can be derived from a first Ad and can include hexon HVRs from one or more different Ads. The HVRs may be derived from any species C Ads, for example Ad1, Ad2, Ad5, Ad6 and Ad57. In an embodiment, a recombinant Ad can be derived from a first Ad and can include one or more hexon HVRs from at least one other Ad, wherein at least one hexon HVR is different from the HVR(s) of the first Ad. The first Ad strain can be a human Ad6 strain, and the second Ad strain can be a human Ad57 strain. Hexon shuttle plasmid maps (FIG. 34) show the combination of the insertion of individual HVRs from different Ad serotypes with the insertion of cell targeting/detargeting peptides or novel amino acids such as cysteine into the hexon for targeted chemical modification and shielding. In an embodiment, the recombinant Ads comprise amino acid substitutions, for example, substitution of cysteines into polypeptides, and modifications such as PEGylation and BAPylation. The ability to target polymer and other chemical modifications to cysteines inserted in Ad657 hexon is demonstrated herein.

Ad657 as an oncolytic against human prostate cancer is demonstrated. The Ad6 HVRs were replaced with those from Ad57 to generate a chimeric species C oncolytic virus called Ad657. Ad657 and Ad6 were tested as systemic oncolytic therapies by single i.v. injection in nude mice bearing human cancerous tumors. Ad657 may be used as a local or systemic oncolytic virotherapy for cancers. These data also demonstrate surprising effects of serotype-switching with oncolytic species C Ads.

In some cases, this invention provides methods for using one or more recombinant Ads provided herein to treat a mammal having, or at risk of having, cancer, an infectious disease, and/or a genetic disease. For example, one or more recombinant Ads can be administered to a mammal having, or at risk of having, cancer to reduce the number of cancer cells (e.g., by infecting and killing cancer cells) in the mammal (e.g., a human). For example, one or more recombinant Ads can be administered to a mammal having, or at risk of having, cancer to stimulate anti-cancer immune responses in the mammal (e.g., a human).

In some cases, recombinant Ads described herein (e.g., recombinant Ads having oncolytic anti-cancer activity such as recombinant Ad657 and variants thereof) are not destroyed by a mammal's immune system. For example, a recombinant Ad is not destroyed by antigen presenting cells (APCs), macrophages, and/or other immune cells in a mammal that the recombinant Ad is administered to.

In some cases, recombinant Ads described herein (e.g., recombinant Ads having oncolytic anti-cancer activity such as recombinant Ad657 and variants thereof) can be administered for multiple (e.g., two or more) rounds of treatment. For example, a first recombinant Ad described herein can avoid antibodies that can neutralize a second recombinant Ad described herein, and vice versa. In cases where a mammal having cancer is treated with one or more recombinant Ads described herein, the mammal can be administered a first round of treatment with a first recombinant Ad and can subsequently be administered a second round of treatment with a second recombinant Ad.

In some cases, recombinant Ads described herein (e.g., recombinant Ads having oncolytic anti-cancer activity such as recombinant Ad657 and variants thereof) can be replication competent Ads (RC-Ads). For example, a RC-Ad can be a RC-Ad that includes a nucleic acid encoding an E1 polypeptide (e.g., an E1+RC-Ad). For example, a RC-Ad can be a single-cycle Ad (SC-Ad) that includes a deletion of one or more nucleic acids encoding one or more polypeptides associated with the production of infectious viral progeny (e.g., pIIIa and E3). For example, a RC-Ad can be a conditionally-replicating Ad (CRAd). Examples of single-cycle Ads and how to make and use them are provided elsewhere (International Patent Application Publication No. WO2009/111738).

In some cases, recombinant Ads described herein (e.g., recombinant Ads having oncolytic anti-cancer activity such as recombinant Ad657 and variants thereof) can be replication defective Ads (RD-Ads). For example, a RD-Ad can be a RD-Ad that includes a deletion of a nucleic acid encoding an E1 polypeptide (e.g., an E1-deleted RD-Ad).

It is demonstrated in the examples herein that CRAd 657 and variants thereof are conditionally-replicating Ads (CRAds) in cancerous cells and that infection of cells with CRAd 657 and variants thereof reduces cell viability and tumor volume. Thus, CRAd 657 ADZE 1 US SEQ DIV 1 and variants thereof may be used as a local or systemic oncolytic virotherapy in subjects with cancer.

What is more, it is demonstrated that CRAds can be used for expression of antigens and used as a vaccine for vaccinating against viruses, for example, against Human Immunodeficiency Virus (HIV), Human Papilloma Virus (HPV) and Hepatitis C Virus (HCV).

In some cases, recombinant Ads described herein (e.g., recombinant Ads having oncolytic anti-cancer activity such as recombinant Ad657 and variants thereof) can bind to a cell surface receptor (e.g., to facilitate viral entry to a cell). For example, a recombinant Ad described herein can bind to coxsackie-adenovirus receptors (CARs) and/or Fc receptors (e.g., FcpR and FcTR), complement receptors (e.g., CR3 and/or C2qR).

In an aspect of the invention, CRAds may comprise nucleic acids encoding polypeptides heterologous to the Ad, for example, antigens, cell surface receptors, cell targeting polypeptides and the like. For example, CRAd-657-dl1101/1107-FolR is a recombinant Ad comprising intact E3 and expressing the human folate receptor alpha. It is demonstrated herein that CRAds may be used to generate antibodies against known cancer antigens, for example, folate receptor alpha.

In some cases, recombinant Ads described herein (e.g., recombinant Ads having oncolytic anti-cancer activity such as recombinant Ad657s) can avoid binding (e.g., do not bind) to a scavenger receptor (e.g., to facilitate viral entry to a cell). For example, a recombinant Ad described herein avoid binding to a SREC receptors and/or SR-A receptors.

In some cases, recombinant Ads described herein (e.g., recombinant Ads having oncolytic anti-cancer activity such as recombinant Ad657s) can avoid phagocytosis.

In some cases, recombinant Ads described herein (e.g., recombinant Ads having oncolytic anti-cancer activity such as recombinant Ad657s) are non-pathogenic (e.g., to a mammal being treated as described herein).

In some cases, recombinant Ads described herein (e.g., recombinant Ads having oncolytic anti-cancer activity such as recombinant Ad657s) can infect dividing cells (e.g., can infect only dividing cells).

A recombinant Ad described herein can be any appropriate recombinant Ad (e.g., a recombinant Ad having oncolytic anti-cancer activity) generated by recombinant DNA technology and methods known to those skilled in the art. A recombinant Ad can be any Ad generated by recombining material (e.g., nucleic acid and/or polypeptide) from any organism other than the Ad from which the recombinant Ad is derived. For example, a recombinant Ad can include one or more materials that do not naturally occur in that Ad (e.g., do no naturally occur in that Ad prior to recombination). In some cases, a recombinant Ad provided herein can be a chimeric Ad (e.g., can include viral elements from two or more (e.g., two, three, four, five, or more) different Ad genomes).

These embodiments have been applied also in the context of Ads which combine different HVRs from different Ads (i.e., shuffling HVRs). For example, HVR1 of Ad6 with HVRs 2-7 of Ad57 or HVR1 and 7 of Ad6 with HVRs 2-6 of Ad57, or HVRs 1 and 7 from Ad6 and HVRs 2-6 from Ad657.

Nucleic acid and/or polypeptides that do not naturally occur in the Ad can be from any appropriate source. In some cases, a nucleic acid and/or a polypeptide that does not naturally occur in that Ad can be from a non-viral organism. In some cases, a nucleic acid and/or a polypeptide that does not naturally occur in that Ad can be from a virus other than an Ad. In some cases, a nucleic acid and/or a polypeptide that does not naturally occur in that Ad can be from an Ad obtained from a different species. In some cases, a nucleic acid and/or a polypeptide that does not naturally occur in that Ad can be from a different strain of Ad (e.g., serotypically distinct strains). In some cases, a nucleic acid and/or a polypeptide that does not naturally occur in that Ad can be a synthetic nucleic acid and/or a synthetic polypeptide.

A recombinant Ad described herein (e.g., a recombinant Ad having oncolytic anti-cancer activity such as a recombinant Ad657) can be derived from (e.g., can include a genomic backbone from) any appropriate Ad. In some cases, a recombinant Ad described herein can be derived from an Ad having low seroprevalence. For example, 50% or fewer (e.g., 50%, 45%, 40%, 35%, 30%, 25%, 20%, 15%, 10%, 5%, or fewer) of mammals (e.g., human) can have been exposed to an Ad from which a recombinant Ad described herein is derived. With regard to seroprevalence, species C adenoviruses, Ad6 and Ad657 have lower prevalence than archetype Ad5 virus. In some cases, a recombinant Ad described herein can be derived from an Ad having reduced or eliminated side effects (e.g., phagocytosis and liver damage). A recombinant Ad can be derived from an Ad isolated from any appropriate species of animal. For example, Ads can be isolated from humans, non-human primates (e.g., monkeys such as Old World monkey species like rhesus macaques), fish, frogs, and snakes. In some cases, a recombinant Ad described herein can be derived from a human Ad (HAd or HAdV). A recombinant Ad can be derived from any species of Ad (e.g., A, B, C, D, E, F, or G). In some cases, a recombinant Ad described herein can be derived from an Ad C species (e.g., a human Ad C species (HAd-C)). A recombinant Ad can be derived from any appropriate Ad serotype (e.g., 2, 5, 6, or 57). In some cases, a recombinant Ad described herein can be derived from an Ad serotype 6 (Ad6; e.g., a human Ad6).

In some cases, a recombinant Ad described herein (e.g., a recombinant Ad having oncolytic anti-cancer activity such as a recombinant Ad657 and variants thereof) can include an Ad genome containing one or more modifications to one or more nucleic acids encoding a polypeptide (or fragments thereof) and/or one or more viral elements of the Ad genome. The one or more modifications can be any appropriate modification. In some cases, a modification can be effective to inhibit the ability of the modified polypeptide to bind another polypeptide such as p300 and/or pRB. In some cases, a modification can be effective to neutralize one or more interferon pathways. Examples of modifications that can be made to a nucleic acid encoding a polypeptide or to a viral element include, without limitation, substitutions, deletions, insertions, and mutations.

Ads, for example Ad657 and variants thereof, may be modified and retain all E1A genes, or modified to delete selected regions and functions of their encoded proteins.

Figure 57:
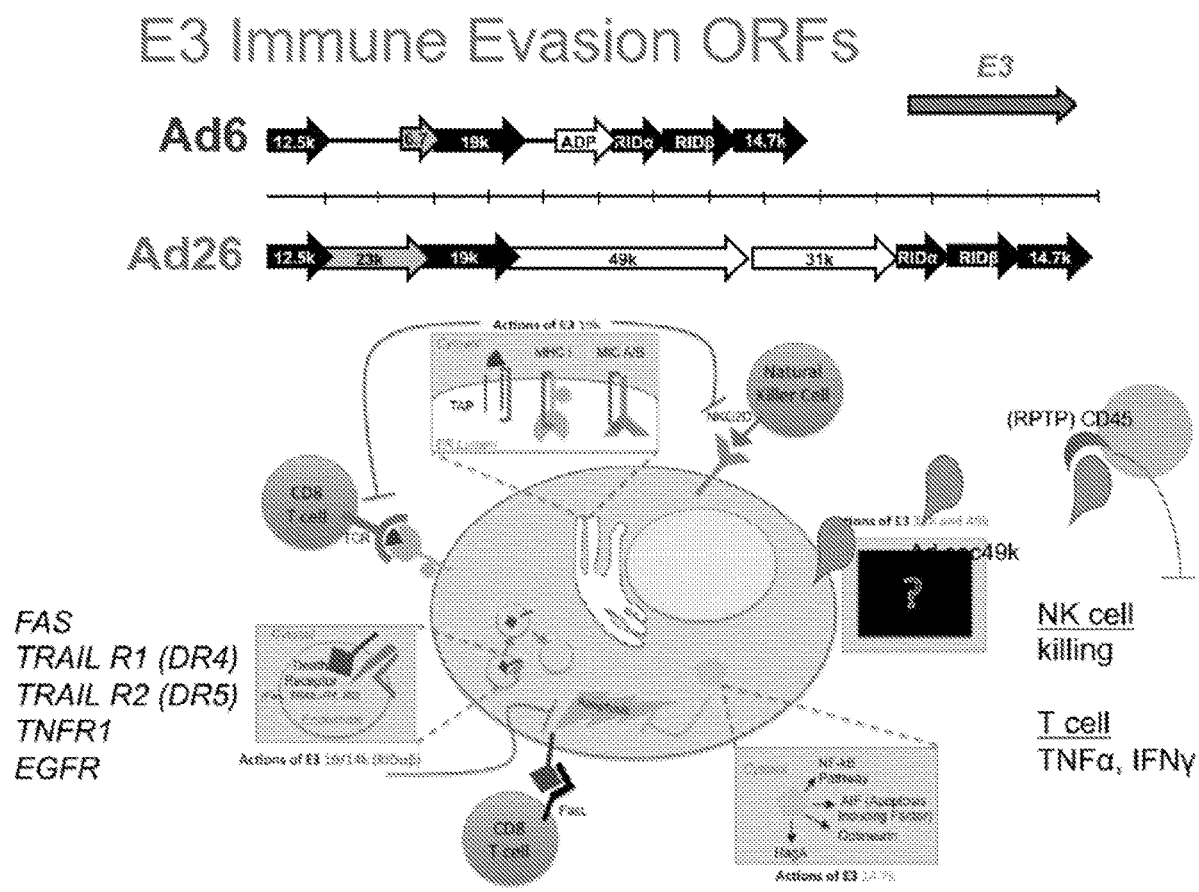
FIG. 57 shows as schematic of different E3 immune evasion genes in Ad species C exemplar Ad6 and Ad species D exemplar Ad26. Both Ads express size and sequence variants of E3 12.5K, 6.7K, 19K, 10.4K (RIDα), 14.5K (RIDβ), and 14.7K genes, as well as a depiction of the functions of these E3 encoded proteins.

FIG. 57 shows as schematic of different E3 immune evasion genes in Ad species C exemplar Ad6 and Ad species D exemplar Ad26, as well as a depiction of the functions of these E3 encoded proteins. Both Ads express size and sequence variants of E3 12.5K, 6.7K, 19K, 10.4K (RIDα), 14.5K (RIDβ), and 14.7K genes. 19K reduces display of MHC I and MIC proteins on the cell surface to protect infected cells from T cells and NK cells. RID proteins protect infected cells from death-inducing ligands (FAS, TRAIL, TNFR, and EGFR). 14.7K inhibits intrinsic activation of apoptosis in infected cells. Species C Ads also express the 11.6K known as the adenovirus death protein (ADP). Over-expression of ADP accelerates cell death, but overall cell death is equal. Species D viruses also express two novel variants called 49K and 31K. The secreted form of 49K binds to CD46 on T cells and NK cells leading to down-regulation of these cells and less-efficient cell killing of cells deficient in class I MHC by NK cells. Ad657 plasmids have been modified to retain all native E3 immune evasion genes (12.5K, 6.7K, 19K, 11.6K (ADP), 10.4K (RIDα), 14.5K (RIDβ), and 14.7K) and E4 34K or to delete selected regions. Ad657 and its variants are also modified with the addition of 49K and 31K to provide these extra functions to these species C viral platforms.

Ads, for example Ad657 and variants thereof, may be modified to retain all E3 immune evasion genes, or to delete selected regions and functions of their encoded proteins. With respect to E3 mutations: 19k downregulates MHCI and MIC proteins on infected cells; ADP over expression accelerates cell death, but does not increase the number of cells that are killed; 10k and 14k proteins (RIDα and RIDβ) combine to block cell killing by extrinsic apoptosis proteins like FAS, TRAIL, TNF, TNFR, and EGFR; 14.7k protein inhibits intrinsic apoptosis signaling.

Retaining these E3 proteins may allow oncolytic to persist longer, and deleting them may increase immune stimulation.

Data testing oncolytic efficacy suggests intact E3 mediates better efficacy.

DE3 constructs have deleted part of 12.5k through and including 14.7k, DE3A constructs have deleted part of E3 12.5k through and including 19k, and DE3ADP constructs have deleted part of E3 12.5k through and including ADP.

Surprisingly, deleting all E3 genes makes the oncolytic virus less effective in repressing tumor growth.

In an embodiment, the invention encompasses single-cycle adenovirus, for example SC-Ad657 and variants thereof. Recombinant SC-Ad viruses with heterologous nucleic acids encoding polypeptides were evaluated for use as a vaccine. SC-Ad657 vaccines by themselves generated significant circulating antibody titers against an HIV envelope protein after only a single immunization.

Similarly, Ad657 carrying genes for hepatitis B and C antigens is able to generate cytotoxic T lymphocyte (CTL) responses against hepatitis and cytomegalovirus.

Ad657 was modified by insertion of synthetic peptides from human papilloma virus into HVR5. In an embodiment, the amino acid sequence of the variant Ad657-HVR5-HPV hexon is defined in SEQ ID NO:57. The modification allows display of this antigen for vaccine purposes as well as retargeting by binding to proteins that interact with HPV peptides.

In a further embodiment, expression of Human Granulocyte-Macrophage Colony Stimulating Factor (GMCSF) by Ad657 is demonstrated herein.

Thus, from the examples herein, it is demonstrated that recombinant Ads, for example Ad657 and variants thereof, may be utilized for expression of heterologous proteins, for example, polypeptide antigens and cell targeting polypeptides.

In some cases, a recombinant Ad described herein (e.g., a recombinant Ad having oncolytic anti-cancer activity such as a recombinant Ad657) can include an Ad genome containing one or more substitutions. For example, one or more nucleic acids encoding a polypeptide (or fragments thereof) and/or one or more viral elements encoded by the Ad genome can be substituted. A substitution can be any appropriate substitution. In some cases, one or more nucleic acids encoding a capsid polypeptide of a genome of a first Ad can be substituted with one or more nucleic acids encoding a capsid polypeptide of a second Ad to generate a chimeric Ad. For example, when a recombinant Ad includes a genome from a first Ad where a nucleic acid encoding a capsid polypeptide in the genome is substituted for a nucleic acid encoding a capsid polypeptide from a second Ad (e.g., an Ad different from the Ad backbone), the nucleic acid encoding a capsid polypeptide form the second Ad can express one or more capsid polypeptides, and the expressed capsid polypeptide(s) can be incorporated into the capsid of the recombinant Ad. Examples of capsid polypeptides include, without limitation, hexon polypeptides, fiber polypeptides, penton base polypeptides, IIIa polypeptides, IX polypeptides, and pVI polypeptides.

The Ad fiber protein is a complex of three apparently identical subunits which mediates the initial cell attachment step. The native Ad6 fiber protein comprises the amino acid sequence set forth in SEQ ID NO:60 and binds CAR.

In an aspect of the invention, fiber-modified recombinant and chimeric Ads having fiber proteins which are not native to the parental or "backbone" Ad were generated.

A chimeric Ad, AdF35 fiber chimera, has the amino acid sequence of SEQ ID NO:61 and is shorter than Ad5 and Ad6 fiber proteins and retargets virus to CD46.

A fiber-modified recombinant Ad, comprising K7 Fiber having the sequence of SEQ ID NO:62, targets virus to heparin sulfate proteoglycans and negative charges on cells.

A recombinant, chimeric Ad, 6/FC68 Fiber comprising the sequence of SEQ ID NO:63, is a chimeric Ad having a fiber protein from chimpanzee adenovirus C68. The fiber protein is shorter than Ad5 or Ad6 fiber proteins and binds CAR.

A recombinant, chimeric Ad, 6/FC68-K7 Fiber comprising the sequence of SEQ ID NO:64, is a chimeric Ad having a fiber protein from chimpanzee adenovirus C68. The fiber protein is shorter than Ad5 or Ad6 fiber proteins. The 6/FC68-K7 Fiber binds CAR and is retargeted to heparin sulfate and negative charges.

A recombinant, chimeric Ad, 6/FC68-HI-K7 Fiber comprising the sequence of SEQ ID NO:65, is a chimeric Ad having a fiber protein from chimpanzee adenovirus C68. The fiber protein is shorter than Ad5 or Ad6 fiber proteins. The 6/FC68-HI-K7 Fiber binds CAR and is retargeted to heparin sulfate and negative charges.

In some cases, a recombinant Ad can include a genome from a first Ad where a nucleic acid encoding a hexon polypeptide (e.g., HVRs of a nucleic acid encoding a hexon polypeptide) in the genome is substituted for a nucleic acid encoding a hexon polypeptide (e.g., HVRs of a nucleic acid encoding a hexon polypeptide) from a second Ad. In some cases, a recombinant Ad described herein can include a genome from a first Ad that has one or more HVRs substituted for one or more HVRs from a second Ad. For example, a recombinant Ad can be a chimera, in particular Ad657 (e.g., can include an Ad6 genome where the hexon HVRs are substituted for Ad57 hexon HVRs). In cases where a recombinant Ad includes a genome from a first Ad where a nucleic acid encoding a hexon polypeptide in the genome is substituted for a nucleic acid encoding a hexon polypeptide from a second Ad, the recombinant Ad can include from about 1 to about 720 hexon polypeptides from the second Ad. For example, when a recombinant Ad is an Ad657, the Ad657 can include an Ad6 genome and 720 hexon polypeptides including Ad57 hexon HVRs.

In some cases, a recombinant Ad described herein (e.g., a recombinant Ad having oncolytic anti-cancer activity such as a recombinant Ad657) can include an Ad genome containing one or more nucleic acid deletions. A nucleic acid deletion can be any appropriate nucleic acid deletion. A nucleic acid deletion can be a full deletion (e.g., deletion of a nucleic acid encoding a polypeptide) or a partial deletion (e.g., deletion of one or more nucleotides within a nucleic acid encoding a polypeptide). A nucleic acid deletion can reduce or eliminate transcription and translation of a polypeptide encoded by the deleted nucleic acid. Any appropriate nucleic acid can be deleted. In some cases, a nucleic acid encoding a polypeptide associated with production of infectious progeny can be deleted. Examples of nucleic acids that can be deleted and/or modified in a recombinant Ad described herein may encode E1 (e.g., E1A and E1B), E2, E3, E4, pIIIA, fiber, E1B, and include viral enhancers and promoters. For example, a recombinant Ad described herein (e.g., a recombinant Ad having oncolytic anti-cancer activity such as a recombinant Ad657) can include an Ad genome containing a deletion of one or more nucleotides within a nucleic acid encoding an E1 polypeptide. In some cases, a recombinant Ad described herein can include one or more substitutions in a nucleic acid encoding an E1 polypeptide.

In particular embodiments, a recombinant Ad described herein is modified to comprise a probasin promoter comprising, for example, a nucleic acid of SEQ ID NO:48; a recombinant Ad described herein is modified to comprise a dl1101 deletion in a nucleic acid encoding an E1 polypeptide; a recombinant Ad described herein is modified to comprise a dl1107 deletion in a nucleic acid encoding an E1 polypeptide; a recombinant Ad described herein is modified to comprise a dl1101 deletion and a dl1107 deletion. See the examples herein and FIG. 56 for N-terminal amino acid sequences of the E1A polypeptide, for example, wild-type Ad E1A, and CRAd-657-dl1101, CRAd-657-dl1107 and CRAd-657-dl1101/1107 variants.

In an embodiment, a variant CRAd-657-dl1101/1107-FoIR comprises intact E3 and expresses the human folate receptor alpha found on cancer cells.

In general, Ads may be modified to include CRAd modifications described herein.

In some cases, a recombinant Ad described herein (e.g., a recombinant Ad having oncolytic anti-cancer activity such as a recombinant Ad657) can include an Ad genome containing one or more nucleic acid insertions. For example, a nucleic acid insertion can include a nucleic acid encoding a polypeptide. A nucleic acid can be inserted into any appropriate location within a genome of a recombinant Ad described herein. In some cases, a nucleic acid encoding a polypeptide can be inserted into a HVR (e.g., HVR 5 loop) of a genome of a recombinant Ad described herein. For example, when a nucleic acid encoding a polypeptide is inserted into a HVR of a genome of a recombinant Ad described herein, the nucleic acid encoding a polypeptide can express one or more polypeptides, and the expressed polypeptide(s) can be incorporated into the capsid of the recombinant Ad. In cases where a nucleic acid encoding a polypeptide is inserted into a HVR of a genome of a recombinant Ad described herein, the recombinant Ad can present from about 1 to about 720 polypeptides encoded by the inserted nucleic acid on its surface. A nucleic acid insertion can be nucleic acid encoding any appropriate polypeptide. In some cases, a nucleic acid insertion can encode a polypeptide antigen.

In some cases, a nucleic acid insertion can encode a targeting polypeptide. Examples of targeting polypeptides that can be included in a recombinant Ad described herein include, without limitation peptide 12.51 (TARGEH-KEEELI; SEQ ID NO: 1), peptide 12.52 (LRQT-GAASAVWG; SEQ ID NO:2), 12.53 (ARRADTQWRGLE; SEQ ID NO:3), VSV (GTWLNPGFPPQSCGYATVT; SEQ ID NO:4), RGD (CDCRGDCFC; SEQ ID NO:5), alpha4 integrin binding peptide (NMSLDVNRKA; SEQ ID NO:6), Met 3-4 (ISLSSHRATWVV; SEQ ID NO:7), L10.1F (WTMGLDQLRDSSWAHGGFSA; SEQ ID NO:8), L10.1RGDF (WTMGLDQLRGDSSWAHGGFS; SEQ ID NO:9), L10.2F (RSVSGTEWVPMNEQHRGAIW; SEQ ID NO:10), L10.5F (TELRTHTSKELTIRTAASSD; SEQ ID NO:11), S5.1 (DRAIGWQDKLYKLPLGSIHN; SEQ ID NO:12), DU9C.1 (MGSWEKAALWNRVSASSGGA; SEQ ID NO:13), DU9C.2 (MAMGGKPERPADSDNVQVRG; SEQ ID NO:14), DU9A.7 (MASRGDAGEG-STQSNTNVPS; SEQ ID NO:15), XS.1 (GPEDTSRAPENQQKTFHRRW; SEQ ID NO:16), REDVmyc (MGREDVGEQKLISEEDLGGS; SEQ ID NO:17), RGD-4C (ACDCRGDCFCG; SEQ ID NO:18), REDV-4C (ACDCREDVCFCG; SEQ ID NO:19), SKBR5C1 (GQIPITEPELCCVPWTEAFY; SEQ ID NO:20), 231R10.1 (PQPPNSTAHPNPHKAPPNTT; SEQ ID NO:21), HepaCD8 (VRWFPGGEWGVTHPESLPPP; SEQ ID NO:22), $K_2O$ (KKKKKKKKKKKKKKKKKKKK; SEQ ID NO:23), BAP (GLNDIFEAQKIEWH; SEQ ID NO:24), CALM BP (CAAARWKKAFIAVSAANRFKKIS; SEQ ID NO:25), EBV (EDPGFFNVEIPEFP; SEQ ID NO:26), #1-5 (GGHGRVLWPDGWFSLVGISP; SEQ ID NO:27), ##4*-5 (MARTVTANVPGMGEGMVVVPC; SEQ ID NO:28), 1-1 (GVSKRGLQCHDFISCSGVPW; SEQ ID NO:29), 1-2 (NQSIPKVAGDSKVFCWWCAL; SEQ ID NO:30), 1-3 (QSTPPTKHLTIPRHLRNTLI; SEQ ID NO:31), 1-4 (DMSFQLVTPFLKALPTGWRG; SEQ ID NO:32), 1-5 (GGHGRVLWPDGWFSLVGISP; SEQ ID NO:33), 1-5con (FSLVGISP; SEQ ID NO:34), 1-6 (QIMMGPSLGYYMPSESIFAY; SEQ ID NO:35), 2-11 (ISWDIWRWWYTSEDRDAGSA; SEQ ID NO:36), 2-14 (VWGMTTSDHQRKTERLDSPE; SEQ ID NO:37), 2-20 (MTSAQTSEKLKAETDRHTAE; SEQ ID NO:38), 2-9 (MGSRSAVGDFESAEGSRRP; SEQ ID NO:39), 3b-6 (MGRTVQSGDGTPAQTQPSVN; SEQ ID NO:40), 4*-5 (MARTVTANVPGMGEGMVVVP; SEQ ID NO:41), CLL peptides, PD-1, GLA polypeptides (e.g., Factor X), antigen genes, fusion proteins, fusogenic glycoproteins, single-chain antibodies, and capsid proteins from other viruses. A targeting polypeptide can target any appropriate type of cell. Examples of types of cells that can be targeted by a targeting polypeptide included in a recombinant Ad described herein include, without limitation, muscle cells (e.g., skeletal muscle cells), tumors, cancer cells, kidney cells, liver cells, mucosal cells, carbohydrates, and cell membranes.

This example demonstrates that peptides selected in a compatible structural context on phage libraries can be translated into the Ad hexon protein. For example, for the 12.51 peptide, this insertion site increases muscle transduction while decreasing off target infection in the liver. Thus, such a recombinant Ad which targets muscle tissue may be used as a vector for gene-based muscle vaccination or for gene therapy application/delivery to the muscle.

In some cases, a nucleic acid insertion can detarget the virus (e.g., by disrupting cell and protein interactions that occur on a given HVR). In some cases, a nucleic acid insertion can encode a detectable label. Examples of detectable labels include, without limitation, fluorophores (e.g., green fluorescent protein (GFP), mCherry, and mBFP), and enzymes (e.g., luciferase, DNAses, proteases, transporters, and polymerases).

Also provided herein are expression vectors containing a recombinant Ad described herein (e.g., a recombinant Ad having oncolytic anti-cancer activity such as a recombinant Ad657 and variants thereof). Expression vectors can carry a recombinant Ad described herein into another cell (e.g., a cancer cell), where it can be replicated and/or expressed. An expression vector, also commonly referred to as an expression construct, is typically a plasmid or vector having an enhancer/promoter region controlling expression of a specific nucleic acid. When introduced into a cell, the expression vector can use cellular protein synthesis machinery to produce the virus in the cell. In some cases, expression vectors containing recombinant Ads described herein can be viral vectors. For example, an expression vector containing a recombinant Ad described herein can be a retroviral vector. In some cases, expression vectors including a recombinant Ad described herein also can be designed to allow insertion of one or more transgenes (e.g., at a multi-cloning site). For example, expression vectors including a recombinant Ad described herein also can include a nucleic acid encoding a detectable label. Examples of detectable labels include, without limitation, fluorophores (e.g., green fluorescent protein (GFP), mCherry, and mBFP), and enzymes (e.g., luciferase, recombinases, nucleases, and transcription factors).

This invention also provides methods and materials for using one or more recombinant Ads described herein (e.g., recombinant Ads having oncolytic anti-cancer activity such as recombinant Ad657s). In some cases, a recombinant Ad provided herein can used for treating a mammal having, or at risk of having, cancer. For example, methods for treating a mammal having, or at risk of having, cancer can include administering one or more recombinant Ads described herein to the mammal. In some cases, methods for treating a ADZE 1 US SEQ DIV 1 mammal having, or at risk of having, cancer can include administering one or more expression vectors that encode a recombinant Ad described herein or nucleic acid encoding a recombinant Ad described herein to the mammal. In some cases, one or more recombinant Ads described herein can be administered to a mammal to reduce the number of cancer cells in the mammal (e.g., suppress and/or delay tumor growth) and/or to increase survival of the mammal.

Figure 9:
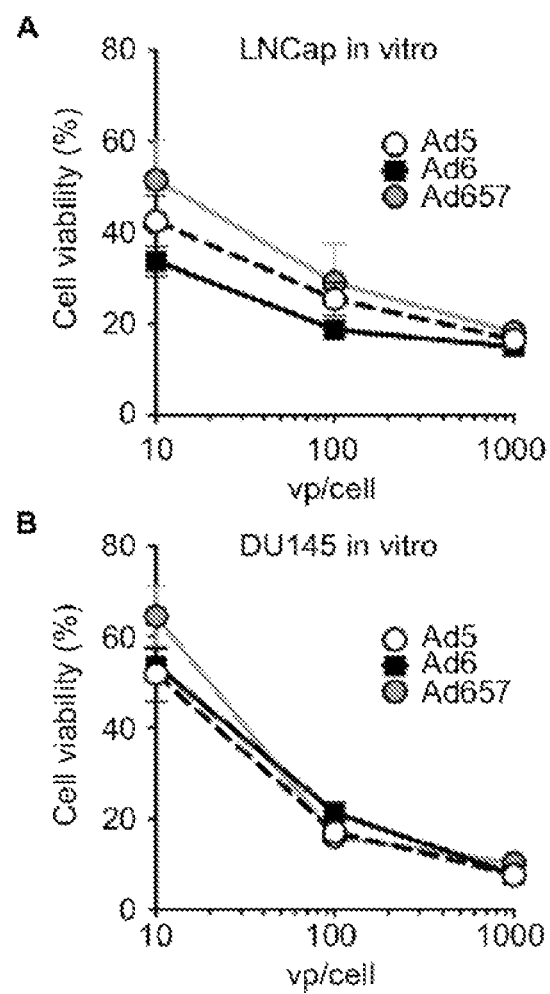
FIG. 9 shows in vitro oncolytic activity. LNCaP and DU145 cells were treated with the indicated viruses with the indicated vp/cell for 5 days. The cells were stained with crystal violet and cell viability was measured by OD595. Cell viability (%) was calculated by dividing the OD of the samples by the mean OD of untreated control cells on the same 96-well plate and multiplying this number by 100. (A) LNCaP cell killing. (B) DU145 killing. Abbreviation: vp, viral particle.

Targeting a cancerous tumor by serotype-switching oncolytic adenoviruses is demonstrated. Mice bearing DU145 or LNCaP prostate tumors on their flanks were treated one by intravenous (IV) injection with Ad657. These mice were treated a second time with alternate Ad6 or Ad6/57/6 oncolytic virus variants with fiber modifications and expressing GFPLuciferase and luciferase activity was measured by imaging. Ad6 has Ad6 hexon and fiber that targets CAR. Ad6-F35 has Ad6 hexon and the Ad35 fiber that targets CD46. Ad6/57/6 has HVR1 and 7 from Ad6 and HVRs 2-6 from Ad57. Ad6/57/6 viruses have Ad6 fiber, AdC68 fiber, or Ad35 fiber. These data in FIG. 9 show the surprising ability to serotype-switch oncolytics with viruses targeting the tumor with lower off-target infection of the liver.

Figure 70:
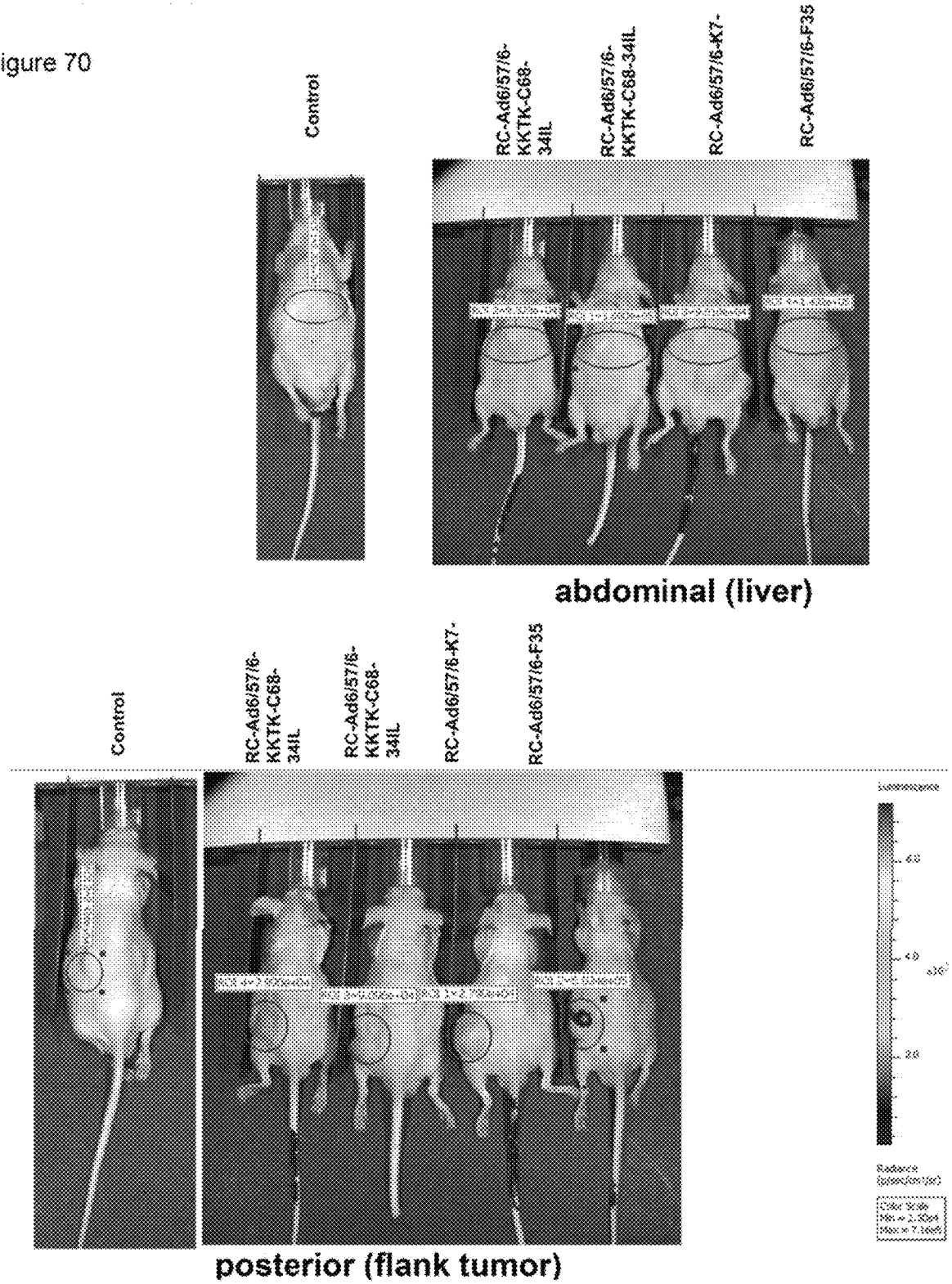
FIG. 70 shows luciferase imaging after serotype switching. Mice bearing LNCaP prostate tumors on their flanks were treated by a single IV injection of Ad657 or CRAd657. Mice with residual tumors 5 months after single IV injection were treated by serotype-switching of the indicated Ad6/57/6 variants expressing GFPLuciferase with and without variant fibers and a codon-optimized E4 34K gene. The indicated Ad6/57/6 variants include Ad6/57/6 virus having different fiber modifications including an added 7 lysine on fiber (K7), chimpanzee C68 fiber grafted onto Ad6 fiber after its KKTK flexibility domain and with an Ad35 fiber. Mice were imaged for luciferase activity 7 days later.
Figure 71:
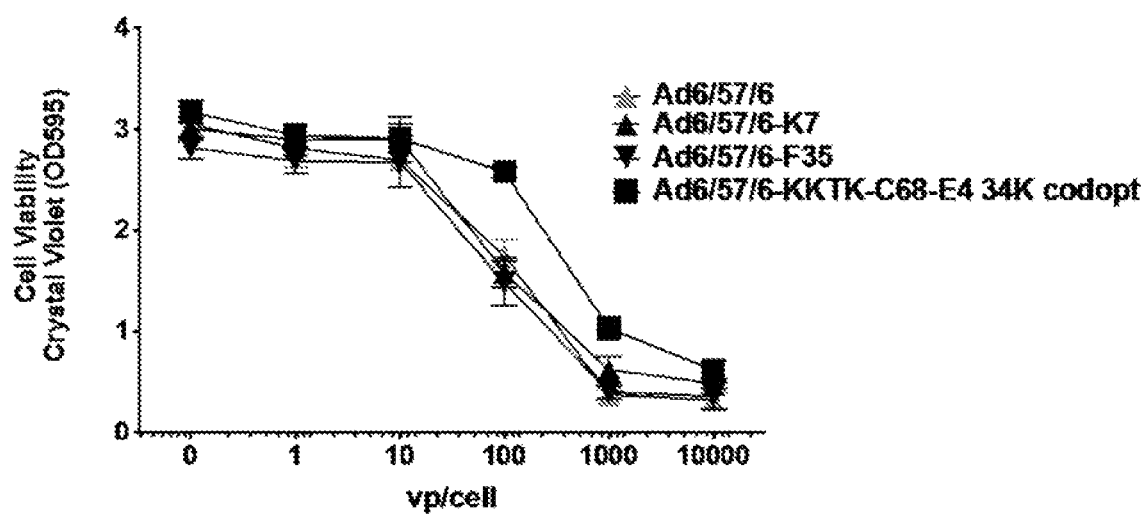
FIG. 71 shows A549 human lung cancer cells which were treated with the indicated viral particles (vp) per cell of Ad6/57/6 with and without variant fibers and a codon-optimized E4 34K gene. 7 days later, the cells were stained with crystal violet and the wells were analyzed in a plate reader. High OD indicates the presence of viable cells. Low OD indicates death and loss of adherent cells.

In another example of serotype-switching, mice bearing LNCaP prostate tumors on their flanks were treated by a single intravenous (IV) injection with Ad657 or CRAd657. These mice were treated a second time 5 months later with alternate Ad6/57/6 oncolytic virus expressing GFPLuciferase and fiber variants K7 (with 7 lysines added), F35 (with the Ad35 fiber), or KKTK-C68 (chimpanzee C68 fiber fused after the Ad6 KKTK flexibility domain. KKTK-C68 virus also has an added codon-optimized E4 34K gene to enhance viral productivity. Luciferase activity was measured by imaging. All Ad6/57/6's have a hexon with HVR1 and 7 from Ad6 and HVRs 2-6 from Ad57. Ad6/57/6 and KKTK-C68 have fibers that targets CAR. Ad6/57/6-F35 has the Ad35 fiber that targets CD46. K7 increases binding to negative charges on cells including binding heparin sulfate proteoglycans. FIG. 70 demonstrates the capability to serotype-switch oncolytics with viruses targeting a tumor with lower off-target infection of the liver.

Any appropriate mammal having, or at risk of having, cancer, an infectious disease, and/or a genetic disease can be treated as described herein. For example, humans, non-human primates (e.g., monkeys), horses, bovine species, porcine species, dogs, cats, mice, rats, and feed animals having cancer, an infectious disease, and/or a genetic disease can be treated for cancer as described herein. In some cases, a human having cancer can be treated. In some cases, a mammal (e.g., a human) treated as described herein is not a natural host of an Ad used to generate a recombinant Ad described herein (e.g., a recombinant Ad having oncolytic anti-cancer activity such as a recombinant Ad657). For example, a human being treated with a recombinant Ad657 described herein can lack any pre-existing adaptive immunity to Ad6.

A mammal having any type of cancer can be treated as described herein. In some cases, a cancer can include one or more solid tumors. In some cases, a cancer can be a blood cancer. Examples of cancers that can be treated as described herein include, without limitation, prostate cancer, ovarian cancer, lung cancer, hepatocellular carcinoma, pancreatic cancer, kidney cancer, melanoma, brain cancer, colon cancer, lymphoma, myeloma, and leukemias (e.g., lymphocytic leukemias and myelogenous leukemias).

In some cases, methods described herein also can include identifying a mammal as having cancer. Examples of methods for identifying a mammal as having cancer include, without limitation, physical examination, laboratory tests (e.g., blood and/or urine), biopsy, imaging tests (e.g., X-ray, PET/CT, MRI, and/or ultrasound), nuclear medicine scans (e.g., bone scans), endoscopy, and/or genetic tests. Once identified as having cancer, an infectious disease, and/or a genetic disease, a mammal can be administered or instructed to self-administer one or more a recombinant Ads described herein (e.g., recombinant Ads having oncolytic anti-cancer activity such as recombinant Ad657s) or a nucleic acid (e.g., an expression vector) encoding one or more a recombinant Ads described herein (e.g., recombinant Ads having oncolytic anti-cancer activity such as recombinant Ad657s).

One or more recombinant Ads described herein (e.g., recombinant Ads having oncolytic anti-cancer activity such as recombinant Ad657s) can be administered by any appropriate route. In some cases, administration can be local administration. In some cases, administration can be systemic administration. Examples of routes of administration include, without limitation, intravenous, intramuscular, subcutaneous, oral, intranasal, inhalation, transdermal, parenteral, intratumoral, retro-ureter, sub-capsular, vaginal, and rectal administration. In cases where multiple rounds of treatment are administered, a first round of treatment can include administering one or more recombinant Ads described herein to a mammal (e.g., a human) by a first route (e.g., intravenously), and a second round of treatment can include administering one or more recombinant Ads described herein to a mammal (e.g., a human) by a second route (e.g., intramuscularly).

As used herein, the term "pharmaceutical composition" refers to the combination of one or more recombinant and/or chimeric Ads of the present invention with a carrier, inert or active, making the composition especially suitable for therapeutic use. One or more recombinant Ads described herein (e.g., recombinant Ads having oncolytic anti-cancer activity such as recombinant Ad657s) can be formulated into a composition (e.g., a pharmaceutical composition) for administration to a mammal (e.g., a mammal having, or at risk of having, cancer). For example, one or more recombinant Ads can be formulated into a pharmaceutically acceptable composition for administration to a mammal having, or at risk of having, cancer. In some cases, one or more recombinant Ads can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, wafers, and granules. Pharmaceutically acceptable carriers, fillers, and vehicles that may be used in a pharmaceutical composition described herein include, without limitation, saline (e.g., phosphate-buffered saline, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinylpyrrolidone, cellulose-based substances, sodium carboxymethylcellulose, polyacrylates, waxes, polyethylene-polyoxypropylene-block polymers, polyethylene glycol, and wool fat. Suitable pharmaceutical carriers are described in "Remington's Pharmaceutical Sciences" by E.W. Martin, 18th Edition. The selection and use of suitable excipients is taught in Gennaro, ed., Remington: The Science and Practice of Pharmacy, 20th Ed. (Lippincott Williams & Wilkins 2003).

A composition (e.g., a pharmaceutical composition) including one or more recombinant Ads described herein (e.g., recombinant Ads having oncolytic anti-cancer activity such as recombinant Ad657s) can be administered to a mammal (e.g., a mammal having, or at risk of having, cancer) as a vaccine. A vaccine can be prophylactic or therapeutic.

In some cases, methods described herein also can include administering to a mammal (e.g., a mammal having cancer) one or more additional agents used to treat a cancer. The one or more additional agents used to treat a cancer can include any appropriate cancer treatment. In some cases, a cancer treatment can include surgery. In some cases, a cancer treatment can include radiation therapy. In some cases, a cancer treatment can include administration of a pharmacotherapy such as a chemotherapy, hormone therapy, targeted therapy, and/or cytotoxic therapy. For example, a mammal having cancer can be administered one or more a recombinant Ads described herein (e.g., recombinant Ads having oncolytic anti-cancer activity such as recombinant Ad657 and variants thereof) and administered one or more additional agents used to treat a cancer. In cases where a mammal having cancer is treated with one or more a recombinant Ads described herein and is treated with one or more additional agents used to treat a cancer, an infectious disease, and/or a genetic disease, the additional agents used to treat a cancer, an infectious disease, and/or a genetic disease can be administered at the same time or independently. For example, one or more a recombinant Ads described herein and one or more additional agents used to treat a cancer, an infectious disease, and/or a genetic disease can be formulated together to form a single composition. In some cases, one or more a recombinant Ads described herein can be administered first, and the one or more additional agents used to treat a cancer, an infectious disease, and/or a genetic disease administered second, or vice versa.

EXAMPLES

Example 1. Adenoviruses

For 50 years, there were only four known species C human species Ads including Ad1, Ad2, Ad5, and Ad6 (see, e.g., Weaver et al., 2011 Virology. 412:19-27). In 2001, a fifth species C adenovirus was identified as field isolate strain #16700, and virus neutralization testing with antisera against Ad1, 2, 5, and 6 demonstrated high levels of neutralization (reciprocal titers of 500-16,000) when each antisera was used against its cognate virus (Lukashev et al., 2008 J Gen Virol. 89:380-388). In contrast, anti-Ad1, 2, and 5 antibodies have weak cross-reactivity against #16700 (reciprocal titers of 32-64). Anti-Ad6 sera demonstrated higher cross-reactivity against #16700, but neutralization required 10-fold higher concentrations of sera to neutralize #16700 when compared with Ad6 itself. Subsequent sequence comparisons confirmed #16700 as a novel species C adenovirus and renamed it as Ad57 (see, e.g., Walsh et al., 2011 J. Clin Microbiol. 49:3482-3490).

15 human Ads were evaluated for oncolytic activity against breast, ovarian, liver, prostate, kidney, and B cell malignancies. In tests against DU145 human prostate tumors, species C Ad6 was more potent after single intratumoral or intravenous (i.v.) injection than species C Ad5 or species B viruses Ad11 and Ad35. Ad6 was also more effective than Ad5 and Ad11 in immunocompetent Syrian hamsters.

Construction of Recombinant Adenoviruses.

Recombinant adenoviruses were constructed by recombinant DNA technology utilizing methods known to those skilled in the art. A recombinant Ad is derived from a first Ad (e.g., can include a genome of a first Ad, such as Ad6) and may include hexon HVRs from a second Ad such as Ad57. In cases where a recombinant Ad includes an Ad6 genome and Ad57 hexon HVRs, the recombinant Ad can be a chimeric Ad referred to as Ad657.

To obtain Ad657, an Ad57 HVR sequence was synthesized and inserted into the Ad6 hexon in a plasmid with an FRT-Zeocin®-FRT cassette between pVI and hexon. This was recombined into various pAd6 plasmids to generate Ad657 and variants thereof. The amino acid sequence of the Ad657 hexon is set forth in SEQ ID NO:49. See FIGS. 34 and 59-65 for plasmid maps of Ad657 variants.

With respect to variants of Ad657, the Ad57 HVR sequence was synthesized with HVR1 modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants with cysteine in HVR1, the variant referred to as Ad657-HVR1-XXA comprises the hexon having the amino acid sequence of SEQ ID NO:50.

With respect to variants of Ad657, the Ad57 HVR sequence was synthesized with HVR5 modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants with cysteine in HVR5, the variant referred to as Ad657-HVR5-XXA comprises the hexon having the amino acid sequence of SEQ ID NO:51.

With respect to variants of Ad657, the Ad57 HVR sequence was synthesized with HVR1 modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants without cysteine in HVR1, but with restriction sites allowing peptide insertions into HVR1, the variant referred to as Ad657-HVR1-XA comprises the hexon having the amino acid sequence of SEQ ID NO:52.

With respect to variants of Ad657, the Ad57 HVR sequence was synthesized with HVR5 modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants without cysteine in HVR5, but with restriction sites allowing peptide insertions into HVR5, the variant referred to as Ad657-HVR5-XA comprises the hexon having the amino acid sequence of SEQ ID NO:53.

With respect to variants of Ad657, the Ad657 HVR1-XA sequence was modified by insertion of a biotin acceptor peptide into HVR1. This was recombined into various pAd6 plasmids to generate Ad657 variants a BAP in HVR1, the variant referred to as Ad657-HVR1-PSTCD comprises the hexon having the amino acid sequence of SEQ ID NO:54.

The insertion of a biotin acceptor peptide detargets the virus variants from the liver, allows the virus to be retargeted with avidin or streptavidin and biotinylated ligands, and allows the virus to be purified on monomeric avidin or streptavidin columns.

With respect to variants of Ad657, the Ad657 HVR1-XA sequence was modified by insertion of a biotin acceptor peptide into HVR1. This was recombined into various pAd6 plasmids to generate Ad657 variants a BAP in HVR1, the variant referred to as Ad657-HVR5-PSTCD comprises the hexon having the amino acid sequence of SEQ ID NO:55.

With respect to variants of Ad657, the Ad657 HVR5-XA sequence was modified by insertion of a synthetic V1/V2 loop from HIV envelope into HVR5, the variant referred to as Ad657-HVR5-V1/V2 comprises the hexon having the amino acid sequence of SEQ ID NO:56.

The insertion of a synthetic V1/V2 loop from HIV envelope allows display of this antigen to serve as a vaccine as well as retargeting by binding to proteins that interact with HIV envelope.

With respect to variants of Ad657, the Ad657 HVR5-XA sequence was modified by insertion of synthetic peptides from human papilloma virus into HVR5, the variant referred to as Ad657-HVR5-HPV comprises the hexon having the amino acid sequence of SEQ ID NO:57.

The insertion of synthetic peptides from human papilloma virus allows display of HPV peptides as antigens for vaccine purposes as well as for retargeting by binding to proteins that interact with HPV peptides.

In another aspect of the invention, chimeric Ads were generated which have an Ad6 HVR1 and Ad57 HVRs 2-7, the chimera, referred to as Ad6/57 HVR chimera, comprises the hexon having the amino acid sequence of SEQ ID NO:58.

In yet another aspect of the invention, chimeric Ads were generated which have Ad6 HVR1 and 7 and Ad57 HVRs 2-6, the chimera, referred to as Ad6/57/6 HVR chimera, comprises the hexon having the amino acid sequence of SEQ ID NO:59.

Example 2. Retargeted and Detargeted Recombinant Adenovirus for Gene Delivery

Adenoviruses are robust vectors for gene delivery and gene-based immunization. The archetype adenovirus used for the vast majority of these application has been human species C adenovirus serotype 5 (HAdV-C5 or Ad5). In vitro, Ad5 binds and enters cells through the combined interactions of its fiber and penton base proteins with cell surface receptors. The trimeric fiber binds the coxsackie-adenovirus receptor (CAR), and cells that lack CAR are relatively resistant to infection unless they also express av integrins that can be bound by an RGD motif on the penton base.

In vivo, these interactions are still utilized, but their importance varies by injection route. If injected directly into a solid tissue or tumor, CAR and integrin interactions dominate. If injected intravenously (IV), these interactions become secondary due to the effects of Ad5 binding to vitamin-K-dependent blood clotting factors. Blood factor X (FX) binds with subnanomolar affinity to the hexons of Ad5 and, consequently, enables Ad5 to efficiently transduce liver hepatocytes after IV injection. In the absence of FX, liver transduction is drastically reduced.

Adenoviral vectors are somewhat unique in their ability to carry very large cDNA sequences of up to 36 kilobase pairs (kbp) when compared to other vectors like adeno-associated virus (AAV) vectors with only 4.5 kb of DNA sequence. This payload capacity justified early exploration of Ad vectors for muscle gene therapy when delivering very large transgenes like the 14 kbp dystrophin cDNA. IV administration in newborn mice can mediate muscle gene delivery, but this ability is lost in adult mice. The decreased transfection with age is due in part to the very large size of Ad virions (i.e. 100 nm) as well as the loss of CAR receptor on muscle cells with aging. The intramuscular (IM) route is by far the most popular route for gene-based vaccines when using Ad5 and other serotypes despite the fact that CAR is absent on skeletal muscle cells.

Therefore, Ad5 and other Ad serotype transduction of muscle can be adequate for gene therapy or gene-based vaccination. However, the absence of the virus' primary receptor in the muscle reduces the efficacy of the virus and requires more vector to be delivered to achieve desired effects.

Construction of Peptide-Modified Hexons in Adenovirus.

12 amino acid (12-mer) peptides on C2C12 mouse muscle cells were selected from a random peptide library displayed between the H and Iβ sheets from the knob region of Ad5 (FIG. 1A). Peptides 12.51 (TARGEHKEEELI; SEQ ID NO:1) and 12.52 (LRQTGAASAVWG; SEQ ID NO:2) were selected against myoblasts with pre-clearing against non-target cells to obtain peptides which would be specific for binding muscle cells. In most cases, small peptides have relatively low affinity. It was therefore reasoned that displaying these muscle-selected peptides on the 720 copies of the Ad5 hexon might enable better muscle gene delivery. This insertion site might also have the benefit of inactivating FX binding to the hexon to "detarget" the vector from the liver if any vector leaked into the blood after IM injection.

Inserting these muscle-selected peptides between two other R sheets which also constrains a hypervariable loop on the virus, the ability of the modified Ads to modulate tropism was evaluated. Peptides 12.51 and 12.52 were introduced into the hypervariable region (HVR) 5 loop constrained by the β7 and β8 sheets in Ad5 hexon. The in vivo ability of these viruses to transduce tissues after intravenous and intramuscular injections in mice and in hamsters was evaluated.

Adenoviruses

E1-deleted Ad5-GL (RD-Ad5-GL) expresses a green fluorescent protein-luciferase (GFP-Luciferase, GL) fusion protein as described elsewhere (see., e.g., Crosby et al., 2002 J. Virol., 76:6893-6899; Khare et al., 2011 Mol. Ther., 19:1254-1262; and Khare et al., 2012 J. Virol., 86:2293-2301). Muscle selected peptides 12.51 and 12.52 were inserted in place of HVR5 on Ad5 hexon between its 37 and p8 sheets which structurally similar to the H and Iβ sheets from the knob region of Ad5 (FIG. 1A) according to methods known to those skilled in the art. The peptides with a flexibility leader replaced the entire HVR5 loop in Ad5 (FIG. 1B). These modified hexon sequences were introduced into replication-defective Ad5 expressing a green fluorescent protein-luciferase (RD-Ad5-GL) fusion protein by red recombination in bacteria (see, e.g., Campos et al., 2004 Hum. Gene Ther., 15:1125-1130). Peptide modified Ads were constructed by insertion of annealed oligonucleotides encoding the peptides 12.51 and 12.52 (FIG. 1B) into the plasmid pHVR5 display (FIG. 1A bottom) to yield recombinant Ads, Ad5-HVR5-12.51 and Ad5-HVR5-12.52.

The resulting plasmids were digested and used for red recombination into pAd5-GL. These vectors were rescued in 293 cells, purified on two consecutive CsCl gradients and were desalted on Econopac 10-DG chromatography columns (Bio-Rad) into 50 mM Tris pH 8 with 0.5 M sucrose and stored at −80° C.

In Vitro Virus Testing

C2C12 mouse myoblasts were purchased from American Type Tissue Culture (Manassas, VA). 293 cells were obtained from Microbix, Toronto, Ontario, Canada. Cells were maintained in DMEM with 10% FBS Invitrogen.

C2C12 muscle cells were plated in 6 well plates (Corning) the day before infection. Viruses were used to infect cells in DMEM with 5% FBS. The cells were incubated for 2 days prior to observation under green fluorescence.

Animal experiments were performed with approval by the Mayo Clinic Institutional Animal Care and Use Committee under the provisions of the Animal Welfare Act, PHS Animal Welfare Policy and principles of the NIH Guide for the Care and Use of Laboratory Animals. Female CD-1 mice (Charles River) were anesthetized and injected intramuscularly (IM) or intravenously (IV) with $10^{10}$ vp of the indicated viruses at indicated times. The animals were anesthetized and injected with 3 mg of d-luciferin (Molecular Imaging Products) and were imaged on a Xenogen imaging system. At later times, the animals were anesthetized and blood was collected in serum separators for ELISA.

ELISA was performed as follows. Immulon 4 HBX plates (Thermo) were incubated with 100 ng per well of GFP protein in 1X phosphate-buffered saline (PBS) at 4° C. overnight, washed, and blocked with 5% milk in TRIS-buffered saline with 0.1% Tween 20 (TBST) at room temperature for 2 hours. 1:100,000 to 1:1,1000 dilutions of each serum sample were prepared in blocking buffer. Wells were washed and 100 μL of each were added to GFP-coated plates in triplicate and incubated for 3 hours at room temperature. Wells were washed and a 1/10,000 dilution of goat anti-mouse-HRP secondary antibody (Pierce Chemical) was added to each well. Plates were incubated for 2 hours at room temperature, washed, and 50 μL of 1 Step Ultra TMB ELISA (Thermo Fisher Scientific Inc.) was added for HRP detection followed by 50 μL of 2 M $H_2SO_4$. Absorbance at 450 nm was determined with a Beckman Coulter DTX 880.

Statistical analyses were performed with Prism (Graphpad). Statistical significance was calculated by one-way ANOVA followed by Tukey's HSD In Vitro Transduction in Mouse C2C12 Muscle Cells RD-Ad5-GL, RD-Ad5-GL-HVR5-12.51, and RD-Ad5-HVR5-12.52 were used to infect mouse C2C12 myoblast cells at varied multiplicities of infection (MOI) in terms of virus particles (vp)/cell. When green fluorescence from the GFP fusion protein was observed by fluorescence microscopy, both of the peptide-modified vectors mediated significantly better transduction than RD-Ad5-GL (FIG. 2A). When luciferase activity was measured, significant increases were observed in RD-Ad5-GL-12.51 and 12.52 infected cells (FIG. 2B). When one of the peptides, 12.51, was inserted back into the knob region of Ad5, the peptide increased in vitro transduction 14-fold on C2C12 myoblasts.

In Vivo Transduction after Intramuscular Injection in Mice

Figure 3:
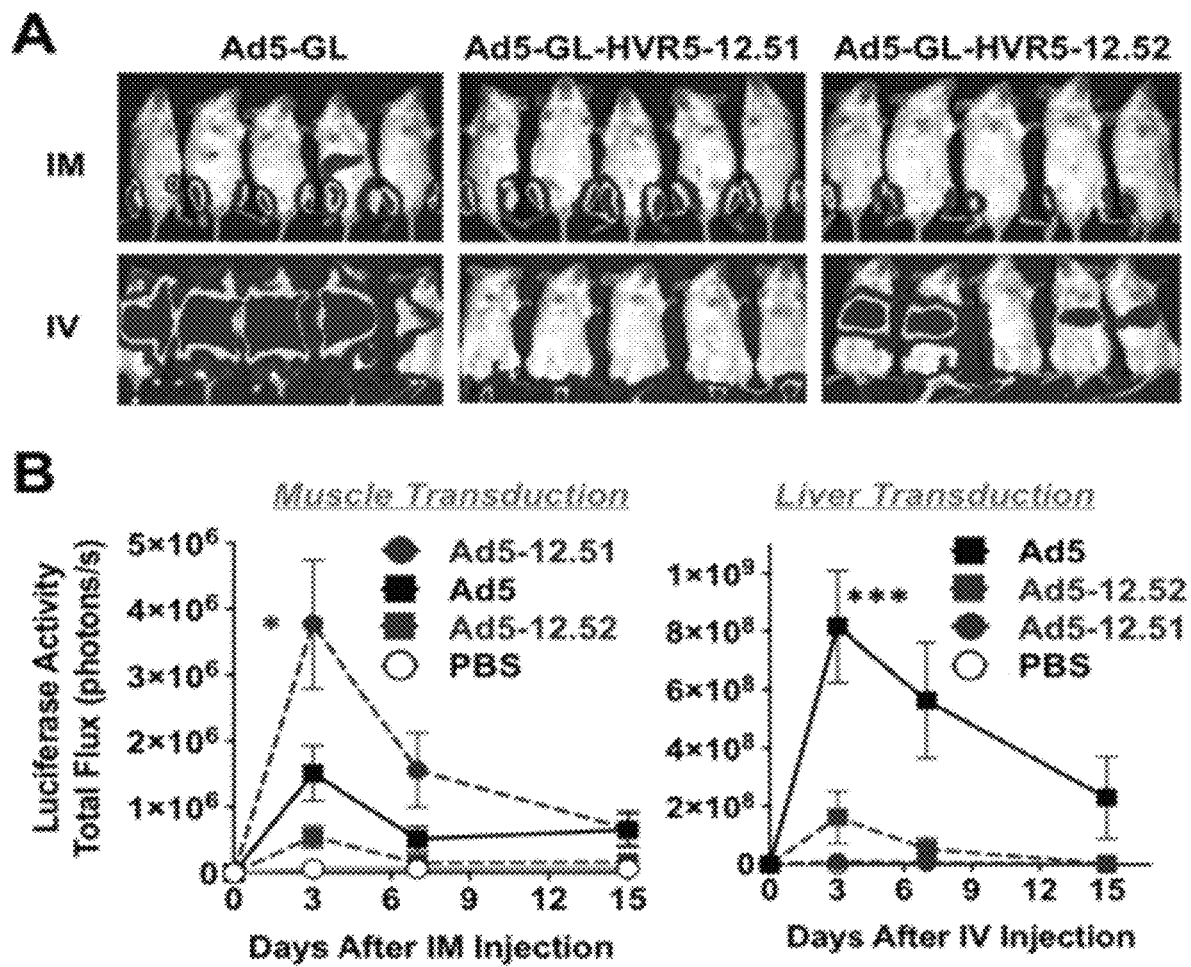
FIG. 3 shows in vivo transduction in mice. A) Luciferase imaging of mice 1 day after injection by the intravenous (IV) or intramuscular (IM) routes. IM injected mice received 109 vp into each quadricep. IV injected mice received $10^{10}$ vp by tail vein. B) Quantitation of luciferase activity by imaging on the indicated days after injection. * $p<0.05$ by one way ANOVA. *** $p<0.001$ by one way ANOVA.

10⁹ vp of Ad5-GL, Ad5-GL-HVR5-12.51, and Ad5-GL-HVR5-12.52 were injected by the IM route into both quadriceps muscles in mice and luciferase imaging was performed at varied times (FIG. 3A top). Ad5-GL-HVR5-12.51 produced 2 to 3-fold higher luciferase activity than Ad5-GL at all the time points (p<0.05 at day 1 by one-way ANOVA) (FIG. 3B left). Ad5-GL-HVR5-12.52 activity in the muscle was lower than both Ad5-GL and HVR5-12.51 in contrast to its stronger activity in vitro.

In Vivo Transduction after Intravenous Injection in Mice

3×10¹⁰ vp of Ad5-GL, Ad5-GL-HVR5-12.51, and Ad5-GL-HVR5-12.52 were injected by the IV route in mice and luciferase imaging was performed (FIG. 3A bottom). In contrast to the results in the muscle, only unmodified Ad5-GL mediated strong liver transduction. Liver transduction by Ad5-GL was 60-fold higher than both Ad5-GL-HVR5-12.51 and Ad5-GL-HVR5-12.52 (p<0.001 at day 1 by one-way ANOVA) (FIG. 3B right) demonstrating that the recombinant Ads target muscle tissue while decreasing off target infection in the liver.

In Vivo Transduction after Intramuscular Injection in Hamsters

Figure 4:
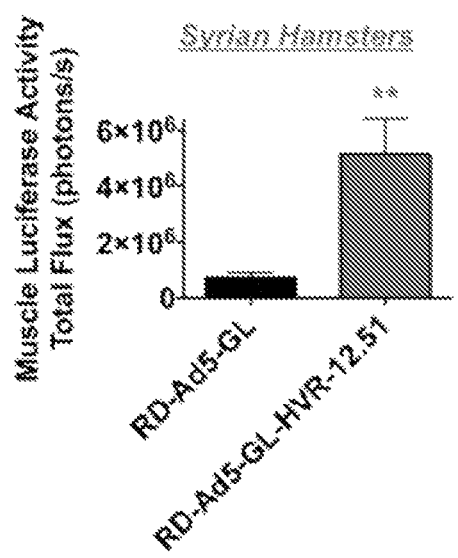
FIG. 4 shows in vivo transduction in hamsters. A) Luciferase activity in the muscles of hamsters 1 day after injection with $10^{10}$ vp by the IM route. ** $p<0.01$ by T test.

To test if the 12.51 modified vector works in other species than mice, 10¹⁰ vp of Ad5-GL and Ad5-GL-HVR5-12.51 were injected IM into both quadriceps of larger Syrian hamsters and luciferase imaging was performed 24 hours later (FIG. 4). In this case, Ad5-GL-HVR5-12.51 mediated 7-fold higher luciferase activity than Ad5-GL (p<0.01 at day 1 by one-way ANOVA).

Figure 5:
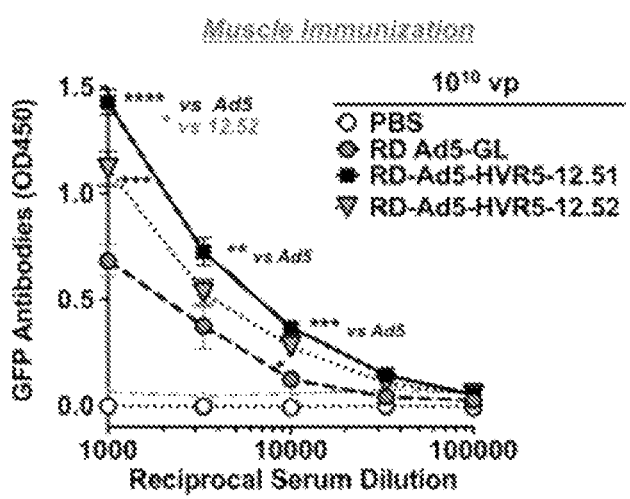
FIG. 5 shows gene-based immune responses 16 weeks after single IM immunization. Mice from FIG. 3 were bled 16 weeks after IM injection and their sera were analyzed in serial dilutions by ELISA to detect antibodies against GFP protein. * $p<0.05$,  $p<0.01$, * $p<0.001$ by one-way ANOVA. **** $p<0.0001$ by one-way ANOVA. All Ad-injected mice generated significant anti-GFP antibodies when compared to the PBS group at sera dilutions of 1:10,000 to 1:1000. Comparisons of Ad5-GL-HVR-12.51 and 12.52 to Ad5-GL are shown with black asterisks. Comparison between Ad5-GL-HVR-12.51 and Ad5-GL-HVR-12.52 are shown with a gray asterisk. A gray dashed and dotted line at OD 0.06 shows the 95% confidence interval discriminating antibodies that are different from the PBS group.

Gene-Based Immunization after Intramuscular Injection in Mice 16 weeks after IM injection, sera were collected the mice treated as described above and as shown in FIG. 3 and analyzed in serial dilutions by ELISA for antibodies against transgene-encoded GFP (FIG. 5). All Ad-injected mice generated significant anti-GFP antibodies when compared to the PBS group at sera dilutions of 1:10,000 to 1:1000 (p<0.0001 by one-way ANOVA). However, Ad5-GL-HVR-12.51 produced higher antibodies than either Ad5 or Ad5-HVR5-12.52. At 1:1000 to 1:10,000 dilutions of sera, Ad5-GL-HVR-12.51 was significantly higher than Ad5-GL (p<0.01 to 0.0001 by one-way ANOVA). At a 1:1000 dilution of sera, 12.51 was significantly higher than 12.52 (p<0.05). Ad5-GL-12.52 was significantly higher than Ad5-GL at 1:1000 and 1:10,000 dilutions of sera (p<0.05 to 0.001).

This example demonstrates that peptides selected in a compatible structural context on phage libraries can be translated into the Ad hexon protein. For example, for the 12.51 peptide, this insertion site increases muscle transduction while decreasing off target infection in the liver. Thus, such a recombinant Ad which targets muscle tissue may be used as a vector for gene-based muscle vaccination or for gene therapy application/delivery to the muscle.

A further aspect of the invention relates to recombinant and/or chimeric Ads which comprise other cell targeting peptides inserted into Ad657 HVRs and into Ad6 and C68 HI loops are described in Table 1.

TABLE 1

Other Cell Targeting Peptides Inserted into Ad657 HVRs and into Ad6 and C68 HI Loops

| | |
|---|---|
| VSV cell binding peptide | GTWLNPGFPPQSCGYATVT (SEQ ID NO: 4) |
| RGD-4C integrin binding peptide | CDCRGDCFC (SEQ ID NO: 5) |
| 12.51 phage-selected peptide | TARGEHKEEELI (SEQ ID NO: 1) |
| 12.52 phage-selected peptide | LRQTGAASAVWG (SEQ ID NO: 2) |
| 12.53 phage-selected peptide | ARRADTQWRGLE (SEQ ID NO: 3) |
| alpha4 binding peptide | NMSLDVNRKA (SEQ ID NO: 6) |
| L10.1 lung binding peptide | WTMGLDQLRDSSWAHGGFSA (SEQ ID NO: 9) |
| L10.2 lung binding peptide | RSVSGTEWVPMNEQHRGAIW (SEQ ID NO: 10) |
| L10.5 lung binding peptide | TELRTHTSKELTIRTAASSD (SEQ ID NO: 11) |
| S5.1 muscle binding peptide | DRAIGWQDKLYKLPLGSIHN (SEQ ID NO: 12) |
| DU9C.1 prostate cancer binding peptide | MGSWEKAALWNRVSASSGGA (SEQ ID NO: 13) |
| DU9C.2 prostate cancer binding peptide | MAMGGKPERPADSDNVQVRG (SEQ ID NO: 14) |
| DU9A.7 prostate cancer binding peptide | MASRGDAGEGSTQSNTNVPS (SEQ ID NO: 15) |
| XS.1 dendritic cell binding peptide | GPEDTSRAPENQQKTFHRRW (SEQ ID NO: 17) |
| REDV endothelial cell binding peptide | REDVY (SEQ ID NO: 46) |
| SKBR5C1 breast cancer cell binding peptide | GQIPITEPELCCVPWTEAFY (SEQ ID NO: 20) |
| 231R10.1 breast cancer cell binding peptide | PQPPNSTAHPNPHKAPPNTT (SEQ ID NO: 21) |
| HepaCD8 hepatocellular cancer binding peptide | VRWFPGGEWGVTHPESLPPP (SEQ ID NO: 22) |
| HI Met 231 3-4 breast cancer binding peptide | ISLSSHRATWVV (SEQ ID NO: 47) |

TABLE 1-continued

Other Cell Targeting Peptides Inserted into Ad657
HVRs and into Ad6 and C68 HI Loops B Cell Cancer Selected Peptides:

| | |
|---|---|
| 1-1 | GVSKRGLQCHDFISCSGVPW (SEQ ID NO: 29) |
| 1-2 | NQSIPKVAGDSKVFCWWCAL (SEQ ID NO: 30) |
| 1-3 | QSTPPTKHLTIPRHLRNTLI (SEQ ID NO: 31) |
| 1-4 | DMSFQLVTPFLKALPTGWRG (SEQ ID NO: 32) |
| 1-5 | GGHGRVLWPDGWFSLVGISP (SEQ ID NO: 33) |
| 1-6 | QIMMGPSLGYYMPSESIFAY (SEQ ID NO: 35) |
| 2-11 | ISWDIWRWWYTSEDRDAGSA (SEQ ID NO: 36) |
| 2-14 | VWGMTTSDHQRKTERLDSPE (SEQ ID NO: 37) |
| 2-20 | MTSAQTSEKLKAETDRHTAE (SEQ ID NO: 38) |
| 2-9 | MGSRSAVGDFESAEGSRRP (SEQ ID NO: 39) |
| 3b-6 | MGRTVQSGDGTPAQTQPSVN (SEQ ID NO: 40) |
| 4*-5 | MARTVTANVPGMGEGMVVVP (SEQ ID NO: 41) |
| Small BAP biotin acceptor peptide | GLNDIFEAQKIEWH (SEQ ID NO: 24) |
| calmodulin binding peptide | CAAARWKKAFIAVSAANRFKKIS (SEQ ID NO: 25) |

DNA encoding the indicated peptides and its complementary DNA was synthesized flanked by cohesive ends for ligation into Ad plasmids, for example, XA hexon plasmids or pAd6-NdePfl fiber shuttle plasmids. These annealed oligonucleotides were ligated into HVRs or the HI loop of Ads. These plasmids were used to recombine into various Ad backbone plasmids.

Some peptides serve to target novel receptors on cells. Others like the small BAP can be used for avidin targeting and purification if the virus is grown in cells expressing bacterial biotin ligase BirA. The calmodulin peptide allows the virus to bind to calmodulin or calmodulin-fusion proteins for retargeting or for virus purification.

Thus, such a recombinant Ads which targets specific tissues/cell receptors may be used as a vector for gene-based vaccination or for gene therapy application in the targeted cells and/or tissues.

Example 3. Insertion of Individual HVRs from Different Ad Serotypes with the Insertion of Cell Targeting/Detargeting Peptides or Novel Amino Acids Hexon shuttle plasmid maps (FIG. 34) show the combination of the insertion of individual HVRs from different Ad serotypes with the insertion of cell targeting/detargeting peptides or novel amino acids such as cysteine into the hexon for targeted chemical modification and shielding.

Figure 34:
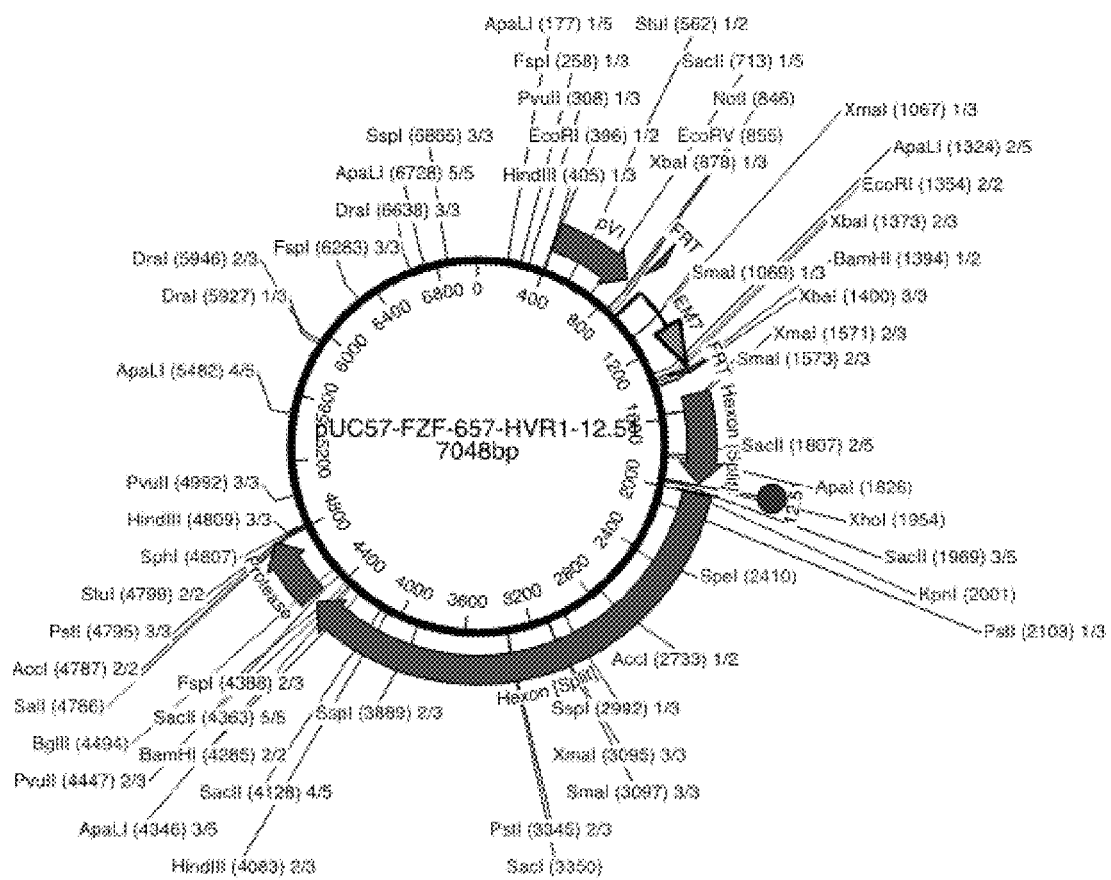
FIG. 34 shows plasmid maps for representative combinatorial hexons and peptide combinations. Shown are hexons with HVR1 from Ad6 and HVRs 2-7 from Ad57 as well as insertions of cell targeting peptides into individual HVRs.
Figure 34:
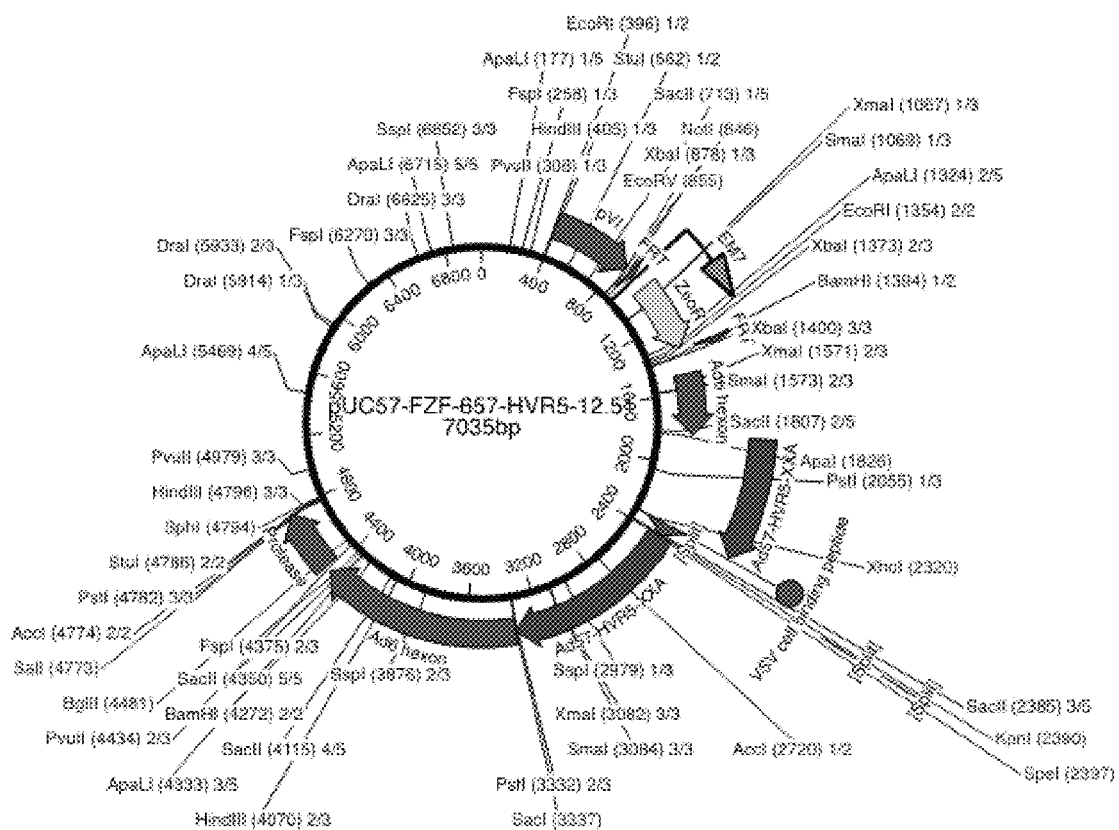
Figure 34:
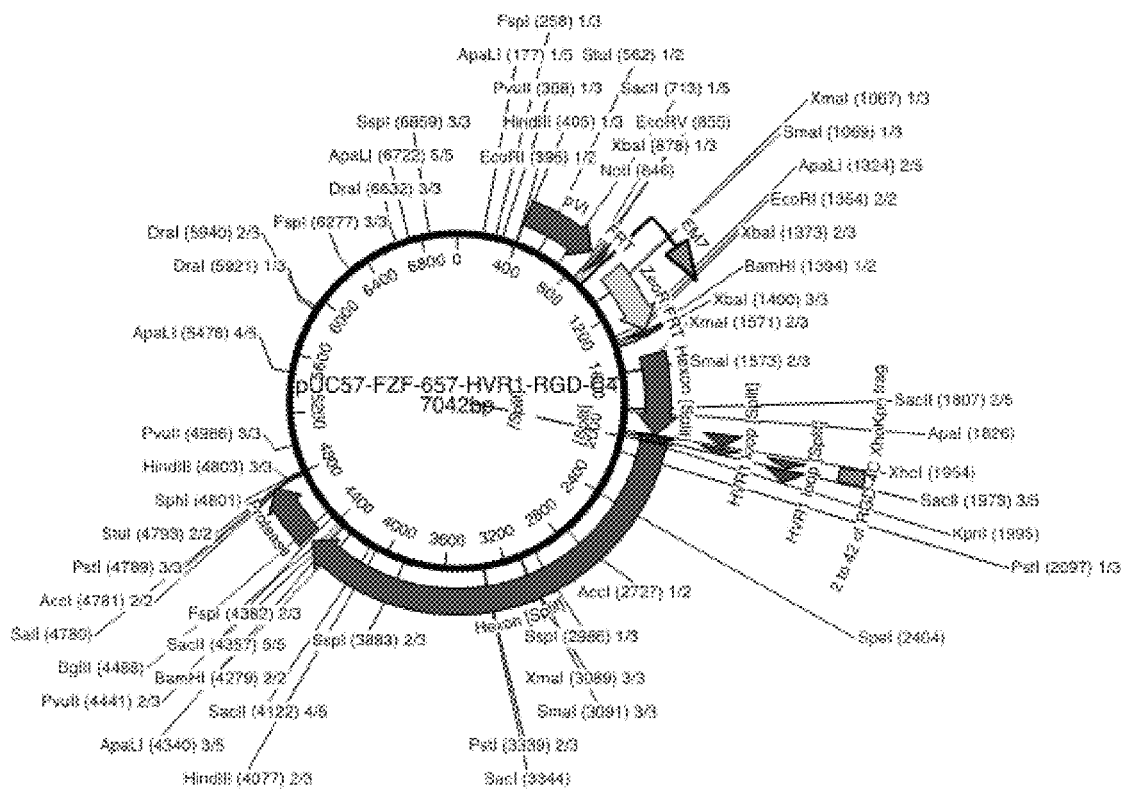
Figure 34:
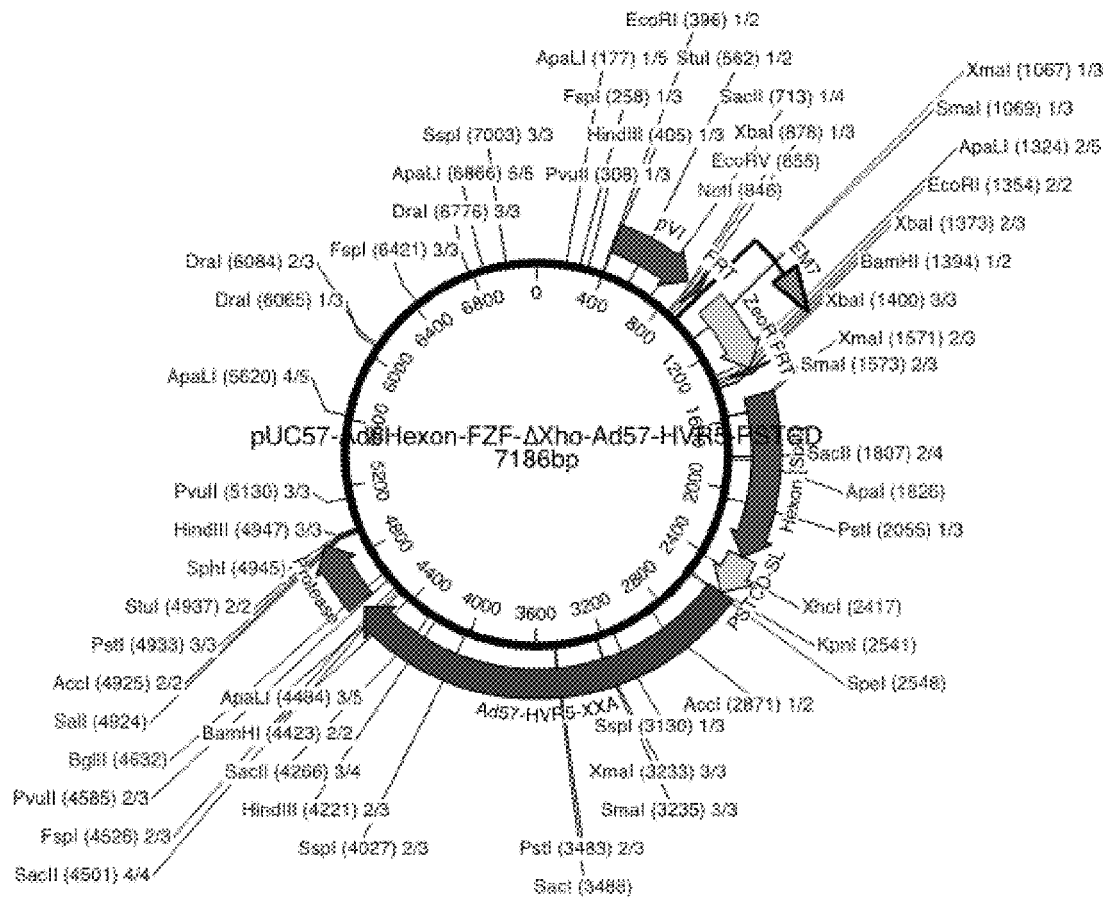
Figure 34:
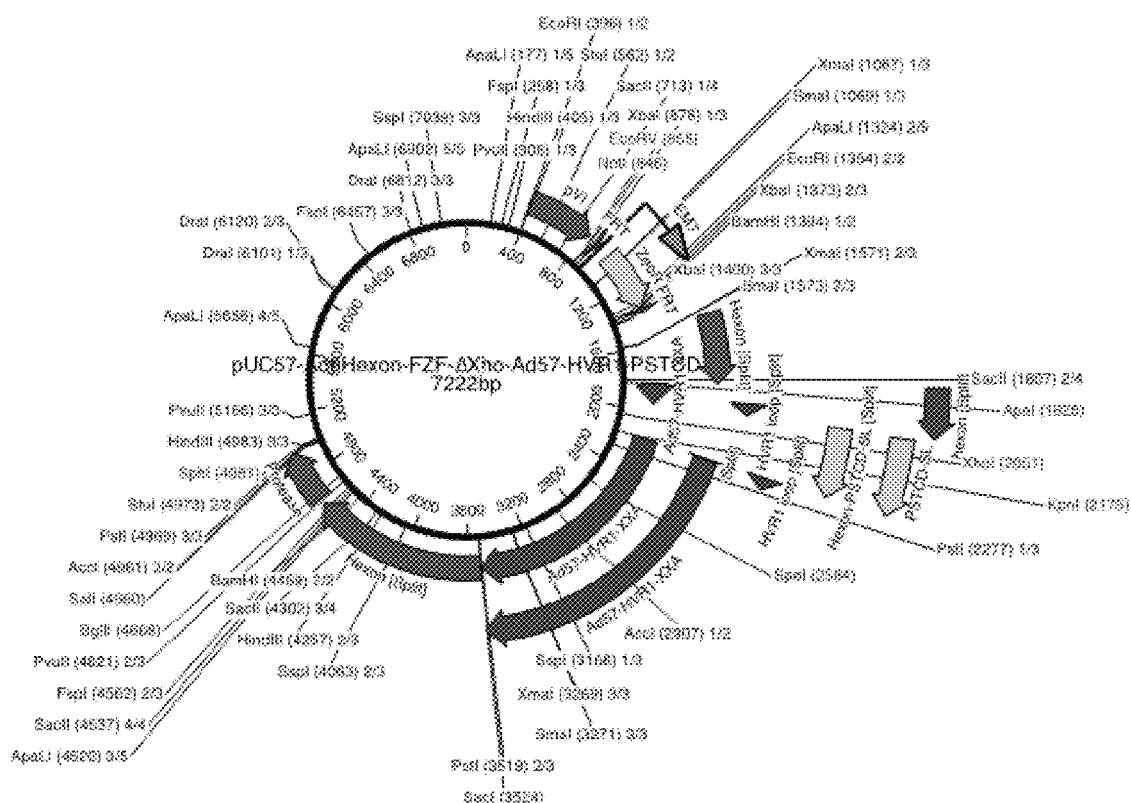
Figure 34:
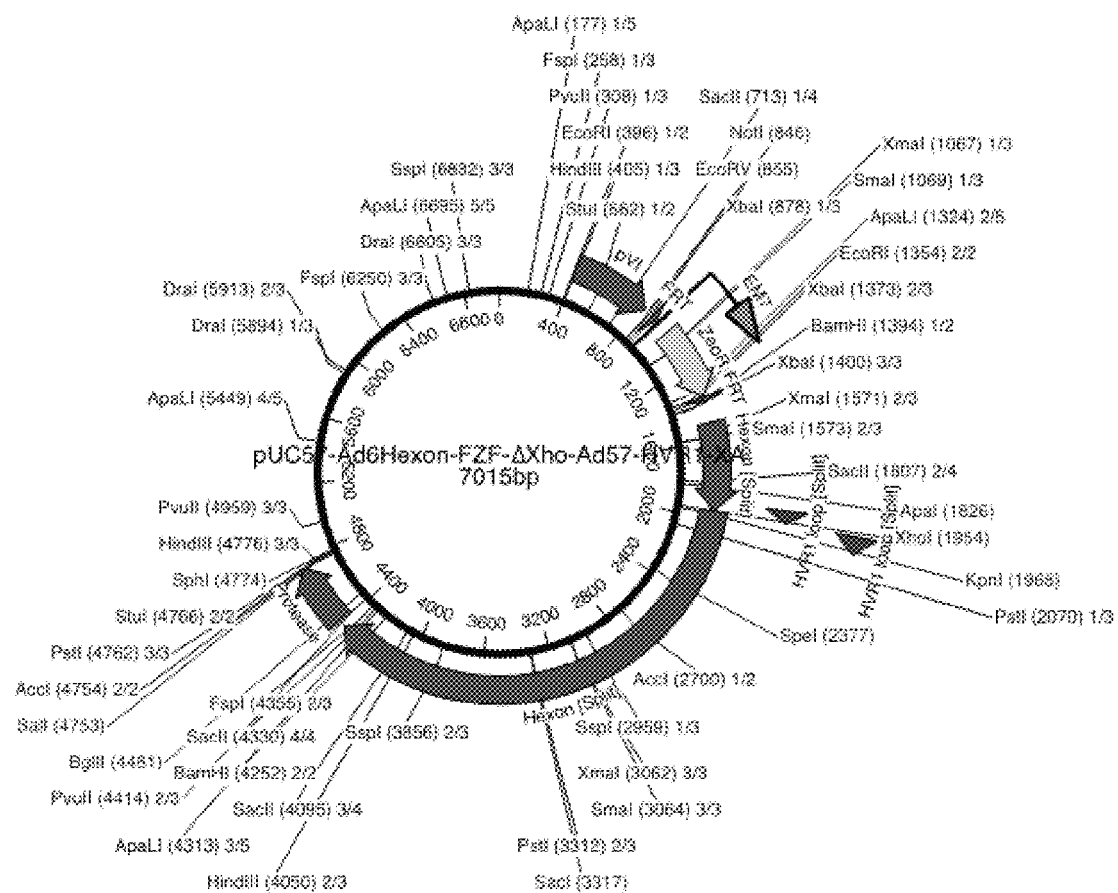
Figure 34:
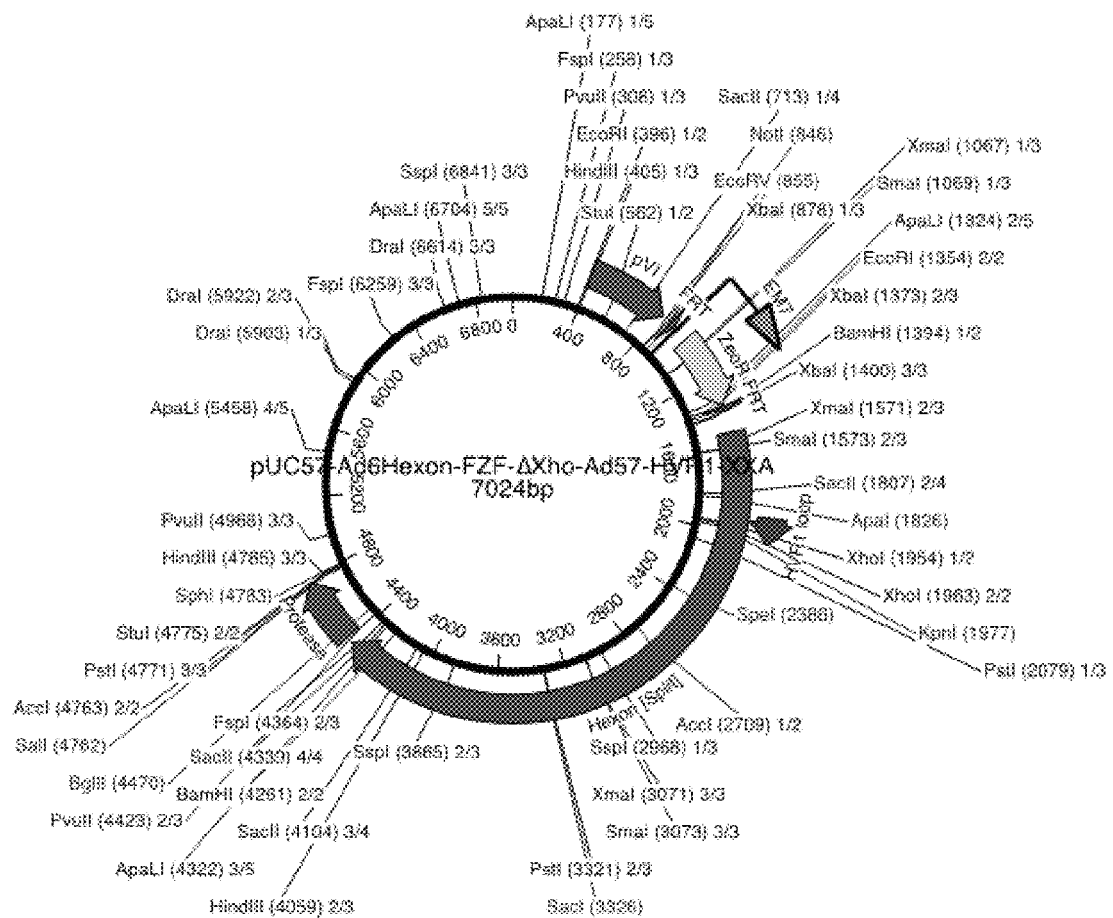
Figure 34:
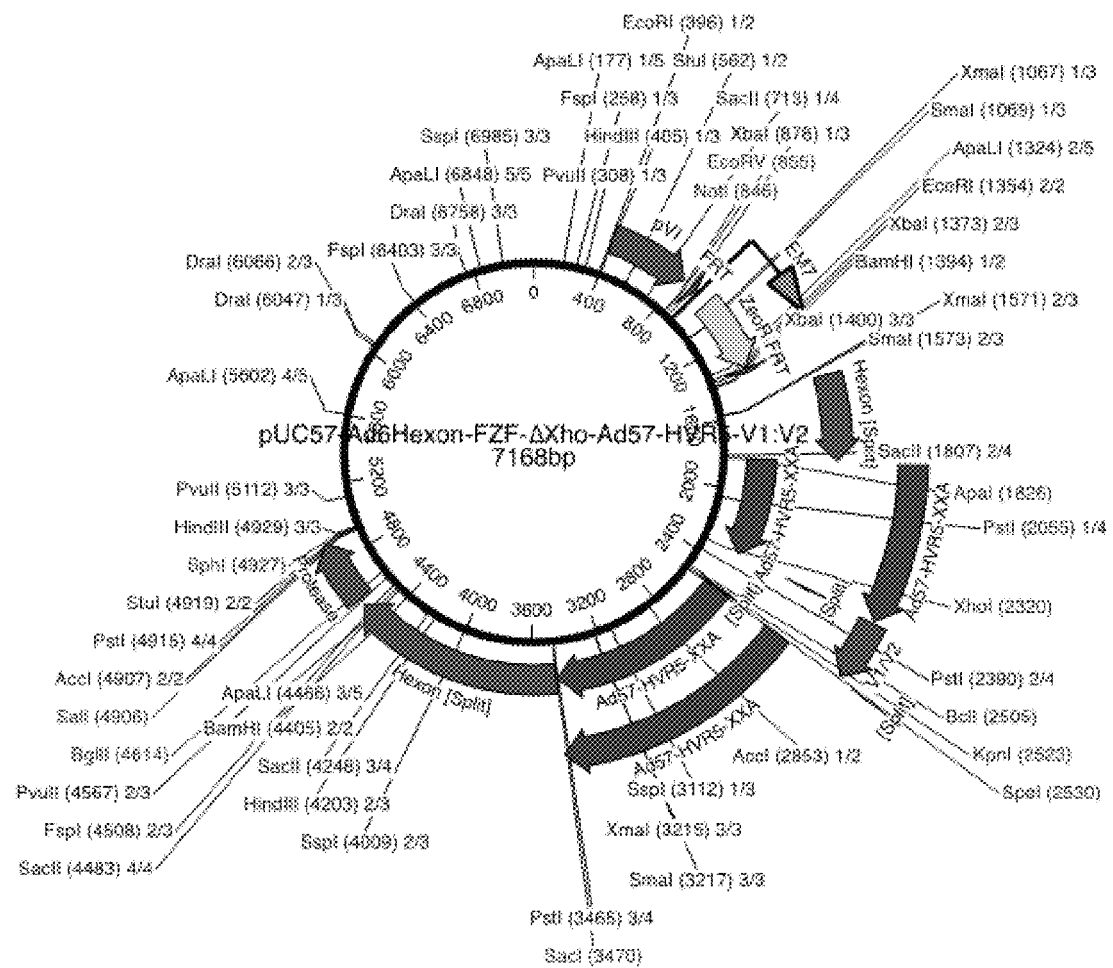

In certain embodiments, cell binding peptides 12.51, VSV, RGD (see Table 1) are inserted into HVR 1 or HVR 5, which embodiments serve as examples of inserting these and other peptides in any of the HVRs of an Ad (FIG. 34). Another example shows insertion of a biotin acceptor peptide (BAP) is inserted into these HVRs allowing for vector retargeting with avidin or streptavidin and biotinylated ligands or with avidin- or streptavidin fusion proteins. BAP insertion also allows the viruses to be purified on monomeric avidin or streptavidin columns for vector production. Likewise, Ad57-HVR1-XXA and XA shows the example of inserting a cysteine into this site to allow targeted chemical modification with maleimide or other cysteine-reactive agents (FIG. 34).

These embodiments have been applied also in the context of Ads which combine different HVRs from different Ads (i.e., shuffling HVRs). For example, HVR1 of Ad6 with HVRs 2-7 of Ad57 or HVR1 and 7 of Ad6 with HVRs 2-6 of Ad57. In a further embodiment, a 6/57/6 virus has HVRs 1 and 7 from Ad6 and HVRs 2-6 from Ad657.

Figure 35:
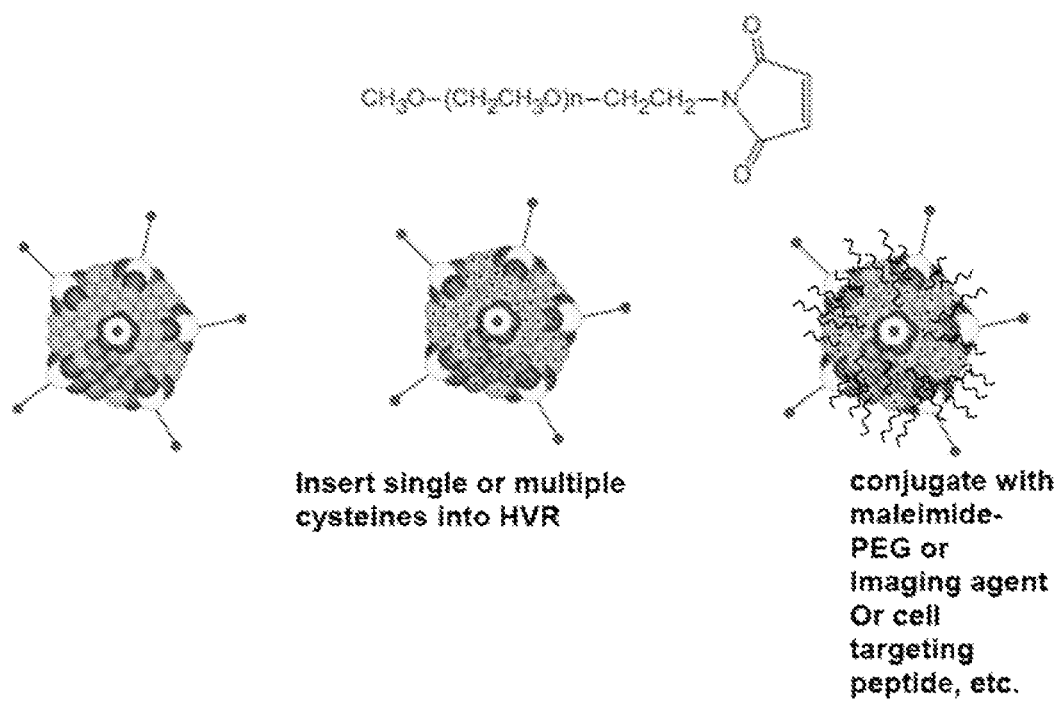
FIG. 35 shows chimeric HVR constructs that combine different HVRs from different Ad serotypes to modulate natural interactions with cells and blood factors improve pharmacology combined with insertion of cell binding and cell detargeting peptides in different HVRs to change cell entry and cell avoidance. In this example, a single cysteine amino acid is inserted into the HVR1 and HVR5 of Ad657 to modulate pharmacology and allow targeted conjugation of polymers like polyethylene glycol or other moieties like imaging agents like fluorophores.

Example 4. Targeted Chemical Conjugation of Cysteine-modified Hexon-modified Ad657-HVR5C FIG. 35 is a depiction of Ad variants showing the combination of insertion of individual HVRs from different Ad serotypes with the insertion of novel amino acids such as cysteine into the hexon for targeted chemical modification and shielding.

Figure 36:
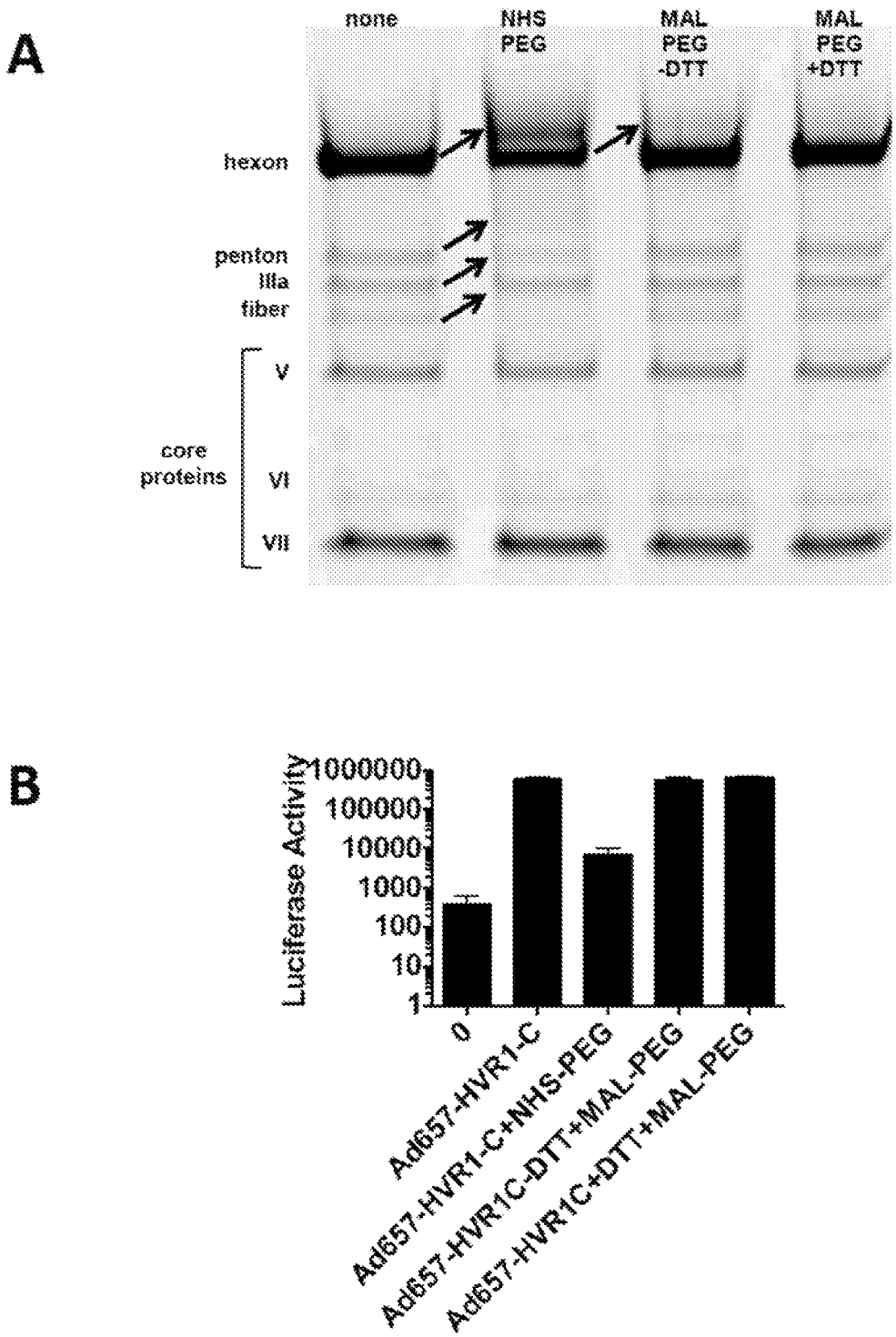
FIG. 36 shows conjugation of polyethylene glycol (PEG) to Ad657-HVR1-C. A) SDS-PAGE of Ad proteins with and without PEGylation. Arrows show size increases due to chemical attachment of PEG to hexon. B) Effects of targeted PEGylation by maleimide-PEG and non-targeting NHS-PEG on virus infection.

Comparison of the effects of non-targeted chemical conjugation to targeted chemical conjugation on shielding and function of cysteine-modified hexon-modified Ad657-HVR1C (FIG. 36). This example demonstrates the ability to target polymer and other chemical modifications to cysteines inserted into an Ad hexon. Untargeted PEG inactivates virus infection whereas cysteine-targeting PEGylation retains virus functions.

Figure 54:
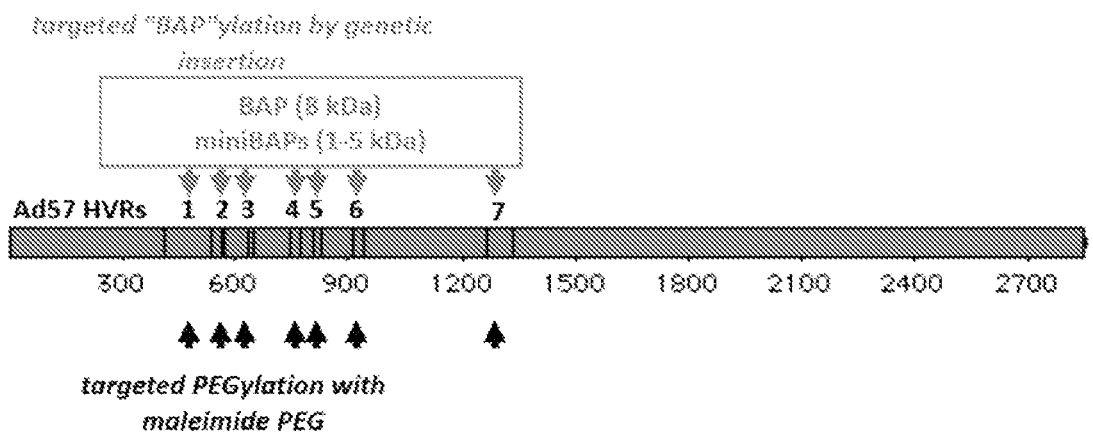
FIG. 54 depicts sites on Ad HVRs which may be modified, for example, by PEGylation or "BAPylation" with biotin acceptor peptides (BAPs).

In an aspect of the invention, the use of polymers or inserted peptides/proteins to detarget, retarget, and shield from antibodies, proteins, cells is contemplated. FIG. 54 depicts sites of Ad HVRs which may be modified, for example, by PEGylation or "BAPylation".

In an embodiment, the different Ad serotypes and/or variants comprise polymer shielding to allow multi dosing of Ad6 and Ad657 variants. An exemplary therapeutic cycle where Ad6 and Ad657 can be used for multiple rounds of treatment by serotype-switching in combination with covalent polymer conjugation is shown (FIG. 41B).

Ad657-HVR1C expressing GFPLuciferase was produced from a cells and purified on CsCl gradients. The virus was covalently modified with 5 kDa polyethylene glycol (PEG). The virus was treated with either NHS-PEG that reacts randomly with amines/lysines on viral proteins or with maleimide PEG that reacts specifically with cysteine that was inserted into HVR1 using the XXA shuttle plasmid. These unmodified or modified viruses were then purified by a final CsCl spin followed by desalting. The indicated virus were separated on SDS-PAGE gels, stained with Sypro-Ruby, and visualized by imaging (FIG. 36A). This ADZE 1 US SEQ DIV 1 shows that NHS-PEGylation randomly modifies many viral proteins as demonstrated by increases in the apparent mass of the proteins (indicated by arrows). In contrast, targeted maleimide PEG reaction with the cysteine in HVR1 modifies only hexon and does not damage other viral capsomer proteins. The effects of PEGylation on virus function was evaluated.

The indicated viruses were incubated with A549 cells and their ability to infect the cells was measured by luciferase assay. This shows that random NHS-PEGylation reduces virus activity more than 90% whereas maleimide-PEG does not (FIG. 36B).

Figure 58:
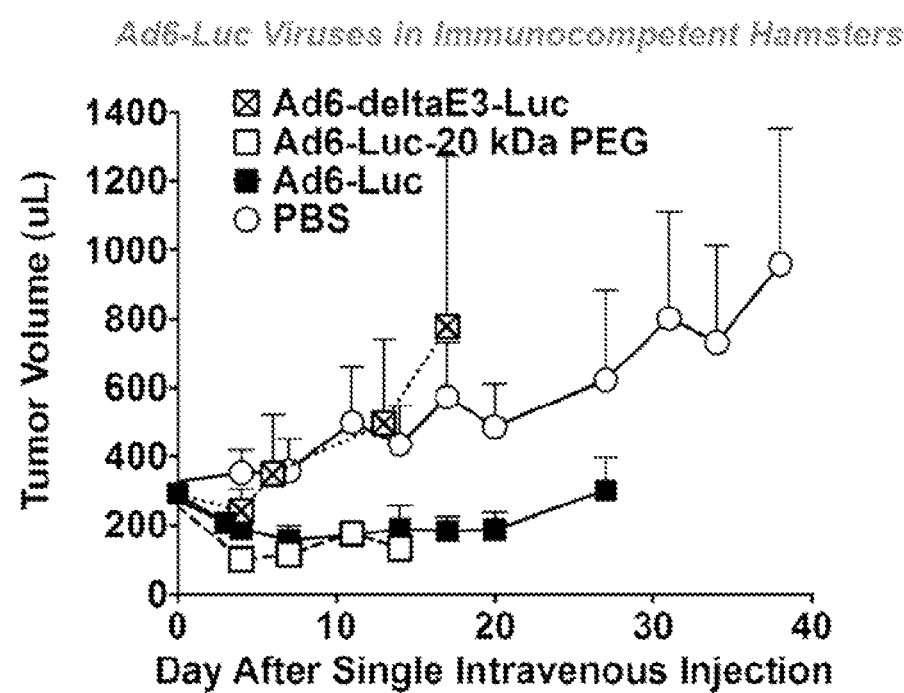
FIG. 58 demonstrates the effects of PEGylation and E3 deletion on oncolytic viral anti-tumor activity by Ad6-Luc viruses in immunocompetent hamsters. Ad6-Luc and Ad6-Luc-20K PEG both have all E3 genes and E4 34K intact. Ad6-deltaE3-Luc has partial deletion of E3 12.5K and E4 34K and full deletion of E3 6.7K, 19K, 11.6K (ADP), 10.4K (RIDα), 14.5K (RIDβ), and 14.7K genes. Oncolytic efficacy is lost in this immunocompetent animal model when these immune evasion genes are not present in oncolytic adenovirus.

Immune competent Syrian hamsters were engrafted with subcutaneous HaK kidney cancer tumors. When these reached 200 µl volume, they were injected a single time by the intravenous route with the indicated Ad6 viruses constructed with and without E3 (DE3) and with or without random NHS-PEGylation. Tumor sizes were measured over time. The data shows that deleting all E3 genes in the oncolytic virus Ad6-deltaE3-Luc makes the virus less effective at reducing tumor volume than the oncolytic parent virus, Ad6-Luc. The data also shows that Ad6 can be PEGylated and retain efficacy (see Ad6-Luc vs. Ad6-Luc-20 kDa PEG) (FIG. 58).

Targeted chemical conjugation of cysteine-modified hexon-modified Ads, for example Ad657-HVR5C. Ad657-HVR5C expressing GFPLuciferase was produced from cells and purified on CsCl gradients. The virus was covalently modified with maleimide-IR800 near-infrared fluorophore, maleimide-biotin, or 5 kDa maleimide-PEG that reacts specifically with cysteine that was inserted into HVR5 using its XXA shuttle plasmid. The indicated Ads and modified Ads were separated on SDS-PAGE gels, stained with Sypro-Ruby, and visualized by imaging (FIG. 37A). SDS-PAGE of viral proteins followed by near infrared imaging demonstrates that the HVR-C can be tagged with an imaging agent (FIG. 37B). The effects of PEGylation on in vivo Ad virus function was demonstrated by injecting PEGylated Ad virus intraperitoneally. The ability to infect cells in tumor bearing mice is demonstrated by detectable luciferase activity by imaging. FIG. 37C demonstrates the ability to target polymer and other chemical modifications to cysteines inserted into the Ad657 hexon region. What is more, it is demonstrated that PEGylation de-targets adenovirus to liver in vivo (FIG. 50).

Example 5. Expression of Human Granulocyte-Macrophage Colony Stimulating Factor (GMCSF) by Ad657

Figure 27:
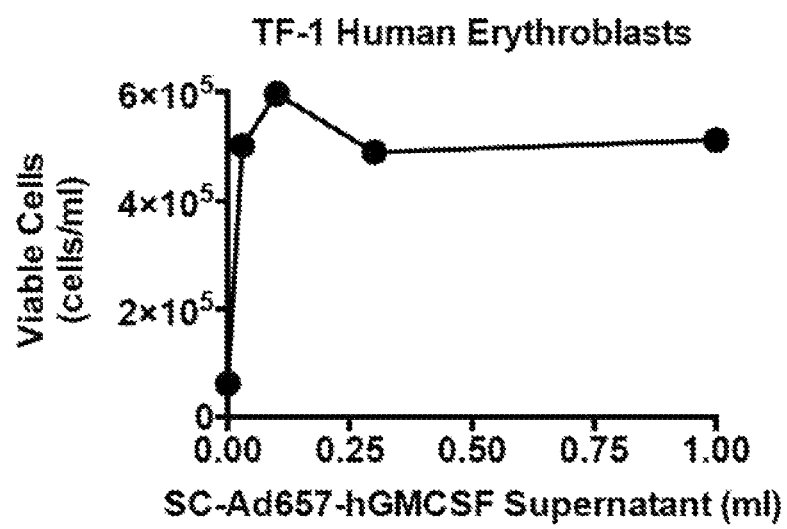
FIG. 27 shows expression of human GMCSF from Ad657 inducing proliferation of GMCSF-dependent TF-1 human erythroblasts.

Ad657 carrying the cDNA for human GMCSF was used to infect A549 cells and varied amounts of the supernatant were added to GMCSF growth-dependent TF-1 cells. Increased cell number indicates expression of the functional human cytokine (FIG. 27). The data demonstrates that recombinant Ads may be utilized for expression of heterologous proteins.

Figure 6:
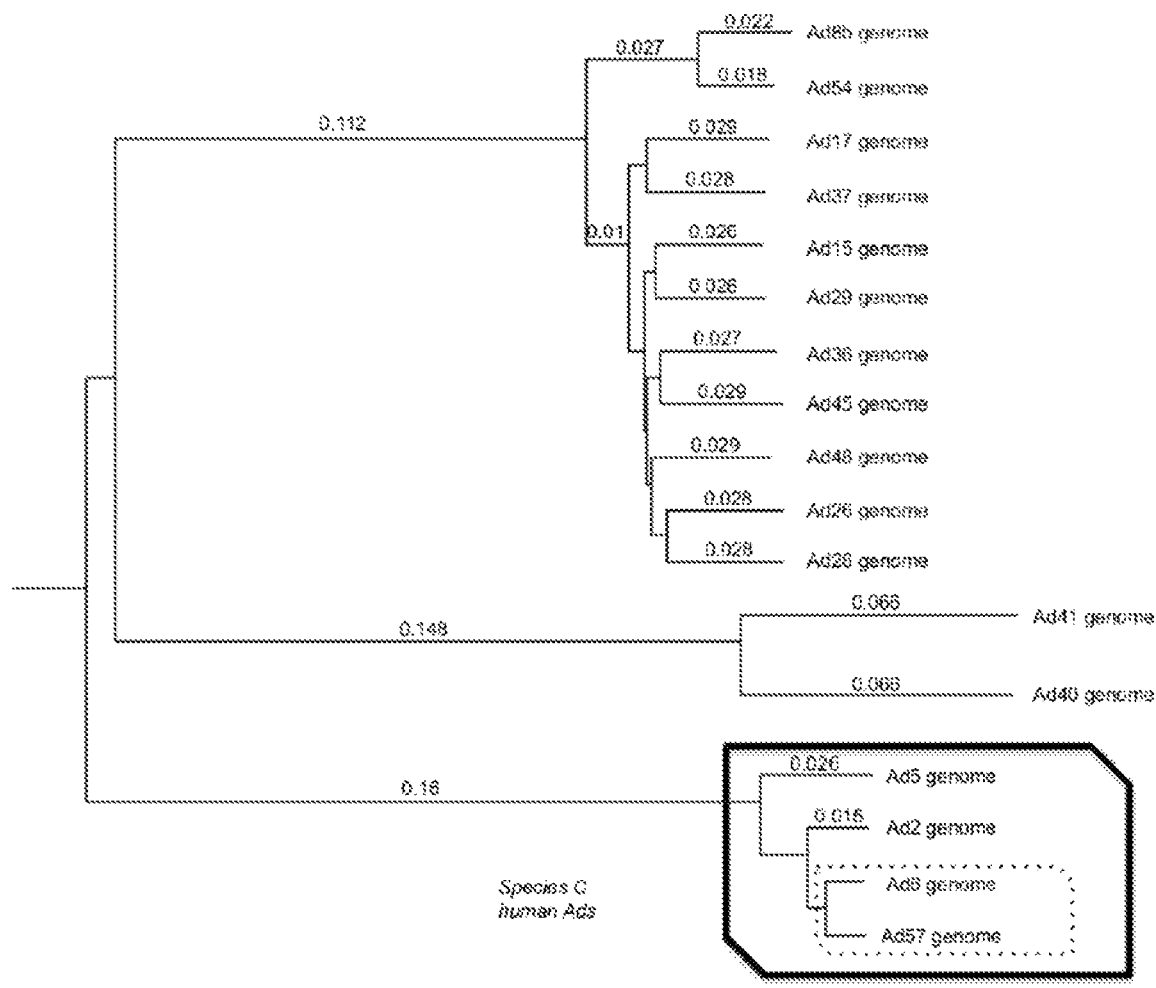
FIG. 6 shows a phylogenetic tree of whole genome sequences of human adenovirus serotypes.

Example 6. Oncolytic Adenovirus Ad657 for Systemic Virotherapy Against Cancer Cells An alignment of selected full Ad genomes produces a phylogenetic tree that clusters Ad57 with other species C viruses with most homology with Ad6 is shown in FIG. 6.

Figure 7:
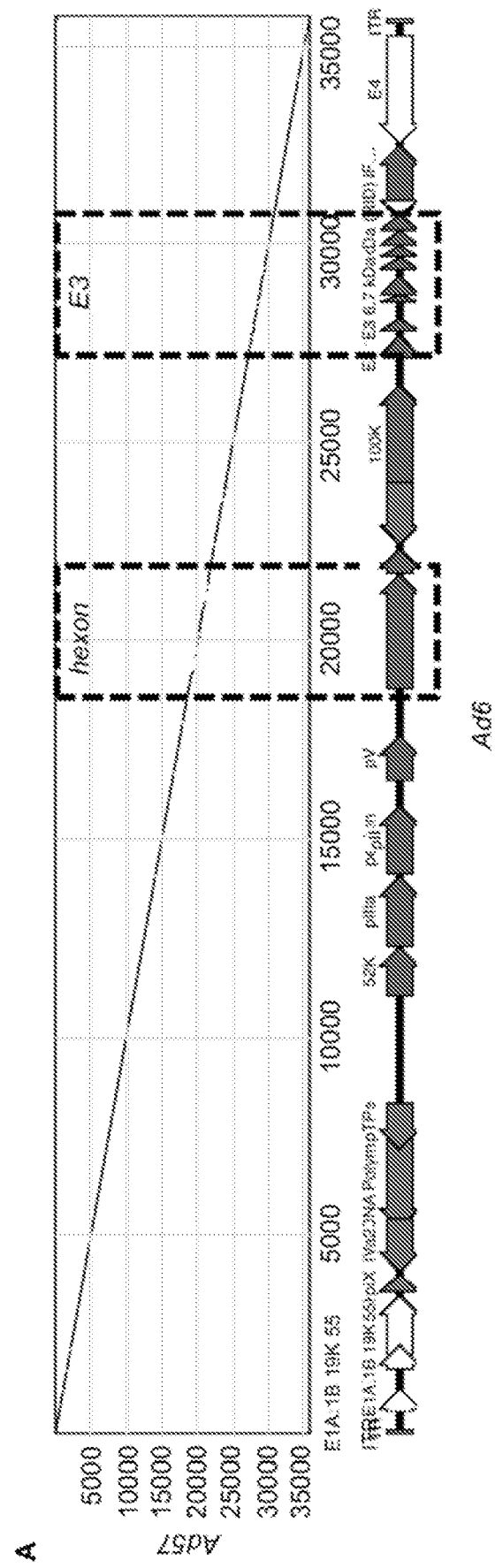
FIG. 7 shows an alignment of Ad5, 6, and 57 showing variation in hexon and E3 regions. (A) A Pustell DNA alignment of the genomes of Ad6 and Ad57. Boxes indicate hexon and E3 regions where variation is highest between the two viruses. (B) ClustalW amino acid alignment of the hypervariable region in hexon proteins from Ad5, Ad6, and Ad57. Alignments were performed on MacVector.

Ad57 appears nearly identical to Ad6 with sequence divergence in hexon hypervariable regions (HVRs) and in E3 immune evasion genes (FIG. 7). Other exposed viral capsid proteins including fiber, penton base, IIIa, and IX are virtually identical between Ad6 and Ad57. The neutralization data are consistent with the fact that most adenovirus-neutralizing antibodies target the HVRs on Ads. The low cross-reactivity between Ad6 antisera and Ad57 is thought to be due to antibodies that may target their common fiber protein (Lukashev et al., 2008 J Gen Virol. 89:380-388).

In this example, the utility of Ad657 as an oncolytic against human prostate cancer is demonstrated. The Ad6 HVRs were replaced with those from Ad57 to generate a chimeric species C oncolytic virus called Ad657. Ad657 and Ad6 were tested as systemic oncolytic therapies by single i.v. injection in nude mice bearing human prostate cancer tumors. The liver and tumor tropism of this virus were evaluated in mouse models of prostate cancer as follows.

DU145 human prostate carcinoma cells were purchased from American Type Culture Collection (ATCC; Manassas, VA, USA) and verified to be specific pathogen free by IMPACT testing by RADIL. 293 cells were obtained from Microbix, Toronto, Ontario, Canada. Cells were maintained in DMEM with 10% FBS (Invitrogen, Grand Island, NY, USA).

Figure 59:
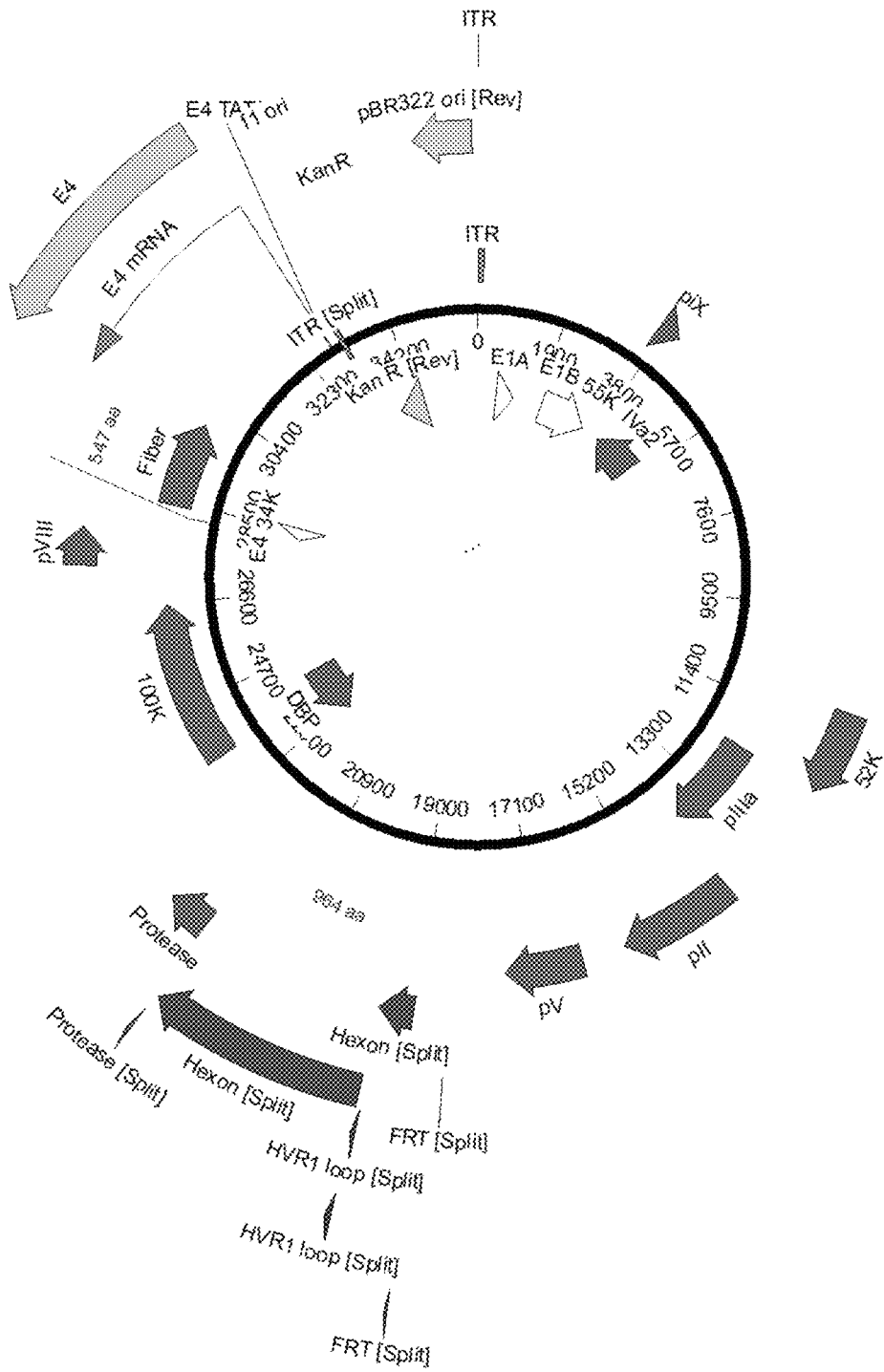
FIG. 59 is a plasmid map of Ad657 with partial deletion of E3 12.5K and E4 34K and full deletion of E3 6.7K, 19K, 11.6K (ADP), 10.4K (RIDα), 14.5K (RIDβ), and 14.7K genes.
Figure 60:
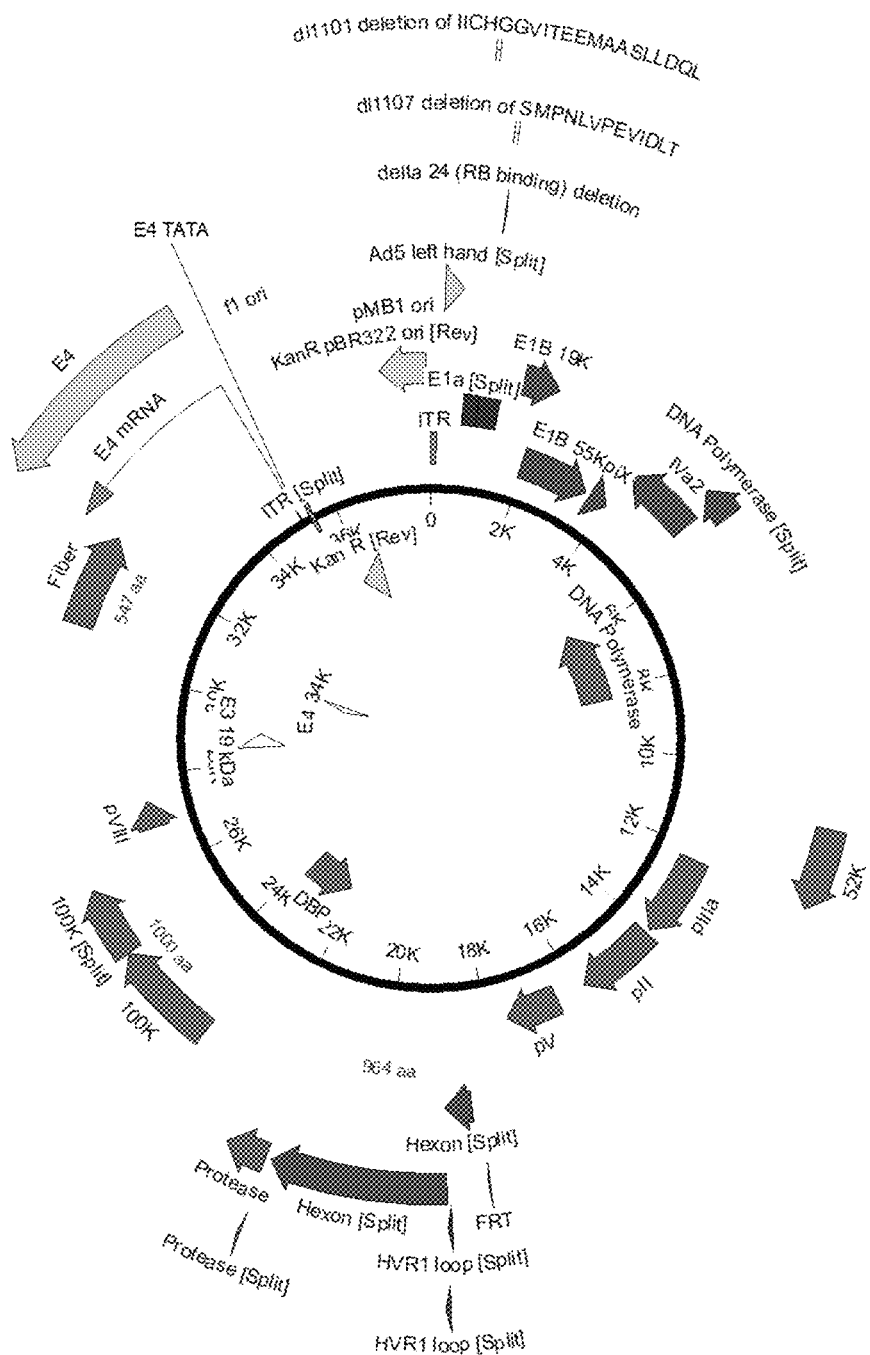
FIG. 60 depicts CRAd 657 constructs with and without dl1101/1107 CRAd modifications and with and without deletions of selected E3 immune evasion genes.
Figure 61:
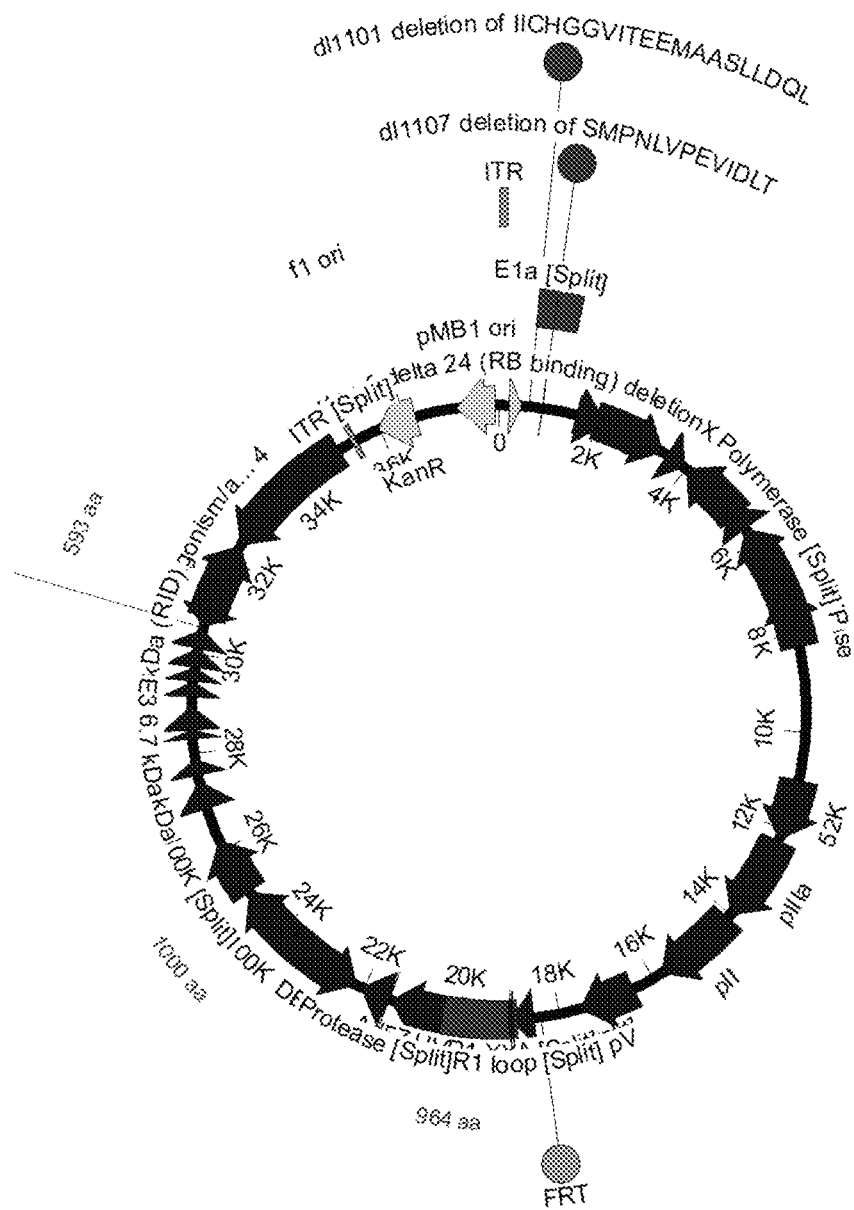
FIG. 61 depicts CRAd657 with E3 insertion site. These are with and without dl1101/1107 CRAd modifications described herein and with and without E3 immune evasion modifications.
Figure 62:
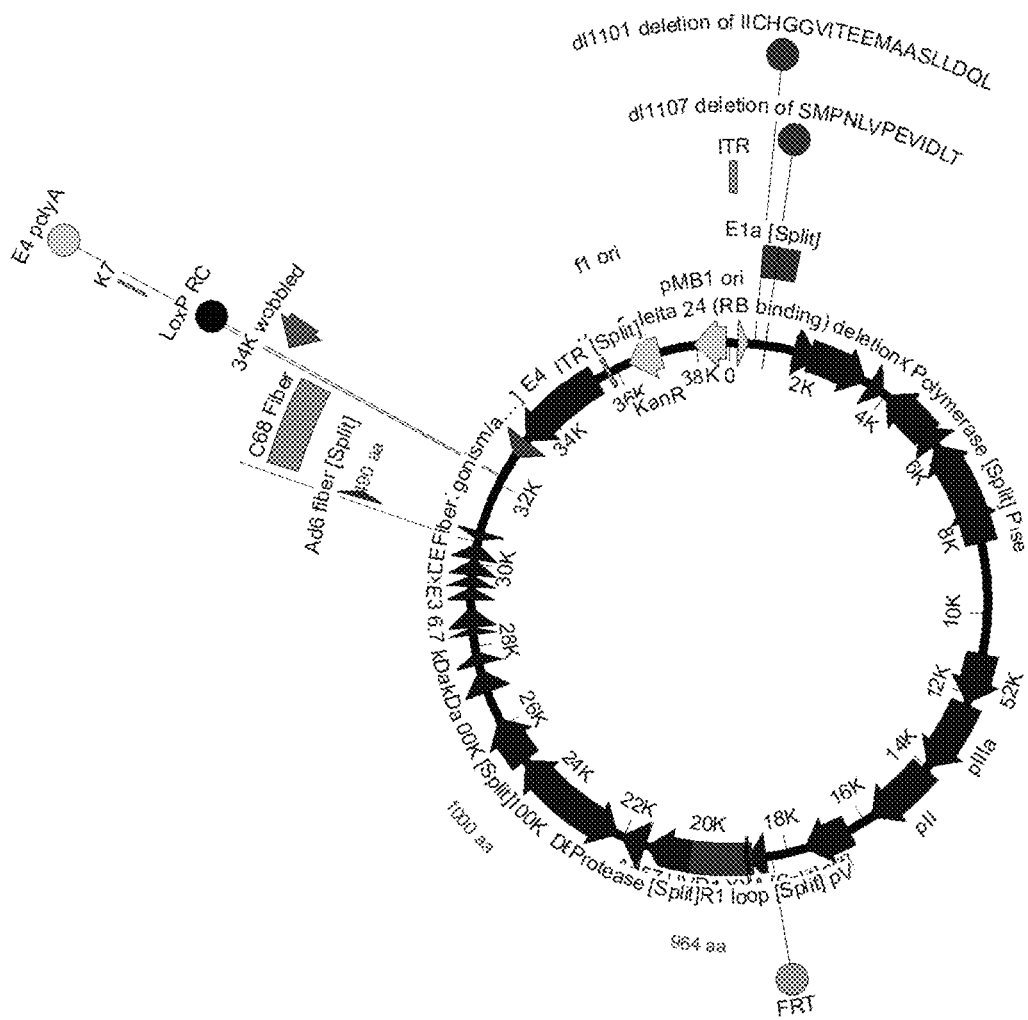
FIG. 62 depicts CRAd657+/−Ad35 Fiber or Chimpanzee C68 Fiber+/−K7 peptide. These are with and without dl1101/1107 CRAd modifications described in previous slides and with and without E3 immune evasion modifications. In some cases, a codon-wobbled E4 34K gene is included after E4 and before fiber to compensate for E4 34K partial deletion when deleted E3B genes.
Figure 63:
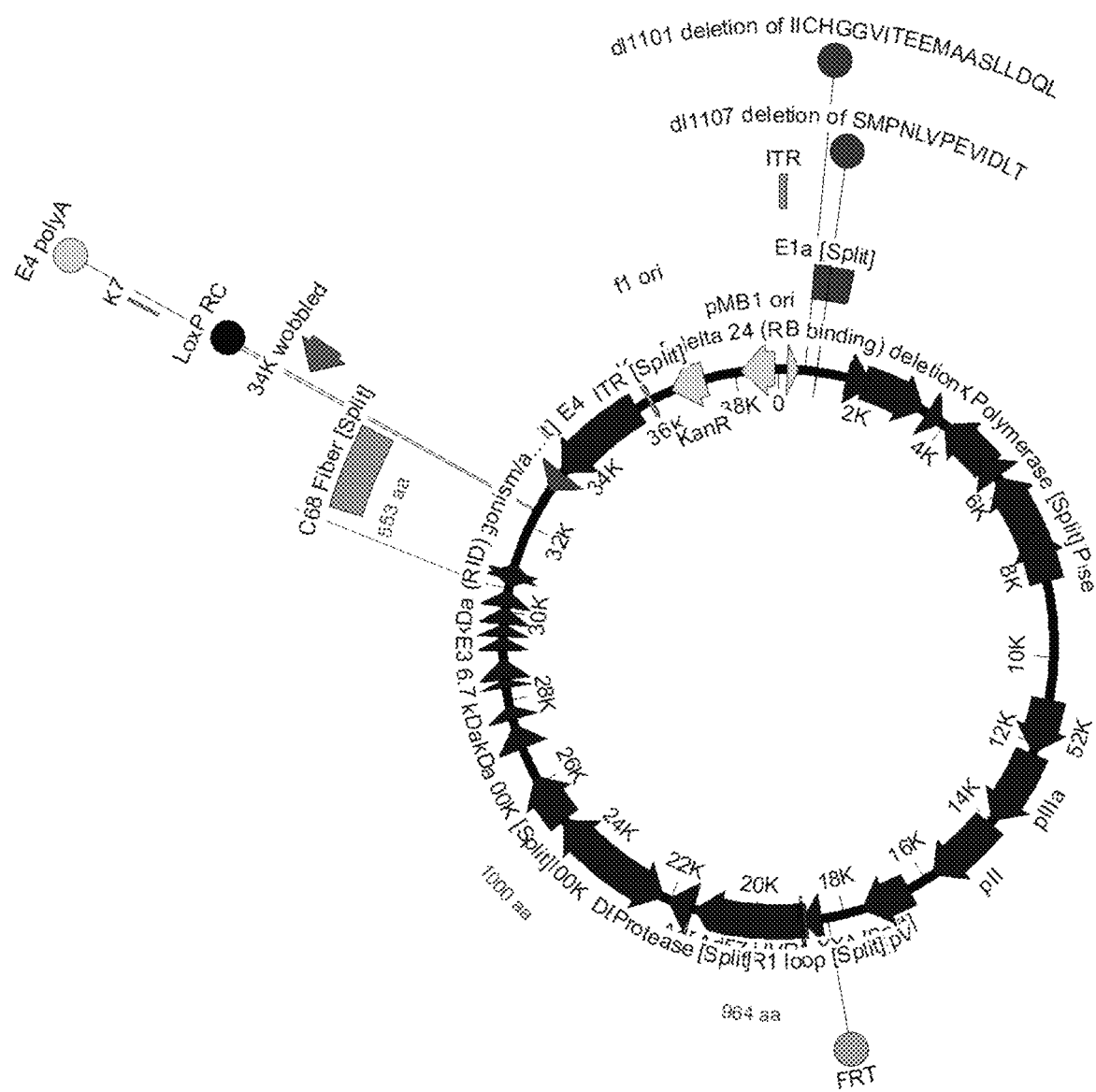
FIG. 63 depicts CRAd657+/−Ad35 Fiber or Chimpanzee C68 Fiber+/−K7 peptide. These are with and without dl1101/1107 CRAd modifications described in previous slides and with and without E3 immune evasion modifications.
Figure 64:
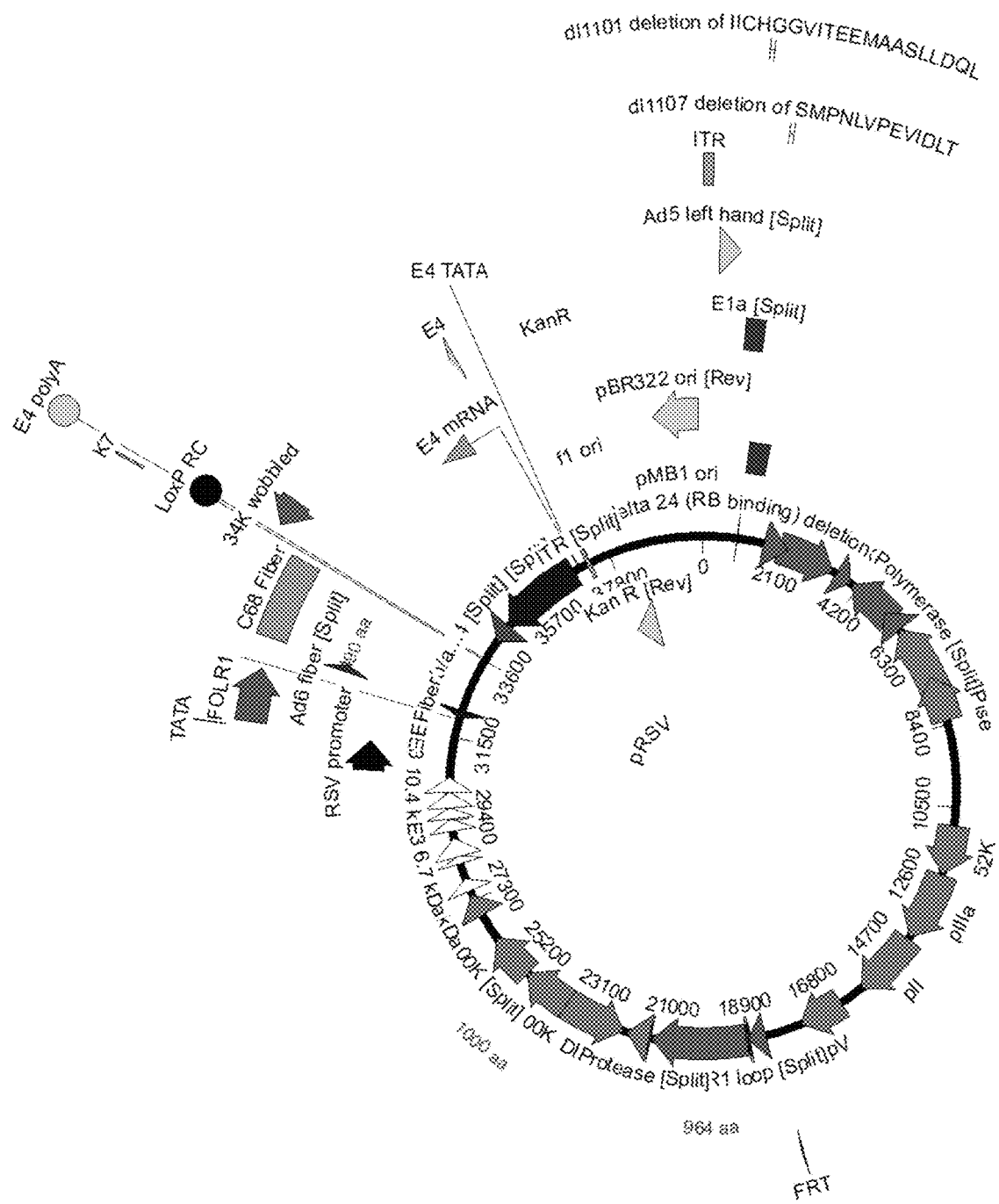
FIG. 64 depicts CRAd657+/−Ad35 Fiber or Chimpanzee C68 Fiber+/−K7 peptide Expressing Folate Receptor alpha.
Figure 65:
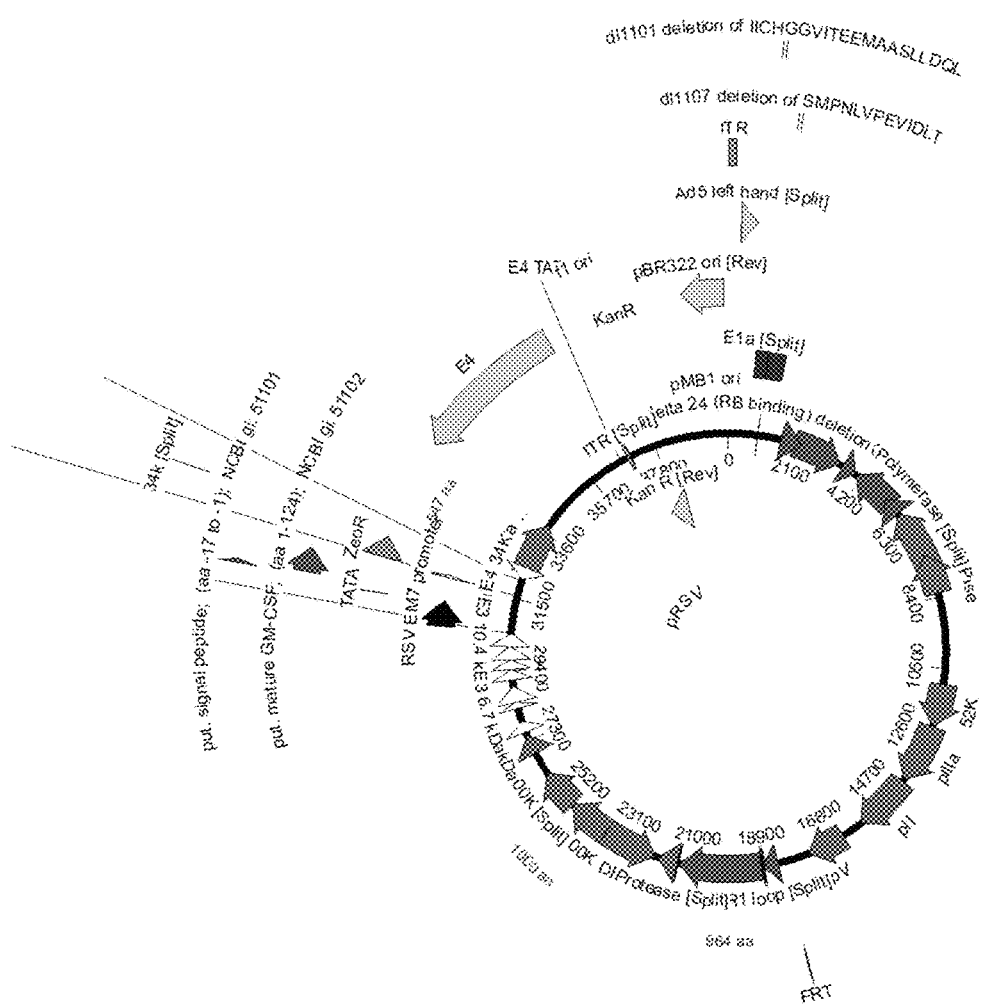
FIG. 65 depicts CRAd657+/−Ad35 Fiber or Chimpanzee C68 Fiber+/−K7 peptide Expressing Granulocyte Macrophage Colony Stimulating Factor (GMCSF).
Figure 66:
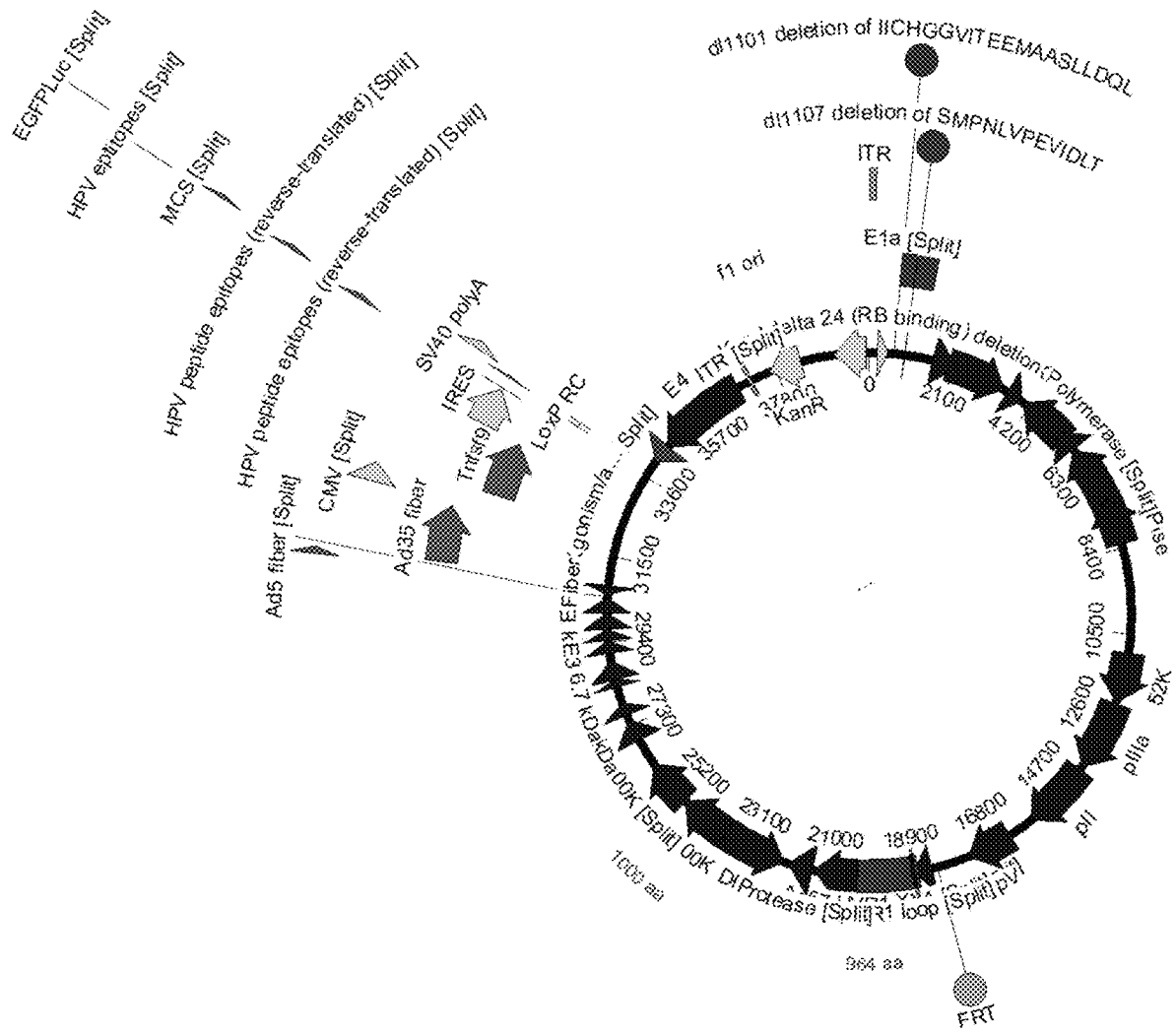
FIG. 66 depicts CRAd657+/−Ad35 Fiber or Chimpanzee C68 Fiber+/−K7 peptide Expressing 4-1BBL or GMCSF or IL21 or CD40L and combinations in one virus.
Figure 67:
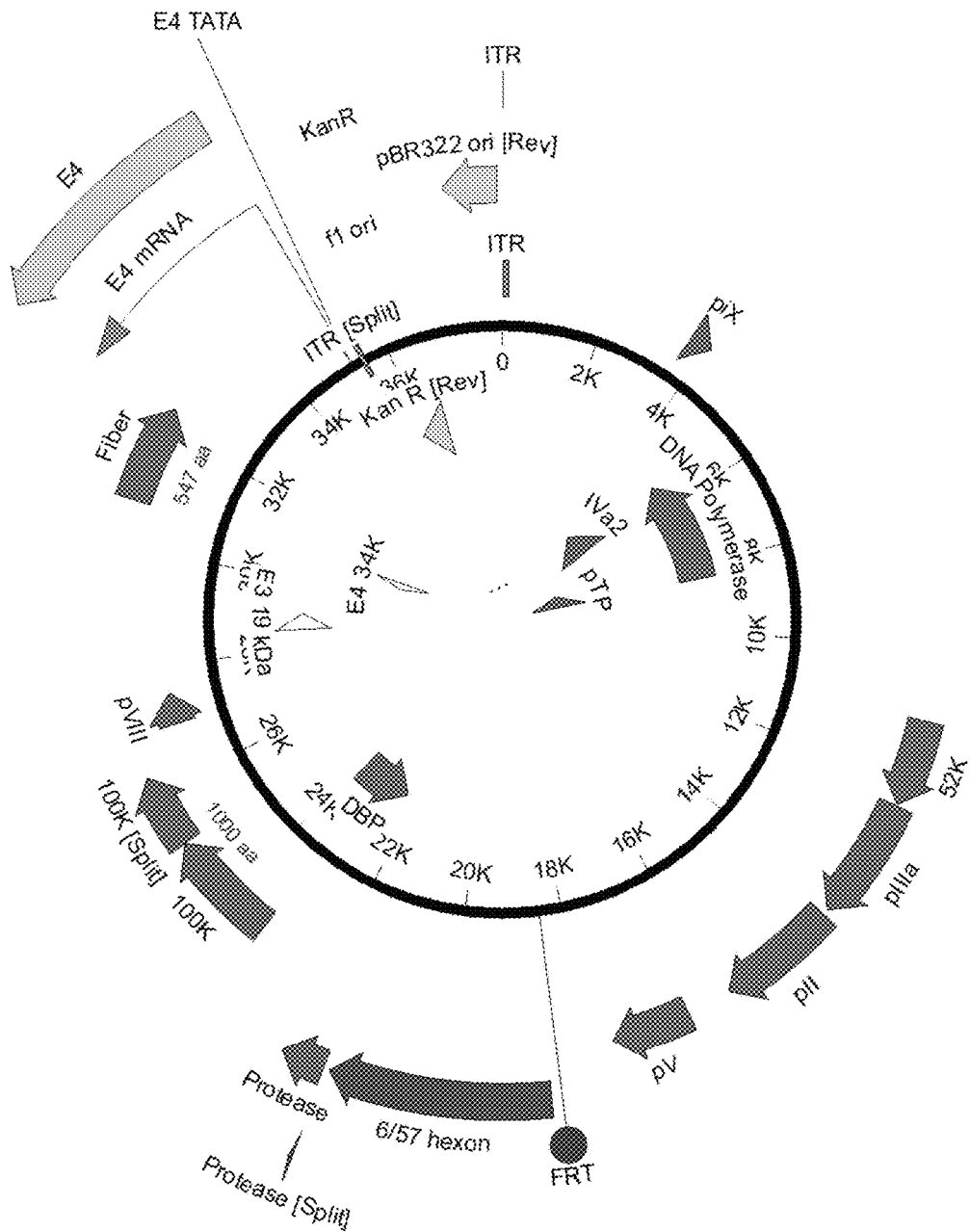
FIG. 67 depicts Ad6/57 with Ad6 HVR1 and Ad57 HVRs2-7+/−Ad35 Fiber or Chimpanzee C68 Fiber+/−K7 peptide.
Figure 68:
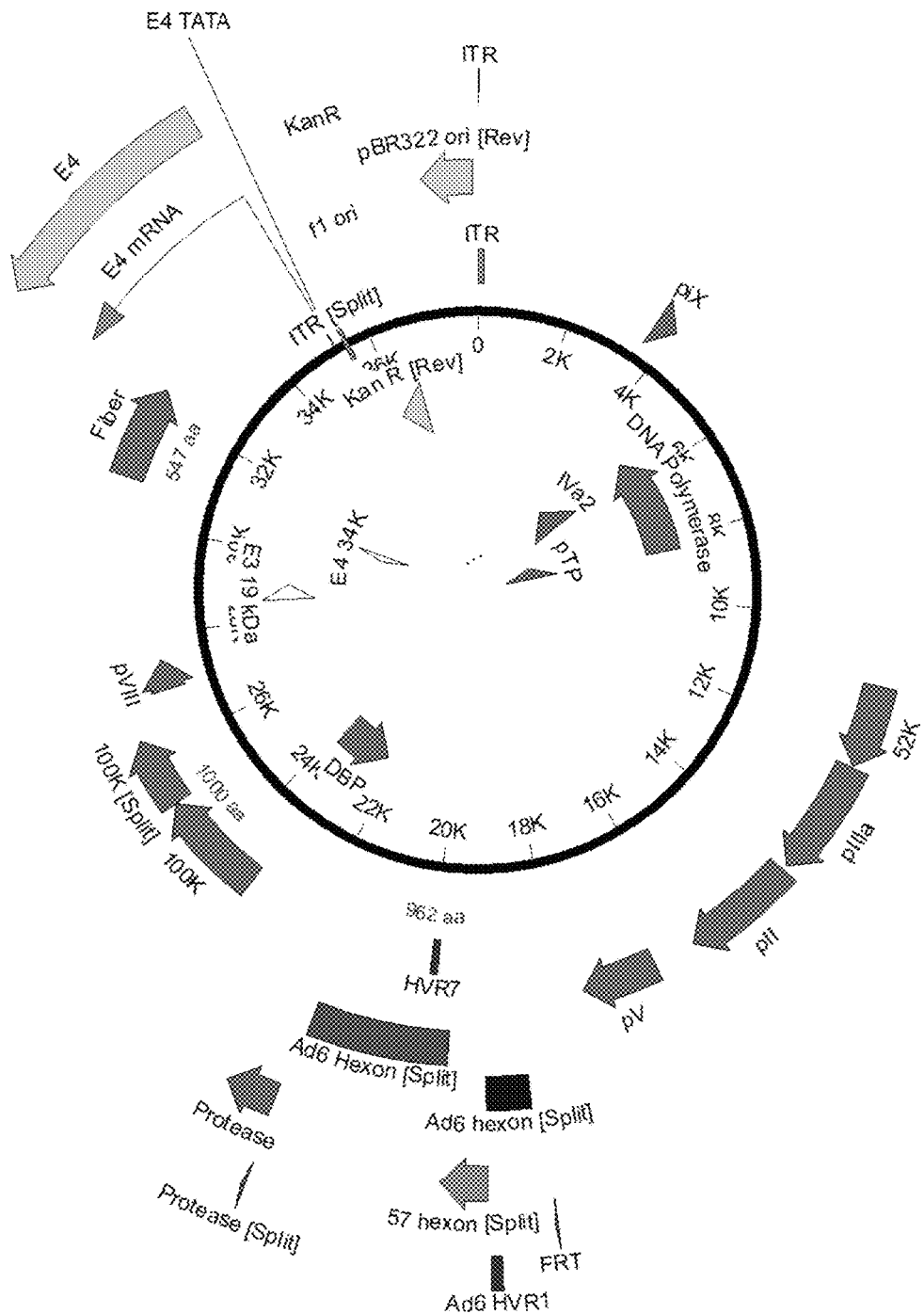
FIG. 68 depicts Ad6/57/6 with Ad6 HVR1, Ad57 HVRs2-6, Ad6 HVR7+/−Ad35 Fiber or Chimpanzee C68 Fiber+/−K7 peptide.
Figure 69:
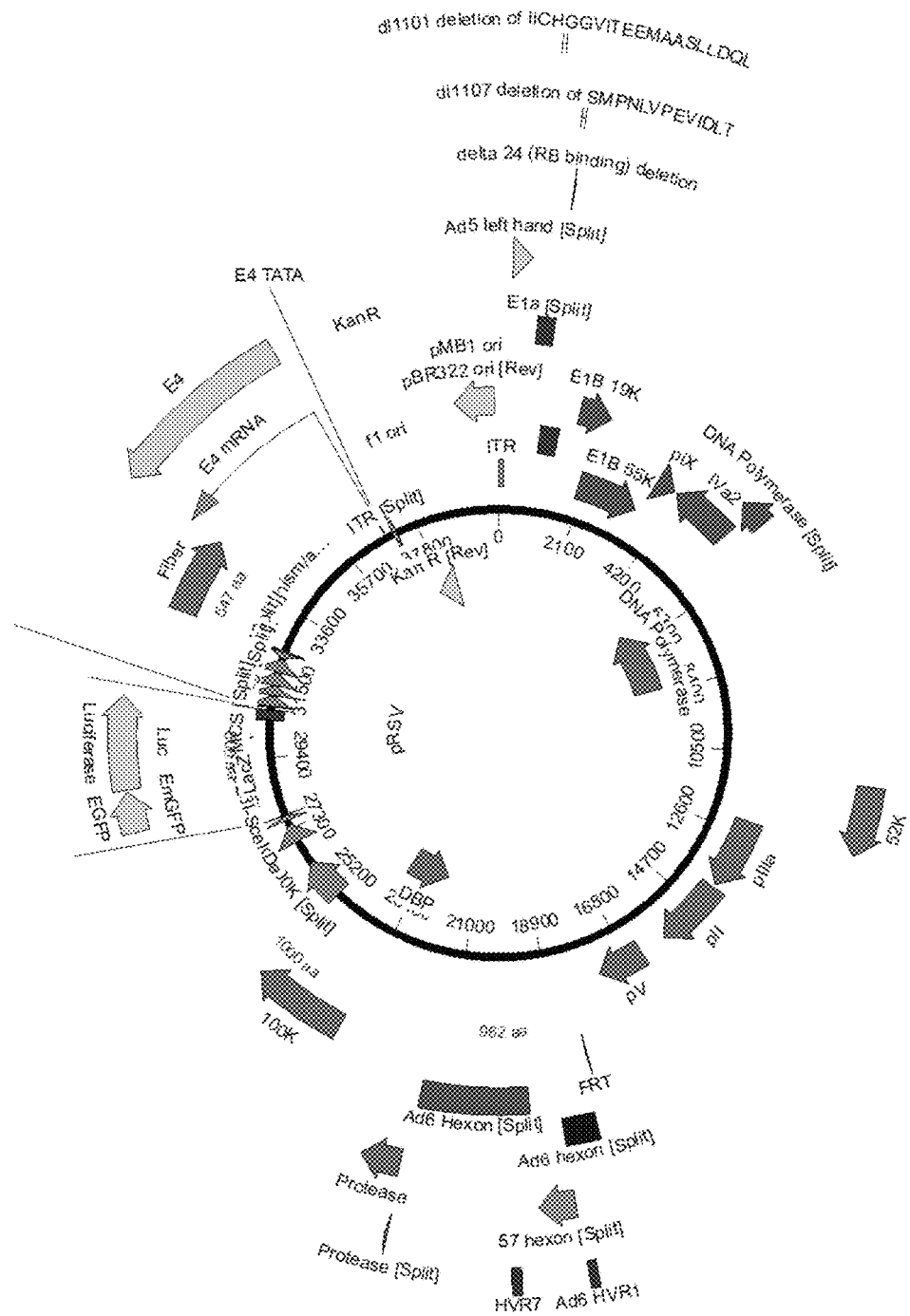
FIG. 69 depicts Ad6/57/6 with Ad6 HVR1, Ad57 HVRs2-6, Ad6 HVR7+/−Ad35 Fiber or Chimpanzee C68 Fiber+/−K7 peptide expressing GFPLuciferase.

The genome of Ad6, Tonsil 99 strain (ATCC VR-1083), was cloned as described elsewhere (see, e.g., Weaver et al., 2013 PLoS One. 8:e73313). A cassette corresponding to the Ad57 hexon between a natural ApaI and SacI sites was synthesized by Genscript. This fragment was cloned into the shuttle plasmid pUC57-Ad6 Hexon-FZF containing the Ad6 pVI and hexon genes with a FRT-Zeocin® resistance gene-FRT cassette between them for homologous recombination in bacteria as described elsewhere (see, e.g., Campos et al., 2004 Hum Gene Ther. 15:1125-1130; and Khare et al., 2012 J Virol. 86:2293-2301). The Ad6 ApaI-SacI fragment was replaced with the Ad57 fragment generating the plasmid pUC57-Ad6/57 Hexon-FZF. This was recombined into the Ad6 genome by red recombination (Campos et al., 2004 Hum Gene Ther. 15:1125-1130). FIG. 59 shows a plasmid map of Ad657 with E3 deletion. Viruses were rescued by transfection into 293 cells and produced from a 10 plate CellStack (Corning Life Sciences, Lowell, MA, USA). Viruses expressing a green fluorescent protein-luciferase (GFP-Luc) fusion protein have a CMV-GFP-Luc expression cassette inserted between the Ad fiber and E4 and an E3 deletion to make space for this insertion. Viruses were purified on two CsCl gradients, and viral particle (vp) numbers were calculated by OD260.

To examine in vitro oncolytic activity, cells were treated at the indicated multiplicities of infection (MOI) in terms of vp/cell in DMEM with 5% FBS and antibiotic-antimycotic (Invitrogen, Grand Island, NY, USA). Five days later, media was removed and the cells were treated with crystal violet (0.05% crystal violet, 3.7% formaldehyde, in phosphate-buffered saline; Invitrogen, Grand Island, NY, USA) for 10 minutes. The cells were washed twice with PBS and then incubated overnight at 37° C. in 0.1% sodium dodecyl sulfate in PBS to solubilize the crystal violet. Crystal violet absorbance was measured at OD595 on a Beckman Coulter DTX 880 plate reader. Cell viability (%) was calculated by dividing the OD of the samples by the mean OD of untreated control cells on the same 96-well plate and multiplying this number by 100.

Animals were housed in the Mayo Clinic Animal Facility under Association for Assessment and Accreditation of Laboratory Animal Care guidelines. The studies were approved by the Mayo Clinic Animal Use and Care Committee under the provisions of the Animal Welfare Act, PHS Animal Welfare Policy. Subcutaneous tumors were initiated in 4-week-old nude mice (Harlan Sprague Dawley, Indianapolis, IN, USA) by injecting subcutaneously (s.c.) with $1\times10^7$ DU145 cells in 100 µL of DMEM/50% Matrigel (BD Biosciences, San Jose, CA, USA). Tumor volumes were calculated using the equation width$^2$×length×1/2. When tumors reached ~200 μL in volume, mice were distributed into different groups and were treated by a single i.v. injection tail vein. Animals were euthanized when the tumor volume reached 2000 μL or if animals were moribund, in distress, or if the skin ruptured over the tumor.

For blood alanine aminotransferase (ALT) measurements, groups of six C57BL/6 mice were injected i.v. with $10^{11}$ vp of Ad5, Ad6, or Ad657 by tail vein and blood was collected 3 days later for ALT measurement using ALT Activity Assay (Sigma-Aldrich, St. Louis, MO, USA).

Statistical analysis was performed with Prism (Graphpad) by repeated measures ANOVA or one-way ANOVA followed by Tukey's HSD test. Kaplan-Meier survival curves were plotted and compared by log rank test.

Figure 8:
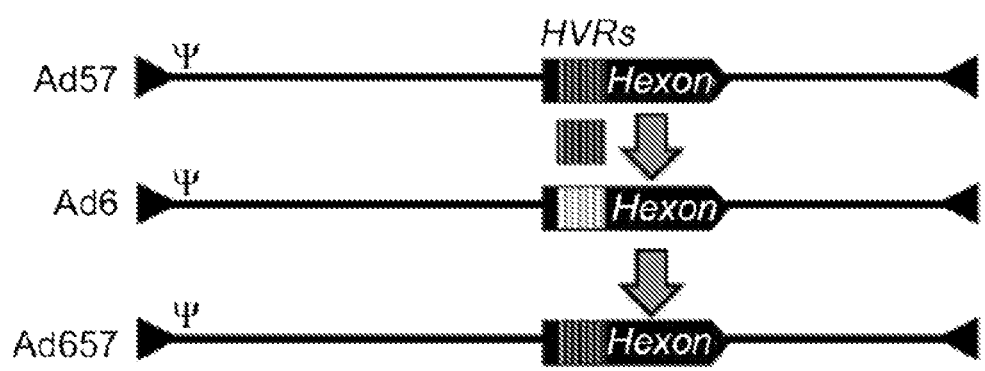
FIG. 8 shows a cartoon of the construction of Ad657 by replacement of the Ad6 HVRs with Ad57 HVRs. Abbreviation: HVRs, hypervariable regions.

The capsomer genes of Ad57 are nearly identical to Ad6 with the exception of their hexon HVRs (FIGS. 6 and 7). To generate a chimeric virus of Ad57 and Ad6, a cassette corresponding to the Ad57 hexon HVRs was recombined into the wild-type Ad6 genome (FIG. 8). This virus was rescued and produced in 293 cells and purified on CsCl gradients. Given that the base viral genome is Ad6, these hexon chimeric viruses are referred to as Ad657 (FIG. 59).

Figure 10:
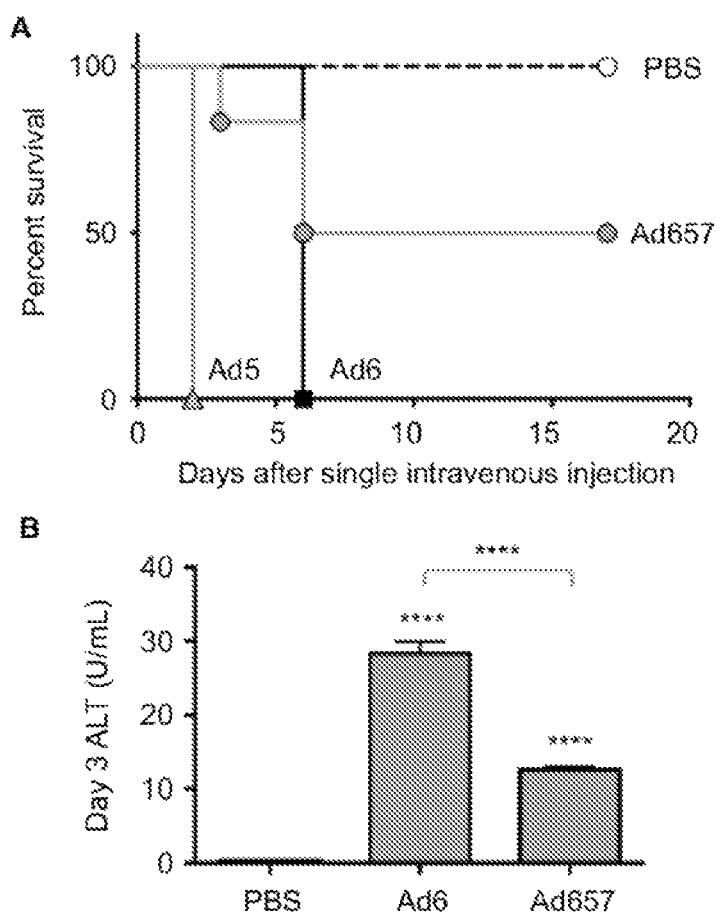
FIG. 10 shows effects of oncolytic Ads on liver damage. C57BL/6 mice (n=6 per group) were injected with 1011 vp of each virus by tail vein. (A) Kaplan-Meier survival. (B) Blood was drawn for ALT measurements 3 days after injection (****$p<0.001$ by ANOVA). Abbreviations: ALT, alanine aminotransferase; vp, viral particle.

In vitro oncolytic activity was evaluated by infecting LNCap and DU145 cells with 10, 100 or 1000 vp/cell. To compare liver damage by Ad5, Ad6, and Ad657, a high dose of $10^{11}$ vp of each virus were injected by tail vein into immunocompetent C57BL/6 mice. Ad5-injected animals became moribund within 2 days and had to be euthanized (FIG. 10A). Survival for Ad5 and Ad6 was significantly lower when compared with PBS (p=0.0001 and 0.0009, respectively, by log-rank analysis). Survival for Ad657 was also reduced when compared with PBS (p=0.0578). Survival after exposure to Ad6 or Ad657 was significantly better than in Ad5-treated mice (p=0.0001 and 0.0001, respectively). Ad6 and Ad657 survival were not statistically different (p=0.248).

Figure 12:
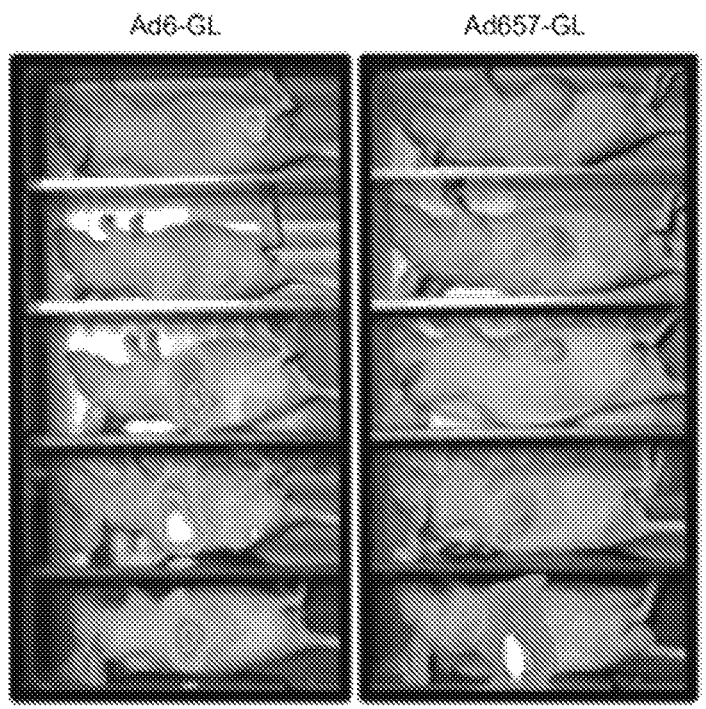
FIG. 12 shows luciferase imaging nude mice. Four days after single i.v. injection of $3 \times 10^{10}$ vp of Ad6 and Ad657-GFP-Luc with deletions of part of 12.5K, 6.7K, 19K, 11.6K (ADP), 10.4K (RIDα), 14.5K (RIDβ), and 14.7K and a partial deletion of E4 34K. Abbreviations: i.v., intravenous; vp, viral particle.

ALT was measured in the blood 3 days after injection in surviving Ad6 and Ad657 animals. Ad5-treated animals were not tested, since most of the group needed to be sacrificed. This assay showed that Ad6 provoked relatively low levels of liver damage in terms of liver ALT enzyme release in the blood (FIG. 10B). Both Ad6 and Ad657 groups had low, but significant, ALT levels when compared with PBS-treated mice (p<0.001 by one-way ANOVA with Tukey's multiple comparison test for both viruses). Ad657 had lower ALT levels than Ad6 (p<0.001 by ANOVA). This is consistent with higher levels of Ad6 infection in the liver than Ad657 after i.v. injection of luciferase expressing viruses (FIG. 12). One Ad657 animal was lost following bleeding on day 3. By 6 days, most of the Ad6 animals became moribund (FIG. 10A). In contrast, 50% of Ad657 animals survived beyond 2 weeks of the treatment.

Figure 11:
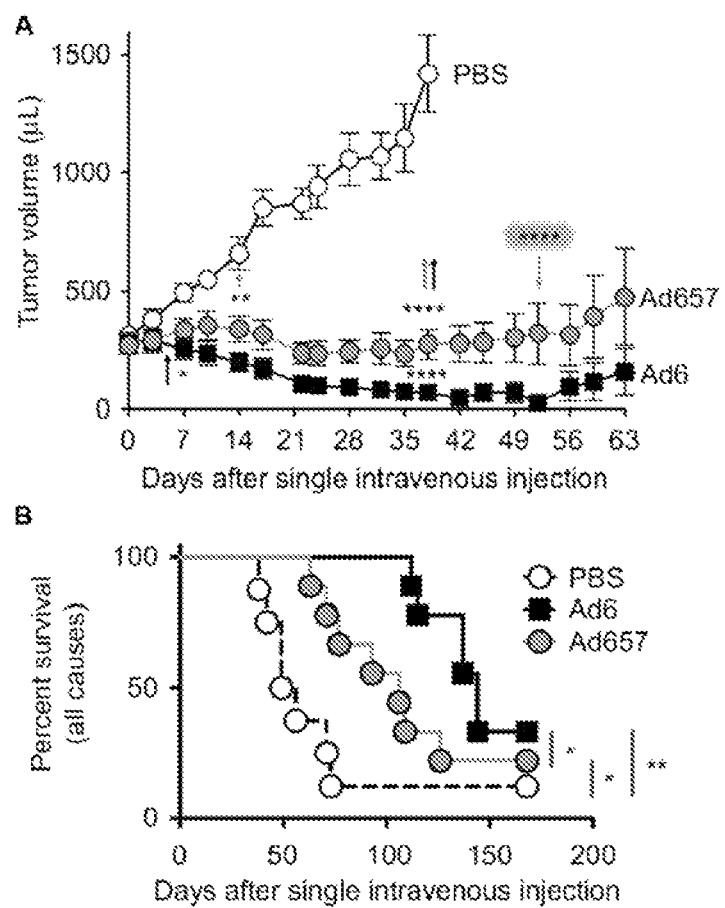
FIG. 11 shows anticancer activity of Ad6 and Ad657 in DU145 tumor xenografts in nude mice after single i.v. administration. Nude mice (n=9 per group) bearing established DU145 tumors were injected i.v. with a single dose of $3 \times 10^{10}$ vp of the indicated viruses or with PBS. (A) Effect of a single i.v. injection on tumor growth. Tumor dimensions were measured with calipers and tumor volume was calculated as width$^2 \times$length$\times 1/2$. The data are shown as mean±SE. *$p<0.05$, ****$p=0.0001$ by ANOVA or by T-test as described in the text. Black asterisks with a black arrow pointing up indicate the statistical difference ADZE 1 US SEQ DIV 1 between the Ad6 group and the PBS group on a selected day described in the text. Gray asterisks and an arrow pointing up indicate differences between the Ad657 group and the PBS group on the indicated day. The shadowed white asterisks with a gray arrow pointing down indicates the statistical difference between the Ad6 and Ad657 groups on the indicated day. (B) Effect of a single i.v. injection on survival. Animals were euthanized when the tumor volume reached 2000 μL or when other sacrifice criteria were met (e.g., ulceration) and Kaplan-Meier survival curves were plotted (*$p<0.05$, **$p<0.01$ by log-rank analysis). Abbreviation: i.v., intravenous.

To compare the oncolytic activity of Ad6 and Ad657 against human DU145 prostate tumors, nude mice were engrafted s.c. with DU145 cells. Animals were distributed into groups with similar tumor sizes averaging 200 μL and groups of nine mice were treated a single time by the i.v. route with a dose of 3×$10^{10}$ vp of Ad6 or Ad657 (FIG. 11).

This single i.v. injection of Ad6 and Ad657 reduced tumor sizes when compared with PBS-injected control animals. Tumors were significantly smaller in the Ad6 group within 7 days when compared with the PBS group (p<0.05 by two-way ANOVA with Tukey's multiple comparison test). Tumors in the Ad657 group were significantly different from those in the PBS group by day 14 (p<0.01 by ANOVA). Both Ad6 and Ad657 maintained significant differences with PBS through day 38 (p<0.0001 by two-way ANOVA). This comparison ended on day 38 when the first animal in the PBS group had to be sacrificed since later comparison would be skewed due to the change in animal numbers. Tumor sizes in the Ad6 and Ad657 groups were not significantly different until day 38, when Ad657 had a significantly higher tumor volume (p<0.05) by two-way ANOVA (FIG. 11A). This difference between Ad6 and Ad657 tumor sizes persisted until day 52 (p=0.04 by T-test), and then the tumors were not significantly different after this time.

Figure 13:
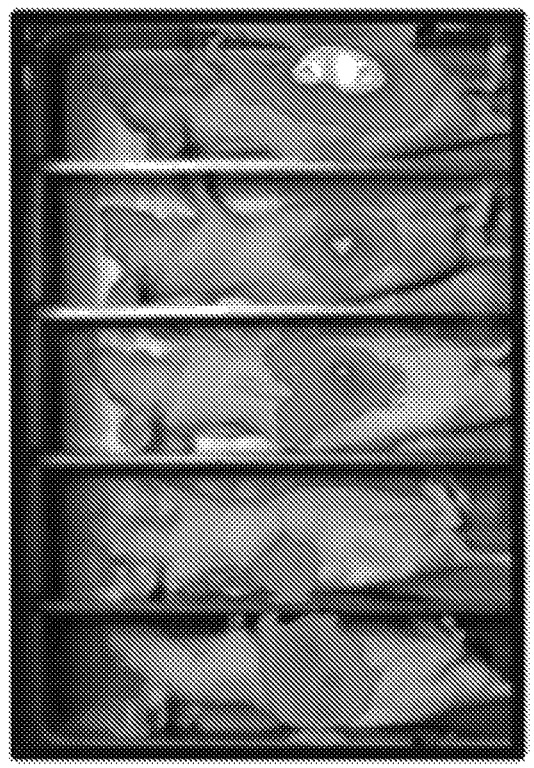
FIG. 13 shows luciferase imaging nude mice. Fourteen days after single i.v. injection of $3 \times 10^{10}$ vp of Ad657-GFP-Luc. Abbreviations: i.v., intravenous; vp, viral particle.

When survival due to all causes was assessed, both Ad6 and Ad657 significantly extended survival when compared with PBS-treated animals (FIG. 11B, p<0.01 and 0.05, respectively, by log-rank analysis). Ad6 survival due to all causes was significantly better than Ad657 (p<0.05). However, this was an artifact of survival attributed to all because three of the Ad657 animals had to be sacrificed per Institutional Animal Care and Use Committee (IACUC) guidelines due to the formation of ulcers on the skin over the tumor rather than due to excess tumor size. In some cases, ulceration is actually associated with effective tumor control. Like Ad6, Ad657 expressing GFP-luciferase produced significant luciferase activity in distant DU145 subcutaneous tumors after a single i.v. injection (FIG. 12 and FIG. 13). This suggests that both Ad6 and Ad657 can mediate oncolytic effects in prostate tumors after a single systemic treatment.

This example demonstrates that Ad657 may be used as a local or systemic oncolytic virotherapy for prostate cancers. These data also demonstrate surprising effects of serotype-switching with oncolytic species C Ads.

Figure 28:
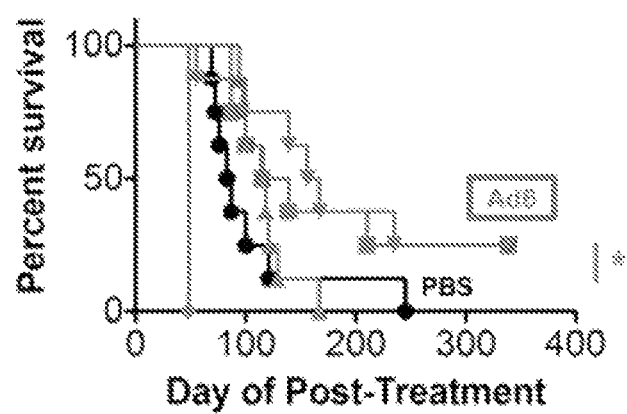
FIG. 28 is a graph showing Ad6 single IV injection vs. A549 lung tumors.
Figure 29:
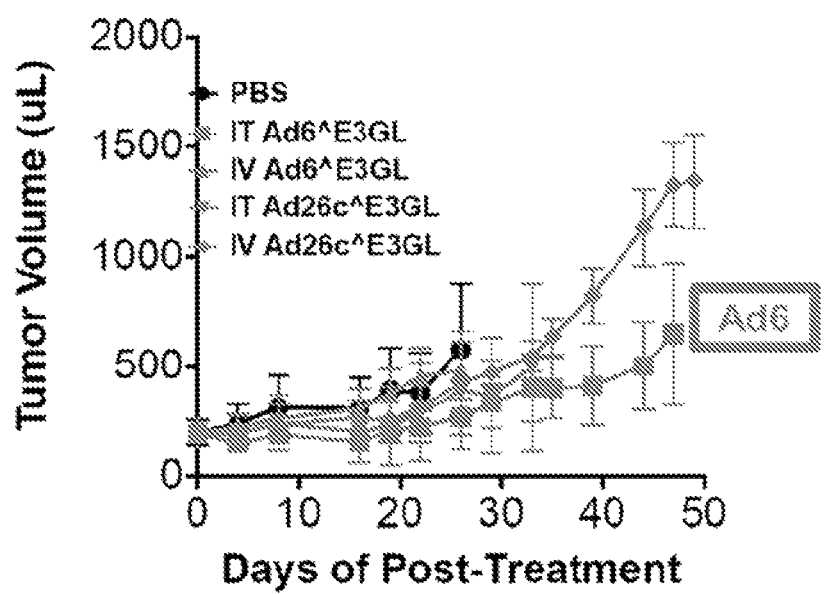
FIG. 29 is a graph showing Ad6 single IV or IT injection vs. Panc1 pancreatic tumors.
Figure 30:
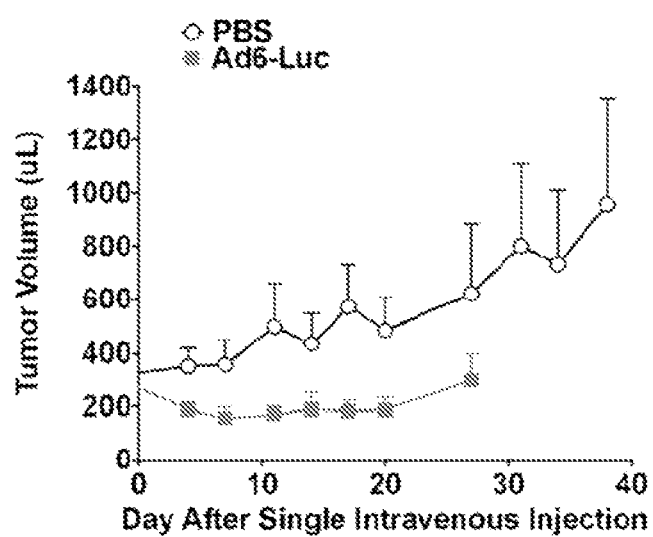
FIG. 30 is a graph showing Ad6 single IV injection vs. kidney cancer in immune competent hamsters.

The oncolytic activity of Ads was evaluated in tumor cells and/or cancerous tumors. Ad6 single IV injection vs. A549 lung tumor cells was evaluated (FIG. 28); Ad6 single IV or intratumoral (IT) injection vs. Panc1 pancreatic tumors was evaluated (FIG. 29), and Ad6 single IV injection vs. kidney cancer in immune competent hamsters was evaluated (FIG. 30).

Figure 38:
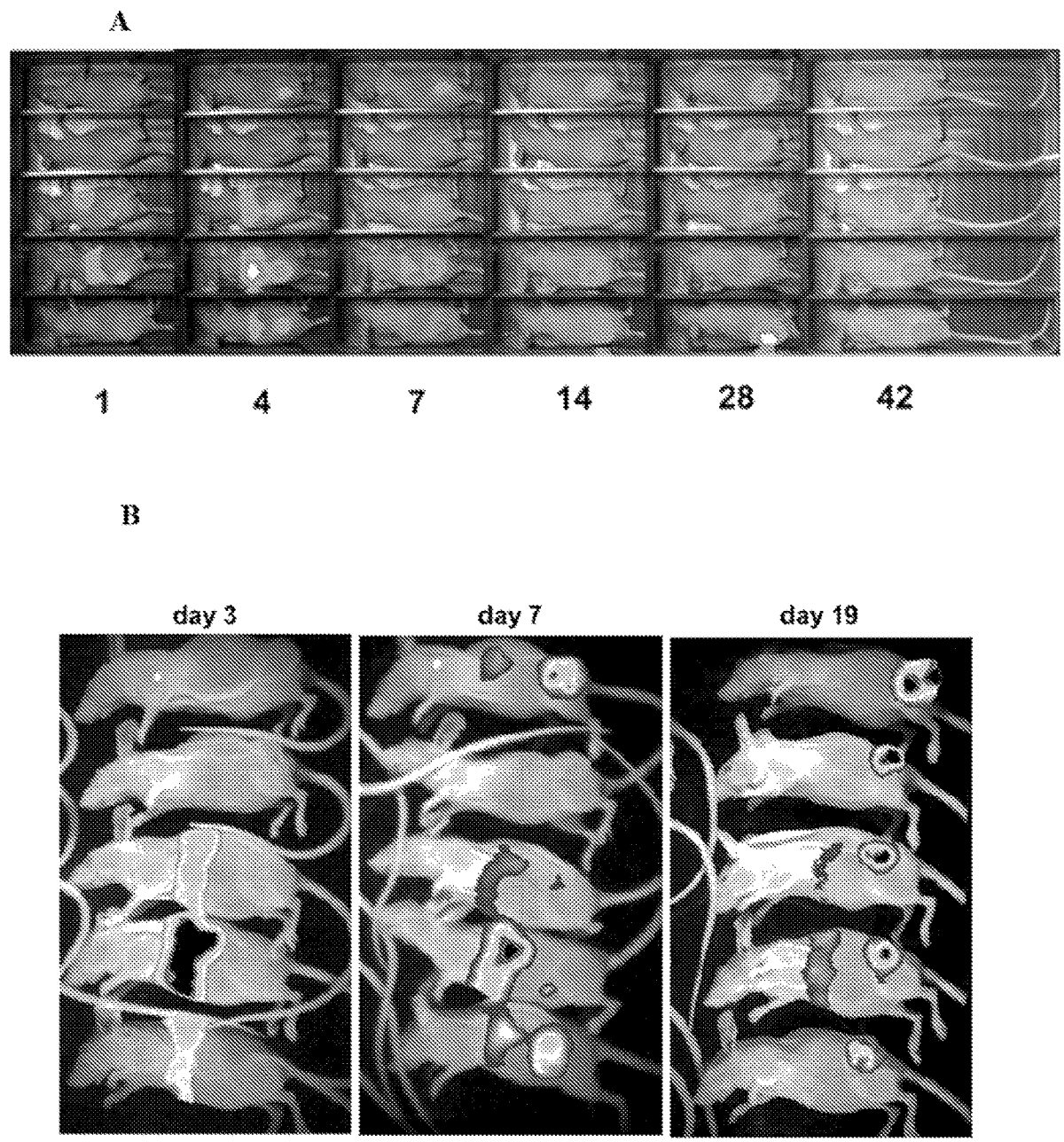
FIG. 38 shows luciferase imaging of nude mice. A) 1, 4, 7, 14, 28, and 42 days after single I.V. injection of Ad6 treatment vs. distant DU145 prostate tumors. B) 3, 7, and 19 days after I.V. injection of replicating Ad5-GFPLUC into mice bearing LNCaP prostate tumors.

FIG. 38 shows luciferase imaging of nude mice. A) 1, 4, 7, 14, 28, and 42 days after single I.V. injection of Ad6 treatment vs. distant DU145 prostate tumors. B) 3, 7, and 19 days after I.V. injection of replicating Ad5-GFPLUC into mice bearing LNCaP prostate tumors.

It may be concluded that Ad6 gets to distant target cells after IV injection.

Figure 31:
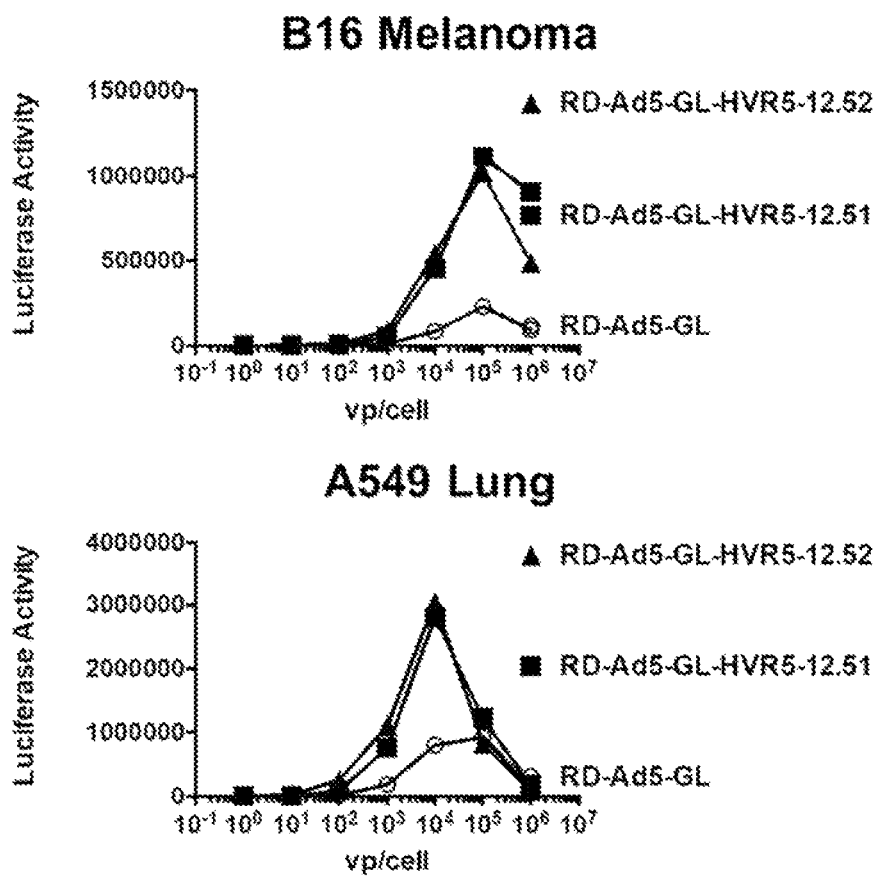
FIG. 31 is a graph showing luciferase activity in B16 melanoma and A549 lung tumor/cancer cells by Ads displaying 12.51 cell binding peptides in HVR5 of the hexon.

In another embodiment, Ads expressing luciferase with and without peptide library generated peptides 12.51 and 12.52 inserted in HVR5 of hexon were incubated on indicated cell lines, B16 melanoma and A549 lung carcinoma cells, with the indicated numbers of virus particles (vp) and luciferase activity was measured. Improved infection of cancer cells by Ads bearing peptide-modified hexons is demonstrated (FIG. 31).

Improved Infection of Cancer Cells by Ads Bearing Peptide-Modified Hexons.

Figure 32:
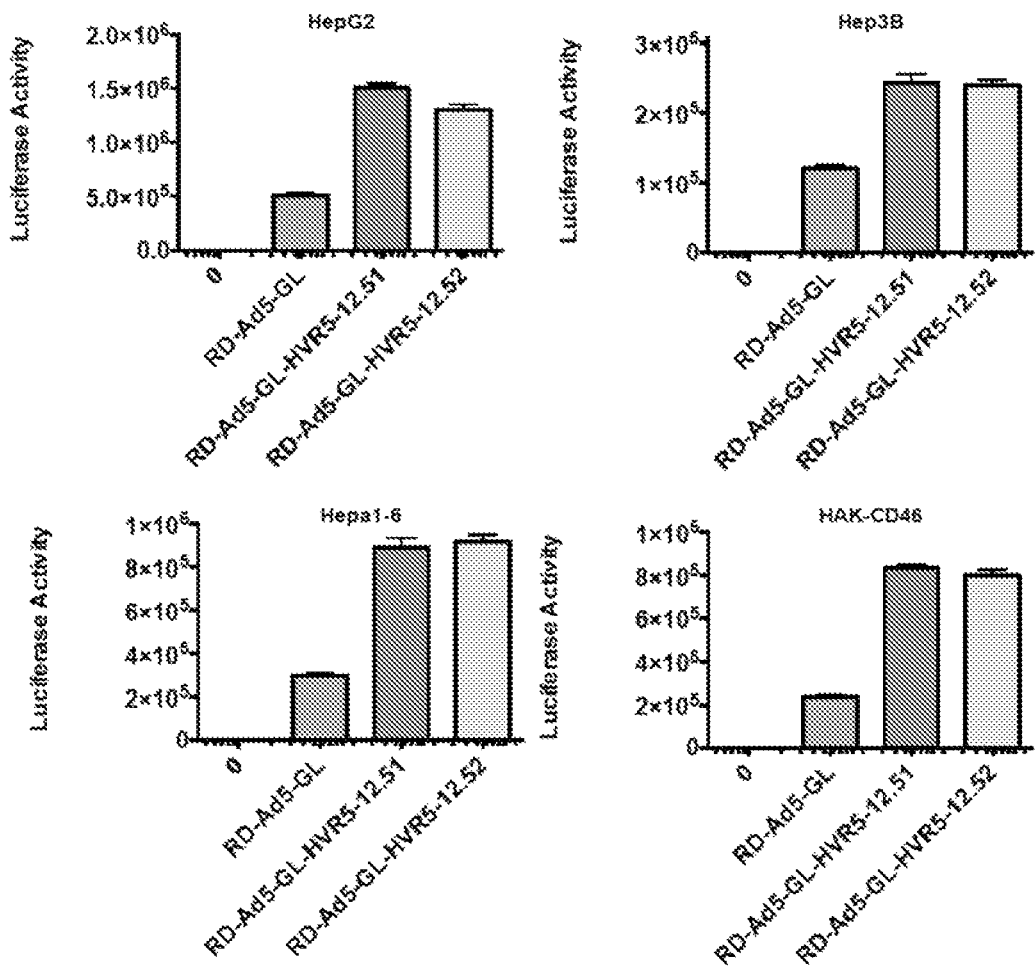
FIG. 32 is a graph showing luciferase activity in hepatocellular carcinoma and kidney cancer by Ads displaying 12.51 cell binding peptides in HVR5 of the hexon.
Figure 33:
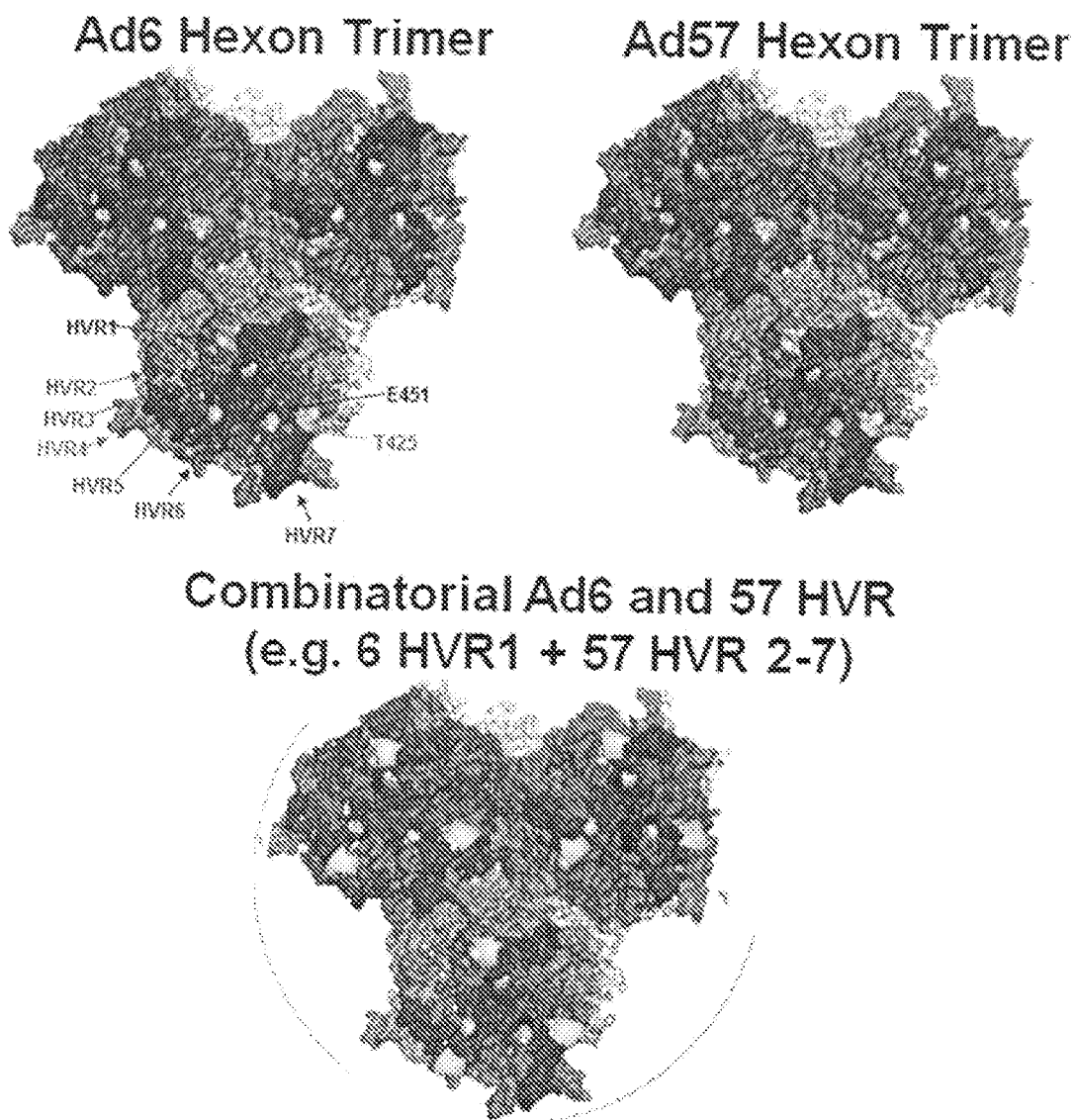
FIG. 33 shows a cartoon combining the insertion of individual HVRs from different Ad serotypes with the insertion of cell targeting/detargeting peptides or novel amino acids such as cysteine into the hexon for targeted chemical modification and shielding. Depicted are chimeric HVR constructs that combine different HVRs from different Ad serotypes to modulate natural interactions with cells and blood factors improve pharmacology combined with insertion of cell binding and cell detargeting peptides in different HVRs to change cell entry and cell avoidance. If one HVR is substituted from 100 Ads, this would create 100 different hexon chimeras. If all 7 HVRs each receive a different Ad HVR, this combinatorial library would equal $7^{100}$ variants. If one 1 peptide were introduced into 7 HVRs this would equal $7 \times 7^{100}$ variants. If 10 different peptides were introduced into 7 HVRs, this would equal $10 \times 7 \times 7^{100}$ variants, etc.
Figure 33:
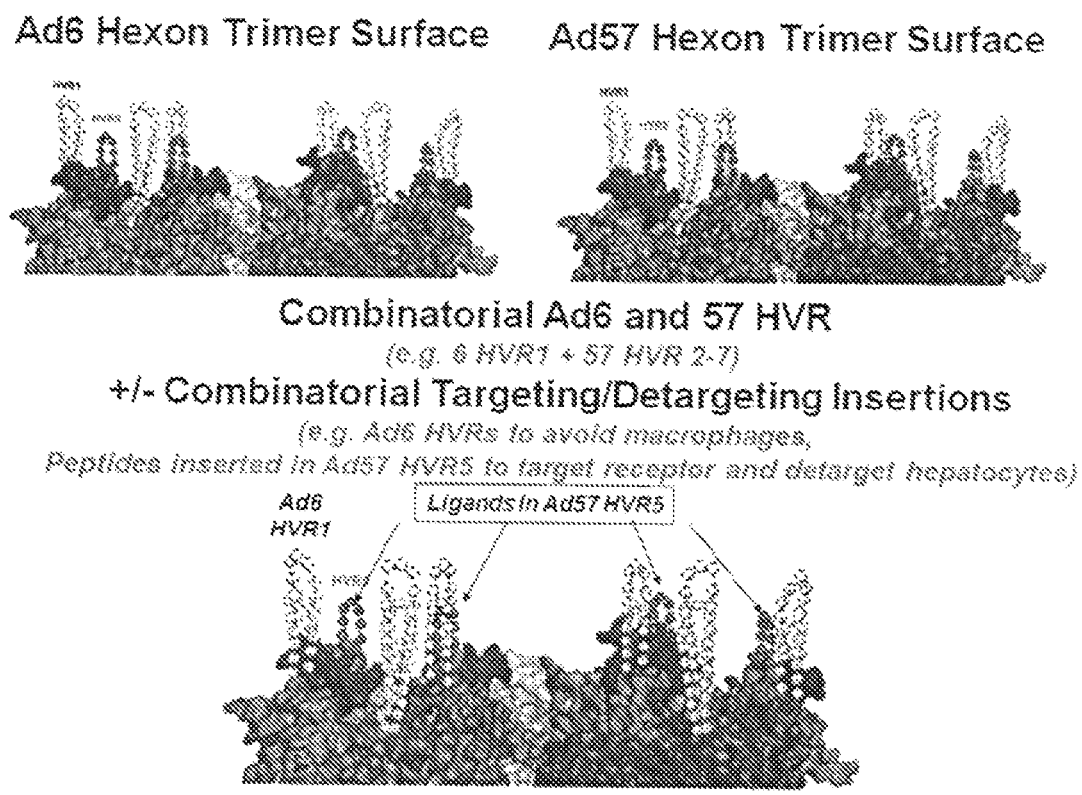

Ads expressing luciferase with and without peptide library generated peptides 12.51 and 12.52 inserted in HVR5 of hexon were incubated on indicated hepatocellular carcinoma cell lines with $10^4$ vp of each virus and luciferase activity was measured. Improved infection of cancer cells by Ads bearing peptide-modified hexons is demonstrated (FIG. 32).

Example 7. Divergent HIV-1 Directed Immune Responses Generated by Systemic and Mucosal Immunization with Replicating Single-Cycle Adenoviruses in Rhesus Macaques Most gene-based adenovirus vaccines are replication-defective Ad (RD-Ad) vectors that have their E1 gene deleted to prevent them from replicating and causing Ad infections. Helper-dependent adenoviruses (HD-Ads) have all Ad genes deleted and are also replication-defective. An E1-deleted Ad vaccine can infect a cell, deliver its one copy of an antigen gene, and express a single copy (e.g., "1X") of this antigen. They are safe, but do not replicate transgenes or their expression.

In contrast, an E1+replication-competent Ad (RC-Ad) vaccine can infect the same cell, replicate the antigen gene DNA 10,000-fold, produce substantially more antigen, and provoke stronger immune responses than E1-deleted vectors. While RC-Ad is more potent than RD-Ad, replication-competent Ads can run the real risk of causing frank adenovirus infections in humans.

To take advantage of transgene DNA replication, but avoid the risk of adenovirus infections, single-cycle Ad (SC-Ad) vectors with a deletion of a gene for a key viral late protein, pIIIa, were developed (Crosby et al., 2014. Virology 462-463:158-165; Crosby et al., 2015 J Virol 89:669-675; Anguiano-Zarate et al., 2018 J Infectious Dis 218:1883-1889; and Crosby et al., 2017 Genes (Basel) 8:E79). SC-Ads retain their E1 genes to allow it to replicate its genome, but the absence of pIIIa blocks the production of infectious progeny viruses. SC-Ads replicate their genomes and transgenes as well as RC-Ad (up to 10,000-fold; Crosby et al., 2014. Virology 462-463:158-165). RC- and SC-Ad produce more transgene protein than RD-Ad vectors (Crosby et al., 2014. Virology 462-463:158-165). SC-Ads generate more robust and more persistent immune responses than either RD-Ad or RC-Ads (Crosby et al., 2015 J Virol 89:669-675). In head-to-head comparisons, SC-Ad produces significantly higher antibodies and better protection against influenza virus (Crosby et al., 2017 J Virol 91:e00720-16).

In this study, rhesus macaques were immunized with SC-Ads expressing clade B envelope sequences that were obtained from an HIV-1 patient before and after their antibody response underwent an expansion neutralization breadth. Macaques were immunized by a single systemic IM immunization or by single mucosal intranasal (IN) immunization. The animals were then boosted by the same or alternative routes with SC-6 Ad followed by protein boost. This example describes how these various SC-Ad immunization strategies affected the generation of HIV binding, antibody-dependent cellular cytotoxicity (ADCC) and neutralizing antibodies as well as their effects on cellular immune responses including T follicular helper (pTfh) cells in blood and lymph nodes.

Single-Cycle Adenovirus Expressing HIV-1 Envelope Protein Gp140.

Clade B gp160 envelope sequences that arose before (G4) and immediately preceding a peak in the expansion of antibody neutralization breadth (F8) from HIV patient VC10014 (Malherbe et al., 2014 *J Virol* 88:12949-12967) were used as immunogens. Motif-optimized G4 and F8 gp160 sequences were recombined into SC-Ads based on human Ad serotypes 6 and 57 (see, e.g., Crosby et al., 2014. *Virology* 462-463:158-165; Crosby et al., 2015 *J Virol* 89:669-675; Anguiano-Zarate et al., 2018 J Infectious Dis 218:1883-1889; and Nguyen et al., 2018 Oncolytic Virotherapy 7:43-51). A control SC-Ad expressing Ebola glycoprotein was also used. Viruses were rescued and purified as described elsewhere (see, e.g., Crosby et al., 2014. *Virology* 462-463:158-165; Crosby et al., 2015 *J Virol* 89:669-675; and Anguiano-Zarate et al., 2018 J Infectious Dis 218:1883-1889).

The envelope gene F8 cloned from an HIV Clade B-infected subject used in the SC-Ad vector was motif-optimized and modified by site-directed mutagenesis to express uncleaved, trimeric gp140. Details of expression, purification, and antigenic characterization have been described elsewhere (see, e.g., Malherbe et al., 2014 *J Virol* 88:12949-12967).

Female adult rhesus macaques (*Macaca* mulatta) of Indian origin were maintained at the Michael Keeling Center for Comparative Medicine and Research at the University of Texas MD Anderson Cancer Center, Bastrop TX in the specific pathogen-free breeding colony. All animal handling was carried out in accordance with the policies and procedures of the Mayo Clinic and the University of Texas MD Anderson Cancer Center, the provisions of the Animal Welfare Act, PHS Animal Welfare Policy, the principles of the NIH Guide for the Care and Use of Laboratory Animals.

Macaques were anesthetized with ketamine and immunized by the intranasal (IN) or intramuscular (IM) route with $2\times10^{10}$ virus particles (vp) of the indicated SC-Ad vaccine. Animals were boosted with 50 μg of purified, trimeric recombinant F8 gp140 combined with Adjuplex™ adjuvant by the IM route as described elsewhere (see, e.g., Malherbe et al., 2014 *J Virol* 88:12949-12967; and Hessell et al., 2016 *J Immunol* 196:3064-3078).

Peripheral venous blood samples were collected in EDTA. Before isolation of peripheral blood mononuclear cells (PBMC), plasma was separated and stored immediately at −80° C. PBMCs were prepared from the blood on Ficoll-Hypaque density-gradients. Saliva and vaginal swabs collected with Wek-Cel Spears in 1 ml of PBS containing protease inhibitors, vortexed, and supernatants were collected after a 2,000 r.p.m. centrifugation as described elsewhere (see, e.g., Kozlowski et al., 1997 *Infect Immun* 65:1387-1394). Samples were kept frozen at −80C until further use.

ELISPOT Assay for Detecting Antigen-Specific IFN-7 Producing Cells

Freshly-isolated PBMCs were stimulated with either F8 gp140 protein (1 μg/mL) or heat inactivated Ad6 ($7.0\times10^8$ vp/well) to determine the numbers of IFN-7-producing cells by the Enzyme Linked Immuno Spot (ELISPOT) assay using the methodology described elsewhere (see, e.g., Nehete et al., 2017 *Comp Med* 67:67-78; Nehete et al., 2013 *PLoS One* 8:e79836; and Nehete et al., 2017 JAm Assoc *Lab Anim Sci* 56:509-519). Briefly, aliquots of PBMCs ($10^5$/well) were seeded in duplicate wells of 96-well plates (polyvinylidene difluoride backed plates, MAIP S 45, Millipore, Bedford, MA) pre-coated with the primary IFN-7 antibody and the lymphocytes were stimulated with either Con A, F8 gp140 protein, or heat inactivated Ad6. After incubation for 30-36 hours at 37° C., the cells were removed and the wells were thoroughly washed with PBS and developed as per protocol provided by the manufacturer. Results are expressed as IFN-γ spot-forming cells (SFCs) per 105 PBMCs after subtraction of the duplicate wells with medium only (negative control) and are considered positive if greater than twice the background and greater than 5 SFCs/$10^5$ PBMCs.

Antibody ELISAs

HIV-1 envelope binding antibody titers were measured in plasma samples collected at regular intervals against F8 gp140 or SF162 gp140 as described elsewhere (Malherbe et al., 2014 *J Virol* 88:12949-12967; and Hessell et al., 2016 J Immunol 196:3064-3078).

Neutralization Assay

HIV neutralization was performed using the TZM-bl neutralization assay as described elsewhere (Malherbe et al., 2014 *J Virol* 88:12949-12967; and Hessell et al., 2016 *J*

*Immunol* 196:3064-3078). All values were calculated as compared to virus-only wells.

Antibody Dependent Cellular Cytotoxicity (ADCC)

CEM.NKR.CCR5.CD4+-Luc, target cells were infected with 50 ng SHIV$_{SF162P3}$ and cultured for 4 days as described elsewhere (see, e.g., Alpert et al., 2012 *PLoS Pathog* 8:e1002890). Two-fold serial dilutions of each sample were added to the infected targets for 20 minutes at room temperature. CD16-KHYG-1 effector cells were added at a 10:1 effector to target ratio and these were incubated for additional 8 hours. The cells were lysed and luciferase activity was measured on the Bio-Tek plate reader.

Flow Cytometry

Cells collected from rectal and lymph node biopsies were incubated overnight with 0.2 µg gp140 or media alone in the presence of GolgiPlug™ (BD Biosciences, San Jose, CA, USA) for the last 4 hours. After culture, cells were harvested and incubated on ice for 45 minutes with a panel of human antibodies that cross-react with rhesus macaque samples. The panels included the following fluorochrome labeled antibodies: CD8 (Qdot655), a407 (PE) and CXCR5 (PE), all obtained from the Nonhuman Primate Reagent Resource; CD69 (BV737, clone FN50) and FoxP3 (PECy5, clone: PCH101) obtained from eBioscience, IL-21 (BV421, clone: 3A3-N2.1), CD45 (BV786, D058-1283) and CD3 (clone SP34-2, PE-Cy7-labeled) all from BD Bioscience (San Jose, CA); CD4 (Pacific Blue, clone OKT4) from ThermoFisher Scientific (Waltham, MA). Dilutions for antibodies were determined by following manufacturer's recommendations. Dead cells were excluded by using live-dead fixable dead cells stain kit obtained from Invitrogen (Carlsbad, CA). Subsequently, the cells were washed twice with PBS containing 2% FBS and 2 mM EDTA and then fixed and permeabilized with FoxP3 Fix/Perm Kit (ThermoFisher Scientific, Waltham, MA). The intracellular markers FoxP3 and IL-21 were stained in permeabilization buffer. Both compensation controls (OneComp eBeads, (ThermoFisher Scientific, Waltham, MA) and fluorescence minus one (FMO) controls were utilized. All the samples were collected on an LSR Fortessa X-20 analyzer (BD Biosciences, San Jose, CA) and were analyzed using FlowJo software (FlowJo, LLC, Ashland, Oregon). Approximately $2\times10^5$ to $1\times10^6$ events were collected per sample.

SHIV$_{SF162P3}$ Rectal Challenge

SHIV$_{SF162P3}$ virus was derived from R157 harvest 3 (3.16.12). This stock had a P27 content of 66 ng/ml, RNA content Log ~9.35, TCID50 in Indian origin rhesus PBMC: 1288/ml, and TCID50 in TZM-bl cells: $4.1\times10^4$/ml. 1 ml of a 1:300 dilution of the stock was used. This equaled 4.3 TCID50 on rhesus PBMCs and 137 TCID50 on TZM-bl cells. This dose was used for weekly intrarectal (IR) challenge. Plasma samples were analyzed for SHIV viral RNA copy numbers by Leidos Biomedical Research, Inc., Frederick National Laboratory. Animals with RNA copies above 10 were considered to be infected and the number of challenges required to infect that animal were used as events for Kaplan-Meier survival analysis. Once infected, the animal was no longer challenged. Plasma viral loads were monitored periodically by the same method until the end of the study.

SHIV$_{SF162P3}$ Viral Load in Tissues

At the end of study PBMCs and post-mortem tissues were collected. PBMC and gut samples were analyzed for SHIV$_{SF162P3}$ viral RNA by qPCR. Prism 7 Graphical software was used for all statistical analyses.

SC-Ad Expressing HIV-1 gp160

Figure 24:
FIG. 24 shows single-cycle adenovirus vaccines used in Example 7. A) Cartoon of SC-Ad serotypes 6 and 657 carrying F8 and G4 clade B HIV envelope genes. B) Alignment of clade C Ad hexons including the Ad6 and 57 hexons displayed on vaccines.

Clade B envelope protein sequences (G4 gp160) were identified before and immediately preceding a peak in the expansion of antibody neutralization breadth (F8 gp160) from HIV patient VC10014. These gp160 sequences were inserted into SC-Ad6 and SC-Ad657 under the control of the strong cytomegalovirus promoter (FIG. 24A). Ad57 is a species C human Ad that is nearly identical to Ad6 with variation in its hexon hypervariable regions (HVRs) and in its E3 immunevasion genes (FIG. 24B). Most Ad neutralizing antibodies target Ad's hexon HVRs (Pichla-Gollon et al., 2007 *J Virol* 81:1680-1689; and Sumida et al., 2005 *J Immunol* 174:7179-7185). Given this, Ad6's HVRs were replaced with those from Ad57 to generate a chimeric species C Ad vector termed Ad657. Both SC-Ad6 and SC-Ad657 retain all Ad genes including E1 and lack functional pIIIA and E3 genes (FIG. 24A). Both SC-Ads can therefore replicate their genomes to amplify gp160 expression, but do not generate progeny Ad viruses. Both viruses were rescued and produced in 293-IIIA cells and purified on CsCl gradients. When used to infect A549 cells, both vectors produced gp160 as determined by Western blotting.

Different Ad vectors were previously tested in rhesus macaques by the systemic intramuscular (IM) route and by a variety of mucosal routes including oral gavage, oral enteric coated capsules, intranasal (IN), and intravaginal (IVAG). Testing of SC-Ad-G4 by IM, IN, and IVAG routes in small animals revealed that priming by IVAG route generated negligible antibody responses. In contrast, IN immunization in both mice and hamsters generated strong antibody responses. Given these data and the potential difficulty in performing IVAG immunizations in humans, the IN route was selected for the mucosal immunization route in the subsequent macaque studies.

Figure 14:
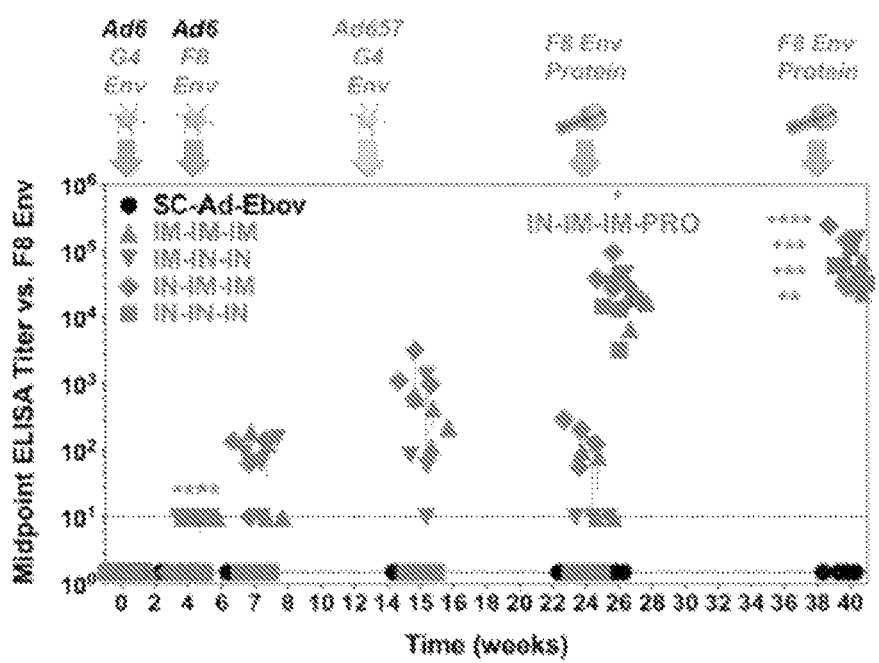
FIG. 14 shows plasma HIV Env binding titers. Immunizations with different SC-Ads and gp140 proteins are shown above the graph with large arrows. Midpoint F8 gp140 binding titers by ELISA are shown for each animal before and after each immunization. The dashed line indicates the minimal detection limit for antibodies in this assay. Symbols are scattered in the x direction at each time point to allow individual measurements to be observed. SC-Ad6-Ebov is a negative control Ad vaccine. This group of animals was not boosted with gp140. * $p<0.05$,  $p<0.01$, * $p<0.001$, **** $p<0.0001$ by one way ANOVA in comparison to the SC-Ad6-Ebov group.

Single Mucosal and Systemic Immunization in Rhesus Macaques $2\times10^{10}$ vp of SC-Ad6-G4 Env was used to vaccinate groups of 8 female rhesus macaques by single IM or IN immunization (FIG. 14). This dose is relatively low, being approximately 7.5-fold lower than recent use of RC-Ad HIV envelope vaccines delivered by mixed IN and IM immunization. A negative control vector group was immunized IN with SC-Ad6 expressing Ebola glycoprotein (gp). Four weeks later, plasma samples were assayed for Env binding antibodies against F8 gp140 (FIG. 14). This showed significantly higher midpoint binding titers in the IM immunized route group after single immunization (p<0.01 by ANOVA). SF162 neutralizing antibody (NAb) titers were also elevated at this time point, but did not reach significance by ANOVA for the individual route groups.

IM vs. IN Boost with SC-Ad6 at Week 4

It was been reported that anti-adenovirus neutralizing antibodies that are produced by one Ad IM immunization can be avoided by boosting by a different route (Xiang et al., 2003 *J Virol* 77:10780-10789). To test this route concept to enable the re-use of the same Ad serotype in macaques, each SC-Ad6-primed group was divided into 2 groups of 4. These were each boosted with SC-Ad6 expressing the alternate F8 Env at week 4 by either the IM or the IN route. Plasma samples collected 3 weeks after this boost showed elevations in midpoint binding titers in the animals that were primeboosted by the IM-IM, IM-IN, and IN-IM groups. No detectable antibodies were observed in the IN-IN group (FIG. 14).

SC-Ad657 Boost at Week 13

The animals were then boosted by serotype-switching with SC-Ad657 expressing G4 Env at week 13. The same route was used as in the previous boost. Week 15 titers showed that IM primed animals had elevated Env binding titers near 350, but these levels were not significantly different than controls (FIG. 14). In contrast, antibodies in the IN-IM-IM group were significantly higher than both the vector control and the IN-IN-IN group (p<0.01). The IN-IN-IN group again showed no Env antibodies even after 3 immunizations.

Recombinant Trimeric Env Protein Boost at Week 24

Most HIV vaccine studies augment Ad immunizations with protein boosts to amplify antibody responses. For example, in a recent study, RD-Ad26 vectors were used twice and boosted three times with adjuvanted gp140 protein (Barouch et al., 2015 Science 349(6245):320-4). In an effort to determine whether this strategy would enhance the SC-Ad vaccines, all of the SC-Ad-Env groups were boosted with 50 μg of recombinant F8 trimeric gp140 protein mixed with ADJUPLEX™ adjuvant by the IM route. The F8 trimeric protein boosted midpoint binding titers by two orders of magnitude in all of the groups (FIG. 14). This protein immunization also boosted the IN-IN-IN to levels comparable to the other groups even though Env binding antibodies were not detected after the earlier SC-Ad immunizations.

Binding and Neutralizing Antibodies in Plasma after a Second Protein Boost

Figure 15:
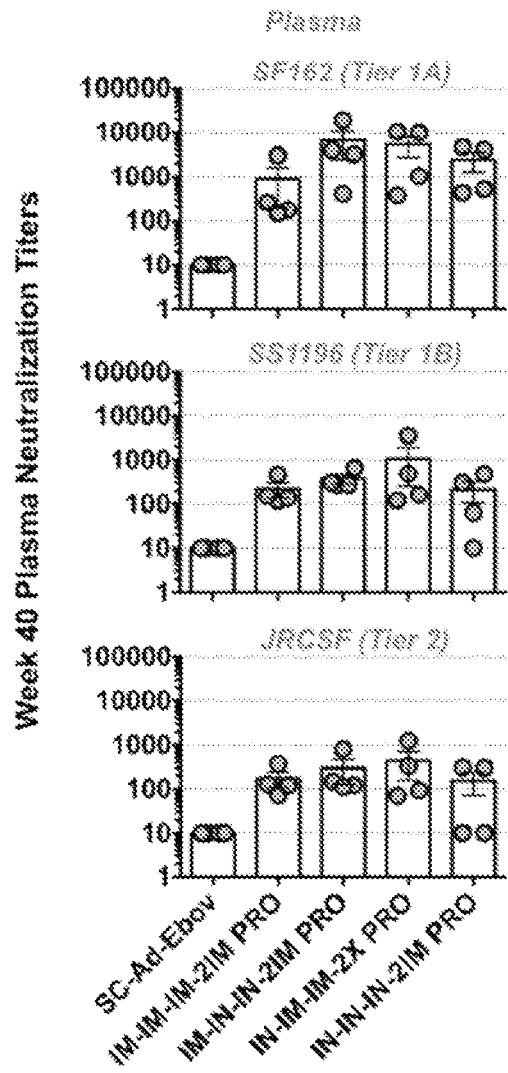
FIG. 15 shows plasma HIV neutralization titers. Neutralization of the indicated viruses was performed using the TZM-bl neutralization assay. All values were calculated as compared to virus-only wells. Each dot represents the mean value for each animal.

The animals were boosted with protein a second time at week 38. This increased F8 binding plasma antibody titers to nearly 10' by week 40 and all groups became significantly different than controls (FIG. 14). Neutralizing antibody (NAb) titers against Tier 1A SF162 virus were increased to 100 to 10,000 at week 40 (FIG. 15). NAbs against Tier 1B virus SS1196 and Tier 2 JRCSF virus increased to 100 in most animals with the exception of two animals in the IN-IN-IN group whose titers were at background levels (FIG. 15).

ADCC Activity after the Second Protein Boost

Figure 16:
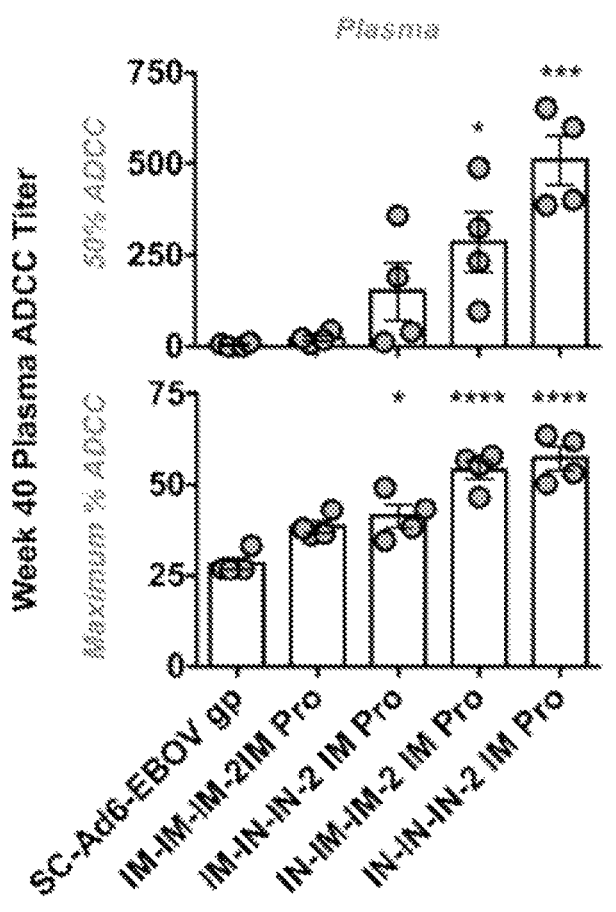

Antibody-dependent cellular cytotoxicity (ADCC) activity in week 40 plasma was tested against $SHIV_{SF162P3}$ infected cells. ADCC activity was generally higher in animals that had at least one IN mucosal SC-Ad immunization (FIG. 16). All animals that received a mucosal immunization had significantly higher maximum % ADCC than SC-Ad-Ebola control animals (p<0.05, 0.0001, 0.0001 for IM-IN-IN, IN-IM-IM, and IN-IN-IN, respectively). When compared by 50% ADCC titers, only the IN SC-Ad primed groups had significantly higher ADCC activity than controls (p<0.05 and 0.001 by ANOVA for (IN-IM-IM and IN-IN-IN groups).

Antibody Responses in Saliva and Vaginal Washes after a Second Protein Boost

Figure 25:
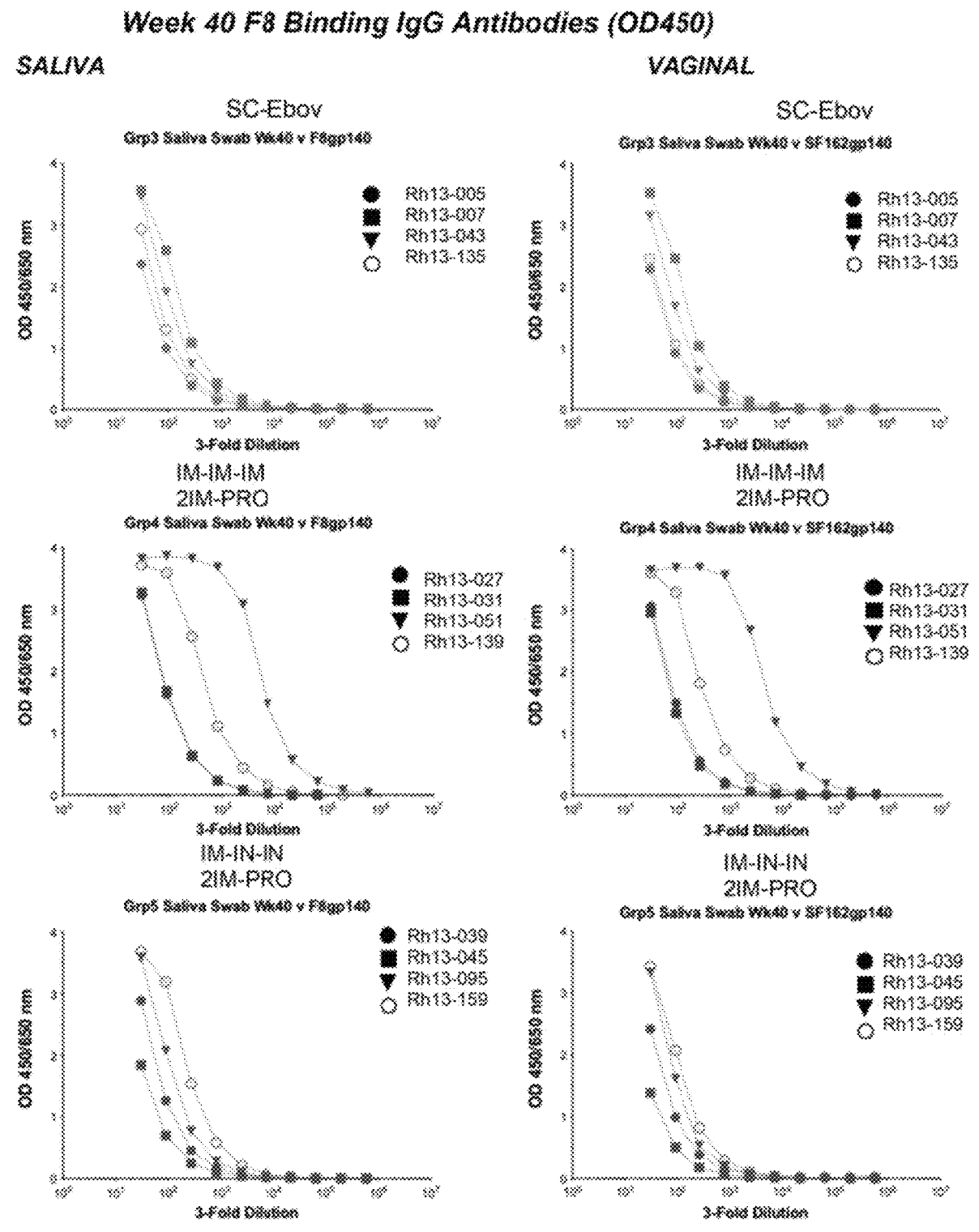

The data above monitored systemic antibody responses in plasma. Saliva and vaginal wash samples were also collected at week 40 and measured for antibodies in these mucosal sites. When saliva and vaginal washes were assayed for F8 and SF162 env binding by ELISA, these responses were observed in most groups with the exception of the SC-Ad-Ebola control group (FIG. 25).

Figure 17:
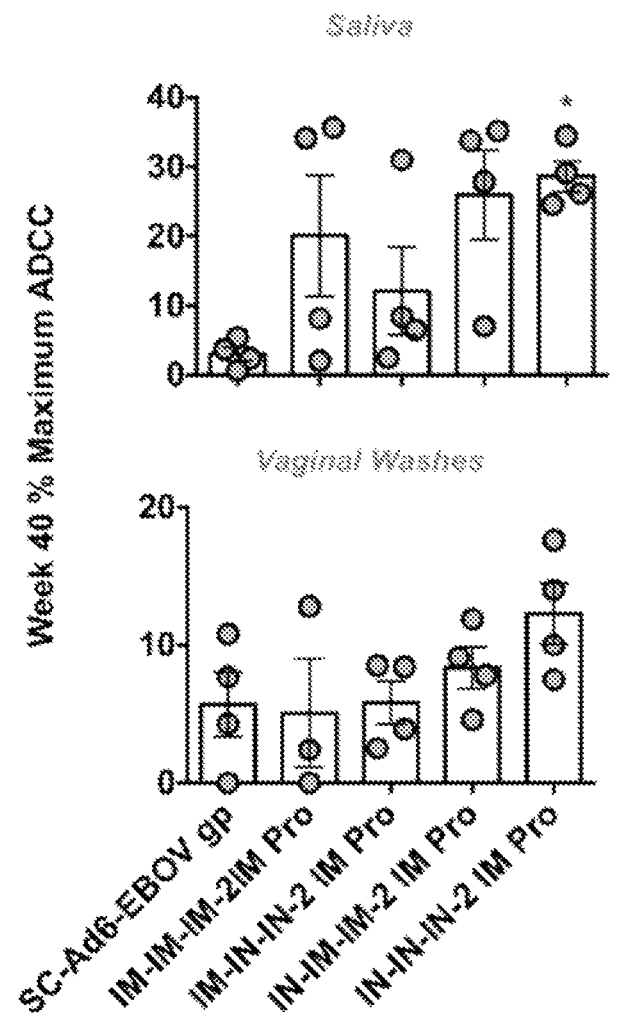

There appeared to be a regional effect on these mucosal antibodies. In animals that were immunized with SC-Ad mostly by the IN route (IM-IN-IN and IN-IN-IN), binding antibodies were higher in the saliva near this site of immunization, but lower in the more distant vaginal site (FIG. 25). When ADCC activity was measured in these mucosal samples, these responses were highly variable (FIG. 17). Despite this, higher ADCC activity was observed in the IN-IN-IN group when compared to control animals (p<0.05 by ANOVA).

Systemic Cellular Immune Responses after One Protein Boost

Figure 18:
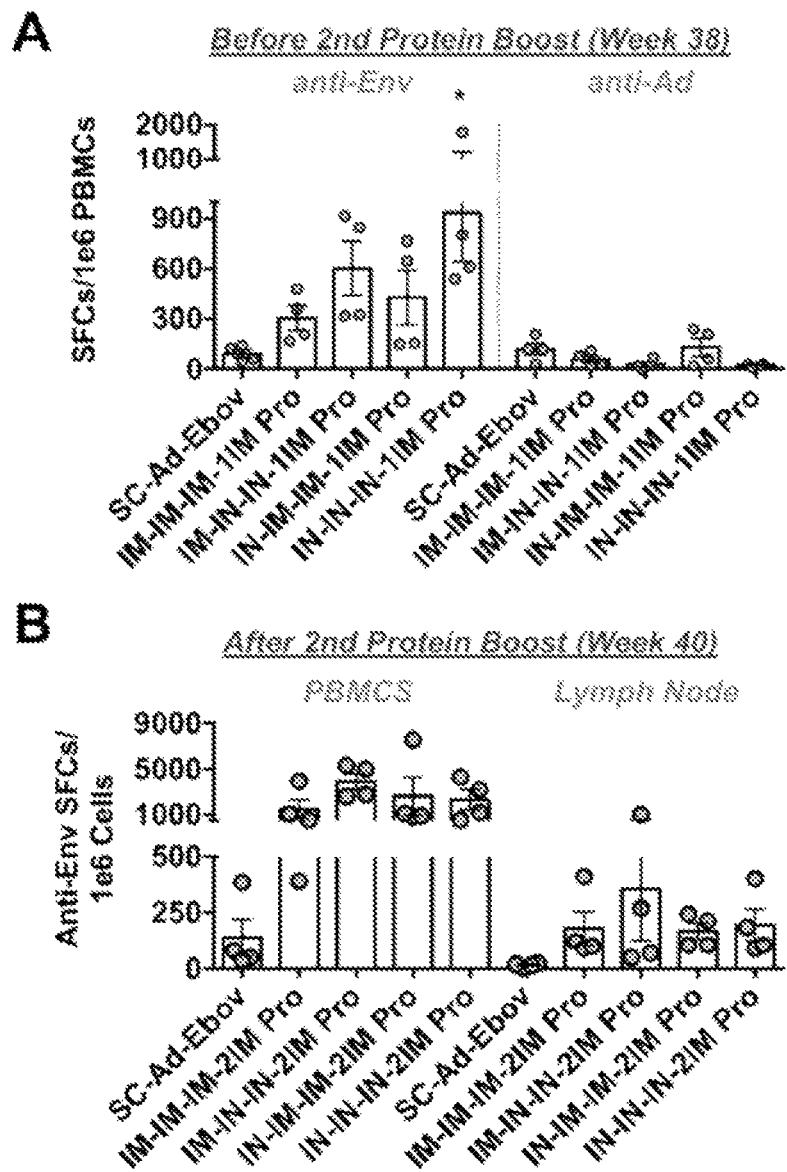
FIG. 18 shows IFN-7 Secreting Cells from PBMCs and Lymph Nodes. PBMCs and lymph node cells were analyzed by ELISPOT by staining for IFN-7. Anti-Env indicates cells that were stimulated with conserved HIV Env peptides, and SC-Ads. The total number of spot forming cells (SFCs) in each of the stimulated wells were counted and adjusted to control medium as background. Each dot represents the mean value for each animal. * $p<0.05$ by one-way ANOVA.

Week 38 PBMCs were assayed for T cells against Env and against adenovirus by ELISPOT on samples collected just prior to a second F8 Env protein boost. All Env-immunized animals had Env-specific IFN-7 secreting cells in their PBMCs (FIG. 18A). The level of Env-specific IFN-7 SFCs were generally increased in animals that received at least one mucosal immunization. However, IFN-7 SFCs were only significantly higher only in the IN-IN-IN SC-Ad group when they were compared to SC-Ad Ebola immunized control animals (p<0.05 by ANOVA). Anti-Ad SFCs were relatively low in all groups when compared to anti-Env SFCs at this time point.

Systemic Cellular Immune Responses after a Second Protein Boost

At week 40, PBMCs and inguinal lymph node cells were assayed for Env-specific IFN-7 SFCs by ELISPOT (FIG. 18B). This protein boost increased Env-specific SFCs in PBMCs and in lymph nodes to similar levels in all of the Env-immunized animals.

Mucosal Cellular Trafficking

Figure 19:
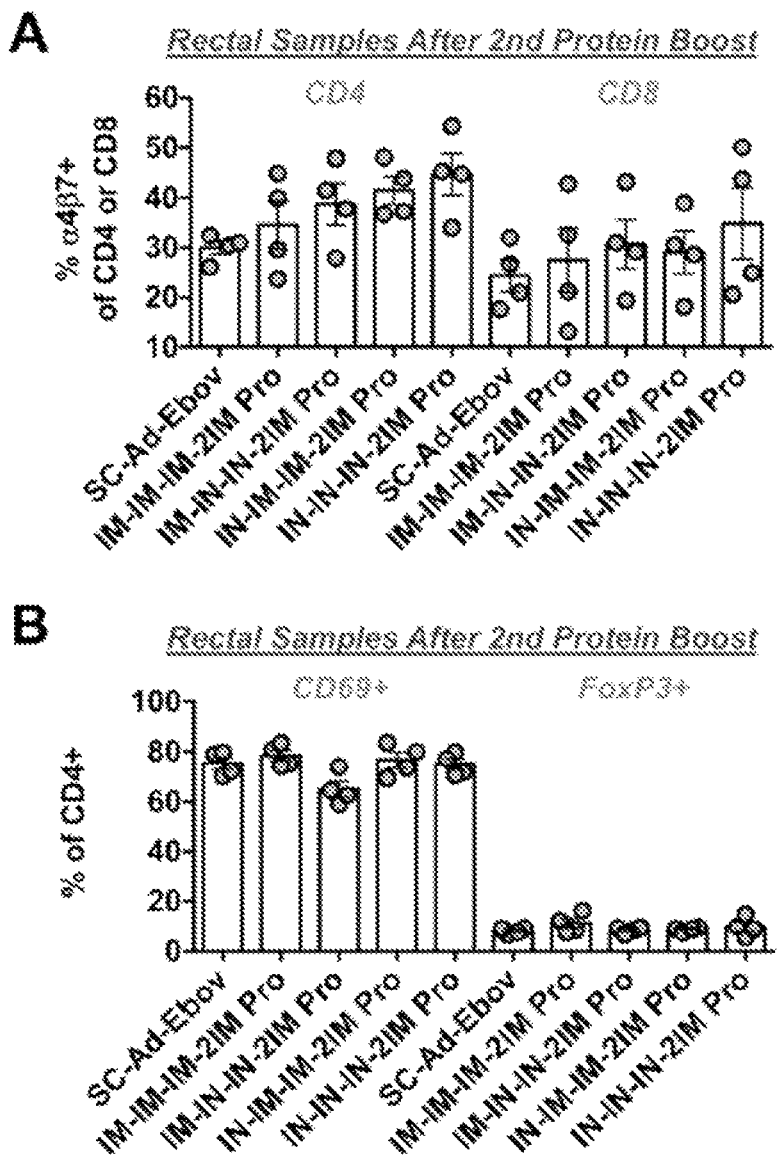
FIG. 19 shows mucosal T cell trafficking and activation. T cells were harvested from rectal biopsies collected after the second protein boost and analyzed by flow cytometry for CD4, CD8, α4β7 integrin, CD69, and FoxP3. Each dot represents the mean value for each animal.

Flow cytometry on rectal biopsy samples at week 40 showed similar numbers of a407 CD4 and CD8 cells in rectal sites (FIG. 19A). There was a trend towards increasing numbers in the IN primed groups, but these did not reach significance. The numbers of activated CD69+CD4+cells in rectal tissues were similar between the groups (FIG. 19B). Similarly, FoxP3+CD4+cells in this mucosal site were not appreciably different (FIG. 19B).

Antigen-specific Tfh Cell Distributions

Figure 20:
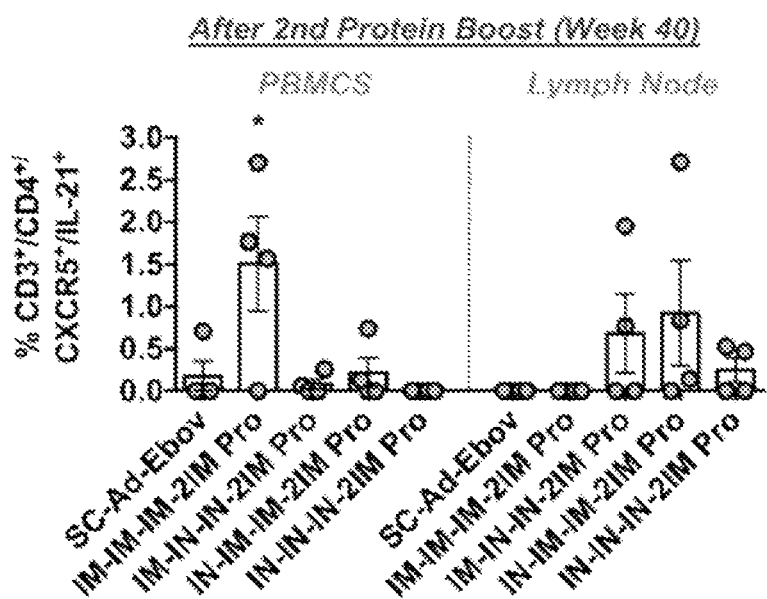
FIG. 20 shows Tfh cell response in the blood and in lymph nodes. PBMCs and lymph node cells collected at week 40 were stimulated with HIV-1 Env protein and then examined for co-expression of CD3+, CD4+, CXCR5+, and IL-21. Each dot represents the mean value for each animal. * $p<0.05$ by one-way ANOVA.

CXCR5+IL-21+CD4+T follicular helper (Tfh) cells were measured in PBMCs and lymph node samples at week 40 (FIG. 20). The animals that were immunized by Ad and protein by only the IM route had significantly higher peripheral Tfh (pTfh) cells in PBMCs than other groups (FIG. 20). In lymph nodes, Tfh cells were lowest in the control and IM only group. In contrast, approximately one half of the animals that received at least one IN mucosal immunization have detectable Tfh in their lymph nodes after the last protein boost (FIG. 20).

Rectal Challenge with SHIVSF162P3

Figure 21:
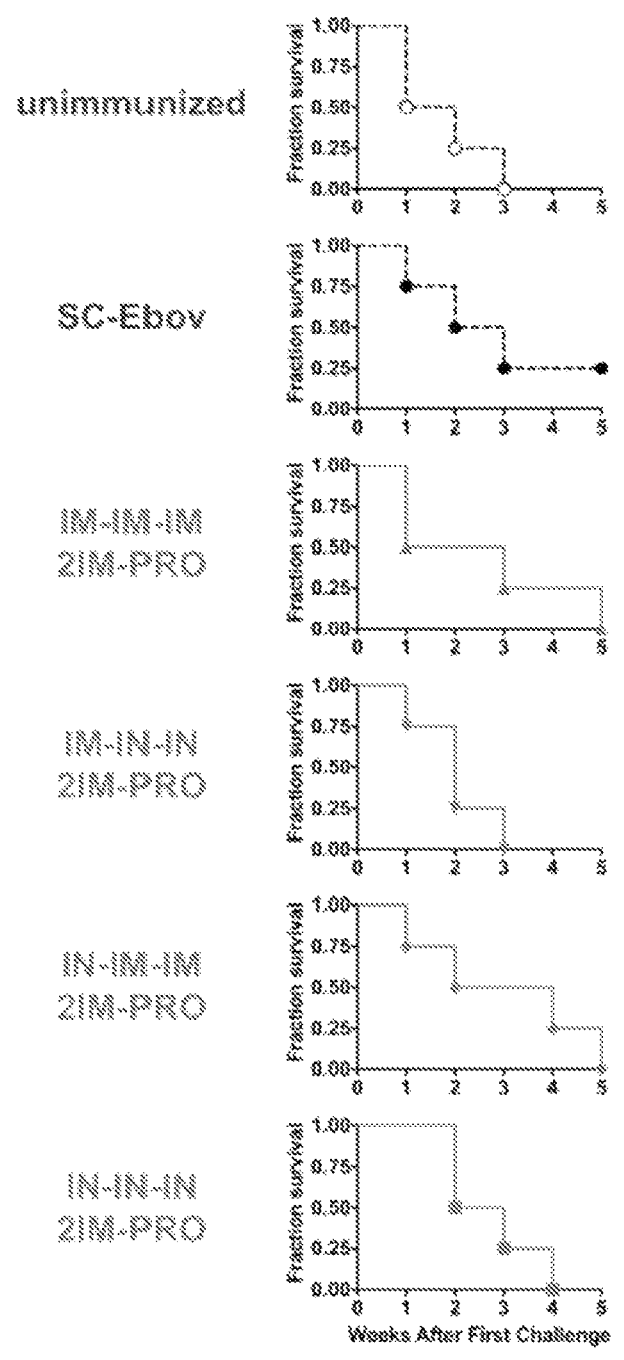
Figure 22:
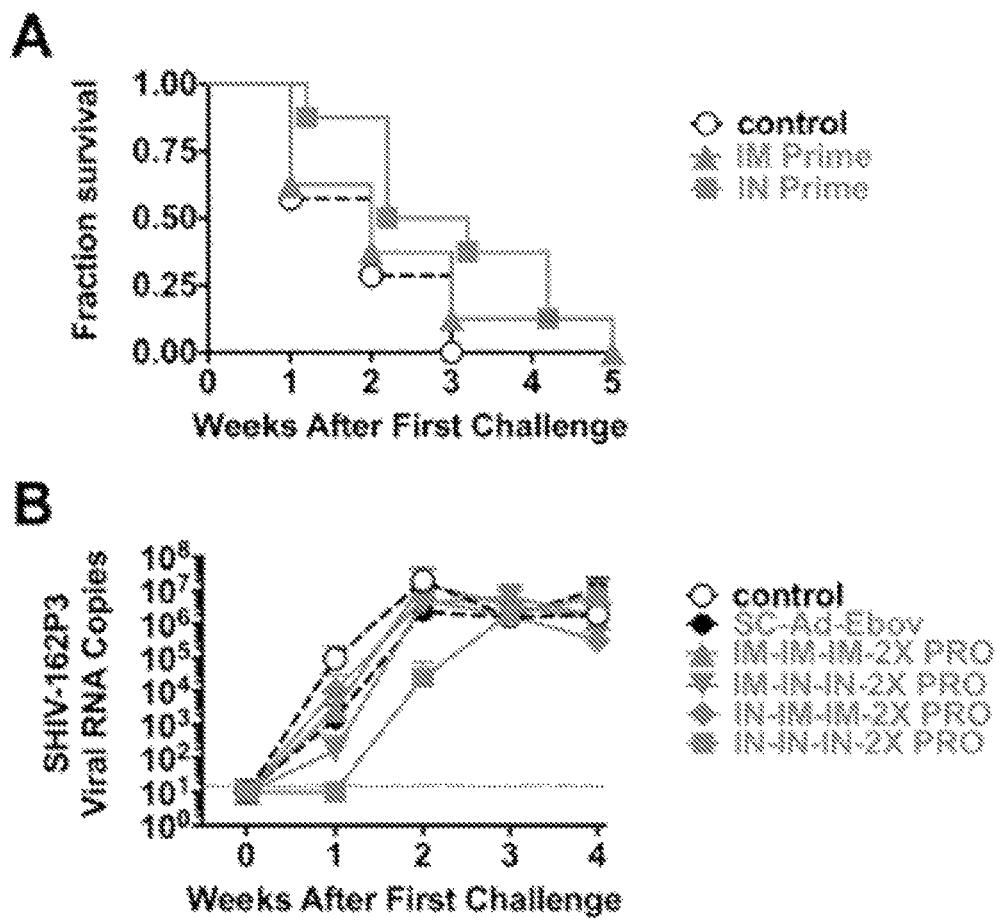
FIG. 22 shows SHIV$_{SF162P3}$ acquisition and viral loads. A) Animals from FIG. 8 were grouped by their initial SC-Ad priming route (IM or IN) yielding groups of 8 and Kaplan-Meier analysis was performed. B) Plasma SHIVSF162P3 viral RNA levels over the course of the challenge study.

The immunized macaques were challenged rectally with HIV isolate SHIVSF162P3. Four unimmunized control animals were added to the study and each group was challenged weekly by rectal inoculation with 1 ml a 1:300 dilution of SHIVSF162P3 challenge stock provided by NIH. This challenge equaled 4.3 $TCID_{50}$ on rhesus PBMCs and 137 $TCID_{50}$ on TZM-bl cells. After the first challenge, 2 animals in an unimmunized control group and 2 animals in the IM-IM-IM group became infected (FIG. 21). One animal in each of the mixed route groups (IM-IN-IN and IN-IM-IM) became infected after one challenge. None of the animals in the IN-IN-IN group were infected after the first challenge. Viral loads in plasma indicated that all animals except the Ebola group animal reached high viral loads after 3 challenges (FIG. 22B). Animals in the IN-IN-IN group had a delay in reaching these high viral loads.

As challenges continued, animals in all groups became infected with the exception of one animal in the Ebola group that remained uninfected after 7 challenges. Trim5α and MHC alleles were examined retrospectively (Table 2). This analysis did not reveal overtly protective genes in the resistant Ebola group animal. Most animals could not be classified with alleles that might keep them moderately protected, but most groups had at least one animal with a higher likelihood of protection by virtue of these alleles. It should be noted that 2/4 animals in the IM-IM-IM and IN-IN-IN groups had Trim5a and MHC alleles that might predict a higher likelihood of innate protection against SIVsmm and perhaps SHIVSF162P3 (Table 2).

TABLE 2

Retrospective Screening for SIV Protective Gene Alleles.

| Vaccine Group | Animal Number | MHC typing | TRIM5alpha | Degree of viral protection |
|---|---|---|---|---|
| Unimmunized | RHJ663 | Not done | Cyp A/TFP | High |
| | RH3-39 | Not done | Q/TFP | Moderate |
| | RHJ403 | Not done | CypA/Q | Moderate |
| | RHJ791 | Not done | Q/TFP | Moderate |
| SC-Ad-Ebov | RH13-005 | A11, B01, B17 | Q/TFP | Moderate |
| | RH13-007 | A08, A11, B01, B17 | Q/TFP | Moderate |
| | RH13-043 | A08, A11, B17 | Q/TFP | Moderate |
| | RH13-135 | A08, A11, B17 | Q/TFP | Moderate |
| IM-IM-IM | RH13-027 | A11, B01, B17 | TFP/TFP | High |
| | RH13-031 | A08, A11, B01 | Cyp A/Q | Moderate |
| | RH13-051 | A08, A11, B17 | Cyp A/Q | Moderate |
| | RH13-139 | A08, A11, B17 | TFP/TFP | High |
| IM-IN-IN | RH13-039 | A11, B01, B17 | Cyp A/Q | Moderate |
| | RH13-045 | A08, A11, B01, B17 | Q/Q | Susceptible |
| | RH13-095 | A08, A11, B17 | Q/TFP | Moderate |
| | RH13-159 | A08, A11 | Cyp A/TFP | High |
| IN-IM-IM | RH13-013 | A11, B17 | Cyp A/Q | Moderate |
| | RH13-067 | A08, A11, B01, B17 | Q/TFP | Moderate |
| | RH13-091 | A11, B01, B17 | TFP/TFP | High |
| | RH13-121 | A08, A11, B17 | Q/TFP | Moderate |
| IN-IN-IN | RH13-025 | A11, B17 | Cyp A/Q | Moderate |
| | RH13-033 | A08, A13, B17 | Cyp A/TFP | High |
| | RH13-087 | A08, A11, B01, B17 | TFP/TFP | High |
| | RH13-125 | A08, A11, B17 | Q/TFP | Moderate |

When the animals were grouped based on whether they were primed by the IM or IN route with SC-Ad and Kaplan Meier survival was analyzed, infection of the eight IM primed animals paralleled that of control animals (FIG. 22A). In contrast, infection was somewhat delayed in the eight animals that were primed with SC-Ad-Env by the mucosal IN route.

Post-Mortem Viral Loads in Tissues

Figure 23:
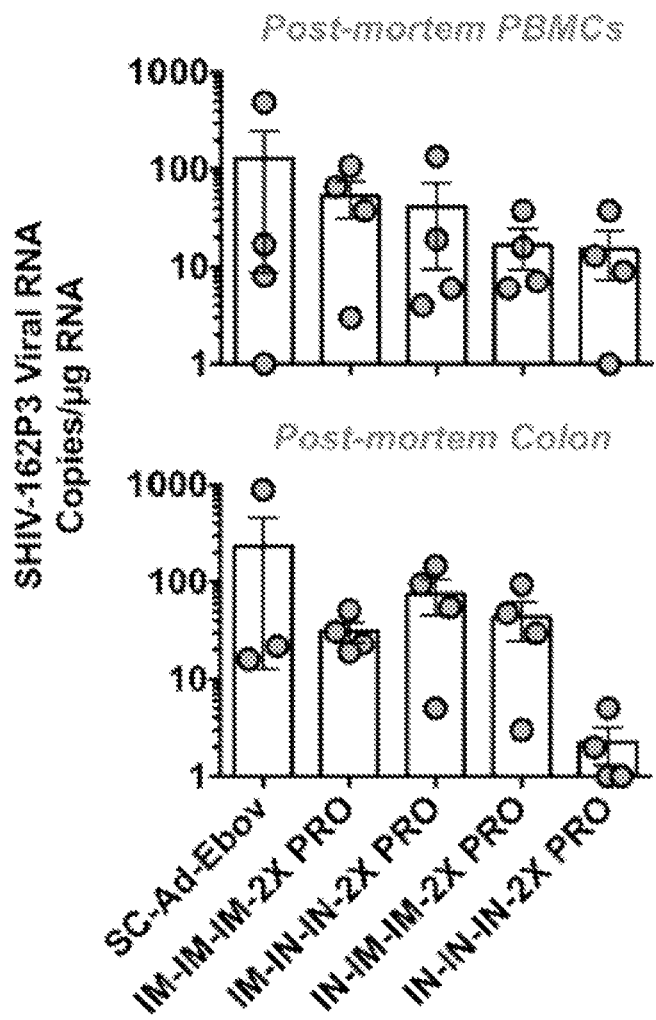
FIG. 23 shows SHIV viral load in tissues. RNA from PBMCs and post-mortem tissues were collected and qPCR was performed to detect analyzed for SHIV viral RNA.

The challenge study was terminated 9 weeks after first challenge. PBMCs and gut tissues were isolated, RNA was purified, and evaluated for SHIV viral genomes (FIG. 22B). Post-mortem PBMCs had varied levels of SHIV viral RNA with somewhat lower levels in the IN-IN-IN group than in the IM-IM-IM group. Mean viral RNA in the colon was 15-fold lower in the IN-IN-IN group than the IM-IM-IM group (FIG. 23). This difference did not reach significance by ANOVA, but two-tailed T test gave a p value of 0.0079.

This example demonstrates that replicating SC-Ad vectors can be used as a robust and safe platform for vaccination against HIV-1 and other infectious diseases. SC-Ad is able to amplify antigen and cytokine genes up to 10,000-fold in infected human cells. The immune response is amplified well-above those mediated by RD-Ad vectors that are currently being tested as HIV-1 vaccines in humans. HIV vaccines can be transitioned to vaccine platforms that amplify HIV antigen genes by utilizing SC-Ad vectors, for example, SC-Ad vectors based on recombinant Ads having low seroprevelance.

Figure 26:
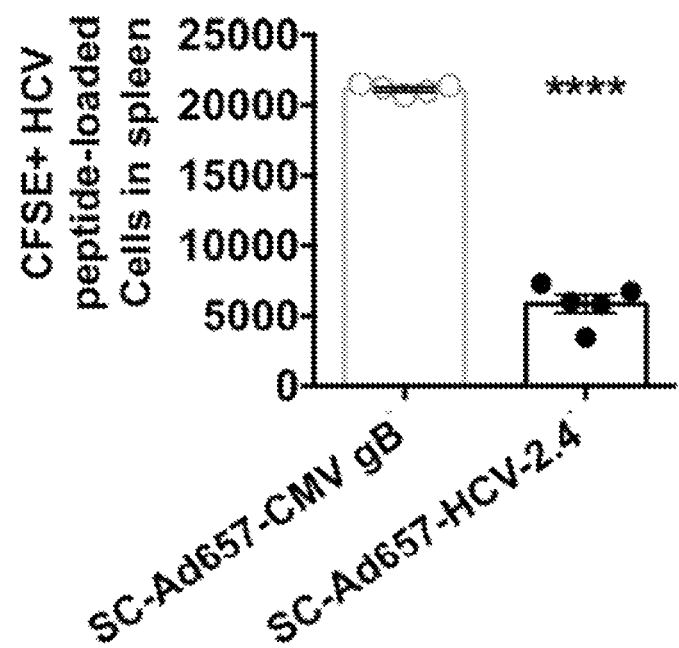
FIG. 26 shows Ad657 expressing antigen genes from hepatitis C and cytomegalovirus (CMV) gB generating in vivo cytotoxic T lymphocyte (CTL) activity. Shown is killing of hepatitis C peptide-loaded target cells in mice vaccinated with Ad657-HCV rather than CMV gB.

Example 8. In Vivo Cytotoxic T Lymphocyte (CTL) Assay for Immune Responses Against Hepatitis C Virus (HCV) Antigen Mice were immunized with Ad657 expressing the CMV cytomegalovirus (CMV) glycoprotein B (gB) cDNA or HCV antigen 2.4. Syngeneic cells were pulsed with HCV peptide and labeled with carboxyfluorescein succinimidyl ester (CFSE) prior to injection into the immunized mice. Cognate CTL activity is observed against HCV by loss of labeled cells in the HCV, but not CMV immunized animals (FIG. 26).

Example 9. Conditionally Replicating Ads (CRAds)

Figure 39:
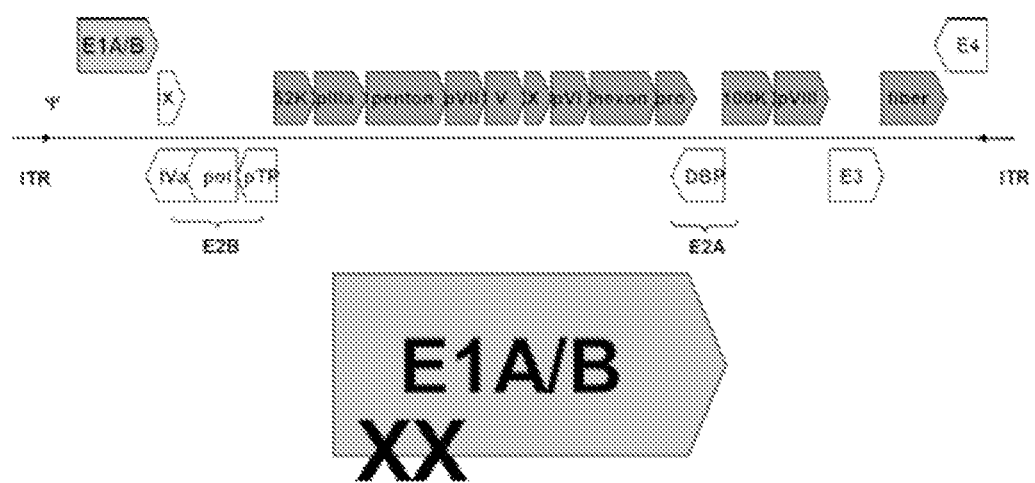
FIG. 39 shows a schematic of cancer-specific conditionally-replicating Ads (CRAds) dl1101+dl1107 having a modification in the E1A gene.

Schematic of mutations in Ad6, Ad657 and variants thereof involving mutations in the E1 protein to convert the virus to a conditionally-replicating Ad (CRAd) is shown in FIG. 39 and FIG. 43. These include dl1101 and/or the dl1107 that block binding to p300 and pRB, respectively.

FIG. 56 shows the N-terminal amino acid sequences of E1A in a wild-type Ad, as well as Ad variants E1A dl1101, E1A dl1107 and E1A dl1101/1107.

Also shown is the replacement of the Ad E1 promoter with the prostate-specific promoter probasin-E1 DNA sequence of SEQ ID NO:48 to generate the CRAd, Ad-PB (FIG. 55). The probasin promoter is androgen dependent, so will work in androgen-sensitive tumors like LNCaP, but not in androgen-resistant tumors like DU145.

Figure 40:
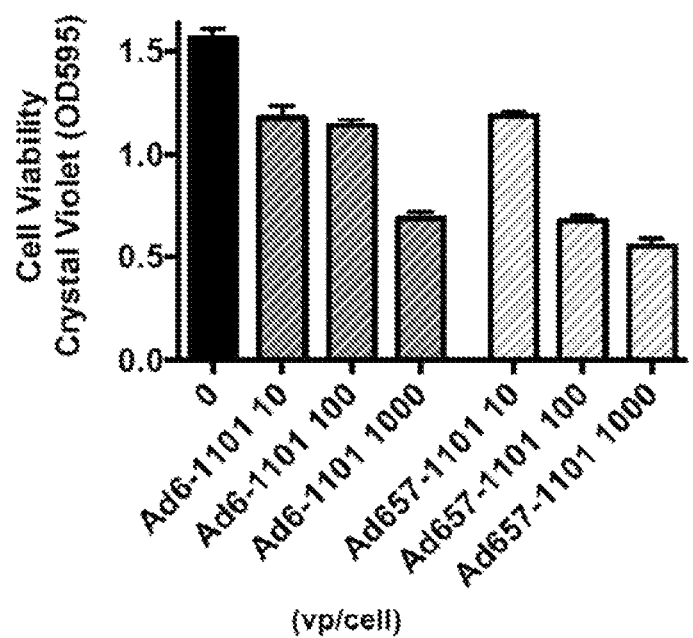
FIG. 40 is a graph showing that Ad6 and Ad657 can both be used as CRAds for targeted cancer therapy.

A549 cells were infected with the indicated Ad6 or Ad657 variants at the indicated concentrations of virus (vp/cell) and cell viability was measured by crystal violet staining after 5 days (FIG. 40).

Killing of non-cancerous cells by replication-defective Ad (RD-Ad), Ad6, CRAd6-dl1101/dl1107 or CRAd6-PB. Modification of Ad6 and Ad657 to be conditionally-replicating Ads (CRAds) is demonstrated (FIG. 44).

Killing of cancerous cells by replication-competent Ad5, Ad6, Ad657, and the indicated CRAds is shown in FIG. 45. The modification of Ad6 and Ad657 to be conditionally-replicating Ads (CRAds) is demonstrated.

Figure 46:
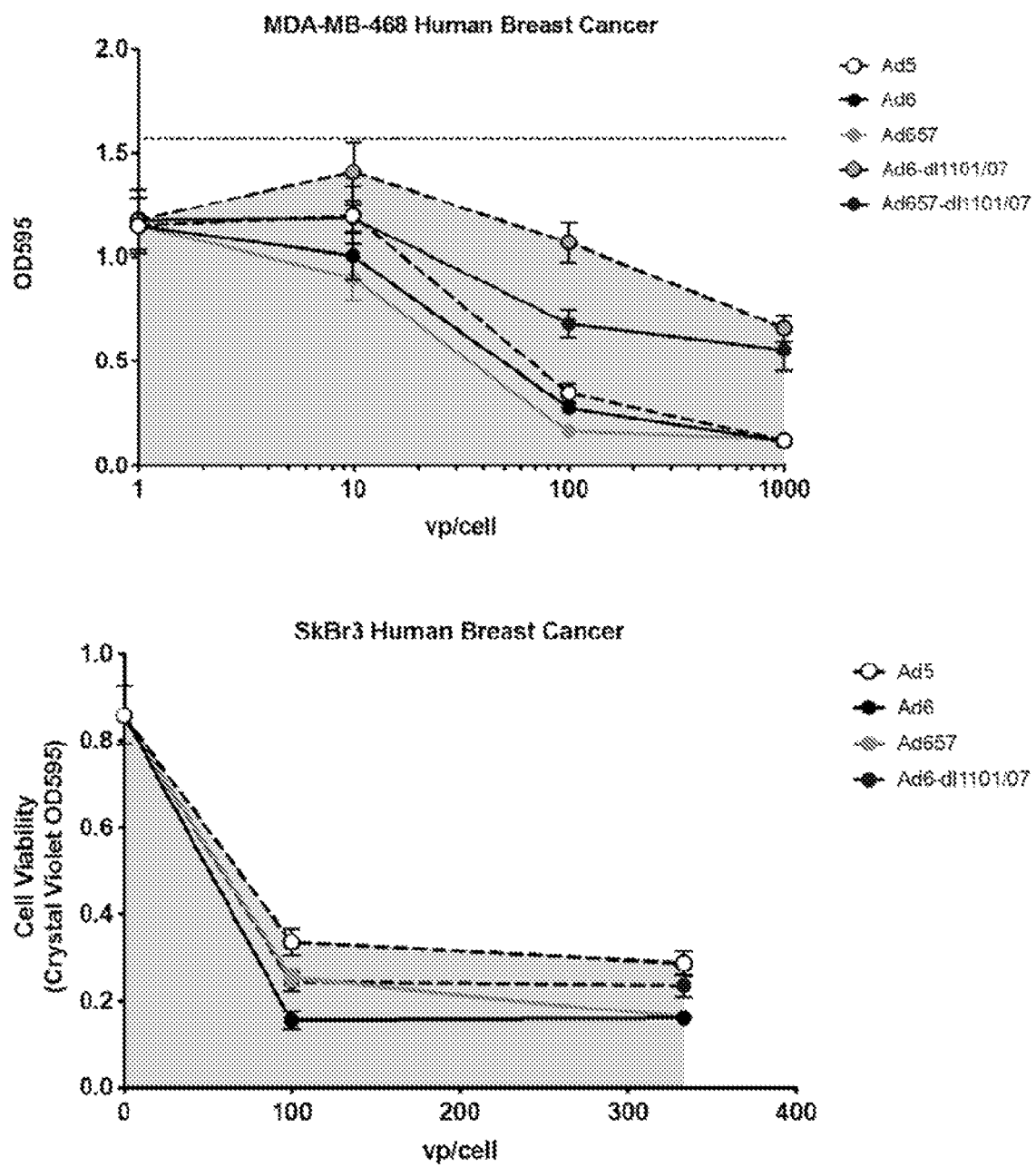
FIG. 46 demonstrates modification of Ad6 and Ad657 to be conditionally-replicating Ads (CRAds).

The results shown in FIG. 46 demonstrate modification of Ad6 and Ad657 to be conditionally-replicating Ads (CRAds) in breast cancer cells.

Figure 47:
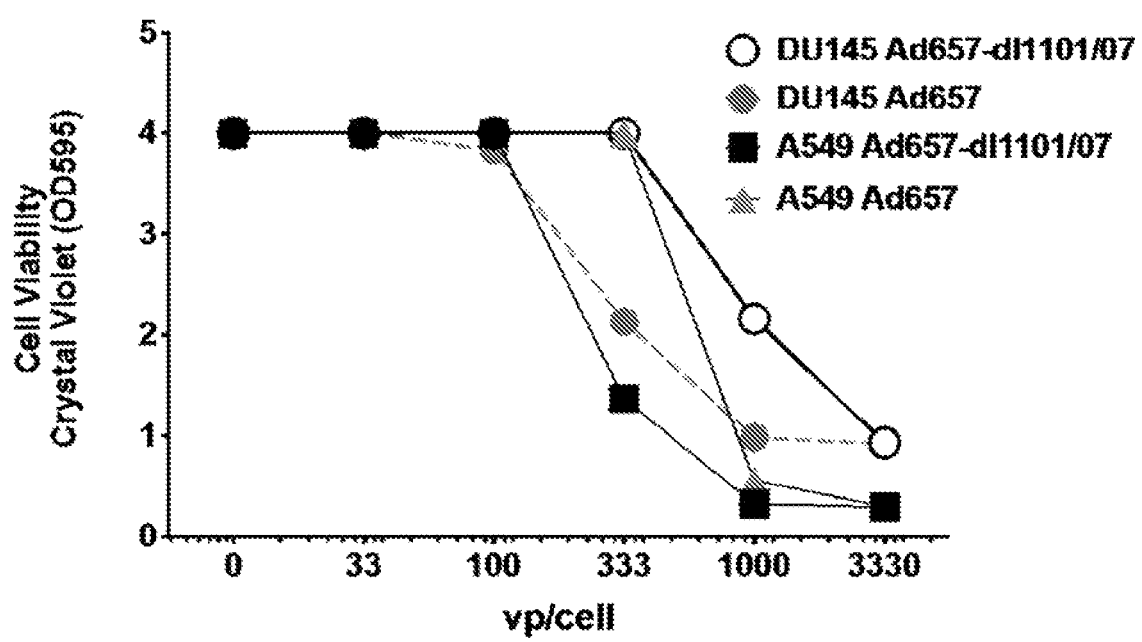
FIG. 47 demonstrates modification of Ad6 and Ad657 to be conditionally-replicating Ads (CRAds).

The results shown in FIG. 47 demonstrate modification of Ad6 and Ad657 to be conditionally-replicating Ads (CRAds) in prostate cancer cells and lung cancer cells.

Figure 48:
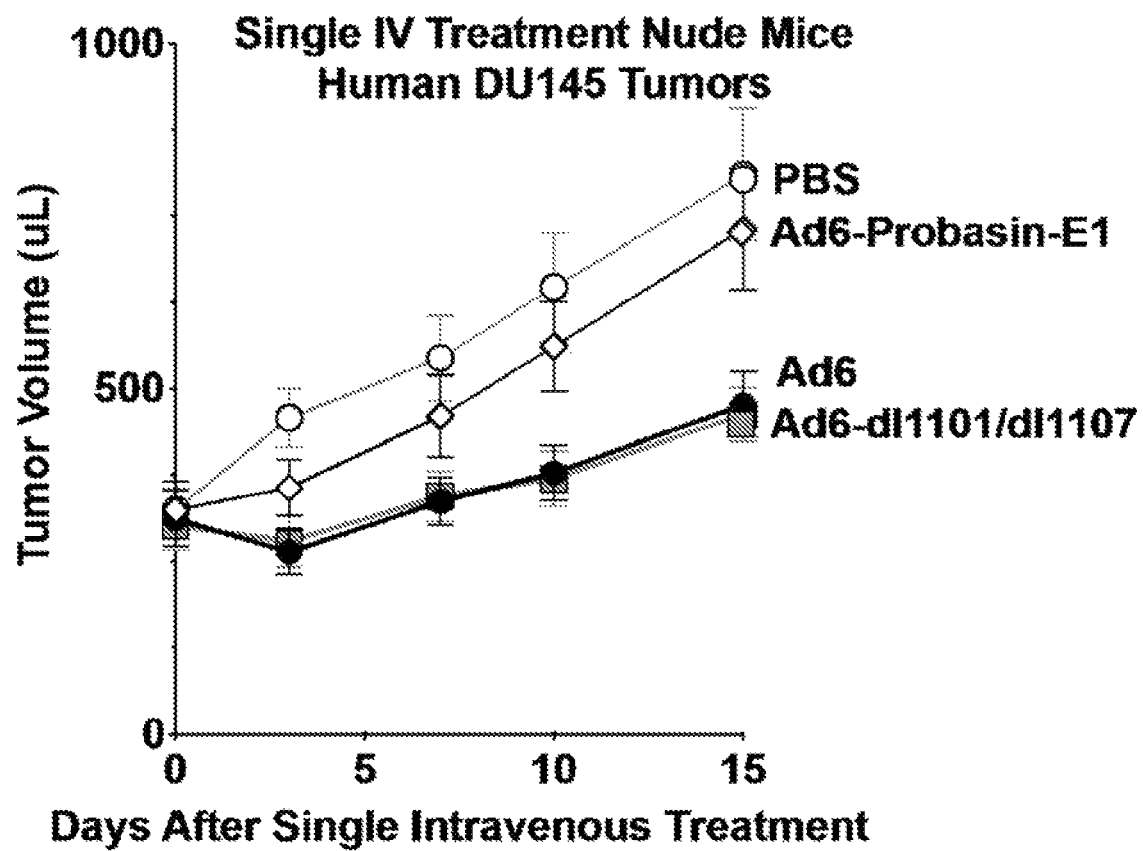
FIG. 48 demonstrates in vivo effects of replication-competent Ad6 or the indicated CRAds on growth of DU145 tumors in mice.

In vivo effects of replication-competent Ad6 or the indicated CRAds on growth of DU145 tumors in mice. FIG. 48 demonstrates modification of Ad6 and Ad657 to be conditionally-replicating Ads (CRAds) in vivo after a single intravenous injection in mice bearing human prostate tumors.

Figure 49:
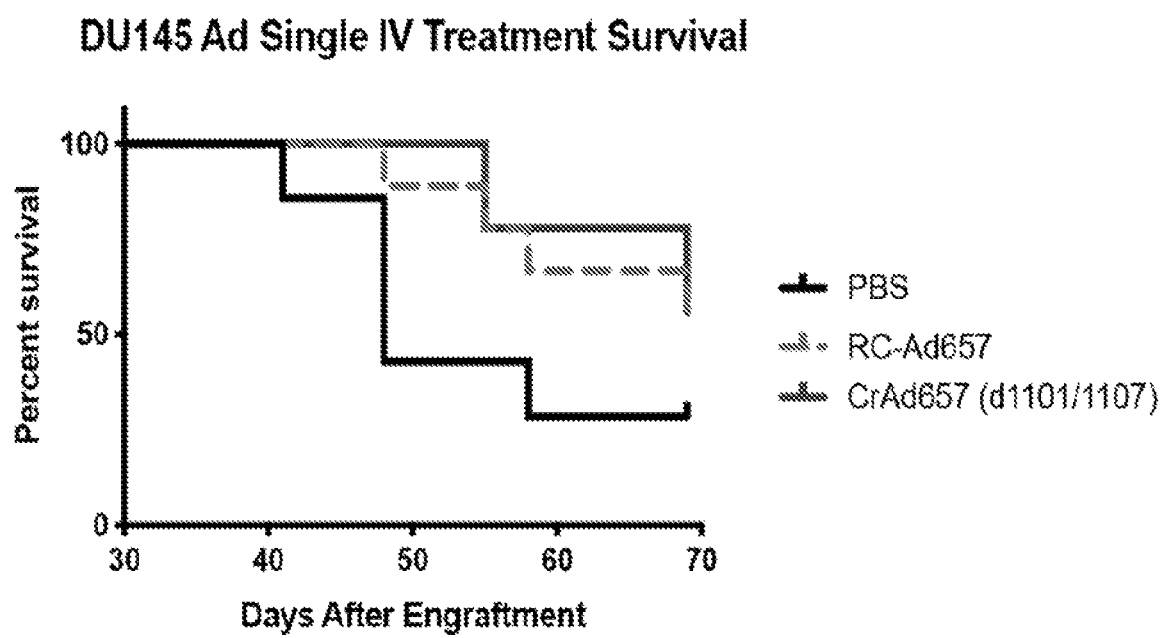
FIG. 49 demonstrates in vivo effects of replication-competent Ad657 and conditionally-replicating Ad657-dl1101/07 both with intact E3 regions in vivo after a single intravenous injection in mice bearing human prostate tumors.

In vivo effects of replication-competent Ad6 or the indicated CRAds on survival of mice with DU145 tumors. FIG. 49 demonstrates modification of Ad6 and Ad657 to be conditionally-replicating Ads (CRAds) in vivo after a single intravenous injection in mice bearing human prostate tumors.

Figure 51:
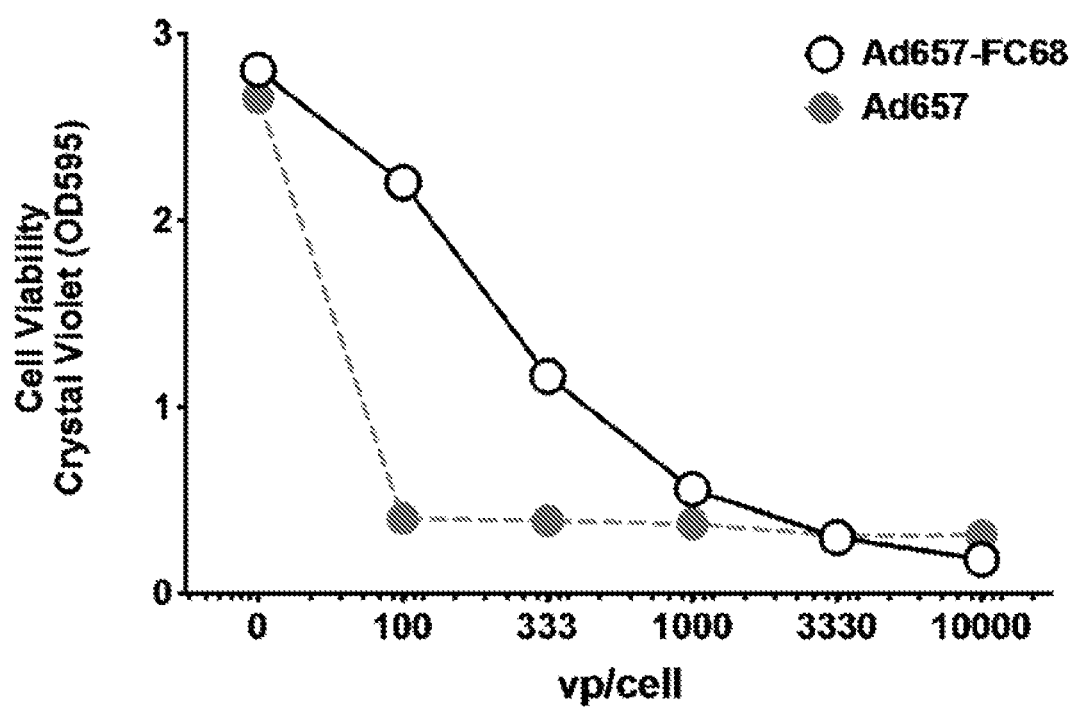
FIG. 51 demonstrates modification of Ad657 with the shorter fiber from chimpanzee AdC68 and the addition of a codon-wobbled E4 34.K gene changes in vitro efficacy.

FIG. 51 demonstrates that modification of Ad657 with the shorter fiber from chimpanzee AdC68 reduces efficacy.

Figure 52:
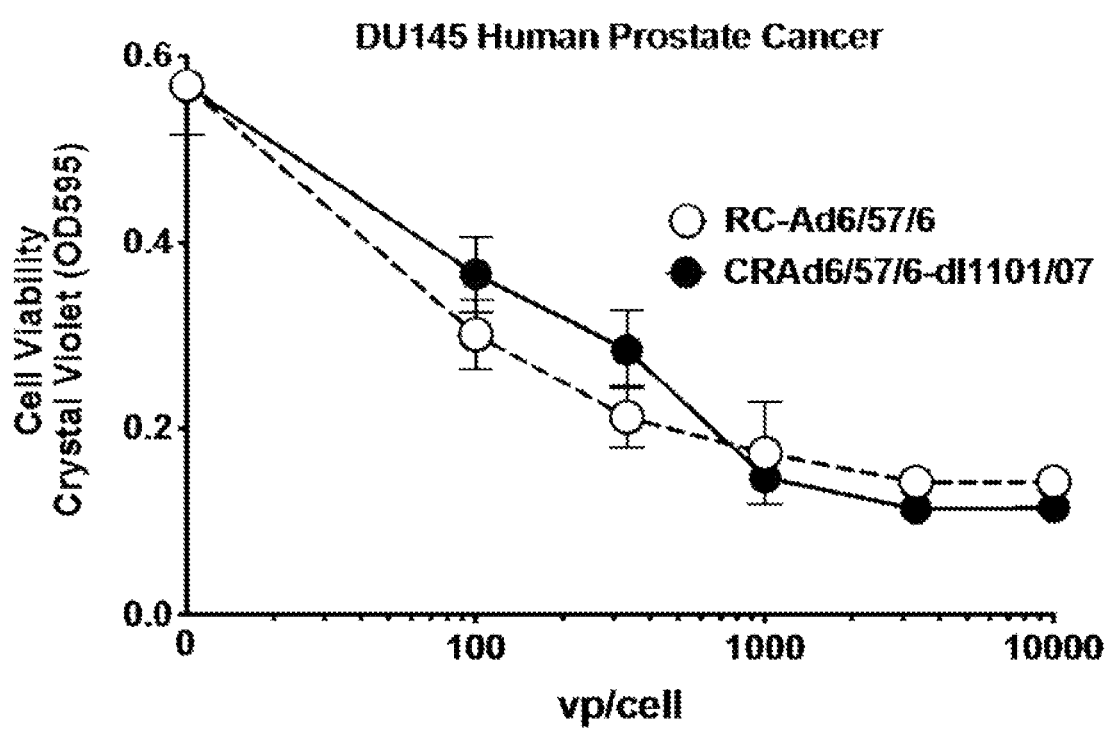
FIG. 52 demonstrates 6/57/6 virus killing human prostate cancer cells with and without CRAd modifications.

In an embodiment, an Ad 6/57/6 virus has HVRs 1 and 7 from Ad6 and HVRs 2-6 from Ad657. FIG. 52 demonstrates Ad 6/57/6 virus killing human lung cancer cells with and without CRAd modifications.

Tumor cell killing by Ad variants involving mutations in the E3 protein. Immune competent Syrian hamsters were engrafted with subcutaneous HaK kidney cancer tumors. When these reached 200 µl volume, they were injected a single time by the intravenous route with the indicated Ad6 viruses constructed with and without E3 (DE3) and with or without random NHS-PEGylation. Tumor sizes were measured over time. The data shows that deleting all E3 genes makes the oncolytic virus less effective (Ad6-deltaE3-Luc vs Ad6-Luc) (FIG. 58).

The Ad fiber protein is a complex of three apparently identical subunits which mediates the initial attachment step. The native Ad6 fiber protein comprises the amino acid sequence set forth in SEQ ID NO:60 and binds CAR.

In a further aspect of the invention, fiber-modified recombinant Ads having different fiber proteins which are not native to the parental Ad were generated. Recombinant Ads, including CRAds, comprising capsid proteins from different Ad strains were generated, for example, recombinant Ads comprising a heterologous Ad35 fiber polypeptide or Chimpanzee C68 fiber polypeptide, +/–a K7 peptide (FIGS. 62-69).

A chimeric Ad, AdF35 fiber chimera, has the amino acid sequence of SEQ ID NO:61 and is shorter than Ad5 and Ad6 fiber proteins and retargets virus to CD46.

A fiber-modified recombinant Ad, comprising K7 Fiber having the sequence of SEQ ID NO:62, targets virus to heparin sulfate proteoglycans and negative charges on cells.

A recombinant, chimeric Ad, 6/FC68 Fiber comprising the sequence of SEQ ID NO:63, is a chimeric Ad having a fiber protein from chimpanzee adenovirus C68. The fiber protein is shorter than Ad5 or Ad6 fiber proteins and binds CAR.

A recombinant, chimeric Ad, 6/FC68-K7 Fiber comprising the sequence of SEQ ID NO:64, is a chimeric Ad having a fiber protein from chimpanzee adenovirus C68. The fiber protein is shorter than Ad5 or Ad6 fiber proteins. The 6/FC68-K7 Fiber binds CAR and is retargeted to heparin sulfate and negative charges.

A recombinant, chimeric Ad, 6/FC68-HI-K7 Fiber comprising the sequence of SEQ ID NO:65, is a chimeric Ad having a fiber protein from chimpanzee adenovirus C68. The fiber protein is shorter than Ad5 or Ad6 fiber proteins. The 6/FC68-HI-K7 Fiber binds CAR and is retargeted to heparin sulfate and negative charges.

Example 10. Serotype-switching of Adenoviruses

Figure 41:
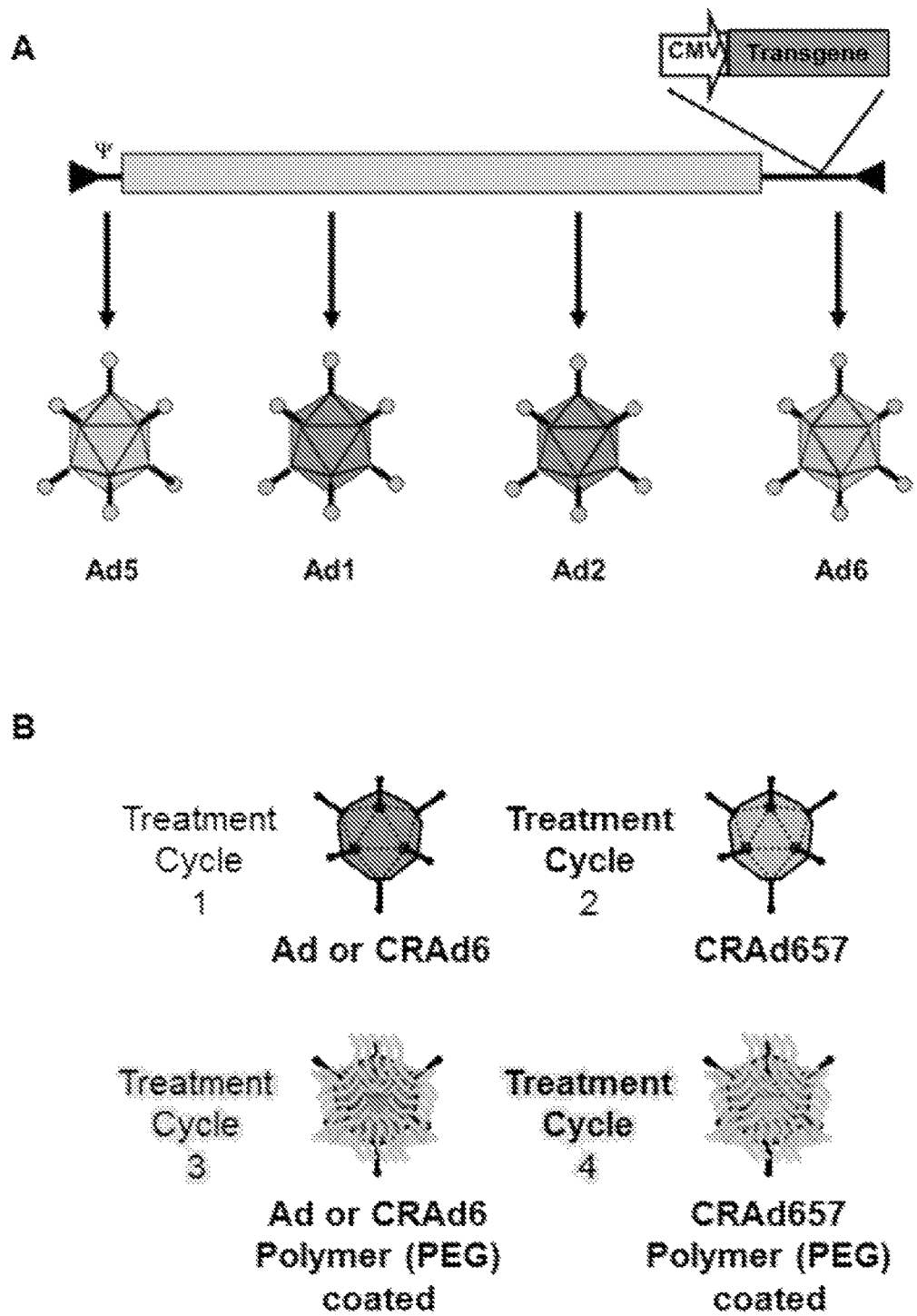
FIG. 41 is a schematic showing Ad therapeutic cycles. A) A schematic of serotype-switching with Ads. B) A schematic of an exemplary therapeutic cycle where Ad6 and Ad657 can be used for multiple rounds of treatment by serotype-switching in combination with covalent polymer conjugation.

FIG. 41 is a schematic showing Ad therapeutic cycles. In an embodiment serotype-switching with different Ads over the course of a treatment is exemplified (FIG. 41A).

Prostate Tumor Targeting after Serotype-switching of Oncolytic Adenoviruses.

Figure 42:
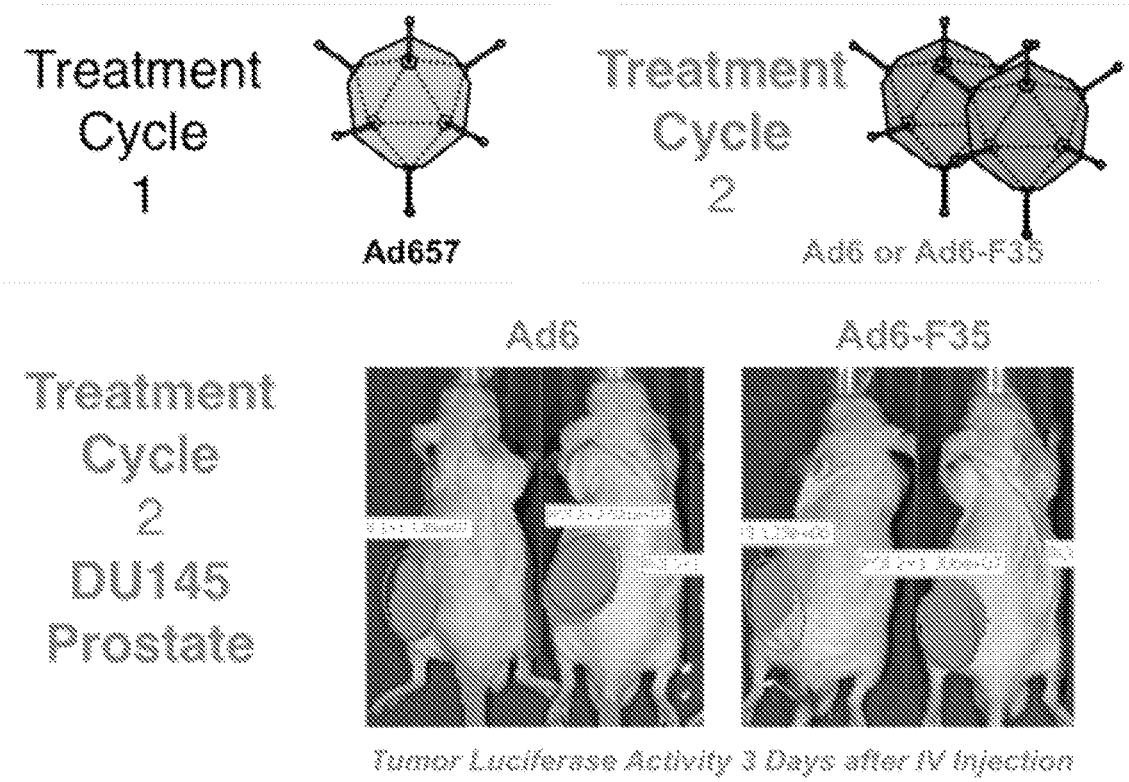
FIG. 42 demonstrates serotype-switching and on-target luciferase activity in the DU145 prostate tumors after a single IV injection of Ad6 and Ad6-F35 with deletions in E3A genes (12.5K, 6.7K, 19K, 11.6K), but retention of E3B genes (10.4K, 14.5K, and 14.7K) and retention of E4 34K. Mice whose tumors resisted prior single IV injection with Ad657 and CRAd657 both with intact E3 genes were injected with the indicated vectors by single IV injection.

Mice bearing DU145 prostate tumors on their flanks were treated by a single intravenous (IV) injection with Ad657 or CRAd657. These mice were treated a second time with alternate Ad6 oncolytic virus or Ad6-F35 expressing GFPLuciferase and luciferase activity was measured by imaging. Ad6 has Ad6 hexon and fiber that targets CAR. Ad6-F35 has Ad6 hexon and the Ad35 fiber that targets CD46. FIG. 42 demonstrates the capability to serotype-switch oncolytics with viruses targeting a tumor with lower off-target infection of the liver.

In another example of serotype-switching, mice bearing LNCaP prostate tumors on their flanks were treated by a single intravenous (IV) injection with 3e10 viral particles (vp) of Ad657 or CRAd657. These mice were treated a second time 5 months later with 3e10 vp alternate Ad6/57/6 oncolytic virus expressing GFPLuciferase and fiber variants K7 (with 7 lysines added), F35 (with the Ad35 fiber), or KKTK-C68 (chimpanzee C68 fiber fused after the Ad6 KKTK flexibility domain. KKTK-C68 virus also has an added codon-optimized E4 34K gene to enhance viral productivity. Luciferase activity was measured by imaging 7 days later. All Ad6/57/6's have a hexon with HVR1 and 7 from Ad6 and HVRs 2-6 from Ad57. Ad6/57/6 and KKTK-C68 have fibers that targets CAR. Ad6/57/6-F35 has the Ad35 fiber that targets CD46. K7 increases binding to negative charges on cells including binding heparin sulfate proteoglycans. FIG. 70 demonstrates the capability to serotype-switch oncolytics with viruses targeting a tumor with lower off-target infection of the liver.

Serotype-Switching During Vaccination of Non-Human Primates.

In FIGS. 14 through 25, rhesus macaques were immunized with replicating single-cycle Ad6 expressing HIV envelope and then boosted by serotype-switching with single-cycle Ad657 expressing HIV envelope. Following these immunizations, each animal was boosted with envelope protein. Each figure shows the generation of adaptive antibody or cellular immune responses and how the animals repelled rectal challenge with SHIV $S_{F162P3}$virus. FIG. 14 documents the value of the serotype-switch where changing to Ad657 generated marked increases in antibody responses.

Example 11. Oncolytic Cancer Vaccines

Figure 53:
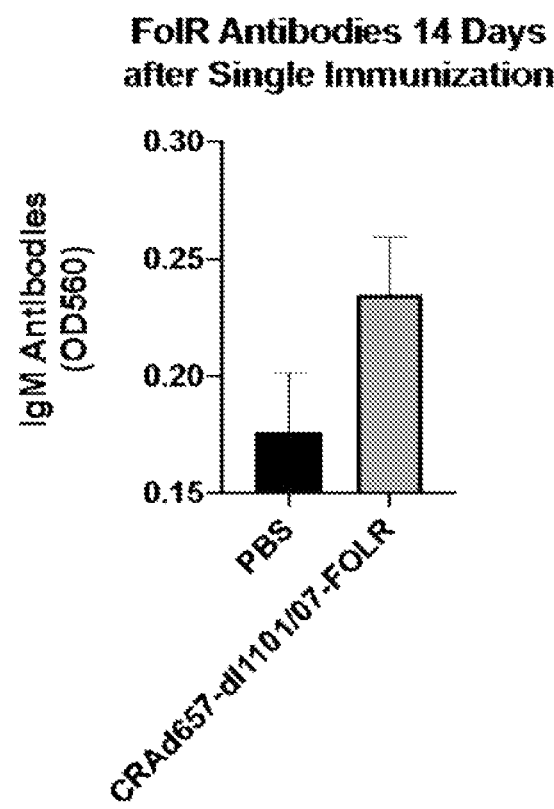
FIG. 53 demonstrates the production of antibody responses against the human cancer antigen folate receptor alpha after a single intramuscular immunization of BALB/c mice by CRAd657-dl1101/07-FOLR with an intact E3 region.

BALB/c mice were immunized with $10^{10}$ virus particles of CRAd-657-dl1101/1107-FolR with intact E3 and expressing the human folate receptor alpha or with PBS by the intramuscular route. Sera was collected 2 weeks after one immunization and analyzed for anti-Folate Receptor alpha antibodies by ELISA using anti-IgM antibody for detection (all antibodies are IgM at this type of early time point after immunization). Data shows the generation of antibodies against the known cancer antigen folate receptor alpha by this CRAd. p-0.07 by T test (FIG. 53).

Example 12. Effects of E3 Immune Evasion Genes on Oncolytic Activity

FIG. 57 shows as schematic of different E3 immune evasion genes in Ads. E3 19K protects infected cells from T cells and NK cells. RID proteins protect infected cells from death-inducing ligands (FAS, TRAIL, TNFR, and EGFR). 14.7K inhibits intrinsic activation of apoptosis in infected cells. Species C Ads also express the 11.6K known as the adenovirus death protein (ADP). Over-expression of ADP accelerates cell death, but overall cell death is equal. Species 49K binds to CD46 on T cells and NK cells leading to down-regulation of these cells and less-efficient cell killing of cells deficient in class I MHC by NK cells.

FIG. 58 demonstrates that partial deletion of E3 12.5K and full deletion of E3 6.7K, 19K, 11.6K (ADP), 10.4K (RIDα), 14.5K (RIDβ), and 14.7K genes reduces oncolytic efficacy in an immunocompetent hamster model of kidney cancer when these immune evasion genes are not present in oncolytic adenovirus.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method for treating cancer in a mammal, comprising administering to a mammal, a recombinant adenovirus (Ad) comprising capsid hexon polypeptides of an Ad strain Ad6 and at least two capsid hexon hypervariable region (HVR) polypeptides from Ad strain Ad57.

2. The method of claim 1, wherein the cancer is selected from the group consisting of prostate cancer, ovarian cancer, lung cancer, hepatocellular carcinoma, pancreatic cancer, kidney cancer, melanoma, brain cancer, colon cancer, lymphoma, myeloma, lymphocytic leukemia, and myelogenous leukemia.

3. The method of claim 1, wherein the administering comprises systemic administration.

4. The method of claim 3, wherein the systemic administration comprises intramuscular, intranasal, or intravenous administration.

5. The method of claim 1, wherein the administering comprises local administration.

6. The method of claim 5, wherein the local administration comprises intratumoral injection.

7. The method of claim 1, further comprising administering one or more additional agents used to treat cancer.

8. The method of claim 7, wherein the one or more additional agents used to treat cancer is selected from the group consisting of chemotherapy, hormone therapy, targeted therapy, and cytotoxic therapy.

9. The method of claim 1, wherein the recombinant Ad is a conditionally-replicating Adenovirus (CRAd) which has been modified in an E1A gene encoding an E1A polypeptide, wherein the CRAd exhibits amino acid substitutions in the E1A polypeptide relative to wild-type E1A polypeptide of an Ad strain.

10. The method of claim 9, wherein the recombinant Adenovirus (Ad) has been modified in an E1A gene to comprise a dl1101 deletion in a nucleic acid encoding an E1 polypeptide, modified to comprise a dl1107 deletion in a nucleic acid encoding an E1 polypeptide, or modified to comprise a dl1101 deletion and a dl1107 deletion in a nucleic acid encoding an E1 polypeptide.

11. The method of claim 9, wherein an N-terminal portion of the E1A polypeptide comprises an amino acid sequence set forth in SEQ ID NO:43, SEQ ID NO:44 or SEQ ID NO:45.

\* \* \* \* \*

SEQUENCE LISTING

```
Sequence total quantity: 78
SEQ ID NO: 1              moltype = AA   length = 12
FEATURE                   Location/Qualifiers
REGION                    1..12
                          note = targeting polypeptide
source                    1..12
                          mol_type = protein
                          organism = synthetic construct
SEQUENCE: 1
TARGEHKEEE LI                                                             12

SEQ ID NO: 2              moltype = AA   length = 12
FEATURE                   Location/Qualifiers
REGION                    1..12
                          note = targeting polypeptide
source                    1..12
                          mol_type = protein
                          organism = synthetic construct
SEQUENCE: 2
LRQTGAASAV WG                                                             12

SEQ ID NO: 3              moltype = AA   length = 12
FEATURE                   Location/Qualifiers
REGION                    1..12
                          note = targeting polypeptide
source                    1..12
                          mol_type = protein
                          organism = synthetic construct
SEQUENCE: 3
ARRADTQWRG LE                                                             12

SEQ ID NO: 4              moltype = AA   length = 19
FEATURE                   Location/Qualifiers
REGION                    1..19
                          note = targeting polypeptide
source                    1..19
                          mol_type = protein
                          organism = synthetic construct
SEQUENCE: 4
GTWLNPGFPP QSCGYATVT                                                      19

SEQ ID NO: 5              moltype = AA   length = 9
FEATURE                   Location/Qualifiers
REGION                    1..9
                          note = targeting polypeptide
source                    1..9
                          mol_type = protein
                          organism = synthetic construct
SEQUENCE: 5
CDCRGDCFC                                                                 9

SEQ ID NO: 6              moltype = AA   length = 10
FEATURE                   Location/Qualifiers
REGION                    1..10
                          note = targeting polypeptide
source                    1..10
                          mol_type = protein
                          organism = synthetic construct
SEQUENCE: 6
NMSLDVNRKA                                                                10

SEQ ID NO: 7              moltype = AA   length = 12
FEATURE                   Location/Qualifiers
REGION                    1..12
                          note = targeting polypeptide
source                    1..12
                          mol_type = protein
                          organism = synthetic construct
SEQUENCE: 7
ISLSSHRATW VV                                                             12

SEQ ID NO: 8              moltype = AA   length = 20
FEATURE                   Location/Qualifiers
```

-continued

```
REGION                    1..20
                          note = targeting polypeptide
source                    1..20
                          mol_type = protein
                          organism = synthetic construct
SEQUENCE: 8
WTMGLDQLRD SSWAHGGFSA                                                   20

SEQ ID NO: 9              moltype = AA  length = 20
FEATURE                   Location/Qualifiers
REGION                    1..20
                          note = targeting polypeptide
source                    1..20
                          mol_type = protein
                          organism = synthetic construct
SEQUENCE: 9
WTMGLDQLRG DSSWAHGGFS                                                   20

SEQ ID NO: 10             moltype = AA  length = 20
FEATURE                   Location/Qualifiers
REGION                    1..20
                          note = targeting polypeptide
source                    1..20
                          mol_type = protein
                          organism = synthetic construct
SEQUENCE: 10
RSVSGTEWVP MNEQHRGAIW                                                   20

SEQ ID NO: 11             moltype = AA  length = 20
FEATURE                   Location/Qualifiers
REGION                    1..20
                          note = targeting polypeptide
source                    1..20
                          mol_type = protein
                          organism = synthetic construct
SEQUENCE: 11
TELRTHTSKE LTIRTAASSD                                                   20

SEQ ID NO: 12             moltype = AA  length = 20
FEATURE                   Location/Qualifiers
REGION                    1..20
                          note = targeting polypeptide
source                    1..20
                          mol_type = protein
                          organism = synthetic construct
SEQUENCE: 12
DRAIGWQDKL YKLPLGSIHN                                                   20

SEQ ID NO: 13             moltype = AA  length = 20
FEATURE                   Location/Qualifiers
REGION                    1..20
                          note = targeting polypeptide
source                    1..20
                          mol_type = protein
                          organism = synthetic construct
SEQUENCE: 13
MGSWEKAALW NRVSASSGGA                                                   20

SEQ ID NO: 14             moltype = AA  length = 20
FEATURE                   Location/Qualifiers
REGION                    1..20
                          note = targeting polypeptide
source                    1..20
                          mol_type = protein
                          organism = synthetic construct
SEQUENCE: 14
MAMGGKPERP ADSDNVQVRG                                                   20

SEQ ID NO: 15             moltype = AA  length = 20
FEATURE                   Location/Qualifiers
REGION                    1..20
                          note = targeting polypeptide
source                    1..20
                          mol_type = protein
                          organism = synthetic construct
SEQUENCE: 15
MASRGDAGEG STQSNTNVPS                                                   20

SEQ ID NO: 16             moltype = AA  length = 20
```

```
FEATURE                 Location/Qualifiers
REGION                  1..20
                        note = targeting polypeptide
source                  1..20
                        mol_type = protein
                        organism = synthetic construct
SEQUENCE: 16
GPEDTSRAPE NQQKTFHRRW                                                      20

SEQ ID NO: 17           moltype = AA  length = 20
FEATURE                 Location/Qualifiers
REGION                  1..20
                        note = targeting polypeptide
source                  1..20
                        mol_type = protein
                        organism = synthetic construct
SEQUENCE: 17
MGREDVGEQK LISEEDLGGS                                                      20

SEQ ID NO: 18           moltype = AA  length = 11
FEATURE                 Location/Qualifiers
REGION                  1..11
                        note = targeting polypeptide
source                  1..11
                        mol_type = protein
                        organism = synthetic construct
SEQUENCE: 18
ACDCRGDCFC G                                                               11

SEQ ID NO: 19           moltype = AA  length = 12
FEATURE                 Location/Qualifiers
REGION                  1..12
                        note = targeting polypeptide
source                  1..12
                        mol_type = protein
                        organism = synthetic construct
SEQUENCE: 19
ACDCREDVCF CG                                                              12

SEQ ID NO: 20           moltype = AA  length = 20
FEATURE                 Location/Qualifiers
REGION                  1..20
                        note = targeting polypeptide
source                  1..20
                        mol_type = protein
                        organism = synthetic construct
SEQUENCE: 20
GQIPITEPEL CCVPWTEAFY                                                      20

SEQ ID NO: 21           moltype = AA  length = 20
FEATURE                 Location/Qualifiers
REGION                  1..20
                        note = targeting polypeptide
source                  1..20
                        mol_type = protein
                        organism = synthetic construct
SEQUENCE: 21
PQPPNSTAHP NPHKAPPNTT                                                      20

SEQ ID NO: 22           moltype = AA  length = 20
FEATURE                 Location/Qualifiers
REGION                  1..20
                        note = targeting polypeptide
source                  1..20
                        mol_type = protein
                        organism = synthetic construct
SEQUENCE: 22
VRWFPGGEWG VTHPESLPPP                                                      20

SEQ ID NO: 23           moltype = AA  length = 19
FEATURE                 Location/Qualifiers
REGION                  1..19
                        note = targeting polypeptide
source                  1..19
                        mol_type = protein
                        organism = synthetic construct
SEQUENCE: 23
KKKKKKKKKK KKKKKKKKK                                                       19
```

-continued

| | | |
|---|---|---|
| SEQ ID NO: 24 | moltype = AA  length = 14 | |
| FEATURE | Location/Qualifiers | |
| REGION | 1..14 | |
| | note = targeting polypeptide | |
| source | 1..14 | |
| | mol_type = protein | |
| | organism = synthetic construct | |
| SEQUENCE: 24 | | |
| GLNDIFEAQK IEWH | | 14 |
| | | |
| SEQ ID NO: 25 | moltype = AA  length = 23 | |
| FEATURE | Location/Qualifiers | |
| REGION | 1..23 | |
| | note = targeting polypeptide | |
| source | 1..23 | |
| | mol_type = protein | |
| | organism = synthetic construct | |
| SEQUENCE: 25 | | |
| CAAARWKKAF IAVSAANRFK KIS | | 23 |
| | | |
| SEQ ID NO: 26 | moltype = AA  length = 14 | |
| FEATURE | Location/Qualifiers | |
| REGION | 1..14 | |
| | note = targeting polypeptide | |
| source | 1..14 | |
| | mol_type = protein | |
| | organism = synthetic construct | |
| SEQUENCE: 26 | | |
| EDPGFFNVEI PEFP | | 14 |
| | | |
| SEQ ID NO: 27 | moltype = AA  length = 20 | |
| FEATURE | Location/Qualifiers | |
| REGION | 1..20 | |
| | note = targeting polypeptide | |
| source | 1..20 | |
| | mol_type = protein | |
| | organism = synthetic construct | |
| SEQUENCE: 27 | | |
| GGHGRVLWPD GWFSLVGISP | | 20 |
| | | |
| SEQ ID NO: 28 | moltype = AA  length = 21 | |
| FEATURE | Location/Qualifiers | |
| REGION | 1..21 | |
| | note = targeting polypeptide | |
| source | 1..21 | |
| | mol_type = protein | |
| | organism = synthetic construct | |
| SEQUENCE: 28 | | |
| MARTVTANVP GMGEGMVVVP C | | 21 |
| | | |
| SEQ ID NO: 29 | moltype = AA  length = 20 | |
| FEATURE | Location/Qualifiers | |
| REGION | 1..20 | |
| | note = targeting polypeptide | |
| source | 1..20 | |
| | mol_type = protein | |
| | organism = synthetic construct | |
| SEQUENCE: 29 | | |
| GVSKRGLQCH DFISCSGVPW | | 20 |
| | | |
| SEQ ID NO: 30 | moltype = AA  length = 20 | |
| FEATURE | Location/Qualifiers | |
| REGION | 1..20 | |
| | note = targeting polypeptide | |
| source | 1..20 | |
| | mol_type = protein | |
| | organism = synthetic construct | |
| SEQUENCE: 30 | | |
| NQSIPKVAGD SKVFCWWCAL | | 20 |
| | | |
| SEQ ID NO: 31 | moltype = AA  length = 20 | |
| FEATURE | Location/Qualifiers | |
| REGION | 1..20 | |
| | note = targeting polypeptide | |
| source | 1..20 | |
| | mol_type = protein | |
| | organism = synthetic construct | |
| SEQUENCE: 31 | | |
| QSTPPTKHLT IPRHLRNTLI | | 20 |

-continued

```
SEQ ID NO: 32            moltype = AA   length = 20
FEATURE                  Location/Qualifiers
REGION                   1..20
                         note = targeting polypeptide
source                   1..20
                         mol_type = protein
                         organism = synthetic construct
SEQUENCE: 32
DMSFQLVTPF LKALPTGWRG                                                      20

SEQ ID NO: 33            moltype = AA   length = 20
FEATURE                  Location/Qualifiers
REGION                   1..20
                         note = targeting polypeptide
source                   1..20
                         mol_type = protein
                         organism = synthetic construct
SEQUENCE: 33
GGHGRVLWPD GWFSLVGISP                                                      20

SEQ ID NO: 34            moltype = AA   length = 8
FEATURE                  Location/Qualifiers
REGION                   1..8
                         note = targeting polypeptide
source                   1..8
                         mol_type = protein
                         organism = synthetic construct
SEQUENCE: 34
FSLVGISP                                                                    8

SEQ ID NO: 35            moltype = AA   length = 20
FEATURE                  Location/Qualifiers
REGION                   1..20
                         note = targeting polypeptide
source                   1..20
                         mol_type = protein
                         organism = synthetic construct
SEQUENCE: 35
QIMMGPSLGY YMPSESIFAY                                                      20

SEQ ID NO: 36            moltype = AA   length = 20
FEATURE                  Location/Qualifiers
REGION                   1..20
                         note = targeting polypeptide
source                   1..20
                         mol_type = protein
                         organism = synthetic construct
SEQUENCE: 36
ISWDIWRWWY TSEDRDAGSA                                                      20

SEQ ID NO: 37            moltype = AA   length = 20
FEATURE                  Location/Qualifiers
REGION                   1..20
                         note = targeting polypeptide
source                   1..20
                         mol_type = protein
                         organism = synthetic construct
SEQUENCE: 37
VWGMTTSDHQ RKTERLDSPE                                                      20

SEQ ID NO: 38            moltype = AA   length = 20
FEATURE                  Location/Qualifiers
REGION                   1..20
                         note = targeting polypeptide
source                   1..20
                         mol_type = protein
                         organism = synthetic construct
SEQUENCE: 38
MTSAQTSEKL KAETDRHTAE                                                      20

SEQ ID NO: 39            moltype = AA   length = 19
FEATURE                  Location/Qualifiers
REGION                   1..19
                         note = targeting polypeptide
source                   1..19
                         mol_type = protein
                         organism = synthetic construct
SEQUENCE: 39
```

```
MGSRSAVGDF ESAEGSRRP                                                    19

SEQ ID NO: 40            moltype = AA   length = 20
FEATURE                  Location/Qualifiers
REGION                   1..20
                         note = targeting polypeptide
source                   1..20
                         mol_type = protein
                         organism = synthetic construct
SEQUENCE: 40
MGRTVQSGDG TPAQTQPSVN                                                   20

SEQ ID NO: 41            moltype = AA   length = 20
FEATURE                  Location/Qualifiers
REGION                   1..20
                         note = targeting polypeptide
source                   1..20
                         mol_type = protein
                         organism = synthetic construct
SEQUENCE: 41
MARTVTANVP GMGEGMVVVP                                                   20

SEQ ID NO: 42            moltype = AA   length = 132
FEATURE                  Location/Qualifiers
REGION                   1..132
                         note = Adenovirus E1A N-terminus polypeptide
source                   1..132
                         mol_type = protein
                         organism = synthetic construct
SEQUENCE: 42
MRHIICHGGV ITEEMAASLL DQLIEEVLAD NLPPPSHFEP PTLHELYDLD VTAPEDPNEE        60
AVSQIFPESV MLAVQEGIDL FTFPPAPGSP EPPHLSRQPE QPEQRALGPV SMPNLVPEVI       120
DLTCHEAGFP PS                                                          132

SEQ ID NO: 43            moltype = AA   length = 112
FEATURE                  Location/Qualifiers
REGION                   1..112
                         note = E1A N-terminus polypeptide
source                   1..112
                         mol_type = protein
                         organism = synthetic construct
SEQUENCE: 43
MRHIEEVLAD NLPPPSHFEP PTLHELYDLD VTAPEDPNEE AVSQIFPESV MLAVQEGIDL        60
FTFPPAPGSP EPPHLSRQPE QPEQRALGPV SMPNLVPEVI DLTCHEAGFP PS               112

SEQ ID NO: 44            moltype = AA   length = 119
FEATURE                  Location/Qualifiers
REGION                   1..119
                         note = E1A N-terminus polypeptide
source                   1..119
                         mol_type = protein
                         organism = synthetic construct
SEQUENCE: 44
MRHIICHGGV ITEEMAASLL DQLIEEVLAD NLPPPSHFEP PTLHELYDLD VTAPEDPNEE        60
AVSQIFPESV MLAVQEGIDL FTFPPAPGSP EPPHLSRQPE QPEQRALGPV CHEAGFPPS       119

SEQ ID NO: 45            moltype = AA   length = 99
FEATURE                  Location/Qualifiers
REGION                   1..99
                         note = E1A N-terminus polypeptide
source                   1..99
                         mol_type = protein
                         organism = synthetic construct
SEQUENCE: 45
MRHIEEVLAD NLPPPSHFEP PTLHELYDLD VTAPEDPNEE AVSQIFPESV MLAVQEGIDL        60
FTFPPAPGSP EPPHLSRQPE QPEQRALGPV CHEAGFPPS                              99

SEQ ID NO: 46            moltype = AA   length = 5
FEATURE                  Location/Qualifiers
REGION                   1..5
                         note = Cell Binding Peptide
source                   1..5
                         mol_type = protein
                         organism = synthetic construct
SEQUENCE: 46
REDVY                                                                    5

SEQ ID NO: 47            moltype = AA   length = 12
FEATURE                  Location/Qualifiers
```

```
REGION                    1..12
                          note = Breast Cancer Binding Peptide
source                    1..12
                          mol_type = protein
                          organism = synthetic construct
SEQUENCE: 47
ISLSSHRATW VV                                                       12

SEQ ID NO: 48             moltype = DNA  length = 1608
FEATURE                   Location/Qualifiers
misc_feature              1..1608
                          note = Probasin-E1 nucleic acid
source                    1..1608
                          mol_type = other DNA
                          organism = synthetic construct
SEQUENCE: 48
tcgagcgacg gtatcgataa gcttggagct tatgatagca tcttgttctt agtcttttc     60
ttaataggga cataaagccc acaaataaaa atatgcctga agaatgggac aggcattggg   120
cattgtccat gcctagtaaa gtactccaag aacctatttg tatactagat gacacaatgt   180
tctagccaag cttggtagtc atcatgttta aacatctacc attccagtta agaaaatatg   240
atagcatctt gttcttagtc tttttcttaa tagggacata aagcccacaa ataaaaatat   300
gcctgaagaa tgggacaggc attgggcatt gtccatgcct agtaaagtac tccaagaacc   360
tatttgtata ctagatgaca caatgtcaat gtctgtgtac aactgccaac tgggatgcaa   420
gacactgccc atgccaatca tcctgaaaag cagctataaa aagcaggaag ctactctgca   480
ccttgtcagt gaggtccaga tacctccctc gagcggccgc gacgcgcagt gtatttatac   540
ccggtgagtt cctcaagagg ccactcttga gtgccagcga gtagagtttt ctcctccgga   600
ccgctccgac accgggactg aaaatgagac atattatctg ccacggaggt gttattaccg   660
aagaaatggc cgccagtctt ttggaccagc tgatcgaaga ggtactggct gataatcttc   720
cacctcctag ccattttgaa ccacctaccc ttcacgaact gtatgattta acgtgacgg    780
ccccgaaga tcccaacgag gaggcggttt cgcagatttt cccgagtct gtaatgttcgc    840
cggtgcagga agggattgac ttattcactt ttccgccggc gcccggttct ccggagccgc   900
ctcacctttc ccggcagccc gagcagcgg agcagagagc cttgggtccg gtttctatgc     960
caaaccttgt gccggaggtg atcgatctta cctgccacga ggctggcttt ccacccagtg   1020
acgacgagga tgaagagggt gaggagtttg tgttagatta tgtggagcac cccgggcacg   1080
gttgcaggtc ttgtcattat caccggagga atacggggga cccagatatt atgtgttcgc   1140
tttgctatat gaggacctgt ggcatgtttt tctacagtaa gtgaaaatta tgggcagtcg   1200
gtgatagagt ggtgggtttg gtgtggtaat ttttttttaa ttttttacagt tttgtggttt   1260
aaagaatttt gtattctgat ttttttaaaag gtcctgtgtc tgaacctgag cctgagcccg   1320
agccagaacc ggagcctgca agacctaccc ggcgtcctaa attggtgcct gctatcctga   1380
gacgcccgac atcacctgtg tctagagaat gcaatagtag tacggatagc tgtgactccg   1440
gtccttctaa cacacctcct gagatacacc cggtggtccc gctgtgcccc attaaaccag   1500
ttgccgtgag agttggtggg cgtcgccagg ctgtggaatg tatcgaggac ttgcttaacg   1560
agtctgggca acctttggac ttgagctgta aacgccccag gccataag                1608

SEQ ID NO: 49             moltype = AA  length = 959
FEATURE                   Location/Qualifiers
REGION                    1..959
                          note = Hexon Polypeptide
source                    1..959
                          mol_type = protein
                          organism = synthetic construct
SEQUENCE: 49
MATPSMMPQW SYMHISGQDA SEYLSPGLVQ FARATETYFS LNNKFRNPTV APTHDVTTDR    60
SQRLTLRFIP VDREDTAYSY KARFTLAVGD NRVLDMASTY FDIRGVLDRG PTFKPYSGTA   120
YNALAPKGAP NSCEWDEDDT QVQVAAEDDQ DDDEEEEQLP QQRNGKKTHV YAQAPFGEA    180
INKNGLQIGT NGAATEGNKE IYADKTYQPE PQIGESQWNE AESSVAGGRV LKKTTPMKPC   240
YGSYARPTNS NGGQGVMVEQ NGKLESQVEM QFFSTSVNAM NEANAIQPKL VLYSEDVNME   300
TPDTHLSYKP GKSDDNSKAM LGQQSMPNRP NYIAFRDNFI GLMYYNSTGN MGVLAGQASQ   360
LNAVVDLQDR NTELSYQLLL DSIGDRTRYF SMWNQAVDSY DPDVRIIENH GTEDELPNYC   420
FPLGGIGVTD TYQAIKATNG NGGATTWAQD NTFAERNEIG VGNNFAMEIN LNANLWRNFL   480
YSNIALYLPD KLKYNPTNVE ISDNPNTYDY MNKRVVAPGL VDCYINLGAR WSLDYMDNVN   540
PFNHHRNAGL RYRSMLLGNG RYVPFHIQVP QKFFAIKNLL LLPGSYTYEW NFRKDVNMVL   600
QSSLGNDLRV DGASIKFDSI CLYATFFPMA HNTASTLEAM LRNDTNDQSF NDYLSAANML   660
YPIPANATNV PISIPSRNWA AFRGWAFTRL KTKETPSLGS GYDPYYTYSG SIPYLDGTFY   720
LNHTFKKVAI TFDSSVSWPG NDRLLTPNEF EIKRSVDGEG YNVAQCNMTK DWFLVQMLAN   780
YNIGYQGFYI PESYKDRMYS FFRNFQPMSR QVVDDTKYKD YQQVGIIHQH NNSGFVGYLA   840
PTMREGQAYP ANVPYPLIGK TAVDSITQKK FLCDRTLWRI PFSSNFMSMG ALTDLGQNLL   900
YANSAHALDM TFEVDPMDEP TLLYVLFEVF DVVRVHQPHR GVIETVYLRT PFSAGNATT    959

SEQ ID NO: 50             moltype = AA  length = 967
FEATURE                   Location/Qualifiers
REGION                    1..967
                          note = Hexon Polypeptide
source                    1..967
                          mol_type = protein
                          organism = synthetic construct
SEQUENCE: 50
MATPSMMPQW SYMHISGQDA SEYLSPGLVQ FARATETYFS LNNKFRNPTV APTHDVTTDR    60
SQRLTLRFIP VDREDTAYSY KARFTLAVGD NRVLDMASTY FDIRGVLDRG PTFKPYSGTA   120
```

```
YNALAPKGAP  NSCEWDEDDT  QVQVAAEDDQ  DDDSSCSSGG  TEEEEQLPQQ  RNGKKTHVYA   180
QAPFAGEAIN  KNGLQIGTNG  AATEGNKEIY  ADKTYQPEPQ  IGESQWNEAE  SSVAGGRVLK   240
KTTPMKPCYG  SYARPTNSNG  GQGVMVEQNG  KLESQVEMQF  FSTSVNAMNE  ANAIQPKLVL   300
YSEDVNMETP  DTHLSYKPGK  SDDNSKAMLG  QQSMPNRPNY  IAFRDNFIGL  MYYNSTGNMG   360
VLAGQASQLN  AVVDLQDRNT  ELSYQLLLDS  IGDRTRYFSM  WNQAVDSYDP  DVRIIENHGT   420
EDELPNYCFP  LGGIGVTDTY  QAIKATNGNG  GATTWAQDNT  FAERNEIGVG  NNFAMEINLN   480
ANLWRNFLYS  NIALYLPDKL  KYNPTNVEIS  DNPNTYDYMN  KRVVAPGLVD  CYINLGARWS   540
LDYMDNVNPF  NHHRNAGLRY  RSMLLGNGRY  VPFHIQVPQK  FFAIKNLLLL  PGSYTYEWNF   600
RKDVNMVLQS  SLGNDLRVDG  ASIKFDSICL  YATFFPMAHN  TASTLEAMLR  NDTNDQSFND   660
YLSAANMLYP  IPANATNVPI  SIPSRNWAAF  RGWAFTRLKT  KETPSLGSGY  DPYYTYSGSI   720
PYLDGTFYLN  HTFKKVAITF  DSSVSWPGND  RLLTPNEFEI  KRSVDGEGYN  VAQCNMTKDW   780
FLVQMLANYN  IGYQGFYIPE  SYKDRMYSFF  RNFQPMSRQV  VDDTKYKDYQ  QVGIIHQHNN   840
SGFVGYLAPT  MREGQAYPAN  VPYPLIGKTA  VDSITQKKFL  CDRTLWRIPF  SSNFMSMGAL   900
TDLGQNLLYA  NSAHALDMTF  EVDPMDEPTL  LYVLFEVFDV  VRVHQPHRGV  IETVYLRTPF   960
SAGNATT                                                                 967

SEQ ID NO: 51           moltype = AA  length = 955
FEATURE                 Location/Qualifiers
REGION                  1..955
                        note = Hexon Polypeptide
source                  1..955
                        mol_type = protein
                        organism = synthetic construct
SEQUENCE: 51
MATPSMMPQW  SYMHISGQDA  SEYLSPGLVQ  FARATETYFS  LNNKFRNPTV  APTHDVTTDR   60
SQRLTLRFIP  VDREDTAYSY  KARFTLAVGD  NRVLDMASTY  FDIRGVLDRG  PTFKPYSGTA   120
YNALAPKGAP  NSCEWDEDDT  QVQVAAEDDQ  DDDEEEQLP   QQRNGKKTHV  YAQAPFAGEA   180
INKNGLQIGT  NGAATEGNKE  IYADKTYQPE  PQIGESQWNE  AESSVAGGRV  LKKTTPMKPC   240
YGSYARPTNS  NGGQGVMVEQ  NGKLESQVEM  QFFSTSSCSS  GGTPKLVLYS  EDVNMETPDT   300
HLSYKPGKSD  DNSKAMLGQQ  SMPNRPNYIA  FRDNFIGLMY  YNSTGNMGVL  AGQASQLNAV   360
VDLQDRNTEL  SYQLLLDSIG  DRTRYFSMWN  QAVDSYDPDV  RIIENHGTED  ELPNYCFPLG   420
GIGVTDTYQA  IKATNGNGGA  TTWAQDNTFA  ERNEIGVGNN  FAMEINLNAN  LWRNFLYSNI   480
ALYLPDKLKY  NPTNVEISDN  PNTYDYMNKR  VVAPGLVDCY  INLGARWSLD  YMDNVNPFNH   540
HRNAGLRYRS  MLLGNGRYVP  FHIQVPQKFF  AIKNLLLLPG  SYTYEWNFRK  DVNMVLQSSL   600
GNDLRVDGAS  IKFDSICLYA  TFFPMAHNTA  STLEAMLRND  TNDQSFNDYL  SAANMLYPIP   660
ANATNVPISI  PSRNWAAFRG  WAFTRLKTKE  TPSLGSGYDP  YYTYSGSIPY  LDGTFYLNHT   720
FKKVAITFDS  SVSWPGNDRL  LTPNEFEIKR  SVDGEGYNVA  QCNMTKDWFL  VQMLANYNIG   780
YQGFYIPESY  KDRMYSFFRN  FQPMSRQVVD  DTKYKDYQQV  GIIHQHNNSG  FVGYLAPTMR   840
EGQAYPANVP  YPLIGKTAVD  SITQKKFLCD  RTLWRIPFSS  NFMSMGALTD  LGQNLLYANS   900
AHALDMTFEV  DPMDEPTLLY  VLFEVFDVVR  VHQPHRGVIE  TVYLRTPFSA  GNATT        955

SEQ ID NO: 52           moltype = AA  length = 964
FEATURE                 Location/Qualifiers
REGION                  1..964
                        note = Hexon Polypeptide
source                  1..964
                        mol_type = protein
                        organism = synthetic construct
SEQUENCE: 52
MATPSMMPQW  SYMHISGQDA  SEYLSPGLVQ  FARATETYFS  LNNKFRNPTV  APTHDVTTDR   60
SQRLTLRFIP  VDREDTAYSY  KARFTLAVGD  NRVLDMASTY  FDIRGVLDRG  PTFKPYSGTA   120
YNALAPKGAP  NSCEWDEDDT  QVQVAAEDDQ  DDDSSGGTEE  EEQLPQQRNG  KKTHVYAQAP   180
FAGEAINKNG  LQIGTNGAAT  EGNKEIYADK  TYQPEPQIGE  SQWNEAESSV  AGGRVLKKTT   240
PMKPCYGSYA  RPTNSNGGQG  VMVEQNGKLE  SQVEMQFFST  SVNAMNEANA  IQPKLVLYSE   300
DVNMETPDTH  LSYKPGKSDD  NSKAMLGQQS  MPNRPNYIAF  RDNFIGLMYY  NSTGNMVLA    360
GQASQLNAVV  DLQDRNTELS  YQLLLDSIGD  RTRYFSMWNQ  AVDSYDPDVR  IIENHGTEDE   420
LPNYCFPLGG  IGVTDTYQAI  KATNGNGGAT  TWAQDNTFAE  RNEIGVGNNF  AMEINLNANL   480
WRNFLYSNIA  LYLPDKLKYN  PTNVEISDNP  NTYDYMNKRV  VAPGLVDCYI  NLGARWSLDY   540
MDNVNPFNHH  RNAGLRYRSM  LLGNGRYVPF  HIQVPQKFFA  IKNLLLLPGS  YTYEWNFRKD   600
VNMVLQSSLG  NDLRVDGASI  KFDSICLYAT  FFPMAHNTAS  TLEAMLRNDT  NDQSFNDYLS   660
AANMLYPIPA  NATNVPISIP  SRNWAAFRGW  AFTRLKTKET  PSLGSGYDPY  YTYSGSIPYL   720
DGTFYLNHTF  KKVAITFDSS  VSWPGNDRLL  TPNEFEIKRS  VDGEGYNVAQ  CNMTKDWFLV   780
QMLANYNIGY  QGFYIPESYK  DRMYSFFRNF  QPMSRQVVDD  TKYKDYQQVG  IIHQHNNSGF   840
VGYLAPTMRE  GQAYPANVPY  PLIGKTAVDS  ITQKKFLCDR  TLWRIPFSSN  FMSMGALTDL   900
GQNLLYANSA  HALDMTFEVD  PMDEPTLLYV  LFEVFDVVRV  HQPHRGVIET  VYLRTPFSAG   960
NATT                                                                    964

SEQ ID NO: 53           moltype = AA  length = 952
FEATURE                 Location/Qualifiers
REGION                  1..952
                        note = Hexon Polypeptide
source                  1..952
                        mol_type = protein
                        organism = synthetic construct
SEQUENCE: 53
MATPSMMPQW  SYMHISGQDA  SEYLSPGLVQ  FARATETYFS  LNNKFRNPTV  APTHDVTTDR   60
SQRLTLRFIP  VDREDTAYSY  KARFTLAVGD  NRVLDMASTY  FDIRGVLDRG  PTFKPYSGTA   120
YNALAPKGAP  NSCEWDEDDT  QVQVAAEDDQ  DDDEEEQLP   QQRNGKKTHV  YAQAPFAGEA   180
INKNGLQIGT  NGAATEGNKE  IYADKTYQPE  PQIGESQWNE  AESSVAGGRV  LKKTTPMKPC   240
```

```
YGSYARPTNS NGGQGVMVEQ NGKLESQVEM QFFSTSSGGT PKLVLYSEDV NMETPDTHLS    300
YKPGKSDDNS KAMLGQQSMP NRPNYIAFRD NFIGLMYYNS TGNMGVLAGQ ASQLNAVVDL    360
QDRNTELSYQ LLLDSIGDRT RYFSMWNQAV DSYDPDVRII ENHGTEDELP NYCFPLGGIG    420
VTDTYQAIKA TNGNGGATTW AQDNTFAERN EIGVGNNFAM EINLNANLWR NFLYSNIALY    480
LPDKLKYNPT NVEISDNPNT YDYMNKRVVA PGLVDCYINL GARWSLDYMD NVNPFNHHRN    540
AGLRYRSMLL GNGRYVPFHI QVPQKFFAIK NLLLLPGSYT YEWNFRKDVN MVLQSSLGND    600
LRVDGASIKF DSICLYATFF PMAHNTASTL EAMLRNDTND QSFNDYLSAA NMLYPIPANA    660
TNVPISIPSR NWAAFRGWAF TRLKTKETPS LGSGYDPYYT YSGSIPYLDG TFYLNHTFKK    720
VAITFDSSVS WPGNDRLLTP NEFEIKRSVD GEGYNVAQCN MTKDWFLVQM LANYNIGYQG    780
FYIPESYKDR MYSFFRNFQP MSRQVVDDTK YKDYQQVGII HQHNNSGFVG YLAPTMREGQ    840
AYPANVPYPL IGKTAVDFSIT QKKFLCDRTL WRIPFSSNFM SMGALTDLGQ NLLYANSAHA    900
LDMTFEVDPM DEPTLLYVLF EVFDVVRVHQ PHRGVIETVY LRTPFSAGNA TT            952

SEQ ID NO: 54           moltype = AA   length = 1033
FEATURE                 Location/Qualifiers
REGION                  1..1033
                        note = Hexon Polypeptide
source                  1..1033
                        mol_type = protein
                        organism = synthetic construct
SEQUENCE: 54
MATPSMMPQW SYMHISGQDA SEYLSPGLVQ FARATETYFS LNNKFRNPTV APTHDVTTDR     60
SQRLTLRFIP VDREDTAYSY KARFTLAVGD NRVLDMASTY FDIRGVLDRG PTFKPYSGTA    120
YNALAPKGAP NSCEWDEDDT QVQVAAEDDQ DDDSTGEIPA PLAGTVSKIL VKEGDTVKAG    180
QTVLVLEAMK METEINAPTD GKVEKVLVKE RDAVQGGQGL IKIGGGTEEE EQLPQQRNGK    240
KTHVYAQAPF AGEAINKNGL QIGTNGAATE GNKEIYADKT YQPEPQIGES QWNEAESSVA    300
GGRVLKKTTP MKPCYGSYAR PTNSNGGQGV MVEQNGKLES QVEMQFFSTS VNAMNEANAI    360
QPKLVLYSED VNMETPDTHL SYKPGKSDDN SKAMLGQQSM PNRPNYIAFR DNFIGLMYYN    420
STGNMGVLAG QASQLNAVVD LQDRNTELSY QLLLDSIGDR TRYFSMWNQA VDSYDPDVRI    480
IENHGTEDEL PNYCFPLGGI GVTDTYQAIK ATNGNGGATT WAQDNTFAER NEIGVGNNFA    540
MEINLNANLW RNFLYSNIAL YLPDKLKYNP TNVEISDNPN TYDYMNKRVV APGLVDCYIN    600
LGARWSLDYM DNVNPFNHHR NAGLRYRSML GNGRYVPFH IQVPQKFFAI KNLLLLPGSY    660
TYEWNFRKDV NMVLQSSLGN DLRVDGASIK FDSICLYATF FPMAHNTAST LEAMLRNDTN    720
DQSFNDYLSA ANMLYPIPAN ATNVPISIPS RNWAAFRGWA FTRLKTKETP SLGSGYDPYY    780
TYSGSIPYLD GTFYLNHTFK KVAITFDSSV SWPGNDRLLT PNEFEIKRSV DGEGYNVAQC    840
NMTKDWFLVQ MLANYNIGYQ GFYIPESYKD RMYSFFRNFQ PMSRQVVDDT KYKDYQQVGI    900
IHQHNNSGFV GYLAPTMREG QAYPANVPYP LIGKTAVDSI TQKKFLCDRT LWRIPFSSNF    960
MSMGALTDLG QNLLYANSAH ALDMTFEVDP MDEPTLLYVL FEVFDVVRVH QPHRGVIETV   1020
YLRTPFSAGN ATT                                                     1033

SEQ ID NO: 55           moltype = AA   length = 1021
FEATURE                 Location/Qualifiers
REGION                  1..1021
                        note = Hexon Polypeptide
source                  1..1021
                        mol_type = protein
                        organism = synthetic construct
SEQUENCE: 55
MATPSMMPQW SYMHISGQDA SEYLSPGLVQ FARATETYFS LNNKFRNPTV APTHDVTTDR     60
SQRLTLRFIP VDREDTAYSY KARFTLAVGD NRVLDMASTY FDIRGVLDRG PTFKPYSGTA    120
YNALAPKGAP NSCEWDEDDT QVQVAAEDDQ DDDEEEEQLP QQRNGKKTHV YAQAPFAGEA    180
INKNGLQIGT NGAATEGNKE IYADKTYQPE PQIGESQWNE AESSVAGGRV LKKTTPMKPC    240
YGSYARPTNS NGGQGVMVEQ NGKLESQVEM QFFSTSTGEI PAPLAGTVSK ILVKEGDTVK    300
AGQTVLVLEA MKMETEINAP TDGKVEKVLV KERDAVQGGQ GLIKIGGGTP KLVLYSEDVN    360
METPDTHLSY KPGKSDDNSK AMLGQQSMPN RPNYIAFRDN FIGLMYYNST GNMGVLAGQA    420
SQLNAVVDLQ DRNTELSYQL LLDSIGDRTR YFSMWNQAVD SYDPDVRIIE NHGTEDELPN    480
YCFPLGGIGV TDTYQAIKAT NGNGGATTWA QDNTFAERNE IGVGNNFAME INLNANLWRN    540
FLYSNIALYL PDKLKYNPTN VEISDNPNTY DYMNKRVVAP GLVDCYINLG ARWSLDYMDN    600
VNPFNHHRNA GLRYRSMLLG NGRYVPFHIQ VPQKFFAIKN LLLLPGSYTY EWNFRKDVNM    660
VLQSSLGNDL RVDGASIKFD SICLYATFFP MAHNTASTLE AMLRNDTNDQ SFNDYLSAAN    720
MLYPIPANAT NVPISIPSRN WAAFRGWAFT RLKTKETPSL GSGYDPYYTY SGSIPYLDGT    780
FYLNHTFKKV AITFDSSVSW PGNDRLLTPN EFEIKRSVDG EGYNVAQCNM TKDWFLVQML    840
ANYNIGYQGF YIPESYKDRM YSFFRNFQPM SRQVVDDTKY KDYQQVGIIH QHNNSGFVGY    900
LAPTMREGQA YPANVPYPLI GKTAVDSITQ KKFLCDRTLW RIPFSSNFMS MGALTDLGQN    960
LLYANSAHAL DMTFEVDPMD EPTLLYVLFE VFDVVRVHQP HRGVIETVYL RTPFSAGNAT   1020
T                                                                  1021

SEQ ID NO: 56           moltype = AA   length = 1015
FEATURE                 Location/Qualifiers
REGION                  1..1015
                        note = Hexon Polypeptide
source                  1..1015
                        mol_type = protein
                        organism = synthetic construct
SEQUENCE: 56
MATPSMMPQW SYMHISGQDA SEYLSPGLVQ FARATETYFS LNNKFRNPTV APTHDVTTDR     60
SQRLTLRFIP VDREDTAYSY KARFTLAVGD NRVLDMASTY FDIRGVLDRG PTFKPYSGTA    120
YNALAPKGAP NSCEWDEDDT QVQVAAEDDQ DDDEEEEQLP QQRNGKKTHV YAQAPFAGEA    180
INKNGLQIGT NGAATEGNKE IYADKTYQPE PQIGESQWNE AESSVAGGRV LKKTTPMKPC    240
```

```
YGSYARPTNS NGGQGVMVEQ NGKLESQVEM QFFSTSSSNF TREGNVTYKE EMDKVKNCSF        300
NVTTGIRDKK QKVNALFYRL DITPLDENNN NSSEYRLINS GGTPKLVLYS EDVNMETPDT        360
HLSYKPGKSD DNSKAMLGQQ SMPNRPNYIA FRDNFIGLMY YNSTGNMGVL AGQASQLNAV        420
VDLQDRNTEL SYQLLLDSIG DRTRYFSMWN QAVDSYDPDV RIIENHGTED ELPNYCFPLG        480
GIGVTDTYQA IKATNGNGGA TTWAQDNTFA ERNEIGVGNN FAMEINLNAN LWRNFLYSNI        540
ALYLPDKLKY NPTNVEISDN PNTYDYMNKR VVAPGLVDCY INLGARWSLD YMDNVNPFNH        600
HRNAGLRYRS MLLGNGRYVP FHIQVPQKFF AIKNLLLLPG SYTYEWNFRK DVNMVLQSSL        660
GNDLRVDGAS IKFDSICLYA TFFPMAHNTA STLEAMLRND TNDQSFNDYL SAANMLYPIP        720
ANATNVPISI PSRNWAAFRG WAFTRLKTKE TPSLGSGYDP YYTYSGSIPY LDGTFYLNHT        780
FKKVAITFDS SVSWPGNDRL LTPNEFEIKR SVDGEGYNVA QCNMTKDWFL VQMLANYNIG        840
YQGFYIPESY KDRMYSFFRN FQPMSRQVVD DTKYKDYQQV GIIHQHNNSG FVGYLAPTMR        900
EGQAYPANVP YPLIGKTAVD SITQKKFLCD RTLWRIPFSS NFMSMGALTD LGQNLLYANS        960
AHALDMTFEV DPMDEPTLLY VLFEVFDVVR VHQPHRGVIE TVYLRTPFSA GNATT           1015

SEQ ID NO: 57           moltype = AA  length = 987
FEATURE                 Location/Qualifiers
REGION                  1..987
                        note = Hexon Polypeptide
source                  1..987
                        mol_type = protein
                        organism = synthetic construct
SEQUENCE: 57
MATPSMMPQW SYMHISGQDA SEYLSPGLVQ FARATETYFS LNNKFRNPTV APTHDVTTDR         60
SQRLTLRFIP VDREDTAYSY KARFTLAVGD NRVLDMASTY FDIRGVLDRG PTFKPYSGTA        120
YNALAPKGAP NSCEWDEDDT QVQVAAEDDQ DDDEEEEQLP QQRNGKKTHV YAQAPFAGEA        180
INKNGLQIGT NGAATEGNKE IYADKTYQPE PQIGESQWNE AESSVAGGRV LKKTTPMKPC        240
YGSYARPTNS NGGQGVMVEQ NGKLESQVEM QFFSTSSQAE PDRAHYNIVT FCCKCDQLLR        300
REVYDFAFRD LSGGTPKLVL YSEDVNMETP DTHLSYKPGK SDDNSKAMLG QQSMPNRPNY        360
IAFRDNFIGL MYYNSTGNMG VLAGQASQLN AVVDLQDRNT ELSYQLLLDS IGDRTRYFSM        420
WNQAVDSYDP DVRIIENHGT EDELPNYCFP LGGIGVTDTY QAIKATNGNG GATTWAQDNT        480
FAERNEIGVG NNFAMEINLN ANLWRNFLYS NIALYLPDKL KYNPTNVEIS DNPNTYDYMN        540
KRVVAPGLVD CYINLGARWS LDYMDNVNPF NHHRNAGLRY RSMLLGNGRY VPFHIQVPQK        600
FFAIKNLLLL PGSYTYEWNF RKDVNMVLQS SLGNDLRVDG ASIKFDSICL YATFFPMAHN        660
TASTLEAMLR NDTNDQSFND YLSAANMLYP IPANATNVPI SIPSRNWAAF RGWAFTRLKT        720
KETPSLGSGY DPYYTYSGSI PYLDGTFYLN HTFKKVAITF DSSVSWPGND RLLTPNEFEI        780
KRSVDGEGYN VAQCNMTKDW FLVQMLANYN IGYQGFYIPE SYKDRMYSFF RNFQPMSRQV        840
VDDTKYKDYQ QVGIIHQHNN SGFVGYLAPT MREGQAYPAN VPYPLIGKTA VDSITQKKFL        900
CDRTLWRIPF SSNFMSMGAL TDLGQNLLYA NSAHALDMTF EVDPMDEPTL LYVLFEVFDV        960
VRVHQPHRGV IETVYLRTPF SAGNATT                                           987

SEQ ID NO: 58           moltype = AA  length = 959
FEATURE                 Location/Qualifiers
REGION                  1..959
                        note = Hexon Polypeptide
source                  1..959
                        mol_type = protein
                        organism = synthetic construct
SEQUENCE: 58
MATPSMMPQW SYMHISGQDA SEYLSPGLVQ FARATETYFS LNNKFRNPTV APTHDVTTDR         60
SQRLTLRFIP VDREDTAYSY KARFTLAVGD NRVLDMASTY FDIRGVLDRG PTFKPYSGTA        120
YNALAPKGAP NSCEWDEDDT QVQVAAEDDQ DDDEEEEQLP QQRNGKKTHV YAQAPFAGEA        180
INKNGLQIGT NGAATEGNKE IYADKTYQPE PQIGESQWNE AESSVAGGRV LKKTTPMKPC        240
YGSYARPTNS NGGQGVMVEQ NGKLESQVEM QFFSTSVNAM NEANAIQPKL VLYSEDVNME        300
TPDTHLSYKP GKSDDNSKAM LGQQSMPNRP NYIAFRDNFI GLMYYNSTGN MGVLAGQASQ        360
LNAVVDLQDR NTELSYQLLL DSIGDRTRYF SMWNQAVDSY DPDVRIIENH GTEDELPNYC        420
FPLGGIGVTD TYQAIKATNG NGGATTWAQD NTFAERNEIG VGNNFAMEIN LNANLWRNFL        480
YSNIALYLPD KLKYNPTNVE ISDNPNTYDY MNKRVVAPGL VDCYINLGAR WSLDYMDNVN        540
PFNHHRNAGL RYRSMLLGNG RYVPFHIQVP QKFFAIKNLL LLPGSYTYEW NFRKDVNMVL        600
QSSLGNDLRV DGASIKFDSI CLYATFFPMA HNTASTLEAM LRNDTNDQSF NDYLSAANML        660
YPIPANATNV PISIPSRNWA AFRGWAFTRL KTKETPSLGS GYDPYYTYSG SIPYLDGTFY        720
LNHTFKKVAI TFDSSVSWPG NDRLLTPNEF EIKRSVDGEG YNVAQCNMTK DWFLVQMLAN        780
YNIGYQGFYI PESYKDRMYS FFRNFQPMSR QVVDDTKYKD YQQVGIIHQH NNSGFVGYLA        840
PTMREGQAYP ANVPYPLIGK TAVDSITQKK FLCDRTLWRI PFSSNFMSMG ALTDLGQNLL        900
YANSAHALDM TFEVDPMDEP TLLYVLFEVF DVVRVHQPHR GVIETVYLRT PFSAGNATT        959

SEQ ID NO: 59           moltype = AA  length = 962
FEATURE                 Location/Qualifiers
REGION                  1..962
                        note = Hexon Polypeptide
source                  1..962
                        mol_type = protein
                        organism = synthetic construct
SEQUENCE: 59
MATPSMMPQW SYMHISGQDA SEYLSPGLVQ FARATETYFS LNNKFRNPTV APTHDVTTDR         60
SQRLTLRFIP VDREDTAYSY KARFTLAVGD NRVLDMASTY FDIRGVLDRG PTFKPYSGTA        120
YNALAPKGAP NSCEWEQNET AQVDAQELDE EENEANEAQA REQEQAKKTH VYAQAPLSGE        180
AINKNGLQIG TNGAATEGNK EIYADKTYQP EPQIGESQWN EAESSVAGGR VLKKTTPMKP        240
CYGSYARPTN SNGGQGVMVE QNGKLESQVE MQFFSTSVNA MNEANAIQPK LVLYSEDVNM        300
ETPDTHLSYK PGKSDDNSKA MLGQQSMPNR PNYIAFRDNF IGLMYYNSTG NMGVLAGQAS        360
```

```
QLNAVVDLQD RNTELSYQLL LDSIGDRTRY FSMWNQAVDS YDPDVRIIEN HGTEDELPNY   420
CFPLGGIGIT DTFQAVKTTA ANGDQGNTTW QKDSTFAERN EIGVGNNFAM EINLNANLWR   480
NPLYSNIALY LPDKLKYNPT NVEISDNPNT YDYMNKRVVA PGLVDCYINL GARWSLDYMD   540
NVNPFNHPRH AGLRYRSMLL GNGRYVPFHI QVPQKFFAIK NLLLLPGSYT YEWNFRKDVN   600
MVLQSSLGND LRVDGASIKF DSICLYATFF PMAHNTASTL EAMLRNDTND QSFNDYLSAA   660
NMLYPIPANA TNVPISIPSR NWAAFRGWAF TRLKTKETPS LGSGYDPYYT YSGSIPYLDG   720
TFYLNHTFKK VAITFDSSVS WPGNDRLLTP NEFEIKRSVD GEGYNVAQCN MTKDWFLVQM   780
LANYNIGYQG FYIPESYKDR MYSFFRNFQP MSRQVVDDTK YKDYQQVGII HQHNNSGFVG   840
YLAPTMREGQ AYPANVPYPL IGKTAVDSIT QKKFLCDRTL WRIPFSSNFM SMGALTDLGQ   900
NLLYANSAHA LDMTFEVDPM DEPTLLYVLF EVFDVVRVHQ PHRGVIETVY LRTPFSAGNA   960
TT                                                                 962

SEQ ID NO: 60           moltype = AA  length = 528
FEATURE                 Location/Qualifiers
REGION                  1..528
                        note = Fiber Polypeptide
source                  1..528
                        mol_type = protein
                        organism = synthetic construct
SEQUENCE: 60
MKRARPSEDT FNPVYPYDTE TGPPTVPFLT PPFVSPNGFQ ESPPGVLSLR LSEPLVTSHG    60
MLALKMGSGL SLDQAGNLTS NTITVSQPLK KTKSNITLET SAPLTVSSGA LTMATTSPLV   120
VSDNTLTMQS QAPLTVQDSK LSIATKEPLT VLDGKLALQT SAPLSATDNN ALTITASPPL   180
TTANGSLAVT MENPLYNNNG KLGLKIGGPL QVATDSHALT LGTGQGVAVH NNLLHTKVTG   240
AIGFDTSGNM ELKTGDGLYV DSAGPNQKLH INLNTTKGLA FDNTAITINA GKGLEFETDS   300
SNGNPIKTKI GSGIQYNTNG AMVAKLGTGL SFDSSGAITM GSINNDRLTL WTTPDPSPNC   360
RIASDKDCKL TLALTKCGSQ ILGTVSALAV SGNMASINGT LSSVNLVLRF DDNGVLMSNS   420
SLDKQYWNFR NGDSTNGQPY TYAVGFMPNL KAYPKTQSKT AKSNIVSQVY LNGDKSKPLH   480
FTITLNGTDE TNQVSKYSIS FSWSWNSGQY TNDKFATNSY TFSYIAQE                528

SEQ ID NO: 61           moltype = AA  length = 324
FEATURE                 Location/Qualifiers
REGION                  1..324
                        note = Fiber Polypeptide
source                  1..324
                        mol_type = protein
                        organism = synthetic construct
SEQUENCE: 61
MKRARPSEDT FNPVYPYDTE TGPPTVPFLT PPFVSPNGFQ ESPPGVLTLK CLTPLTTTGG    60
SLQLKVGGGL TVDDTDGTLQ ENIRATAPIT KNNHSVELSI GNGLETQNNK LCAKLGNGLK   120
FNNGDICIKD SINTLWTGIN PPPNCQIVEN TNTNDGKLTL VLVKNGGLVN GYVSLVGVSD   180
TVNQMFTQKT ANIQLRLYFD SSGNLLTDES DLKIPLKNKS STATSETVAS SKAFMPSTTA   240
YPFNTTTRDS ENYIHGICYY MTSYDRSLFP LNISIMLNSR MISSNVAYAI QFEWNLNASE   300
SPESNIATLT TSPFFFSYIT EDDN                                         324

SEQ ID NO: 62           moltype = AA  length = 534
FEATURE                 Location/Qualifiers
REGION                  1..534
                        note = Fiber Polypeptide
source                  1..534
                        mol_type = protein
                        organism = synthetic construct
SEQUENCE: 62
MKRARPSEDT FNPVYPYDTE TGPPTVPFLT PPFVSPNGFQ ESPPGVLSLR LSEPLVTSHG    60
MLALKMGSGL SLDQAGNLTS NTITVSQPLK KTKSNITLET SAPLTVSSGA LTMATTSPLV   120
VSDNTLTMQS QAPLTVQDSK LSIATKEPLT VLDGKLALQT SAPLSATDNN ALTITASPPL   180
TTANGSLAVT MENPLYNNNG KLGLKIGGPL QVATDSHALT LGTGQGVAVH NNLLHTKVTG   240
AIGFDTSGNM ELKTGDGLYV DSAGPNQKLH INLNTTKGLA FDNTAITINA GKGLEFETDS   300
SNGNPIKTKI GSGIQYNTNG AMVAKLGTGL SFDSSGAITM GSINNDRLTL WTTPDPSPNC   360
RIASDKDCKL TLALTKCGSQ ILGTVSALAV SGNMASINGT LSSVNLVLRF DDNGVLMSNS   420
SLDKQYWNFR NGDSTNGQPY TYAVGFMPNL KAYPKTQSKT AKSNIVSQVY LNGDKSKPLH   480
FTITLNGTDE TNQVSKYSIS FSWSWNSGQY TNDKFATNSY TFSYIAQEKK KKKK         534

SEQ ID NO: 63           moltype = AA  length = 425
FEATURE                 Location/Qualifiers
REGION                  1..425
                        note = Fiber Polypeptide
source                  1..425
                        mol_type = protein
                        organism = synthetic construct
SEQUENCE: 63
MKRARPSEDT FNPVYPYDTE TGPPTVPFLT PPFVSPNGFQ ESPPGVLSLR LSEPLVTKNG    60
EITLKLGEGV DLDSSGKLIS NTATKAAAPL SFSNNTISLN MDHPFYTKDG KLSLQVSPPL   120
NILRTSILNT LALGFGSGLG LRGSALAVQL VSPLTFDTDG NIKLTLDRGL HVTTGDAIES   180
NISWAKGLKF EDGAIATNIG NGLEFGSSST ETGVDDAYPI QVKLGSGLSF DSTGAIMAGN   240
KEDDKLTLWT TPDDPSPNCQ I LAENDAKLTL CLTKCGSQIL ATVSVLVVGS GNLNPITGTV   300
SSAQVFLRFD ANGVLLTEHS TLKKYWGYRQ GDSIDGTPYT NAVGFMPNLK AYPKSQSSTT   360
KNNIVGQVYM NGDVSKPMLL TITLNGTDDS NSTYSMSFSY TWTNGSYVGA TFGANSYTFS   420
YIAQE                                                              425
```

```
SEQ ID NO: 64           moltype = AA  length = 432
FEATURE                 Location/Qualifiers
REGION                  1..432
                        note = Fiber Polypeptide
source                  1..432
                        mol_type = protein
                        organism = synthetic construct
SEQUENCE: 64
MKRARPSEDT FNPVYPYDTE TGPPTVPFLT PPFVSPNGFQ ESPPGVLSLR LSEPLVTKNG    60
EITLKLGEGV DLDSSGKLIS NTATKAAAPL SFSNNTISLN MDHPFYTKDG KLSLQVSPPL   120
NILRTSILNT LALGFGSGLG LRGSALAVQL VSPLTFDTDG NIKLTLDRGL HVTTGDAIES   180
NISWAKGLKF EDGAIATNIG NGLEFGSSST ETGVDDAYPI QVKLGSGLSF DSTGAIMAGN   240
KEDDKLTLWT TPDPSPNCQI LAENDAKLTL CLTKCGSQIL ATVSVLVVGS GNLNPITGTV   300
SSAQVFLRFD ANGVLLTEHS TLKKYWGYRQ GDSIDGTPYT NAVGFMPNLK AYPKSQSSTT   360
KNNIVGQVYM NGDVSKPMLL TITLNGTDDS NSTYSMSFSY TWTNGSYVGA TFGANSYTFS   420
YIAQEKKKKK KK                                                      432

SEQ ID NO: 65           moltype = AA  length = 441
FEATURE                 Location/Qualifiers
REGION                  1..441
                        note = Fiber Polypeptide
source                  1..441
                        mol_type = protein
                        organism = synthetic construct
SEQUENCE: 65
MKRARPSEDT FNPVYPYDTE TGPPTVPFLT PPFVSPNGFQ ESPPGVLSLR LSEPLVTKNG    60
EITLKLGEGV DLDSSGKLIS NTATKAAAPL SFSNNTISLN MDHPFYTKDG KLSLQVSPPL   120
NILRTSILNT LALGFGSGLG LRGSALAVQL VSPLTFDTDG NIKLTLDRGL HVTTGDAIES   180
NISWAKGLKF EDGAIATNIG NGLEFGSSST ETGVDDAYPI QVKLGSGLSF DSTGAIMAGN   240
KEDDKLTLWT TPDPSPNCQI LAENDAKLTL CLTKCGSQIL ATVSVLVVGS GNLNPITGTV   300
SSAQVFLRFD ANGVLLTEHS TLKKYWGYRQ GDSIDGTPYT NAVGFMPNLK AYPKSQSSTT   360
KNNIVGQVYM NGDVSKPMLL TITLNGTDDS GGSSGKKKKK KKASGGSSTY SMSFSYTWTN   420
GSYVGATFGA NSYTFSYIAQ E                                            441

SEQ ID NO: 66           moltype = AA  length = 27
FEATURE                 Location/Qualifiers
source                  1..27
                        mol_type = protein
                        organism = Mus musculus
SEQUENCE: 66
PVTLTITLTA RGEHKEEELI GAYYSMS                                       27

SEQ ID NO: 67           moltype = AA  length = 27
FEATURE                 Location/Qualifiers
source                  1..27
                        mol_type = protein
                        organism = Mus musculus
SEQUENCE: 67
PVTLTITLLR QTGAASAVWG GAYYSMS                                       27

SEQ ID NO: 68           moltype = AA  length = 23
FEATURE                 Location/Qualifiers
source                  1..23
                        mol_type = protein
                        organism = Adenovirus
SEQUENCE: 68
EMQFFSTTEA TAGNGDNLTP KVV                                           23

SEQ ID NO: 69           moltype = AA  length = 26
FEATURE                 Location/Qualifiers
REGION                  1..26
                        note = Artificial Sequence
source                  1..26
                        mol_type = protein
                        organism = synthetic construct
SEQUENCE: 69
EMQFFSGSTA RGEHKEEELI GTPKVV                                        26

SEQ ID NO: 70           moltype = AA  length = 27
FEATURE                 Location/Qualifiers
REGION                  1..27
                        note = Artificial Sequence
source                  1..27
                        mol_type = protein
                        organism = synthetic construct
SEQUENCE: 70
EMQFFSGSML RQTGAASAVW GGTPKVV                                       27
```

```
SEQ ID NO: 71           moltype = AA  length = 407
FEATURE                 Location/Qualifiers
source                  1..407
                        mol_type = protein
                        organism = Adenovirus
SEQUENCE: 71
YNALAPKGAP NPCEWDEAAT ALEINLEEED DDNEDEVDEQ AEQQKTHVFS QAPYSGINIT    60
KEGIQIGVEG QTPKYADKTF QPEPQIGESQ WYETEINHAA GRVLKKTTPM KPCYGSYAKP   120
TNENGGQGIL VKQQNGKLES QVEMQFFSTT EATAGNGDNL TPKVVLYSED VDIETPDTHI   180
SYMPTIKEGN SRELMGQQSM PNRPNYIAFR DNFIGLMYYN STGNMGVLAG QASQLNAVVD   240
LQDRNTELSY QLLLDSIGDR TRYFSMWNQA VDSYDPDVRI IENHGTEDEL PNYCFPLGGV   300
INTETLTKVK PKTGQENGWE KDATEFSDKN EIRVGNNFAM EINLNANLWR NFLYSNIALY   360
LPDKLKYSPS NVKISDNPNT YDYMNKRVVA PGLVDCYINL GARWSLD                407

SEQ ID NO: 72           moltype = AA  length = 418
FEATURE                 Location/Qualifiers
source                  1..418
                        mol_type = protein
                        organism = Adenovirus
SEQUENCE: 72
YNALAPKGAP NSCEWEQNET AQVDAQELDE EENEANEAQA REQEQAKKTH VYAQAPLSGI    60
KITKEGLQIG TADATVAGAG KEIFADKTFQ PEPQVGESQW NEADATAAGG RVLKKTTPMK   120
PCYGSYARPT NSNGGQGVMV EQNGKLESQV EMQFFSTSTN ATNEVNNIQP TVVLYSEDVN   180
METPDTHLSY KPKMGDKNAK VMLGQQAMPN RPNYIAFRDN FIGLMYYNST GNMGVLAGQA   240
SQLNAVVDLQ DRNTELSYQL LLDSIGDRTR YFSMWNQAVD SYDPDVRIIE NHGTEDELPN   300
YCFPLGGIGI TDTFQAVKTT AANGDQGNTT WQKDSTFAER NEIGVGNNFA MEINLNANLW   360
RNFLYSNIAL YLPDKLKYNP TNVEISDNPN TYDYMNKRVV APGLVDCYIN LGARWSLE    418

SEQ ID NO: 73           moltype = AA  length = 414
FEATURE                 Location/Qualifiers
source                  1..414
                        mol_type = protein
                        organism = Adenovirus
SEQUENCE: 73
YNALAPKGAP NSCEWDEDDT QVQVAAEDDQ DDDEEEEQLP QQRNGKKTHV YAQAPFAGEA    60
INKNGLQIGT NGAATEGNKE IYADKTYQPE PQIGESQWNE AESSVAGGRV LKKTTPMKPC   120
YGSYARPTNS NGGQGVMVEQ NGKLESQVEM QFFSTSVNAM NEANAIQPKL VLYSEDVNME   180
TPDTHLSYKP GKSDDNSKAM LGQQSMPNRP NYIAFRDNFI GLMYYNSTGN MGVLAGQASQ   240
LNAVVDLQDR NTELSYQLLL DSIGDRTRYF SMWNQAVDSY DPDVRIIENH GTEDELPNYC   300
FPLGGIGVTD TYQAIKATNG NGGATTWAQD NTFAERNEIG VGNNFAMEIN LNANLWRNFL   360
YSNIALYLPD KLKYNPTNVE ISDNPNTYDY MNKRVVAPGL VDCYINLGAR WSLD        414

SEQ ID NO: 74           moltype = AA  length = 348
FEATURE                 Location/Qualifiers
source                  1..348
                        mol_type = protein
                        organism = Adenovirus
SEQUENCE: 74
YNALAPKGAP NSCEWEQEEP TQEMAEELED EEEAEEEEAE EEAEAPQADQ KVKKTHVYAQ    60
APLAGEKITA NGLQIVSDTQ TEGNPVFADP TYQPEPQVGE SQWNEAEATA SGGRVLKKTT   120
PMKPCYGSYA RPTNKNGGQG ILVANNQGAL ESKVEMQFFA PSGTAMNERN AVQPSIVLYS   180
EDVNMETPDT HISYKPSKTD ENSKAMLGQQ AMPNRPNYIA FRDNFIGLMY YNSTGNMGVL   240
AGQASQLNAV VDLQDRNTEL SYQLLLDSIG DRTRYFSMWN QAVDSYDPDV RIIENHGTED   300
ELPNYCFPLG GIGVTDTYQG IKSNGNGNPQ NWTKNDDFAA RNEIGVGN               348

SEQ ID NO: 75           moltype = AA  length = 352
FEATURE                 Location/Qualifiers
source                  1..352
                        mol_type = protein
                        organism = Adenovirus
SEQUENCE: 75
YNALAPKGAP NSCEWEQTED SGRAVAEDEE EEDEDEEEEE EEQNARDQAT KKTHVYAQAP    60
LSGETITKSG LQIGSDNAET QAKPVYADPS YQPEPQIGES QWNEADANAA GGRVLKKTTP   120
MKPCYGSYAR TNPFGGQSV LVPDEKGVPL PKVDLQFFSN TTSLNDRQGN ATKPKVVLYS   180
EDVNMETPDT HLSYKPGKGD ENSKAMLGQQ SMPNRPNYIA FRDNFIGLMY YNSTGNMGVL   240
AGQASQLNAV VDLQDRNTEL SYQLLLDSIG DRTRYFSMWN QAVDSYDPDV RIIENHGTED   300
ELPNYCFPLG GIGVTDTYQA IKANGNGSGD NGDTTWTKDE TFATRNEIGV GN          352

SEQ ID NO: 76           moltype = AA  length = 336
FEATURE                 Location/Qualifiers
source                  1..336
                        mol_type = protein
                        organism = Adenovirus
SEQUENCE: 76
YNALAPKGAP NPCEWDEAAT ALEINLEEED DDNEDEVDEQ AEQQKTHVFS QAPYSGINIT    60
KEGIQIGVEG QTPKYADKTF QPEPQIGESQ WYETEINHAA GRVLKKTTPM KPCYGSYAKP   120
TNENGGQGIL VKQQNGKLES QVEMQFFSTT EATAGNGDNL TPKVVLYSED VDIETPDTHI   180
SYMPTIKEGN SRELMGQQSM PNRPNYIAFR DNFIGLMYYN STGNMGVLAG QASQLNAVVD   240
LQDRNTELSY QLLLDSIGDR TRYFSMWNQA VDSYDPDVRI IENHGTEDEL PNYCFPLGGV   300
```

```
INTETLTKVK PKTGQENGWE KDATEFSDKN EIRVGN                                336

SEQ ID NO: 77           moltype = AA  length = 347
FEATURE                 Location/Qualifiers
source                  1..347
                        mol_type = protein
                        organism = Adenovirus
SEQUENCE: 77
YNALAPKGAP NSCEWEQNET AQVDAQELDE EENEANEAQA REQEQAKKTH VYAQAPLSGI        60
KITKEGLQIG TADATVAGAG KEIFADKTFQ PEPQVGESQW NEADATAAGG RVLKKTTPMK       120
PCYGSYARPT NSNGGQGVMV EQNGKLESQV EMQFFSTSTN ATNEVNNIQP TVVLYSEDVN       180
METPDTHLSY KPKMGDKNAK VMLGQQAMPN RPNYIAFRDN FIGLMYYNST GNMGVLAGQA       240
SQLNAVVDLQ DRNTELSYQL LLDSIGDRTR YFSMWNQAVD SYDPDVRIIE NHGTEDELPN       300
YCFPLGGIGI TDTFQAVKTT AANGDQGNTT WQKDSTFAER NEIGVGN                    347

SEQ ID NO: 78           moltype = AA  length = 343
FEATURE                 Location/Qualifiers
source                  1..343
                        mol_type = protein
                        organism = Adenovirus
SEQUENCE: 78
YNALAPKGAP NSCEWDEDDT QVQVAAEDDQ DDDEEEEQLP QQRNGKKTHV YAQAPFAGEA        60
INKNGLQIGT NGAATEGNKE IYADKTYQPE PQIGESQWNE AESSVAGGRV LKKTTPMKPC       120
YGSYARPTNS NGGQGVMVEQ NGKLESQVEM QFFSTSVNAM NEANAIQPKL VLYSEDVNME       180
TPDTHLSYKP GKSDDNSKAM LGQQSMPNRP NYIAFRDNFI GLMYYNSTGN MGVLAGQASQ       240
LNAVVDLQDR NTELSYQLLL DSIGDRTRYF SMWNQAVDSY DPDVRIIENH GTEDELPNYC       300
FPLGGIGVTD TYQAIKATNG NGGATTWAQD NTFAERNEIG VGN                        343
```